United States Patent
Lim et al.

(10) Patent No.: US 11,560,561 B2
(45) Date of Patent: Jan. 24, 2023

(54) MODULAR POLYPEPTIDE LIBRARIES AND METHODS OF MAKING AND USING SAME

(71) Applicant: The Regents of the University of California, Oakland, CA (US)

(72) Inventors: Wendell A. Lim, San Francisco, CA (US); Scott M. Coyle, San Francisco, CA (US); Russell M. Gordley, San Francisco, CA (US); Kole T. Roybal, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/751,419

(22) PCT Filed: Aug. 31, 2016

(86) PCT No.: PCT/US2016/049745
§ 371 (c)(1),
(2) Date: Feb. 8, 2018

(87) PCT Pub. No.: WO2017/040694
PCT Pub. Date: Mar. 9, 2017

(65) Prior Publication Data
US 2020/0224191 A1  Jul. 16, 2020

Related U.S. Application Data

(60) Provisional application No. 62/212,999, filed on Sep. 1, 2015.

(51) Int. Cl.
*C12N 15/10* (2006.01)
*C07K 14/725* (2006.01)
*C07K 16/28* (2006.01)

(52) U.S. Cl.
CPC ...... *C12N 15/1079* (2013.01); *C07K 14/7051* (2013.01); *C07K 16/2803* (2013.01);
(Continued)

(58) Field of Classification Search
CPC ............ C12N 15/1079; C12N 15/1037; C07K 14/7051; C07K 16/2803
See application file for complete search history.

(56) References Cited

U.S. PATENT DOCUMENTS

2004/0121324 A1  6/2004  Brenner et al.
2006/0034810 A1  2/2006  Riley et al.
(Continued)

FOREIGN PATENT DOCUMENTS

CN   1610737 A    4/2005
CN   101548034 A  9/2009
(Continued)

OTHER PUBLICATIONS

Dotti et al. "Design and Development of Therapies using Chimeric Antigen Receptor-Expressing T cells" Immunol Rev. Jan. 2014; 257(1):107-126; doi:10.1111/imr.12131, Author manuscript available Jan. 1, 2015, pp. 1-35 (Year: 2014).*

(Continued)

*Primary Examiner* — Richard A Schnizer
*Assistant Examiner* — K. Lau
(74) *Attorney, Agent, or Firm* — James S. Keddie; Bozicevic, Field & Francis LLP

(57) ABSTRACT

The present disclosure provides synthetic modular polypeptide libraries and nucleic acids encoding such synthetic modular polypeptide libraries. Also provided are methods of making synthetic modular polypeptide libraries and nucleic acids encoding synthetic modular polypeptide libraries. Methods of screening a synthetic modular polypeptide library to identify a selected phenotype associated with a (Continued)

member of a synthetic modular polypeptide library are also provided where such methods find use in both in vitro and in vivo assays.

11 Claims, 19 Drawing Sheets

Specification includes a Sequence Listing.

(52) U.S. Cl.
CPC ...... *C12N 15/1037* (2013.01); *C07K 2317/24* (2013.01); *C07K 2319/02* (2013.01); *C07K 2319/033* (2013.01); *C07K 2319/30* (2013.01)

(56) References Cited

U.S. PATENT DOCUMENTS

| | | | |
|---|---|---|---|
| 2008/0152657 A1* | 6/2008 | Horowitz et al. | 424/159.1 |
| 2009/0233806 A1 | 9/2009 | Carr | |
| 2010/0152059 A1 | 6/2010 | Zeichner | |
| 2015/0011405 A1* | 1/2015 | DeFalco et al. | G01N 33/6854 |
| 2015/0315569 A1* | 11/2015 | Weisinger et al. | C12N 15/1065 |

FOREIGN PATENT DOCUMENTS

| | | |
|---|---|---|
| CN | 104769103 A | 7/2015 |
| WO | WO 2005/010198 A2 | 2/2005 |
| WO | WO 2007/076166 A2 | 7/2007 |
| WO | WO 2012/041802 A1 | 4/2012 |
| WO | WO 2012/061832 A1 | 5/2012 |
| WO | WO2012112804 A1 | 8/2012 |
| WO | WO 2013/155119 A1 | 10/2013 |
| WO | WO 2014/127261 A1 | 8/2014 |
| WO | WO 2015/123642 A1 | 8/2015 |
| WO | WO 2015/163744 A1 | 10/2015 |

OTHER PUBLICATIONS

Benhar et al. "Phage display of single chain antibody constructs." Current Protocols in Immunology, (2002) 10.19B.1-10.19B.31 (Year: 2002).*

Camino, et al.; "CARbodies: Human Antibodies Against Cell Surface Tumor Antigens Selected From Repertoires Displayed on T Cell Chimeric Antigen Receptors", Molecular Therapy—Nucleic Acids, vol. 2, No. 5, May 2013, 11 pages.

Korngold, et al.; "Abstract B053: Designing chimeric antigen receptors for personalized immunotherapy: Rapid assembly of CARs from principal components using EZ-CAR_platform", Proceedings of the CRI-CIMT-EATI-AACR Inaugural International Cancer Immunotherapy Conference, Cancer Immunology Research, vol. 4, No. 1, Jan. 2016, 2 pages.

Lipowska-Bhalla, et al.; "Isolation of tumor antigen-specific single-chain variable fragments using a chimeric antigen receptor bicistronic retroviral vector in a Mammalian screening protocol.", Human Gene Therapy Methods, vol. 24, No. 6, Dec. 2013, pp. 381-391.

Rydzek, et al.; "Chimeric Antigen Receptor Library Screening Using a Novel NF-[kappa]B/NFAT Reporter Cell Platform", Molecular Therapy: The Journal of the American Society of Gene & Cell Therapy, vol. 27, No. 2, Feb. 2019, pp. 1-13.

Bernath, et al.; "In vitro compartmentalization by double emulsions: sorting and gene enrichment by fluorescence activated cell sorting"; Analytical Biochemistry; vol. 325, pp. 151-157 (2004).

Chichili, et al.; "Linkers in the structural biology of protein-protein interactions"; Protein Science; vol. 22, pp. 153-167 (2013).

Duong, et al.; "Engineering T Cell Function Using Chimeric Antigen Receptors Identified Using a DNA Library Approach";PLos One; vol. 8, Issue 5, 10 pages (May 2013).

Griffiths, et al.; "Directed evolution of an extremely fast phosphotriesterase by in vitro compartmentalization"; The EMBO Journal; vol. 22, No. 1, pp. 24-35 (2003).

Lim; "Designing Customized Cell Signaling Circuits"; Nat. Rev. Mol. Cell Biol.; vol. 11, No. 6, pp. 393-403 (Jun. 2010).

Lim; "The modular logic of signaling proteins: building allosteric switches from simple binding domains"; Current Opinion in Structural Biology; vol. 12, pp. 61-68 (2002).

Pawson, et al.; "Synthetic modular systems—reverse engineering of signal transduction"; FEBS Letters; vol. 579, pp. 1808-1814 (2005).

Stahelin; "Lipid binding domains: more than simple lipid effectors"; Journal of Lipid Research; April Supplement, 6 pages (2009).

Yachie et al., "Pooled-matrix protein interaction screens using Barcode Fusion Genetics", Molecular Systems Biology, 2016, 12: 863.

Engler et al., "A One Pot, One Step, Precision Cloning Method with High Throughput Capability", PLoS One, 2008, 3(11): e3647.

Sotelo et al., "An efficient method for variable region assembly in the construction of scFv phage display libraries using independent strand amplification", mAbs, 2012, 4(4): 542-550.

Yu et al., "Lentiviral vector of chimeric antigen receptor targeting carcinoembryonic antigen and its application", Journal of Third Military Medical University, Jun. 2015; 37(11): 1096-1101, Only abstract translated.

* cited by examiner

FIG. 3

Before Type IIS restriction enzyme (RE) digestion:

acctgcaacaCTCCGGATCAGGATCtGGTTCGTGGGTGCGCAGCAAGAGAAGCAGACTGCT-GCACAGCGACTACATGAACATGACCCCCAGACGGCCTGGCCCCACCAGAAAGCACTACCAGCCTTACGCC CCTCCCAGAGACTTCGCCGCCTACAGATCTggCTCCGGATCAggatcc*GGCAGTGGTAACACATAT*GTCTGCa *GATCCGGCAGTGGTA**caaggcaggt*

After Type IIS RE digestion:

CTCCGGATCAGGATCtGGTTCGTGGGTGCGCAGCAAGAGAAGCAGACTGCTGCACAGCGAC TACATGAACATGACCCCCAGACGGCCTGGCCCCACCAGAAAGCACTACCAGCCTTACGCCCCTCCCAGAGA CTTCGCCGCCTACAGATCTggCTCCGGATCAggatcc*GGCAGTGGTAACACATAT*GTCTGCa*GATCCGGCAGT GGTA*

Translation of Type IIS RE digested fragment:

SGSGSGSWVRSKRSRLLHSDYMNMTPRRPGPTRKHY-QPYAPPRDFAAYRSGSGSGSGS...

Legend:

*ITALIC*: CD28 co-stimulatory domain
<u>BOLD UNDERLINE</u>: sdfsa:module-specific barcode
<u>UNDERLINE</u>: Type IIS restriction site
<u>DOUBLE UNDERLINE</u>: BamHI site
BOLD: Gly/Ser linker sequence
*BOLD ITALIC*: 3' cloning homology arm

FIG. 4

| Index | Receptor | | Protein Sequence |
|---|---|---|---|
| 1 | CD80 | 19 | RCRERRRNERLRRESVRPV |
| 2 | PD1L | 29 | RKGRMMDVKKCGIQDTNSKKQSDTHLEET |
| 3 | TRML2_human (TLT2) | 32 | KKRHMASYSMCSDPSTRDPPGRPEPYVEVYLI |
| 4 | ICOS_human | 35 | TKKKYSSSVHDPNGEYMFMRAVNTAKKSRLTDVTL |
| 5 | TNF14_human (HVEM) | 35 | MEESVVRPSVFVVDGQTDIPFTRLGRSHRRQSCSV |
| 6 | CTLA4_human | 39 | SLSKMLKKRSPLTTGVYVKMPPTEPECEKQFQPYFIPIN |
| 7 | CD7_human | 40 | artqikklcswrdknsaacvvyedmshsrcntlsspnqyq |
| 8 | TNR9_human (CD137, 41BB) | 42 | KRGRKKLLYIFKQPFMRPVQTTQEEDGCSCRFPEEEEGGCEL |
| 9 | CD28 | 43 | WVRSKRSRLLHSDYMNMTPRRPGPTRKHYQPYAPPRDFAAYRS |
| 10 | CD27_human | 49 | HQRRKYRSNKGESPVEPAEPCHYSCPREEEGSTIPIQEDYRKPEPACSP |
| 11 | LAG3_human | 51 | RRQWRPRRFSALEQGIHPPQAQSKIEELEQEPEPEPEPEPEPEPEPEPEQL |
| 12 | TNR18_human (GITR) | 54 | HIWQLRSQCMWPRETQLLLEVPPSTEDARSCQFPEEERGERSAEEKGRLGDLWV |
| 13 | CD226_human (DNAM-1) | 61 | NRRRRRERRDLFTESWDTQKAPNNYRSPISTSQPTNQSMDDTREDIYVNYPTFSRRPKTRV |
| 14 | TNR5_human (CD40) | 62 | KKVAKKPTNKAPHPKQEPQEINFPDDLPGSNTAAPVQETLHGCQPVTQEDGKESRISVQERQ |
| 15 | HAVR(TIM-3) | 77 | KWYSHSKEKIQNLSLISLANLPPSGLANAVAEGIRSEENIYTIEENVYEVEEPNEYYCYVSSRQQPSQPLGCRFAMP |
| 16 | TIGIT_human | 80 | RKKKALRIHSVEGDLRRKSAGQEEWSPSAPSPPGSCVQAEAAPAGLCGEQRGEDCAELHDYFNVLSYRSLGNCSFFTETG |
| 17 | CRTAM_human | 83 | KLRKAHVIWKKENEVSEHTLESYRSRSNNEETSSEEKNGQSSHPMRCMNYITKLYSEAKTKRKENVQHSKLEEKHIQVPESIV |
| 18 | PDCD1_human (PD-1) | 98 | ICSRAARGTIGARRTGQPLKEDPSAVPVFSVDYGELDFQWREKTPEPPVPCVPEQTEYATIVFPSGMGTSSPARRGSADGPRSAQPLRPEDGHCSWPL |
| 19 | LAIR1_human | 101 | HRQNQIKQGPPRSKDEEQKPQQRPDLAVDVLERTADKATVNGLPEKDRETDTSALAAGSSQEVTYAQLDHWALTQRTARAVSPQSTKPMAESITYAAVARH |
| 20 | CXAR_human (CAR) | 107 | CCRKKRREEKYEKEVHHDIREDVPPPKSRTSTARSYIGSNHSSLGSMSPSNMEGYSKTQYNQVPSEDFERTPQSPTLPPAKVAAPNLSRMGAIPVMIPAQSKDGSIV |
| 21 | BTLA_human | 114 | CCLRRHQGKQNELSDTAGREINLVDAHLKSEQTEASTRQNSQVLLSETGIYDNDPDLCFRMQEGSEVYSNPCLEENKPGIVYASLNHSVIGPNSRLARNVKEAPTEYASICVRS |
| 22 | CD2 | 117 | TKRKKQRSRRNDEELETRAHRVATEERGRKPHQIPASTPQNPATSQHPPPPPGHRSQAPSHRPPPPGHRVQHPQKRPPAPSGTQVHQQKGPPLPRPRVQPKPPHGAAENSLSPSSN |
| 23 | CD244_human (2B4) | 120 | WRRKRKEKQSETSPKEFLTIYEDVKDLKTRRNHEQEQTFPGGGSTIYSMIQSQSSAPTSQEPAYTLYSLIQPSRKSGSRKRNHSPSFNSTIYEVIGKSQPKAQNPARLSRKELENFDVYS |

FIG. 4 (Cont.)

| Index | Receptor | | Protein Sequence |
|---|---|---|---|
| 24 | TNR8_human (CD30) | 187 | RRACRKRIRQKLHLCYPVQTSQPKLELVDSRPRRSSTQLRSGASVTEPVAEERGLMSQPLMETCHSVGAAYLESLPLQDASPAGGPSSPRDLPEPRVSTEHTNNKIEKIYIMKADTVIVGTVKAELPEGRGLAGPAEPELEEELEADHTPHYPEQETEPPLGSCSDVMLSVEEEGKEDPLPTAASGK |
| 25 | TNR25_HUMAN (DR3) | 108 | TYRHCWPHKPLVTADEAGMEALTPPPATHLSPLDSAHTLLAPPDSSEKICTVQLVGNSWTPGYPETQEALCPQVTWSWDQLPSRALGPAAAPTLSPESPAGSPAMMLQ |
| 26 | OX40 | 42 | ALYLLRRDQRLPPDAHKPPGGGSFRTPIQEEQADAHSTLAKI |
| 27 | NKG2D | 51 | MGWIRGRRSRHSWEMSEFHNYNLDLKKSDFSTRWQKQRCPVVKSKCRENAS |
| 28 | TIM-1 | 48 | KKYFFKKEVQQLSVSFSSLQIKALQNAVEKEVQAEDNIYIENSLYATD |
| 29 | CD160 | 22 | SGFLQEKVWVMLVTSLVALQAL |
| 30 | BAFF-R | 85 | SWRRRQRRLRGASSAEAPDGDKDAPEPLDKVIILSPGISDATAPAWPPPGEDPGTTPPGHSVPVPATELGSTELVTTKTAGPEQQ |
| 31 | TACI | 111 | ACFLKKRGDPCSCQPRSRPRQSPAKSSQDHAMEAGSPVSTSPEPVETCSFCFPECRAPTQESAVTPGTPDPTCAGRWGCHTRTTVLQPCPHIPDSGLGIVCVPAQEGGPGA |
| 32 | CD72 | 95 | MAEAITYADLRFVKAPLKKSISSRLGQDPGADDDGEITYENVQVPAVLGVPSSLASSVLGDKAAVKSEQPTASWRAVTSPAVGRILPCRTTCLRY |
| 33 | CD22 | 141 | KLQRRWKRTQSQQGLQENSSGQSFFVRNKKVRRAPLSEGPHSLGCYNPMMEDGISYTTLRFPEMNIPRTGDAESSEMQRPPPDCDDTVTYSALHKRQVGDYENVIPDFPEDEGIHYSELIQFGVGERPQAQENVDYVILKH |
| 34 | CD96 | 45 | RKWCQYQKEIMERPPPFKPPPPPIKYTCIQEPNESDLPYHEMETL |
| 35 | NTB-A | 84 | LRKRRDSLSLSTQRTQGPAESARNLEYVSVSPTNNTVYASVTHSNRETEIWTPRENDTITIYSTINHSKESKPTFSRATALDNV |
| 36 | CRACC | 88 | WFLKRERQEEYIEEKKRVDICRETPNICPHSGENTEYDTIPHTNRTILKEDPANTVYSTVEIPKKMENPHSLLTMPDTPRLFAYENVI |
| 37 | Siglec-3,7,9 | 82 | KTHRRKAARTAVGRNDTHPTTGSASPKHQKKSKLHGPTETSSCSGAAPTVEMDEELHYASLNFHGMNPSKDTSTEYSEVRTQ |
| 38 | KLRG1 | 38 | MTDSVIYSMLELPTATQAQNDYGPQQKSSSSRPSCSCL |
| 39 | NKR-P1A | 45 | MDQQAIYAELNLPTDSGPESSSPSSLPRDVCQGSPWHQFALKLSC |
| 40 | ILT2 | 168 | LRHRRQGKHWTSTQRKADFQHPAGAVGPEPTDRGLQWRSSPAADAQEENLYAAVKHTQPEDGVEMDTRSPHDEDPQAVTYAEVKHSRPRREMASPPSPLSGEFLDTKDRQAEEDRQMDTEAAASEAPQDVTYAQLHSLTLRREATEPPPSQEGPSPAVPSIYATLAIH |
| 41 | KIR2DL1 | 83 | RWCSNKKNAAVMDQESAGNRTANSEDSDEQDPQEVTYTQLNHCVFTQRKITRPSQRPKTPPTDIIVYTELPNAESRSKVVSCP |
| 42 | KIR3DL1 | 84 | HLWCSNKKNAAVMDQEPAGNRTANSEDSDEQDPEEVTYAQLDHCVFTQRKITRPSQRPKTPPTDTILYTELPNAKPRSKVVSCP |
| 43 | CD94-NKG2A | 10 | MAVFKTTLWR |
| 44 | CD300b | 29 | KGSQRVPEEPGEQPIYMNFSEPLTKDMAT |
| 45 | CD300e | 11 | VNRPQWAPPGR |
| 46 | TREM1 | 8 | VTLRSFVP |

FIG. 4 (Cont.)

| Index | Receptor | | Protein Sequence |
|---|---|---|---|
| 47 | TREM2 | 35 | AAWHGQKPGTHPPSELDCGHDPGYQLQTLPGLRDT |
| 48 | ILT7 | 32 | QHSQRSPPRCSQEANSRKDNAPFRVVEPWEQI |
| 49 | ILT3 | 168 | QHWRQGKHRTLAQRQADFQRPPGAAEPEPKDGGLQRRSSPAADVQ GENFCAAVKNTQPEDGVEMDTRQSPHDEDPQAVTYAKVKHSRPRRE MASPPSPLSGEFLDTKDRQAEEDRQMDTEAAASEAPQDVTYAQLHSF TLRQKATEPPPSQEGASPAEPSVYATLAIH |
| 50 | ILT4 | 116 | LRHRRQGKHWTSTQRKADFQHPAGAVGPEPTDRGLQWRSSPAADA QEENLYAAVKDTQPEDGVEMDTRAAASEAPQDVTYAQLHSLTLRRKA TEPPPSQEREPPAEPSIYATLAIH |
| 51 | TLT-1 | 128 | MAKRKQGNRLGVCGRFLSSRVSGMNPSSVVHHVSDSGPAAELPLDV PHIRLDSPPSFDNTTYTSLPLDSPSGKPSLPAPSSLPPLPPKVLVCSKP VTYATVIFPGGNKGGGTSCGPAQNPPNNQTPSS |
| 52 | CD200R | 61 | KVNGCRKYKLNKTESTPVVEEDEMQPYASYTEKNNPLYDTTNKVKASE ALQSEVDTDLHTL |
| 53 | CD300a | 98 | RMFQKWIKAGDHSELSQNPKQAATQSELHYANLELLMWPLQEKPAPP REVEVEYSTVASPREELHYASVVFDSNTNRIAAQRPREEEPDSDYSVIR KT |
| 54 | CD300f | 113 | WRMMKYQQKAAGMSPEQVLQPLEGDLCYADLTLQLAGTSPQKATTKL SSAQVDQVEVEYVTMASLPKEDISYASLTLGAEDQEPTYCNMGHLSSH LPGRGPEEPTEYSTISRP |
| 55 | DC-SIGN | 37 | MSDSKEPRLQQLGLLEEEQLRGLGFRQTRGYKSLAGC |
| 56 | B7-2 | 29 | RKSSGGKGGSYSQAACSDSAQGSDVSLTA |
| 57 | Allergin-1 | 95 | LPKYKTRKAMRNNVPRDRGDTAMEVGIYANILEKQAKEESVPEVGSRP CVSTAQDEAKHSQELQYATPVFQEVAPREQEACDSYKSGYVYSELNF |
| 58 | Pir-B | 178 | RRRHRGKFRKDVQKEKDLQLSSGAEEPITRKGELQKRPNPAAATQEE SLYASVEDMQTEDGVELNSWTPPEEDPQGETYAQVKPSRLRKAGHVS PSVMSREQLNTEYEQAEEGQGANNQAAESGESQDVTYAQLCSRTLR QGAAASPLSQAGEAPEEPSVYATLAAARPEAVPKDMEQ |
| 59 | NC-14xSAG | 42 | SAGSAGSAGSAGSAGSAGSAGSAGSAGSAGSAGSAGSAGSAG |
| 60 | TNR9_2 | 42 | KRGRKKLLYIFKQPFMRPVQTTQEEDGCSCRFPEEEEGGCEL |
| 61 | TNR9_3 | 42 | KRGRKKLLYIFKQPFMRPVQTTQEEDGCSCRFPEEEEGGCEL |
| 62 | TNR9_4 | 42 | KRGRKKLLYIFKQPFMRPVQTTQEEDGCSCRFPEEEEGGCEL |

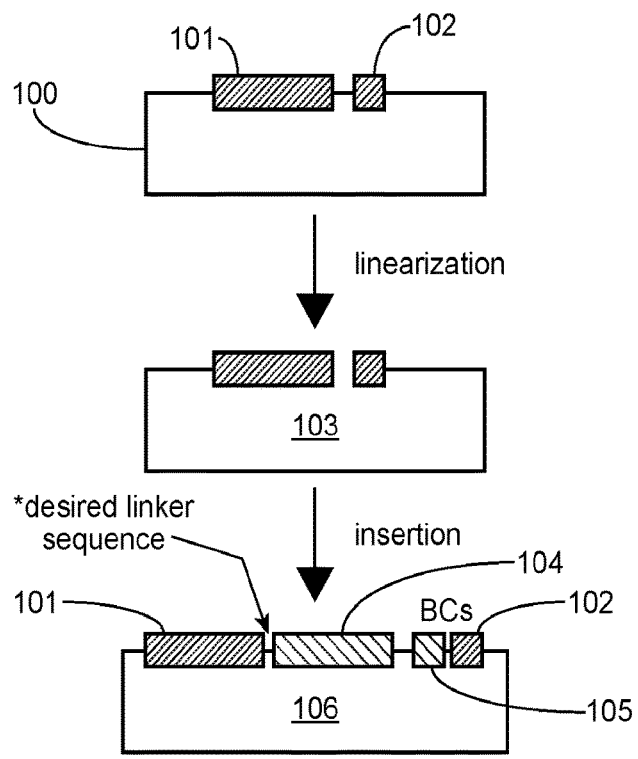
FIG. 12
FIG. 13
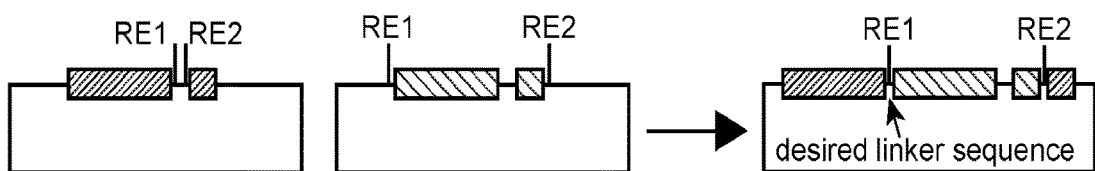
FIG. 14
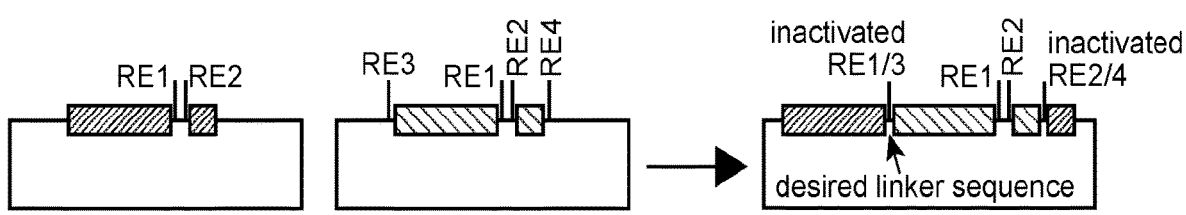

2 restriction enzymes (TypeIIS + In Fusion, Gibson...)

| ID# | Module | ID# | Module | ID# | Module | ID# | Module |
|---|---|---|---|---|---|---|---|
| 1 | CD80 | 17 | CRTAM | 33 | CD96 | 49 | ILT4 |
| 2 | PD1L | 18 | PDCD1 | 34 | NTB-A | 50 | TLT-1 |
| 3 | TRML2 | 19 | LAIR1 | 35 | CRACC | 51 | CD200R |
| 4 | ICOS | 20 | CXAR | 36 | Siglec-3,7,9 | 52 | CD300a |
| 5 | TNF14 | 21 | BTLA | 37 | KLRG1 | 53 | CD300f |
| 6 | CTLA4 | 22 | CD2 | 38 | NKR-P1A | 54 | DC-SIGN |
| 7 | CD7 | 23 | CD244 | 39 | ILT2 | 55 | B7-2 |
| 8 | TNR9 | 24 | TNR8 | 40 | KIR2DL1 | 56 | Allergin-1 |
| 9 | CD28 | 25 | TNR25 | 41 | KIR3DL1 | 57 | Pir-B |
| 10 | CD27 | 26 | OX40 | 42 | CD94-NKG2A | 58 | NC-14xSAG |
| 11 | LAG3 | 27 | NKG2D | 43 | CD300b | 59 | TNR9_2 |
| 12 | TNR18 | 28 | TIM-1 | 44 | CD300e | 60 | TNR9_3 |
| 13 | CD226 | 29 | CD160 | 45 | TREM1 | 61 | TNR9_4 |
| 14 | TNR5 | 30 | BAFF-R | 46 | TREM2 | | |
| 15 | HAVR | 31 | TACI | 47 | ILT7 | | |
| 16 | TIGIT | 32 | CD22 | 48 | ILT3 | | |

$$\overset{-(N-1)}{\begin{bmatrix} -2 & e_2/e_1 & e_3/e_1 \\ e_1/e_2 & -2 & e_3/e_2 \\ e_1/e_3 & e_2/e_3 & -2 \\ 1 & 1 & 1 \end{bmatrix}} \begin{bmatrix} p_1 \\ p_2 \\ p_3 \end{bmatrix} = \begin{bmatrix} 0 \\ 0 \\ 0 \\ 1 \end{bmatrix}$$

$$\quad\quad\quad\quad E \quad\quad\quad\quad F \quad\quad G$$

F = E\G
For original volumes all equal to 1,
F * N = optimized insert volumes

MODULAR POLYPEPTIDE LIBRARIES AND METHODS OF MAKING AND USING SAME

CROSS-REFERENCE

This application claims the benefit of U.S. Provisional Patent Application No. 62/212,999, filed Sep. 1, 2015, which application is incorporated herein by reference in its entirety.

STATEMENT REGARDING FEDERALLY SPONSORED RESEARCH

This invention was made with government support under grant nos. EY016546, P50 GM081879, R01 CA196277, F32 GM006499 and R01 GM055040, awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "UCSF-518WO SeqList_ST25.txt" created on Aug. 29, 2016 and having a size of 145 KB. The contents of the text file are incorporated by reference herein in their entirety.

INTRODUCTION

Many eukaryotic proteins function through modular domains or motifs that control or facilitate input and output functions of the protein as a whole. Rearrangement and recombination of the modular domains of eukaryotic proteins has already begun to provide new proteins with altered input/output relationships and completely novel overall functions. Successful engineering of individual modular proteins by simple recombination of input and output domains has served as proof-of-principle of this modular approach to new protein development.

Construction of new synthetic proteins, e.g., for use in therapeutic cells, has so far been carried out on a construct-by-construct basis. Likewise, transfection and screening of such synthetic proteins has also been performed in a low-throughput approach, using individual constructs screened one at a time or, in some instances, a small number of individual constructs screened in parallel. Parallel screening, while more efficient than screening individual constructs one at a time, has limited scalability due to the requirement that individual constructs must remain physically separate to facilitate end-stage identification of well performing constructs. Individual screening of large numbers of new proteins is burdensome when performing an in vitro assay but becomes even more prohibitively cumbersome and expensive when testing is advanced to assays performed in in vivo models. Such individual production and separate screening greatly limits the rate of development of new synthetic proteins.

SUMMARY

The present disclosure provides synthetic modular polypeptide libraries and nucleic acids encoding such synthetic modular polypeptide libraries. Also provided are methods of making synthetic modular polypeptide libraries and nucleic acids encoding synthetic modular polypeptide libraries. Methods of screening a synthetic modular polypeptide library to identify a selected phenotype associated with a member of a synthetic modular polypeptide library are also provided where such methods find use in both in vitro and in vivo assays.

Provided is a method of identifying a selected phenotype associated with a synthetic modular polypeptide in a cell, the method comprising: a) introducing a barcoded library of nucleic acids into host cells, thereby generating a heterogeneous population of genetically modified host cells, wherein the barcoded library of nucleic acids comprises a plurality of members, each of which plurality of members comprises a nucleotide sequence encoding a different synthetic modular polypeptide; and b) identifying a genetically modified host cell within the heterogeneous population that displays the selected phenotype in response to a stimulus.

Also provided is a method, wherein the synthetic modular polypeptide is a chimeric antigen receptor (CAR) polypeptide and wherein the stimulus is an antigen-presenting cell that displays on its surface an antigen that is bound by the CAR.

Also provided is a method of identifying a selected phenotype associated with a synthetic modular polypeptide in a cell, wherein the stimulus is in contact with a co-stimulatory molecule.

Also provided is a method of identifying a selected phenotype associated with a synthetic modular polypeptide in a cell, wherein the synthetic modular polypeptide is a modular receptor polypeptide.

Also provided is a method of identifying a selected phenotype associated with a synthetic modular polypeptide in a cell, wherein the modular receptor polypeptide is a chimeric Notch receptor polypeptide.

Also provided is a method of identifying a selected phenotype associated with a synthetic modular polypeptide in a cell, wherein the stimulus is a ligand for the chimeric Notch receptor polypeptide.

Also provided is a method of identifying a selected phenotype associated with a synthetic modular polypeptide in a cell, wherein the synthetic modular polypeptide is a modular scaffold protein.

Also provided is a method of identifying a selected phenotype associated with a synthetic modular polypeptide in a cell, wherein the synthetic modular polypeptide is a modular protein kinase or phosphatase protein.

Also provided is a method of identifying a selected phenotype associated with a synthetic modular polypeptide in a cell, wherein the synthetic modular polypeptide is a modular transcriptional regulator protein.

Also provided is a method of identifying a selected phenotype associated with a synthetic modular polypeptide in a cell, wherein the synthetic modular polypeptide is a modular epigenetic regulator protein.

Also provided is a method of identifying a selected phenotype associated with a synthetic modular polypeptide in a cell, wherein the synthetic modular polypeptide is a modular recombinase or nuclease protein.

Also provided is a method of identifying a selected phenotype associated with a synthetic modular polypeptide in a cell, wherein the selected phenotype comprises a phenotypic signature comprising two or more phenotypes.

Also provided is a method of identifying a selected phenotype associated with a synthetic modular polypeptide in a cell comprising sequencing the barcode of the identified genetically modified host cell to identify the synthetic modular polypeptide associated with the phenotype.

Also provided is a method of identifying a selected phenotype associated with a synthetic modular polypeptide in a cell, comprising quantifying the synthetic modular polypeptide associated with the phenotype.

Also provided is a method of identifying a selected phenotype associated with a synthetic modular polypeptide in a cell, comprising quantifying an individual module of the synthetic modular polypeptides of the barcoded library of nucleic acids that is associated with the phenotype.

Also provided is a method of identifying a selected phenotype associated with a synthetic modular polypeptide in a cell, wherein each nucleotide sequence encoding a different synthetic modular polypeptide comprises a sequence encoding a detectable reporter in operable linkage with the nucleotide sequence encoding the synthetic modular polypeptide and the method further comprises partitioning the heterogeneous population of genetically modified host cells based on the expressed detectable reporter.

Also provided is a method of identifying a selected phenotype associated with a synthetic modular polypeptide in a cell, wherein the identifying is performed in vitro or ex vivo.

Also provided is a method of identifying a selected phenotype associated with a synthetic modular polypeptide in a cell, wherein the phenotype is one or more of: a) proliferation; b) cytokine production; c) expression of a cell surface marker; d) expression of a reporter protein.

Also provided is a method of identifying a selected phenotype associated with a synthetic modular polypeptide in a cell, wherein the method includes a barcoded library of nucleic acids that comprises 100 or more unique members and the identifying comprises screening 100 or more unique members of the library for the selected phenotype.

Also provided is a method of identifying a selected phenotype associated with a synthetic modular polypeptide in a cell, wherein the method includes a barcoded library of nucleic acids comprising a plurality of members, wherein the plurality of members comprises a nucleotide sequence encoding a synthetic modular polypeptide comprising a modular domain selected from the group consisting of: an antigen-binding domain, a specific binding domain or a specific binding partner protein, a co-stimulatory domain, a co-inhibitory domain, an intracellular signaling domain, a transmembrane domain, a scaffold protein domain, a protein kinase protein domain, a protein phosphatase protein domain, a receptor tyrosine kinase protein domain, a lipid kinase protein domain, a lipid phosphatase protein domain, an ubiquitinylase protein domain, a deubiquitinylase protein domain, a SUMOylase protein domain, an acetylase protein domain, a deacetylase protein domain, a methylase protein domain, a demethylase protein domain, a nuclease protein domain, a recombinase protein domain, a transcription factor protein domain and combinations thereof.

Provided is a barcoded library of nucleic acids, the library comprising: a plurality of unique polynucleotides each comprising a nucleotide sequence encoding a unique synthetic modular polypeptide wherein each unique polynucleotide comprises: i) a coding region encoding the unique synthetic modular polypeptide comprising a first coding sequence encoding a first module linked in-frame to a second coding sequence encoding a second module, ii) a barcode region comprising a first barcode specific to the first coding sequence linked to a second barcode specific to the second coding sequence, wherein the first and second barcodes are in the reverse 5' to 3' order as compared to the first and second coding sequences; and wherein sequencing of each barcode region allows for the identification each unique synthetic modular polypeptide.

Also provided is a barcoded library of nucleic acids, wherein the first and second coding sequences are directly linked without any intervening non-coding nucleotides.

Also provided is a barcoded library of nucleic acids, wherein the plurality of unique polynucleotides comprises at least 1000 unique polynucleotides.

Also provided is a barcoded library of nucleic acids, wherein the barcode region is 5' of the coding region.

Also provided is a barcoded library of nucleic acids, wherein the coding region is 5' of the barcode region.

Also provided is a barcoded library of nucleic acids, that includes a plurality of unique polynucleotides each comprising a nucleotide sequence encoding a unique synthetic modular polypeptide wherein the unique synthetic modular polypeptide comprises a co-stimulatory domain.

Also provided is a barcoded library of nucleic acids, which includes a plurality of unique polynucleotides each comprising a nucleotide sequence encoding a unique synthetic modular polypeptide that includes a first and second module wherein the first and second modules comprise different co-stimulatory domains.

Also provided is a barcoded library of nucleic acids, which includes a plurality of unique polynucleotides each comprising a nucleotide sequence encoding a unique synthetic modular polypeptide wherein each unique polynucleotide further comprises a promoter sequence operably linked to both the coding region and a reporter sequence encoding a detectable polypeptide, wherein the detectable polypeptide is an optically detectable polypeptide including, e.g., an optically detectable fluorescent polypeptide.

Also provided is a barcoded library of nucleic acids, which includes a plurality of unique polynucleotides each comprising a nucleotide sequence encoding a unique synthetic modular polypeptide that includes a coding region wherein the coding region further comprises a third coding sequence encoding a third module linked in-frame to the second coding sequence and the barcode region comprises a third barcode specific to the third coding sequence linked to the second barcode, wherein the first, second and third barcodes are in reverse 5' to 3' order as compared to the first, second and third coding sequences.

Also provided is a barcoded library of nucleic acids, which includes a plurality of unique polynucleotides each comprising a nucleotide sequence encoding a unique synthetic modular polypeptide wherein the unique synthetic modular polypeptides encoded by each unique polynucleotide of the plurality are chimeric antigen receptor (CAR) polypeptides.

Also provided is a barcoded library of nucleic acids, which includes a plurality of unique polynucleotides each comprising a nucleotide sequence encoding a unique synthetic modular polypeptide wherein the unique synthetic modular polypeptides encoded by each unique polynucleotide of the plurality are modular receptor polypeptides.

Also provided is a barcoded library of nucleic acids encoding modular receptor polypeptides, wherein the modular receptor polypeptides are chimeric Notch receptor polypeptides.

Also provided is a barcoded library of nucleic acids, which includes a plurality of unique polynucleotides each comprising a nucleotide sequence encoding a unique synthetic modular polypeptide wherein the unique synthetic modular polypeptides encoded by each unique polynucleotide of the plurality are modular scaffold proteins.

Also provided is a barcoded library of nucleic acids, which includes a plurality of unique polynucleotides each comprising a nucleotide sequence encoding a unique synthetic modular polypeptide wherein the unique synthetic modular polypeptides encoded by each unique polynucleotide of the plurality are modular protein kinases or phosphatase proteins.

Also provided is a barcoded library of nucleic acids, which includes a plurality of unique polynucleotides each comprising a nucleotide sequence encoding a unique synthetic modular polypeptide wherein the unique synthetic modular polypeptides encoded by each unique polynucleotide of the plurality are modular transcriptional regulator proteins.

Also provided is a barcoded library of nucleic acids, which includes a plurality of unique polynucleotides each comprising a nucleotide sequence encoding a unique synthetic modular polypeptide wherein the unique synthetic modular polypeptides encoded by each unique polynucleotide of the plurality are modular epigenetic regulator proteins.

Also provided is a barcoded library of nucleic acids, which includes a plurality of unique polynucleotides each comprising a nucleotide sequence encoding a unique synthetic modular polypeptide wherein the unique synthetic modular polypeptides encoded by each unique polynucleotide of the plurality are modular recombinase or nuclease proteins.

Also provided is a barcoded library of nucleic acids, which includes a plurality of unique polynucleotides each comprising a nucleotide sequence encoding a unique synthetic modular polypeptide wherein the unique synthetic modular polypeptides encoded by each unique polynucleotide of the plurality comprise a modular domain selected from the group consisting of: an antigen-binding domain, a specific binding domain or a specific binding partner protein, a co-stimulatory domain, a co-inhibitory domain, an intracellular signaling domain, a transmembrane domain, a scaffold protein domain, a protein kinase protein domain, a protein phosphatase protein domain, a receptor tyrosine kinase protein domain, a lipid kinase protein domain, a lipid phosphatase protein domain, an ubiquitinylase protein domain, a deubiquitinylase protein domain, a SUMOylase protein domain, an acetylase protein domain, a deacetylase protein domain, a methylase protein domain, a demethylase protein domain, a nuclease protein domain, a recombinase protein domain, a transcription factor protein domain and combinations thereof.

Provided is a cellular library, the library comprising: a plurality of cells each comprising a unique polynucleotide comprising a nucleotide sequence encoding a unique synthetic modular polypeptide wherein each unique polynucleotide comprises: i) a coding region encoding the unique synthetic modular polypeptide comprising a first coding sequence encoding a first module linked in-frame to a second coding sequence encoding a second module, ii) a barcode region comprising a first barcode specific to the first coding sequence linked to a second barcode specific to the second coding sequence, wherein the first and second barcodes are in the reverse 5' to 3' order as compared to the first and second coding sequences; and wherein sequencing of each barcode region allows for the identification each unique synthetic modular polypeptide of each cell of the library.

Also provided is a cellular library wherein the cells are prokaryotic cells or eukaryotic cells. Also provided is a cellular library wherein the eukaryotic cells are human cells. Also provided is a cellular library wherein the human cells are human T cells.

Also provided is a cellular library, which includes a plurality of cells each comprising a unique polynucleotide comprising a nucleotide sequence encoding a unique synthetic modular polypeptide that includes a coding region encoding the unique synthetic modular polypeptide comprising a first coding sequence encoding a first module linked in-frame to a second coding sequence encoding a second module wherein the first and second coding sequence are directly linked without any intervening non-coding nucleotides.

Also provided is a cellular library, which includes a plurality of cells each comprising a unique polynucleotide comprising a nucleotide sequence encoding a unique synthetic modular polypeptide that includes a coding region encoding the unique synthetic modular polypeptide comprising a first coding sequence encoding a first module linked in-frame to a second coding sequence encoding a second module wherein the coding region further comprises a reporter coding sequence encoding a reporter linked in frame to the second coding sequence.

Also provided is a cellular library that includes a reporter coding sequence encoding a reporter linked in frame to the second coding sequence wherein the reporter is an epitope tag.

Also provided is a cellular library that includes a reporter coding sequence encoding a reporter linked in frame to the second coding sequence wherein the reporter is a fluorescent protein.

Also provided is a cellular library, which includes a plurality of cells each comprising a unique polynucleotide comprising a nucleotide sequence encoding a unique synthetic modular polypeptide wherein the plurality of cells comprises at least 1000 unique polynucleotides.

Also provided is a cellular library, which includes a plurality of cells each comprising a unique polynucleotide comprising a nucleotide sequence that includes a coding region encoding a unique synthetic modular polypeptide wherein the coding region further comprises a third coding sequence encoding a third module linked in-frame to the second coding sequence and the barcode region comprises a third barcode specific to the third coding sequence linked to the second barcode, wherein the first, second and third barcodes are in reverse 5' to 3' order as compared to the first, second and third coding sequences.

Also provided is a cellular library, which includes a plurality of cells each comprising a unique polynucleotide comprising a nucleotide sequence encoding a unique synthetic modular polypeptide wherein the unique synthetic modular polypeptides encoded by each unique polynucleotide of the plurality of cells are chimeric antigen receptor (CAR) polypeptides.

Also provided is a cellular library, which includes a plurality of cells each comprising a unique polynucleotide comprising a nucleotide sequence encoding a unique synthetic modular polypeptide wherein the unique synthetic modular polypeptides encoded by each unique polynucleotide of the plurality of cells are modular receptor polypeptides.

Also provided is a cellular library, which includes a plurality of cells each comprising a unique polynucleotide comprising a nucleotide sequence encoding a unique synthetic modular polypeptide wherein the modular receptor polypeptides are chimeric Notch receptor polypeptides.

Also provided is a cellular library, which includes a plurality of cells each comprising a unique polynucleotide comprising a nucleotide sequence encoding a unique synthetic modular polypeptide wherein the unique synthetic modular polypeptides encoded by each unique polynucleotide of the plurality of cells are modular scaffold proteins.

Also provided is a cellular library, which includes a plurality of cells each comprising a unique polynucleotide comprising a nucleotide sequence encoding a unique synthetic modular polypeptide wherein the unique synthetic modular polypeptides encoded by each unique polynucleotide of the plurality of cells are modular protein kinases or phosphatase proteins.

Also provided is a cellular library, which includes a plurality of cells each comprising a unique polynucleotide comprising a nucleotide sequence encoding a unique synthetic modular polypeptide wherein the unique synthetic modular polypeptides encoded by each unique polynucleotide of the plurality of cells are modular transcriptional regulator proteins.

Also provided is a cellular library, which includes a plurality of cells each comprising a unique polynucleotide comprising a nucleotide sequence encoding a unique synthetic modular polypeptide wherein the unique synthetic modular polypeptides encoded by each unique polynucleotide of the plurality of cells are modular epigenetic regulator proteins.

Also provided is a cellular library, which includes a plurality of cells each comprising a unique polynucleotide comprising a nucleotide sequence encoding a unique synthetic modular polypeptide wherein the unique synthetic modular polypeptides encoded by each unique polynucleotide of the plurality of cells are modular recombinase or nuclease proteins.

Also provided is a cellular library, which includes a plurality of cells each comprising a unique polynucleotide comprising a nucleotide sequence encoding a unique synthetic modular polypeptide wherein the unique synthetic modular polypeptides encoded by each unique polynucleotide of the plurality of cells comprise a modular domain selected from the group consisting of: an antigen-binding domain, a specific binding domain or a specific binding partner protein, a co-stimulatory domain, a co-inhibitory domain, an intracellular signaling domain, a transmembrane domain, a scaffold protein domain, a protein kinase protein domain, a protein phosphatase protein domain, a receptor tyrosine kinase protein domain, a lipid kinase protein domain, a lipid phosphatase protein domain, an ubiquitinylase protein domain, a deubiquitinylase protein domain, a SUMOylase protein domain, an acetylase protein domain, a deacetylase protein domain, a methylase protein domain, a demethylase protein domain, a nuclease protein domain, a recombinase protein domain, a transcription factor protein domain and combinations thereof.

Provided is a method of making a barcoded library of nucleic acids each encoding a unique synthetic modular polypeptide, the method comprising: contacting a first polynucleotide comprising a first module coding sequence linked to a first barcode sequence with a second polynucleotide comprising a second module coding sequence linked to a second barcode sequence under conditions sufficient for insertion of the first polynucleotide into the second polynucleotide at the junction between the second coding sequence and the second barcode sequence thereby generating a barcoded bi-modular polynucleotide, wherein the barcoded bi-modular polynucleotide comprises the second modular coding sequence linked in-frame with the first modular coding sequence linked to the first barcode sequence linked to the second barcode sequence.

Also provided is a method of making a barcoded library of nucleic acids each encoding a unique synthetic modular polypeptide wherein the method further comprises contacting the first and second polynucleotides with a third polynucleotide comprising a third module coding sequence linked to a third barcode sequence wherein the third polynucleotide inserts into the first polynucleotide at the junction between the first coding sequence and the first barcode sequence thereby generating a barcoded tri-modular polynucleotide, wherein the barcoded tri-modular polynucleotide comprises the second modular coding sequence linked in-frame with the first modular coding sequence linked in-frame with the third modular coding sequence linked to the third barcode sequence linked to the first barcode sequence linked to the second barcode sequence.

Also provided is a method of making a barcoded library of nucleic acids each encoding a unique synthetic modular polypeptide wherein the first and second modular coding sequences are linked in-frame without any intervening non-coding nucleotides.

Also provided is a method of making a barcoded library of nucleic acids each encoding a unique synthetic modular polypeptide wherein the barcoded library comprises 1000 or more unique nucleic acids each encoding a unique synthetic modular polypeptide.

Also provided is a method of making a barcoded library of nucleic acids each encoding a unique synthetic modular polypeptide wherein the barcode sequences are 5' to the module coding sequences or 3' to the module coding sequences.

Also provided is a method of making a barcoded library of nucleic acids each encoding a unique synthetic modular polypeptide wherein the insertion of the first polynucleotide into the second polynucleotide at the junction between the second coding sequence and the second barcode sequence is mediated by the activity of a restriction enzyme which recognizes a restriction enzyme recognition site on the second polynucleotide and cleaves the second polynucleotide between the second coding sequence and the second barcode sequence, including wherein the restriction enzyme used is a Type II restriction enzyme, including wherein the restriction enzyme used is a Type IIS restriction enzyme.

Also provided is a method of making a barcoded library of nucleic acids each encoding a unique synthetic modular polypeptide wherein the first polynucleotide also comprises the restriction enzyme recognition site that is present on the second polynucleotide.

Also provided is a method of making a barcoded library of nucleic acids each encoding a unique synthetic modular polypeptide wherein the method further comprises contacting barcoded bi-modular polynucleotides with a reporter encoding polynucleotide under conditions sufficient for insertion of the reporter encoding polynucleotide into the barcoded bi-modular polynucleotide at the junction between the first modular coding sequence and the first barcode sequence thereby generating a reporter-linked barcoded bi-modular polynucleotide, wherein the reporter-linked barcoded bi-modular polynucleotide comprises the second modular coding sequence linked in-frame with the first modular coding sequence linked in-frame with the reporter coding sequence linked to the first barcode sequence linked to the second barcode sequence. Also provided is a method of making a barcoded library wherein the reporter coding sequence encodes an epitope tag or a fluorescent reporter.

Provided is a chimeric antigen receptor (CAR) identified by screening a library of synthetic modular CAR polypeptide encoding nucleic acids, wherein the CAR comprises at least one co-modulatory domain listed in Table 3 or Table 4.

Also provided is a CAR identified by screening a library of synthetic modular CAR polypeptide encoding nucleic acids wherein the CAR comprises a anti-CD19 antigen-binding domain.

Also provided is a CAR identified by screening a library of synthetic modular CAR polypeptide encoding nucleic acids wherein the CAR comprises a CD3 zeta primary signaling domain.

Also provided is a CAR identified by screening a library of synthetic modular CAR polypeptide encoding nucleic acids wherein the CAR stimulates T cell activity and comprises at least one co-stimulatory domain listed in Table 3.

Also provided is a CAR identified by screening a library of synthetic modular CAR polypeptide encoding nucleic acids wherein the CAR inhibits T cell activity and comprises at least one co-inhibitory domain listed in Table 4.

Also provided is a nucleic acid encoding a CAR identified by screening a library of synthetic modular CAR polypeptide encoding nucleic acids, including e.g., any of those CARs described herein.

BRIEF DESCRIPTION OF THE DRAWINGS

FIG. 3 depicts an example sequence fragment according to FIG. 1 (before Type IIS restriction enzyme (RE) digestion; SEQ ID NO:16) and FIG. 2 (after Type IIS RE digestion; SEQ ID NO:17) containing sequence encoding for a CD28 co-stimulatory domain (translation of Type IIS RE digested fragment; SEQ ID NO:18).

FIG. 4 provides Table 1. Sequence identifiers for the sequences in Table 1 are as follows: index 1—SEQ ID NO:19; index 2—SEQ ID NO:20; index 3—SEQ ID NO:21; index 4—SEQ ID NO:22; index 5—SEQ ID NO:23; index 6—SEQ ID NO:24; index 7—SEQ ID NO:25; index 8—SEQ ID NO:26; index 9—SEQ ID NO:27; index 10—SEQ ID NO:28; index 11—SEQ ID NO:29; index 12—SEQ ID NO:30; index 13—SEQ ID NO:31; index 14—SEQ ID NO:32; index 15—SEQ ID NO:33; index 16—SEQ ID NO:34; index 17—SEQ ID NO:35; index 18—SEQ ID NO:36; index 19—SEQ ID NO:37; index 20—SEQ ID NO:38; index 21—SEQ ID NO:39; index 22—SEQ ID NO:40; index 23—SEQ ID NO:41; index 24—SEQ ID NO:42; index 25—SEQ ID NO:43; index 26—SEQ ID NO:44; index 27—SEQ ID NO:45; index 28—SEQ ID NO:46; index 29—SEQ ID NO:47; index 30—SEQ ID NO:48; index 31—SEQ ID NO:49; index 32—SEQ ID NO:50; index 33—SEQ ID NO:51; index 34—SEQ ID NO:52; index 35—SEQ ID NO:53; index 36—SEQ ID NO:54; index 37—SEQ ID NO:55; index 38—SEQ ID NO:56; index 39—SEQ ID NO:57; index 40—SEQ ID NO:58; index 41—SEQ ID NO:59; index 42—SEQ ID NO:60; index 43—SEQ ID NO:61; index 44—SEQ ID NO:62; index 45—SEQ ID NO:63; index 46—SEQ ID NO:64; index 47—SEQ ID NO:65; index 48—SEQ ID NO:66; index 49—SEQ ID NO:67; index 50—SEQ ID NO:68; index 51—SEQ ID NO:69; index 52—SEQ ID NO:70; index 53—SEQ ID NO:71; index 54—SEQ ID NO:72; index 55—SEQ ID NO:73; index 56—SEQ ID NO:74; index 57—SEQ ID NO:75; index 58—SEQ ID NO:76; index 59—SEQ ID NO:77; index 60—SEQ ID NO:26; index 61—SEQ ID NO:26; index 62—SEQ ID NO:26.

FIG. 12 depicts a schematized barcoded module coding sequence assembly strategy as described herein.

FIG. 13 depicts a schematized barcoded module coding sequence assembly strategy as described herein.

FIG. 14 depicts a schematized barcoded module coding sequence assembly strategy as described herein.

DEFINITIONS

Figure 1:
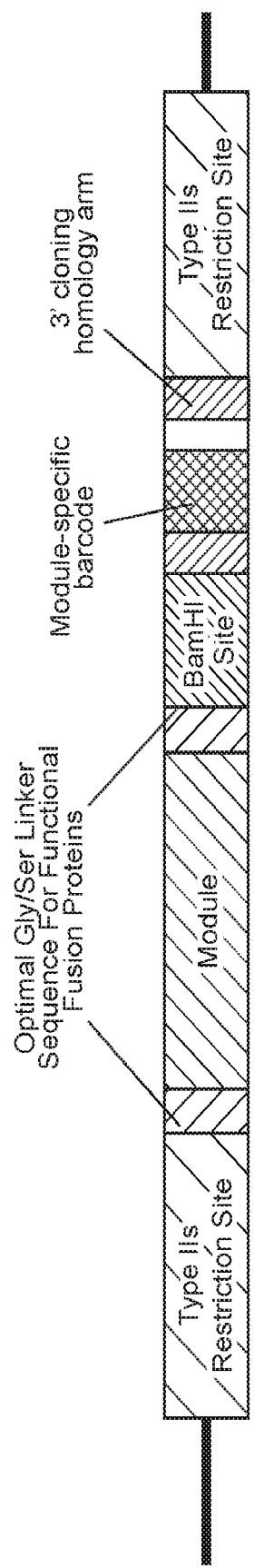
FIG. 1 depicts a barcoded module sequence subcloned for library assembly according to one embodiment of the disclosure.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "domain" and "motif", used interchangeably herein, refer to both structured domains having one or more particular functions and unstructured segments of a polypeptide that, although unstructured, retain one or more particular functions. For example, a structured domain may encompass but is not limited to a continuous or discontinuous plurality of amino acids, or portions thereof, in a folded polypeptide that comprise a three-dimensional structure which contributes to a particular function of the polypeptide. In other instances, a domain may include an unstructured segment of a polypeptide comprising a plurality of two or more amino acids, or portions thereof, that maintains a particular function of the polypeptide unfolded or disordered. Also encompassed within this definition are domains that may be disordered or unstructured but become structured or ordered upon association with a target or binding partner. Non-limiting examples of intrinsically unstructured domains and domains of intrinsically unstructured proteins are described, e.g., in Dyson & Wright. *Nature Reviews Molecular Cell Biology* 6:197-208.

The term "module", as used herein, refers to a contiguous polypeptide sequence, or fragment thereof, that is associated with some function, particularly a biological function.

The terms "chimeric antigen receptor" and "CAR", used interchangeably herein, refer to artificial multi-module molecules capable of triggering or inhibiting the activation of an immune cell which generally but not exclusively comprise an extracellular domain (e.g., an ligand/antigen binding domain), a transmembrane domain and one or more intracellular signaling domains. The term CAR is not limited specifically CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs and OFF-switch CARs which are conditionally activatable/repressible CARs, e.g., comprising a split CAR wherein conditional hetero-dimerization of the two portions of the split CAR is pharmacologically controlled. CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. *Sci Transl Med* (2013); 5(215):215ra172; Glienke et al. *Front Pharmacol* (2015) 6:21; Kakarla & Gottschalk 52 *Cancer J* (2014) 20(2):151-5; Riddell et al. *Cancer J* (2014) 20(2):141-4; Pegram et al. *Cancer J* (2014) 20(2):127-33; Cheadle et al. *Immunol Rev* (2014) 257(1):91-106; Barrett et al. *Annu Rev Med* (2014) 65:333-47; Sadelain et al. *Cancer Discov* (2013) 3(4):388-98; Cartellieri et al., *J Biomed Biotechnol* (2010) 956304; the disclosures of which are incorporated herein by reference in their entirety.

The term "gene" refers to a particular unit of heredity present at a particular locus within the genetic component of an organism. A gene may be a nucleic acid sequence, e.g., a DNA or RNA sequence, present in a nucleic acid genome, a DNA or RNA genome, of an organism and, in some instances, may be present on a chromosome. A gene can be a DNA sequence that encodes for an mRNA that encodes a protein. A gene may be comprised of a single exon and no introns, or can include multiple exons and one or more introns. One of two or more identical or alternative forms of a gene present at a particular locus is referred to as an "allele" and, for example, a diploid organism will typically have two alleles of a particular gene. New alleles of a particular gene may be generated either naturally or artificially through natural or induced mutation and propagated through breeding or cloning. A gene or allele may be isolated from the genome of an organism and replicated and/or manipulated or a gene or allele may be modified in situ through gene therapy methods. The locus of a gene or allele may have associated regulatory elements and gene therapy, in some instances, may include modification of the regulatory elements of a gene or allele while leaving the coding sequences of the gene or allele unmodified.

"Operably linked" refers to a juxtaposition wherein the components so described are in a relationship permitting them to function in their intended manner. For instance, a promoter is operably linked to a coding sequence if the promoter affects its transcription or expression.

A "vector" or "expression vector" is a replicon, such as plasmid, phage, virus, or cosmid, to which another DNA segment, i.e. an "insert", may be attached so as to bring about the replication of the attached segment in a cell.

"Heterologous," as used herein, means a nucleotide or polypeptide sequence that is not found in the native (e.g., naturally-occurring) nucleic acid or protein, respectively.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein.

"Antibody fragments" comprise a portion of an intact antibody, for example, the antigen binding or variable region of the intact antibody. Examples of antibody fragments include Fab, Fab', $F(ab')_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Single-chain Fv" or "sFv" antibody fragments comprise the V$_H$ and V$_L$ domains of antibody, wherein these domains are present in a single polypeptide chain. In some embodiments, the Fv polypeptide further comprises a polypeptide linker between the V$_H$ and V$_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "immune cells" generally includes white blood cells (leukocytes) which are derived from hematopoietic stem cells (HSC) produced in the bone marrow "Immune cells" includes, e.g., lymphocytes (T cells, B cells, natural killer (NK) cells) and myeloid-derived cells (neutrophil, eosinophil, basophil, monocyte, macrophage, dendritic cells).

"T cell" includes all types of immune cells expressing CD3 including T-helper cells (CD4$^+$ cells), cytotoxic T-cells (CD8$^+$ cells), T-regulatory cells (Treg) and gamma-delta T cells.

A "cytotoxic cell" includes CD8$^+$ T cells, natural-killer (NK) cells, and neutrophils, which cells are capable of mediating cytotoxicity responses.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoietic stem cells (HSC); bone marrow derived cells, etc.).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (e.g., rats, mice), lagomorphs (e.g., rabbits), non-human primates, humans, canines, felines, ungulates (e.g., equines, bovines, ovines, porcines, caprines), etc.

A "therapeutically effective amount" or "efficacious amount" refers to the amount of an agent, or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

The terms "control", "control reaction", "control assay", and the like, refer to a reaction, test, or other portion of an experimental or diagnostic procedure or experimental design for which an expected result is known with high certainty, e.g., in order to indicate whether the results obtained from associated experimental samples are reliable, indicate to what degree of confidence associated experimental results indicate a true result, and/or to allow for the calibration of experimental results. For example, in some instances, a control may be a "negative control" such that an essential component of the assay is excluded from the negative control reaction such that an experimenter may have high certainty that the negative control reaction will not produce a positive result. In some instances, a control may be "positive control" such that all components of a particular assay are characterized and known, when combined, to produce a particular result in the assay being performed such that an experimenter may have high certainty that the positive control reaction will not produce a positive negative result.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with their use in synthesis of primer extension products, and may be in the range of between 8 to 100 nucleotides in length, such as 10 to 75, 15 to 60, 15 to 40, 18 to 30, 20 to 40, 21 to 50, 22 to 45, 25 to 40, and so on, including in the range of between 18-40, 20-35, 21-30 nucleotides long, and any length between the stated ranges. In some instances, primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

The terms "hybridize" and "hybridization" refer to the formation of complexes between nucleotide sequences which are sufficiently complementary to form complexes via Watson-Crick base pairing. For example, where a primer "hybridizes" with target (template), such complexes (or hybrids) are sufficiently stable to serve the priming function required by, e.g., the DNA polymerase to initiate DNA synthesis.

A "biological sample" encompasses a variety of sample types obtained from an individual or a population of individuals and can be used in a diagnostic, monitoring or screening assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by mixing or pooling of individual samples, treatment with reagents, solubilization, or enrichment for certain components, such as cells, polynucleotides, polypeptides, etc. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a polypeptide" includes a plurality of such polypeptides and reference to "the antigen" includes reference to one or more antigens and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides synthetic modular polypeptide libraries and nucleic acids encoding such synthetic modular polypeptide libraries. Also provided are methods of making synthetic modular polypeptide libraries and nucleic acids encoding synthetic modular polypeptide libraries. Methods of screening a synthetic modular polypeptide library to identify a selected phenotype associated with a member of a synthetic modular polypeptide library are also provided where such methods find use in both in vitro and in vivo assays.

Libraries

Aspects of the instant disclosure pertain to barcoded libraries of nucleic acids encoding a plurality of synthetic modular polypeptides. Aspects of the instant disclosure also include libraries of cells wherein each cell expresses an individual barcoded nucleic acid encoding a unique synthetic modular polypeptide or a plurality of such individual barcoded nucleic acids. As described in more detail below, aspects of the disclosure also include methods of making such libraries and methods of screening such libraries to detect particular phenotypes.

The nucleic acid libraries of the instant disclosure are generally combinatorially assembled from modular components and include a multi-unit barcode that may be read to identify both the identity and configuration of the modular components of each member of the library. As such, each individual member of the nucleic acid library will at least contain a coding region and a barcode region. As used herein, as it relates to individual members of a nucleic acid library, the term "coding region" refers to the region of each nucleic acid that encodes for a synthetic polypeptide of interest, e.g., a synthetic polypeptide having one or more polypeptide modules that may be screened for influence on a particular desired or undesired phenotype. In some instances, the coding region may further include sequence encoding for a reporter molecule, e.g., as used to detect and/or measure the expression of the synthetic polypeptide of interest.

The coding region will generally encode a single modular polypeptide, described in more detail below; however, this description does not exclude libraries wherein the coding region of each library member encodes two or more separate modular polypeptides. Such library members may include a single coding region that is multicistronic (e.g., bicistronic, polycistronic, etc.), e.g., through the inclusion of a separable linker (e.g., an internal ribosome entry site (IRES), a ribosomal shunting sequence, a nucleic acid encoding a self-cleaving peptide, etc.) between sequences encoding separable module polypeptides. A coding region comprising sequence encoding two or more separate modular polypeptides will be contiguous and will be assembled and screened according to the methods described herein for single modular polypeptide constructs.

The coding region will contain variable modules and non-variable modules, wherein whether a particular portion of a synthetic modular polypeptide is variable or non-variable will depend on the intended use of the library. The variable modules of the coding region are generally those modules being screened, individually or combinatorially, for a functional property and/or influence on a phenotype of interest. In general, variable modules will be associated with a module identifying barcode and non-variable modules will not be associated with a barcode. Any module may serve as a variable module or a non-variable depending on the particular library construction and/or the screen with which the library is associated.

Figure 11:
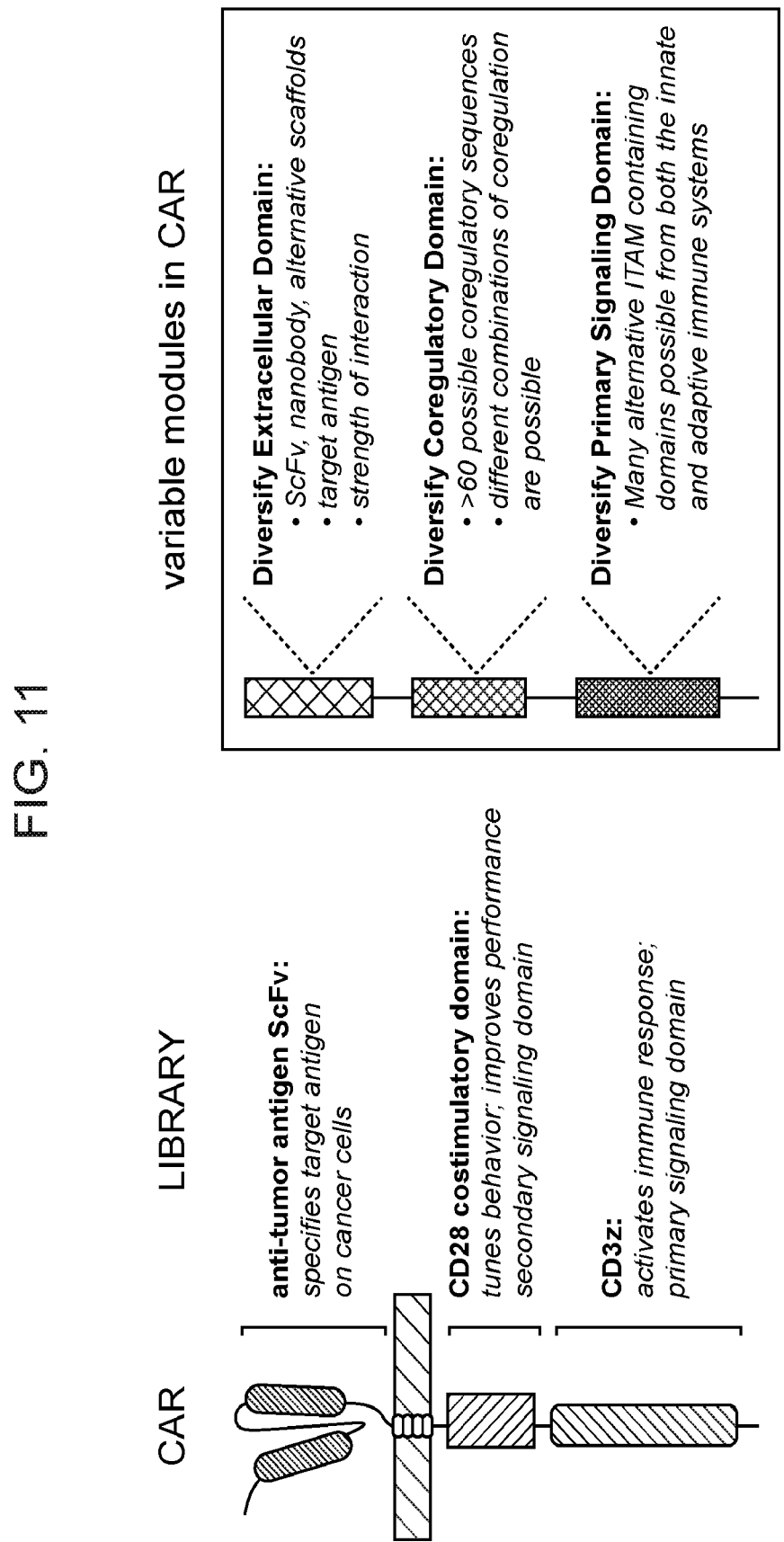
FIG. 11 depicts a non-limiting example of a CAR library, indicating where various domains of the CAR may be varied within the library, according to one embodiment of the instant disclosure.

As a non-limiting example, in certain embodiments where the coding region encodes a chimeric antigen receptor (CAR), any module of the CAR may serve as a variable module depending on the CAR activity being screened, including but not limited to the extracellular domain, the co-regulatory domain or the primary signaling domain. For example, FIG. 11 depicts a single member of a CAR library where each member of the library contains an extracellular domain, a co-regulatory domain and a primary signaling domain and provides non-limiting examples of instances where each domain may serve as a variable module.

In some instances, the extracellular domain may be a variable module, e.g., where antigen targeting is of interest, where the strength of the interaction between the antigen and the extracellular domain are of interest, etc. In some instances, the co-regulatory domain may be a variable module, e.g., where individual or combinations of co-regulatory domains are to be screened for co-modulation of functional activity. In some instances, the primary signaling domain may be a variable module, e.g., where different intracellular signaling activities are to be screened.

As a non-limiting example, in some instances, an encoded synthetic modular polypeptide may be a chimeric Notch receptor polypeptide having an extracellular binding domain, a cleavable Notch receptor polypeptide domain (including a binding-triggered cleavage site) and an intracellular domain Useful chimeric Notch receptor polypeptides, and domains thereof, include but are not limited to e.g., those described in U.S. PCT Application No. US2016/019188; the disclosure of which is incorporated herein by reference in its entirety. In some instances, one or more domains of the chimeric Notch receptor polypeptide serves as a variable domain including but not limited to e.g., the extracellular binding domain, the Notch receptor polypeptide domain, the intracellular domain, the extracellular binding domain and the Notch receptor polypeptide domain, the extracellular binding domain and the intracellular domain or the Notch receptor polypeptide domain and the intracellular domain.

Non-variable modules included in the coding region will be selected where it is desired that all members of the library have the function of the non-variable module, i.e., where the function supplied by the non-variable module is held constant across all members of the library. As non-limiting examples, in some instances, the extracellular domain, co-regulatory domain or primary signaling domain, as described above, may be non-variable modules where it is desired or an assay requires that all members of the library have the function of the extracellular domain, co-regulatory domain or primary signaling domain. As non-limiting examples, in some instances, the extracellular binding domain, cleavable Notch receptor polypeptide domain or intracellular domain, as described above, may be non-variable modules where it is desired or an assay requires that all members of the library have the function of the extracellular binding domain, cleavable Notch receptor polypeptide domain or intracellular domain.

Depending on the particular modules employed and the screening assay for which the subject library is used, the coding region of each library member may encode any combination of variable and non-variable modules with the simplest coding region encoding only a variable module. In some instances, each individual library member, e.g., each vector, into which a variable module is inserted may contain, prior to insertion of the variable module, one or more coding sequences such that upon insertion of the variable module the coding region with then comprise the variable module and the pre-existing coding sequences, which may or may not comprise a non-variable module and/or a non-module coding sequence. In some instances, such pre-existing coding sequence that is present in all library members may be referred to as a "constant domain".

In some instances, the coding region may encode two or more variable modules including but not limited to, e.g., three or more variable modules, four or more variable modules, five or more variable modules, six or more variable modules, seven or more variable modules, eight or more variable modules, etc. In some instances, the coding region may encode two or more non-variable modules including but not limited to, e.g., three or more non-variable modules, four or more non-variable modules, five or more non-variable modules, six or more non-variable modules, seven or more non-variable modules, eight or more non-variable modules, etc. The number of variable and non-variable modules within a coding region may be limited by practical constraints of coding sequence cloning and library construction.

The number of unique library members encoding for unique synthetic modular polypeptides will depend on the number of variable modules used in constructing the library and the overall intended complexity of the library. In some embodiments herein library complexity may be described in terms of library dimensionality where the dimensionality of a library correlates with the number of variable module coding sequences present in the coding region of the library members. Thus, a one-dimensional library contains one variable module coding sequence in each coding region of each library member, a two-dimensional library contains two variable module coding sequences in each coding region of each library member, a three-dimensional library contains three variable module coding sequences in each coding region of each library member, a four-dimensional library contains four variable module coding sequences in each coding region of each library member, and so on.

The dimensionality of a library need not be uniform across the entire library and, thus, in some instances a library may have mixed-dimensionality. By "mixed-dimensionality" is meant that the library contains library members of more than one dimension, as described above. For example, a library may be partly one-dimensional, partly two-dimensional, partly three-dimensional, etc. Such mixed-dimensionality libraries may be mixed one- and two-dimensional libraries, two- and three-dimensional libraries, one-, two- and three-dimensional libraries, and so on. Such descriptions of mixed-dimensional libraries are not intended to be limiting and the ordinary skilled artisan will readily comprehend that the variety of mixed-dimensional libraries encompassed herein extends well beyond those explicitly described.

As such, the number of unique library members encoding for unique synthetic modular polypeptides will vary and will be the product of the library dimensionality and the number of modules used in constructing the library. For example, a one-dimensional library constructed of 20 unique variable modules will contain 20 unique library members. A two-dimensional library constructed of 20 unique variable modules will contain 20-by-20 (i.e., 400) unique library members. A three-dimensional library constructed of 20 unique variable modules will contain 20-by-20-by-20 (i.e., 8000) unique library members. In some instances, a unique library member of a multi-dimensional library may contain two or more sequences encoding for the same variable module.

In some instances, where each library member has two or more variable modules, the modules may be position-specific, meaning a sub-set of the variable modules may only be positioned in a particular location within the synthetic modular polypeptide relative to the other variable modules. For example, a synthetic modular polypeptide having two variable modules may contain a first set and a second set of variable modules where the modules of the first set are always in a particular location relative to the modules of the second set. As such, a two-dimensional library constructed, in a position-specific manner, of 30 unique variable modules, including a first set of 10 unique variable modules and a second set of 20 unique variable modules, may contain 10-by-20 (i.e., 200) unique library members.

One of skill in the art will readily understand the great variability of library configurations given the above described variable dimensionality and variable numbers of modules that may be combined, position-specifically or not, in constructing libraries of the instant disclosure. As such the total number of unique library members will vary greatly and may range from less than 20 to 50,000 or more, including but not limited to, e.g., 20 or more, 30 or more, 40 or more, 50 or more, 60 or more, 70 or more, 80 or more, 90 or more, 100 or more, 150 or more, 200 or more, 250 or more, 300 or more, 350 or more, 400 or more, 450 or more, 500 or more, 550 or more, 600 or more, 650 or more, 700 or more, 750 or more, 800 or more, 850 or more, 900 or more, 950 or more, 1,000 or more, 1,500 or more, 2,000 or more, 2,500 or more, 3,000 or more, 3,500 or more, 4,000 or more, 4,500 or more, 5,000 or more, 5,500 or more, 6,000 or more, 6,500 or more, 7,000 or more, 7,500 or more, 8,000 or more, 8,500 or more, 9,000 or more, 9,500 or more, 10,000 or more, 20,000 or more, 30,000 or more, 40,000 or more, 50,000 or more, etc.

In instances where multi-dimensional libraries are constructed in a pooled assembly, the total number of unique library members within the pool may vary greatly and may range from less than 20 to 50,000 or more, as described above, and to higher degrees of diversity including but not limited to, e.g., $10^5$ or more, $10^6$ or more, $10^7$ or more, $10^8$ or more, or $10^9$ or more.

The unique members of the libraries described herein need not be physically arrayed for the purposes of library construction or screening. As described in more detail below, the combinatorial assembly of nucleic acid components encoding each synthetic modular polypeptide and the co-assembly of the multi-unit barcode in a manner that records the identity and orientation of the assembled modules, allows for one-pot synthesis and pooled screening of the herein described libraries. As such, the library, and the plurality of unique library members, may be present in a single appropriate solution and/or present in a single appropriate container.

Synthetic Modular Polypeptides

Libraries of synthetic modular polypeptides and nucleic acids encoding synthetic modular polypeptides are provided. By "modular polypeptide" is meant a functional protein having two or more operably linked modular components such that the modules are physically joined and function together in a single polypeptide molecule. The modules of a modular polypeptide may have related or unrelated functions or activities. In many embodiments, at least two of the modular components of synthetic modular polypeptides are derived from separate proteins. Modules derived from "separate proteins" may be derived from different proteins that are functionally unrelated or functionally related and may be derived from different species of organism, the same species of organism, different orthologous proteins, different paralogous proteins, etc.

In certain embodiments, individual library members of a synthetic modular polypeptide library, as described herein, will include, at a minimum, a module that is a member of a specific binding pair (e.g., an antigen-antibody binding pair, a ligand-receptor binding pairs, etc.) and a functional or signaling module that functions to induce a cellular response. In some instances, a member of a specific binding pair may be referred to herein as an extracellular domain or an extracellular recognition domain. In some instances, a member of a specific binding pair may refer to a protein involved in a protein-protein signaling interaction or a protein involved in a protein-lipid signaling interaction.

In many embodiments, a member of a specific binding pair that may find use in the individual library members may include an antigen-binding domain. An antigen-binding domain suitable for use in the library members of the present disclosure can be any antigen-binding polypeptide, a wide variety of which are known in the art. In some instances, the antigen-binding domain is a single chain Fv (scFv). Other antibody based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing Vα Vβ) are also suitable for use.

An antigen-binding domain suitable for use in the library members of the present disclosure can have a variety of antigen-binding specificities. In some cases, the antigen-binding domain is specific for an epitope present in an antigen that is expressed by (synthesized by) a cancer cell, i.e., a cancer cell associated antigen. The cancer cell associated antigen can be an antigen associated with, e.g., a breast cancer cell, a B cell lymphoma, a Hodgkin lymphoma cell, an ovarian cancer cell, a prostate cancer cell, a mesothelioma, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer cell associated antigen may also be expressed by a non-cancerous cell.

Non-limiting examples of antigens to which an antigen-binding domain of a subject library member can bind include, e.g., CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, and the like.

In some instances, a member of a specific binding pair suitable for use in the library members of a subject library is a ligand for a receptor. Ligands include, but are not limited to, cytokines (e.g., IL-13, etc.); growth factors (e.g., heregulin; vascular endothelial growth factor (VEGF); and the like); an integrin-binding peptide (e.g., a peptide comprising the sequence Arg-Gly-Asp); Notch ligands (e.g., Delta, Serrate, Delta-like, X-Delta, Jagged, etc. and homologs and orthologs thereof) and the like.

Where the member of a specific binding pair in library members of a subject library is a ligand, the specific library member can be activated in the presence of a second member of the specific binding pair, where the second member of the specific binding pair is a receptor for the ligand. For example, where the ligand is VEGF, the second member of the specific binding pair can be a VEGF receptor, including a soluble VEGF receptor. In another example, where the ligand is a Notch ligand, the second member of the specific binding pair can be a Notch receptor or ligand binding portion thereof. As another example, where the ligand is heregulin, the second member of the specific binding pair can be Her2.

In some instances, the member of a specific binding pair that is included in the members of a subject library is a receptor, e.g., a receptor for a ligand, a co-receptor, etc. The receptor can be a ligand-binding fragment of a receptor. Suitable receptors include, but are not limited to, a growth factor receptor (e.g., a VEGF receptor); a killer cell lectin-like receptor subfamily K, member 1 (NKG2D) polypeptide (receptor for MICA, MICB, and ULB6); a cytokine receptor (e.g., an IL-13 receptor; an IL-2 receptor; etc.); Her2; CD27; a natural cytotoxicity receptor (NCR) (e.g., NKP30 (NCR3/CD337) polypeptide (receptor for HLA-B-associated transcript 3 (BAT3) and B7-H6); etc.); a Notch receptor (e.g., human NOTCH1, human NOTCH2, human NOTCH3, human NOTCH4, etc.), and the like.

Also encompassed within specific binding partners are dimer pairs. Single members of dimer pairs are suitable for use in a library member of subject library and include but are not limited to dimerizer-binding pairs. Dimerizer-binding pairs bind to a different site of the same molecule (referred to herein as a "dimerizer"). In the presence of a dimerizer, both members of the dimerizer-binding pair bind to a different site of the dimerizer and are thus brought into proximity with one another. In some embodiments, binding to the dimerizer is reversible. In some embodiments, binding to the dimerizer is irreversible. In some embodiments, binding to the dimerizer is non-covalent. In some embodiments, binding to the dimerizer is covalent.

Other dimer pairs suitable for use include dimerizer-binding pairs that dimerize upon binding of a first member of a dimer pair to a dimerizing agent, where the dimerizing agent induces a conformational change in the first member of the dimer pair, and where the conformational change allows the first member of the dimer pair to bind (covalently or non-covalently) to a second member of the dimer pair. Other dimer pairs suitable for use include dimer pairs in which exposure to light (e.g., blue light) induces dimerization of the dimer pair.

In some instances, a member of a specific binding pair may include a protein involved in a protein-protein signaling interaction or a protein-lipid signaling interaction and therefore the synthetic modular polypeptides as described herein may include one or more protein-protein interaction domains or protein-lipid interaction domains. Such protein-protein interaction domains or protein-lipid interaction domains include but are not limited to, e.g., a 14-3-3 domain (e.g., as present in PDB (RCSB Protein Data Bank available online at www(dot)rcsb(dot)org) structure 2B05), an Actin-Depolymerizing Factor (ADF) domain (e.g., as present in PDB structure 1CFY), an ANK domain (e.g., as present in PDB structure 1SW6), an ANTH (AP180 N-Terminal Homology) domain (e.g., as present in PDB structure 5AHV), an Armadillo (ARM) domain (e.g., as present in PDB structure 1BK6), a BAR (Bin/Amphiphysin/Rvs) domain (e.g., as present in PDB structure 1I4D), a BEACH (beige and CHS) domain (e.g., as present in PDB structure 1MI1), a BH (Bcl-2 Homology) domains (BH1, BH2, BH3 and BH4) (e.g., as present in PDB structure 1BXL), a Baculovirus IAP Repeat (BIR) domain (e.g., as present in PDB structure 1G73), a BRCT (BRCA1 C-terminal) domain (e.g., as present in PDB structure 1T29), a bromodomain (e.g., as present in PDB structure 1E6I), a BTB (BR-C, ttk and bab) domain (e.g., as present in PDB structure 1R2B), a C1 domain (e.g., as present in PDB structure 1PTQ), a C2 domain (e.g., as present in PDB structure 1A25), a Caspase recruitment domains (CARDs) (e.g., as present in PDB structure 1CWW), a Coiled-coils (CC) domain (e.g., as present in PDB structure 1QEY), a CALM (Clathrin Assembly Lymphoid Myeloid) domain (e.g., as present in PDB structure 1HFA), a calponin homology (CH) domain (e.g., as present in PDB structure 1BKR), a Chromatin Organization Modifier (Chromo) domain (e.g., as present in PDB structure 1KNA), a CUE domain (e.g., as present in PDB structure 1OTR), a Death domains (DD) (e.g., as present in PDB structure 1FAD), a death-effector domain (DED) (e.g., as present in PDB structure 1A1W), a Discheveled, EGL-10 and Pleckstrin (DEP) domain (e.g., as present in PDB structure 1FSH), a Dbl homology (DH) domain (e.g., as present in PDB structure 1FOE), an EF-hand (EFh) domain (e.g., as present in PDB structure 2PMY), an Eps15-Homology (EH) domain (e.g., as present in PDB structure 1EH2), an epsin NH2-terminal homology (ENTH) domain (e.g., as present in PDB structure 1EDU), an Ena/Vasp Homology domain 1 (EVH1) (e.g., as present in PDB structure 1QC6), a F-box domain (e.g., as present in PDB structure 1FS1), a FERM (Band 4.1, Ezrin, Radixin, Moesin) domain (e.g., as present in PDB structure 1GC6), a FF domain (e.g., as present in PDB structure 1UZC), a Formin Homology-2 (FH2) domain (e.g., as present in PDB structure 1UX4), a Forkhead-Associated (FHA) domain (e.g., as present in PDB structure 1G6G), a FYVE (Fab-1, YGL023, Vps27, and EEA1) domain (e.g., as present in PDB structure 1VFY), a GAT (GGA and Tom1) domain (e.g., as present in PDB structure 1O3X), a gelsolin homology domain (GEL) (e.g., as present in PDB structure 1H1V), a GLUE (GRAM-like ubiquitin-binding in EAP45) domain (e.g., as present in PDB structure 2CAY), a GRAM (from glucosyltransferases, Rab-like GTPase activators and myotubularins) domain (e.g., as present in PDB structure 1LW3), a GRIP domain (e.g., as present in PDB structure 1UPT), a glycine-tyrosine-phenylalanine (GYF) domain (e.g., as present in PDB structure 1GYF), a HEAT (Huntington, Elongation Factor 3, PR65/A, TOR) domain (e.g., as present in PDB structure 1IBR), a Homologous to the E6-AP Carboxyl Terminus (HECT) domain (e.g., as present in PDB structure 1C4Z), an IQ domain (e.g., as present in PDB structure 1N2D), a LIM (Lin-1, Isl-1, and Mec-3) domain (e.g., as present in PDB structure 1QLI), a Leucine-Rich Repeats (LRR) domain (e.g., as present in PDB structure 1YRG), a Malignant brain tumor (MBT) domain (e.g., as present in PDB structure 1OYX), a MH1 (Mad homology 1) domain (e.g., as present in PDB structure 1OZJ), a MH2 (Mad homology 2) domain (e.g., as present in PDB structure 1DEV), a MIU (Motif Interacting with Ubiquitin) domain (e.g., as present in PDB structure 2C7M), a NZF (Np14 zinc finger) domain (e.g., as present in PDB structure 1Q5W), a PAS (Per-ARNT-Sim) domain (e.g., as present in PDB structure 1P97), a Phox and Bem1 (PB1) domain (e.g., as present in PDB structure 1IPG), a PDZ (postsynaptic density 95, PSD-85; discs large, Dlg; zonula occludens-1, ZO-1) domain (e.g., as present in PDB structure 1BE9), a Pleckstrin-homology (PH) domain (e.g., as present in PDB structure 1MAI), a Polo-Box domain (e.g., as present in PDB structure 1Q4K), a Phosphotyrosine binding (PTB) domain (e.g., as present in PDB structure 1SHC), a Pumilio/Puf (PUF) domain (e.g., as present in PDB structure 1M8W), a PWWP domain (e.g., as present in PDB structure 1KHC), a Phox homology (PX) domain (e.g., as present in PDB structure 1H6H), a RGS (Regulator of G protein Signaling) domain (e.g., as present in PDB structure 1AGR), a RING domain (e.g., as present in PDB structure 1FBV), a SAM (Sterile Alpha Motif) domain (e.g., as present in PDB structure 1B0X), a Shadow Chromo (SC) Domain (e.g., as present in PDB structure 1E0B), a Src-homology 2 (SH2) domain (e.g., as present in PDB structure 1SHB), a Src-homology 3 (SH3) domain (e.g., as present in PDB structure 3SEM), a SOCS (supressors of cytokine signaling) domain (e.g., as present in PDB structure 1VCB), a SPRY domain (e.g., as present in PDB structure 2AFJ), a steroidogenic acute regulatory protein (StAR) related lipid transfer (START) domain (e.g., as present in PDB structure 1EM2), a SWIRM domain (e.g., as present in PDB structure 2AQF), a Toll/Il-1 Receptor (TIR) domain (e.g., as present in PDB structure 1FYV), a tetratricopeptide repeat (TPR) domain (e.g., as present in PDB structure 1ELW), a TRAF (Tumor Necrosis Factor (TNF) receptor-associated factors) domain (e.g., as present in PDB structure 1F3V), a tSNARE (SNARE (soluble NSF attachment protein (SNAP) receptor) domain (e.g., as present in PDB structure 1SFC), a Tubby domain (e.g., as present in PDB structure 1I7E), a TUDOR domain (e.g., as present in PDB structure 2GFA), an ubiquitin-associated (UBA) domain (e.g., as present in PDB structure 1IFY), an UEV (Ubiquitin E2 variant) domain (e.g., as present in PDB structure 1S1Q), an ubiquitin-interacting motif (UIM) domain (e.g., as present in PDB structure 1Q0W), a VHL domain (e.g., as present in PDB structure 1LM8), a VHS (Vps27p, Hrs and STAM) domain (e.g., as present in PDB structure 1ELK), a WD40 domain (e.g., as present in PDB structure 1NEX), a WW domain (e.g., as present in PDB structure 1I6C), and the like.

The individual library members of the subject libraries as described herein may include a modulatory domain Modulatory domains include domains with stimulatory and inhibitory functions and domains that modulate the activation and/or inhibitory functions of other "upstream" signaling domains. In some instances, modulatory domains include co-stimulatory domains. In some instances, modulatory domains include co-inhibitory domains.

A modulatory domain suitable for inclusion in library members of a subject library may be any functional unit of a polypeptide as short as a 3 amino acid linear motif and as long as an entire protein, where size of the modulatory domain is restricted only in that the domain must be sufficiently large as to retain its function and sufficiently small so as to be compatible with the desired assembly method. Accordingly, a modulatory domain may range in size from 3 amino acids in length to 1000 amino acids or more and, in some instances, can have a length of from about 30 amino acids to about 70 amino acids (aa), e.g., a modulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, modulatory domain can have a length of from about 70 aa to about 100 aa, from about 100 aa to about 200 aa, or greater than 200 aa.

In some instances, "co-stimulatory domains" find use in individual library members a library of the present disclosure. Co-stimulation generally refers to a secondary non-specific activation mechanism through which a primary specific stimulation is propagated. Examples of co-stimulation include antigen nonspecific T cell co-stimulation following antigen specific signaling through the T cell receptor and antigen nonspecific B cell co-stimulation following signaling through the B cell receptor. Co-stimulation, e.g., T cell co-stimulation, and the factors involved have been described in Chen & Flies. *Nat Rev Immunol* (2013) 13(4): 227-42, the disclosures of which are incorporated herein by reference in their entirety. Co-stimulatory domains are generally polypeptides derived from receptors. In some embodiments, co-stimulatory domains homodimerize. A subject co-stimulatory domain can be an intracellular portion of a transmembrane protein (i.e., the co-stimulatory domain can be derived from a transmembrane protein). Non-limiting examples of suitable co-stimulatory polypeptides include, but are not limited to, 4-1BB (CD137), CD28, ICOS, OX-40, BTLA, CD27, CD30, GITR, and HVEM. In some instances, a co-stimulatory domain, e.g., as used in a library member of the instant disclosure may include a co-stimulatory domain listed in Table 1. In some instances, a co-stimulatory domain of a individual member of a library comprises a an amino acid sequence having at least about 75%, at least about 80%, at least about 85%, at least about 90%, at least about 95%, at least about 98%, or 100% amino acid sequence identity to a co-stimulatory domain as described herein.

In some instances, "co-inhibitory domains" find use in individual library members of a library of the present disclosure. Such co-inhibitory domains are generally polypeptides derived from receptors. Co-inhibition generally refers to the secondary inhibition of primary antigen-specific activation mechanisms which prevents co-stimulation. Co-inhibition, e.g., T cell co-inhibition, and the factors involved have been described in Chen & Flies. *Nat Rev Immunol* (2013) 13(4):227-42 and Thaventhiran et al. *J Clin Cell Immunol* (2012) S12, the disclosures of which are incorporated herein by reference in their entirety. In some embodiments, co-inhibitory domains homodimerize. A subject co-inhibitory domain can be an intracellular portion of a transmembrane protein (i.e., the co-inhibitory domain can be derived from a transmembrane protein). Non-limiting examples of suitable co-inhibitory polypeptides include, but are not limited to, CTLA-4 and PD-1. In some instances, a co-inhibitory domain, e.g., as used in a library member of the instant disclosure may include a co-inhibitory domain listed in Table 1. In some instances, a co-stimulatory domain of a individual member of a library comprises a an amino acid sequence having at least about 75%, at least about 80%, at least about 85%, at least about 90%, at least about 95%, at least about 98%, or 100% amino acid sequence identity to a co-stimulatory domain as described herein.

In some instances, individual library members of a synthetic modular polypeptide library may include an intracellular signaling domain module. Intracellular signaling domains suitable for use as modules of the library of the present disclosure include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of an individual library member. The intracellular signaling domain may or may not be covalently attached to the individual library members, e.g., where all library members utilize a common intracellular signaling domain, the intracellular signaling domain may be unbound to the library members, e.g., diffused in the cytoplasm.

In some instances, individual library members of a subject library of the present disclosure will include a transmembrane domain for insertion into a eukaryotic cell membrane. The transmembrane domain may be present at any convenient location within the library members, e.g., N-terminal to the modular components of the library, C-terminal to the modular components of the library, interposed between at least two modular components of the library (e.g., between the antigen-binding domain and the co-stimulatory domain of the members of a CAR modular library), etc.

Any transmembrane (TM) domain that provides for insertion of a polypeptide into the cell membrane of a eukaryotic (e.g., mammalian) cell is suitable for use. As one non-limiting example, the TM sequence IYIWAPLAGTCGVLLLSLVITLYC (SEQ ID NO:1) can be used. Additional non-limiting examples of suitable TM sequences include:

a) CD8 beta derived:
(SEQ ID NO: 2)
LGLLVAGVLVLLVSLGVAIHLCC;

b) CD4 derived:
(SEQ ID NO: 3)
ALIVLGGVAGLLLFIGLGIFFCVRC;

c) CD3 zeta derived:
(SEQ ID NO: 4)
LCYLLDGILFIYGVILTALFLRV;

d) CD28 derived:
(SEQ ID NO: 5)
WVLVVVGGVLACYSLLVTVAFIIFWV;

-continued e) CD134 (OX40) derived:
(SEQ ID NO: 6)
VAAILGLGLVLGLLGPLAILLALYLL;
and f) CD7 derived:
(SEQ ID NO: 7)
ALPAALAVISFLLGLGLGVACVLA.

In some instances, individual synthetic modular polypeptide library members may be configured to include one or more additional modular elements. For example, in instances where the library is a chimeric antigen receptor (CAR) library the individual library members may be configured to contain one or more additional components as described in, e.g., PCT Patent Application Publication No. WO2014/127261, the disclosure of which is incorporated herein by reference in its entirety.

In some instances, individual synthetic modular polypeptide library members may be configured to include one or more modules of a multidomain scaffold protein. The term "scaffold proteins", as used herein, includes anchor proteins and adapter proteins. Such proteins contain multiple binding domains that each recruit or anchor specific members of a signaling pathway, e.g., tethering them into complexes, localizing them within a cell or modulating signaling (e.g., controlling positive and/or negative feedback, stabilizing activated signaling components from inactivation, etc.). As such, domains of multidomain scaffold proteins and multidomain anchor proteins and multidomain adapter proteins generally include signaling pathway member binding domains.

Non-limiting examples of scaffold proteins and the pathways within which they function, include e.g., Ste5 scaffold of the mitogen-activated protein kinase (MAPK) pathway; A-kinase anchor proteins (AKAPs) of the protein kinase A (PKA) signaling pathway; Kinase suppressor of Ras 1(KSR) of the MAPK pathway; B-cell lymphoma 10 (BCL-10) of the JUN N-terminal kinase (JNK) pathway and MAPK pathway; Mitogen-activated protein kinase kinase kinase 1 (MEKK1) of the JNK pathway and MAPK pathway; AHNAK-1 of the calcium signaling pathway; HOMER of the calcium signaling pathway; Pellino proteins of the innate immune signaling pathway; NLR family, pyrine domain-containing (NLRP) proteins of the innate immune signaling pathway; Disks large homolog 1 (DLG1) of the T-cell receptor signaling pathway; Spinophilin of the Dendritic cell signaling pathway; and the like. Scaffold proteins also include but are not limited to e.g., those described in Buday & Tompa. *FEBS Journal* (2010) 277:4348-4355; the disclosure of which is incorporated herein by reference in its entirety. In some instances, a scaffold protein may be a protein associated with Gene Ontology (GO) terms "protein complex scaffold" (GO:0032947), and synonymous terms, which can be used to retrieve information pertaining to protein kinases, including sequences, e.g., online at www(dot)ebi(dot)ac(dot)uk/QuickGO.

In some instances, individual synthetic modular polypeptide library members may be configured to include one or more modules of a protein kinase. Protein kinases are those proteins that function by adding phosphate groups to substrate proteins to direct substrate protein activity, association with other proteins, and/or localization. Protein kinases may include those proteins associated with GO terms "protein phosphorylation" (GO:0006468), "protein kinase activity" (GO:0004672), "protein serine/threonine kinase activity" (GO:0004674), "kinase activity" (GO:0016301), and synonymous terms, which can be used to retrieve information pertaining to protein kinases, including sequences, e.g., online at www(dot)ebi(dot)ac(dot)uk/QuickGO. Protein kinases contain one or more kinase domains that contain the catalytic function of the protein kinase. Protein kinase domains are associated with Pfam identifier PF00069 which can be used to retrieve protein kinase domains those proteins containing protein kinase domains, including sequences and structures online, e.g., at pfam(dot)xfam(dot)org.

In some instances, individual synthetic modular polypeptide library members may be configured to include one or more modules of a protein phosphatase. Protein phosphatases are those proteins that function by removing a phosphate group from the phosphorylated amino acid residue of its substrate protein resulting in dephosphorylation to direct substrate protein activity and act in opposition of protein kinases. Protein phosphatases are grouped into three classes: phosphoprotein phosphatases (e.g., PPP1CA, PPP1CB, PPP1CC, PPP2CA, PPP2CB, PPP3CA, PPP3CB, PPP3CC, PPP4C, PPP5C, PPP6C, etc.), protein Tyr phosphatases (e.g., CDC14A, CDC14B, CDC14C, CDKN3, PTEN, SSH1, SSH2, SSH3, etc.) and dual-specificity protein phosphatases (e.g., DUSP1, DUSP2, DUSP3, DUSP4, DUSP5, DUSP6, DUSP7, DUSP8, DUSP9, DUSP10, DUSP11, DUSP12, DUSP13, DUSP14, DUSP15, DUSP16, DUSP18, DUSP19, DUSP21, DUSP22, DUSP23, DUSP26, DUSP27, DUSP28, etc.); however, some protein phosphatases remain ungrouped. Protein phosphatases may include those proteins associated with the GO term "phosphatase activity" (GO:0016791) and synonymous terms, which can be used to retrieve information pertaining to protein phosphatases, including sequences, e.g., online at www(dot)ebi(dot)ac(dot)uk/QuickGO. Protein phosphatases contain one or more phosphatase domains that contain the dephosphorylation function of the protein phosphatase. Protein phosphatase domains are associated with Pfam identifier PF15698 which can be used to retrieve protein phosphatase domains those proteins containing protein phosphatase domains, including sequences, e.g., at pfam(dot)xfam(dot)org.

In some instances, individual synthetic modular polypeptide library members may be configured to include one or more modules of a tyrosine kinase receptor protein, also referred to as receptor tyrosine kinases (RTKs). RTKs are membrane associated cell surface receptors. A subclass of protein tyrosine kinases, RTKs which function through extracellular ligand binding and subsequent phosphorylation of the cytoplasmic portion of the protein. RTKs can be divided into families including e.g., the epidermal growth factor receptor family, the fibroblast growth factor receptor (FGFR) family, the vascular endothelial growth factor receptor (VEGFR) family, RET receptor family and the discoidin domain receptor (DDR) family. RTKs may include those proteins associated with GO terms "transmembrane receptor protein tyrosine kinase activity" (GO:0004714), "transmembrane receptor protein tyrosine kinase signaling pathway" (GO:0007169), and synonymous terms, which can be used to retrieve information pertaining to RTKs, including sequences, e.g., online at www(dot)ebi(dot)ac(dot)uk/QuickGO. RTKs contain one or more tyrosine kinase domains that contain the kinase function of the RTK. RTK kinase domains are associated with Pfam identifier PF07714 which can be used to retrieve RTK kinase domains and those proteins containing RTK kinase domains, including sequences and structures, e.g., at pfam(dot)xfam(dot)org.

In some instances, individual synthetic modular polypeptide library members may be configured to include one or more modules of a lipid kinase protein. Lipid kinase proteins phosphorylate cellular lipids which results in modulation of the reactivity of the lipid, signal transduction, and/or localization of lipids. Lipid kinases can be divided into families including e.g., phosphatidylinositol kinases and sphingosine kinases. Lipid kinases may include those proteins associated with GO terms "lipid kinase activity" (GO:0001727), "lipid phosphorylation" (GO:0046834), and synonymous terms, which can be used to retrieve information pertaining to lipid kinases, including sequences, e.g., online at www(dot)ebi(dot)ac(dot)uk/QuickGO.

In some instances, individual synthetic modular polypeptide library members may be configured to include one or more modules of a lipid phosphatase protein. Lipid phosphatase proteins dephosphorylate cellular lipids, which acts to reverse the activity of lipid kinases, resulting in the modulation of the reactivity of the lipid, signal transduction, and/or localization of lipids. Lipid phosphatases may include those proteins associated with GO terms "lipid phosphatase activity" (GO:0042577), "phospholipid dephosphorylation" (GO:0046839), and synonymous terms, which can be used to retrieve information pertaining to lipid phosphatases, including sequences, e.g., online at www(dot)ebi(dot)ac(dot)uk/QuickGO.

In some instances, individual synthetic modular polypeptide library members may be configured to include one or more modules of an ubiquitinylase protein. Ubiquitinylase protein are those proteins that mediate the post-translational modification of ubiquitination, the attachment of ubiquitin to a substrate protein. Ubiquitination of a substrate protein can result in degradation of the substrate protein, re-localization of the substrate protein, modulation of the activity of the substrate protein, modulation of protein-protein interaction of the substrate protein, etc. Ubiquitinylases may include those proteins associated with GO terms "protein ubiquitination" (GO:0016567), "ubiquitin-protein transferase activity" (GO:0004842), and synonymous terms, which can be used to retrieve information pertaining to ubiquitinylases, including sequences, e.g., online at www(dot)ebi(dot)ac(dot)uk/QuickGO.

In some instances, individual synthetic modular polypeptide library members may be configured to include one or more modules of a deubiquitinylase protein. Deubiquitinylase protein are those proteins that mediate the reversal of ubiquitination, the removal of ubiquitin from a substrate protein. Deubiquitination of a substrate protein can reverse the effects of ubiquitinylases and prevent degradation of a substrate protein, reverse ubiquitin associated re-localization of the substrate protein, reverse ubiquitin associated modulation of the activity of a substrate protein, reverse ubiquitin associated modulation of protein-protein interaction of a substrate protein, etc. Deubiquitinylases may include those proteins associated with the GO term "protein deubiquitination" (GO:0016579), and synonymous terms, which can be used to retrieve information pertaining to deubiquitinylases, including sequences, e.g., online at www(dot)ebi(dot)ac(dot)uk/QuickGO.

In some instances, individual synthetic modular polypeptide library members may be configured to include one or more modules of a SUMOylase protein. SUMOylase proteins are those proteins that mediate the post-translational modification of SUMOylation, the addition of a Small Ubiquitin-like Modifier (SUMO) protein to a substrate protein. SUMOylation can modulate various protein functions including protein stability, nuclear-cytosolic transport, transcriptional regulation, etc. SUMOylases may include those proteins associated with the GO term "protein sumoylation"

(GO:0016925), and synonymous terms, which can be used to retrieve information pertaining to SUMOylases, including sequences, e.g., online at www(dot)ebi(dot)ac(dot)uk/QuickGO.

In some instances, individual synthetic modular polypeptide library members may be configured to include one or more modules of an acetylase protein, also referred to as acetyltransferases. Acetyltransferases are transferase enzymes that catalyze the transfer of an acetyl group to a substrate protein and are involved in epigenetic and transcriptional modulation. Acetyltransferases may be categorized into groups including e.g., histone acetyltransferases, choline acetyltransferases, chloramphenicol acetyltransferases, serotonin N-acetyltransferases, NatA Acetyltransferases, NatB acetyltransferases. Acetyltransferases may include those proteins associated with the GO term "acetyltransferase activity" (GO:0016407), and synonymous terms, which can be used to retrieve information pertaining to acetyltransferases, including sequences, e.g., online at www(dot)ebi(dot)ac(dot)uk/QuickGO.

In some instances, individual synthetic modular polypeptide library members may be configured to include one or more modules of a deacetylase protein. Deacetylase proteins reverse the effects of acetyltransferases and remove acetyl groups transferred to a substrate protein and are thus likewise involved in epigenetic and transcriptional modulation. Deacetylases include, e.g., histone deacetylases and sirtuins. Deacetylases may include those proteins associated with the GO term "deacetylase activity" (GO:0019213), and synonymous terms, which can be used to retrieve information pertaining to deacetylases, including sequences, e.g., online at www(dot)ebi(dot)ac(dot)uk/QuickGO.

In some instances, individual synthetic modular polypeptide library members may be configured to include one or more modules of a methylase protein, also called methyltransferases. Methyltransferases alkylate substrate substrates (including protein and nucleic acid substrates) by transfer of a methyl group to the substrate and are involved in epigenetic and transcriptional modulation. Methyltransferases can be categorized into classes based on their structure including e.g., Class I, Class II, Class III, and can be grouped according to their substrates or mode of methylation including e.g., protein methyltransferases, DNA methyltransferases, natural product methyltransferases, and non-SAM dependent methyltransferases. Methyltransferases may include those proteins associated with GO terms "DNA-methyltransferase activity" (GO:0009008), "histone methyltransferase activity" (GO:0042054), and synonymous terms, which can be used to retrieve information pertaining to methyltransferases, including sequences, e.g., online at www(dot)ebi(dot)ac(dot)uk/QuickGO.

In some instances, individual synthetic modular polypeptide library members may be configured to include one or more modules of a demethylase protein. Demethylases reverse the effects of methyltransferases and catalyze the removal methyl groups from substrates (including protein and nucleic acid substrates) and are thus also are involved in epigenetic and transcriptional modulation. Demethylases may include those proteins associated with GO terms "demethylase activity" (GO:0032451), "DNA demethylase activity" (GO:0035514), "histone demethylase activity" (GO:0032452), and synonymous terms, which can be used to retrieve information pertaining to demethylases, including sequences, e.g., online at www(dot)ebi(dot)ac(dot)uk/QuickGO.

In some instances, individual synthetic modular polypeptide library members may be configured to include one or more modules of a nuclease protein. Nucleases catalyze the cleaving of phosphodiester bonds between the nucleotide subunits of nucleic acid substrates. Nucleases can be subdivided into non-mutually exclusive categories such as endonucleases and exonucleases. Nucleases may include those proteins associated with GO terms "nuclease activity" (GO:0004518), "deoxyribonuclease I activity" (GO:0004530), "RNA-DNA hybrid ribonuclease activity" (GO:0004523), "nucleic acid phosphodiester bond hydrolysis" (GO:0090305), "endonuclease activity" (GO:0004519), "exonuclease activity" (GO:0004527), and synonymous terms, which can be used to retrieve information pertaining to nucleases, including sequences, e.g., online at www(dot)ebi(dot)ac(dot)uk/QuickGO.

In some instances, individual synthetic modular polypeptide library members may be configured to include one or more modules of a recombinase protein. Recombinases catalyze directionally sensitive nucleic acid exchange reactions between target site sequences specific to each recombinase resulting in excision/insertion, inversion, translocation and nucleic acid fragment exchange. Examples of recombinases include but are not limited to Cre recombinase, Hin recombinase, Tre recombinase, FLP recombinase, and the like. Recombinases may include those proteins associated with GO terms "recombinase activity" (GO:0000150), "DNA recombination" (GO:0006310), and synonymous terms, which can be used to retrieve information pertaining to recombinases, including sequences, e.g., online at www(dot)ebi(dot)ac(dot)uk/QuickGO.

In some instances, individual synthetic modular polypeptide library members may be configured to include one or more modules of a transcription factor protein. Transcription factors are those proteins that bind to specific DNA sequences and control transcription. Transcription factors may be activators, resulting in upregulation of transcription, or repressors resulting in downregulation of transcription. Transcription factors can be classified by the structure of their DNA binding domains into superclasses including e.g., Basic Domain transcription factors, Zinc-coordinating DNA-binding domain transcription factors, Helix-turn-helix transcription factors, beta-Scaffold Factors transcription factors, and those transcription factors that are not included in one of the above superclasses (see e.g., Stegmaier et al. *Genome Inform* (2004) 15(2):276-86). Transcription factors contain one or more DNA binding domains. DNA binding domains of transcription factors may be one or more of the DNA binding domains associated with Pfam identifiers PF00010, PF00170, PF00172, PF00046, PF00319, PF08279, PF00096, PF00105, and the like, which can be used to retrieve domains sequences and structures, e.g., at pfam(dot)xfam(dot)org. Transcription factors may also contain one or more trans-activating domains, one or more signal sensing domains. Transcription factors may include those proteins associated with the GO term "transcription factor complex" (GO:0005667), and synonymous and related terms, which can be used to retrieve information pertaining to transcription factors, including sequences, e.g., online at www(dot)ebi(dot)ac(dot)uk/QuickGO.

Other DNA binding domains, e.g., DNA binding domains not derived from transcription factors or non-transcription factor DNA binding domains, may also find use, in some instances, in one or more modules of individual synthetic modular polypeptide library members as described herein. Such non-transcription factor DNA binding domains include natural and synthetic polypeptide domains that bind non-specifically to DNA or bind specific sequences of DNA. Non-transcription factor DNA binding domains may include but are not limited to e.g., the natural or engineered DNA binding domain of a zinc finger endonuclease polypeptide, the natural or engineered DNA binding domain of a Transcription activator-like effector nuclease (TALEN) polypeptide, the natural or engineered DNA binding domain of a Cas9 polypeptide (including e.g., a nuclease-deficient Cas9 (dCas9) and the like), etc.

In some instances, individual synthetic modular polypeptide library members may be configured to include one or more modules as described in PCT Application No. US2004/019778; the disclosure of which is incorporated herein by reference in its entirety.

Configuration of modules into synthetic modular polypeptides as described herein will generate a library containing a plurality of individual modular functional proteins which may, but need not necessary, share a common function. For example, the individual library members may comprise or may consist of synthetic modular polypeptides that are modular scaffold proteins, synthetic modular polypeptides that are modular receptor proteins, synthetic modular polypeptides that are modular proteins kinase or phosphatase proteins, synthetic modular polypeptides that are modular transcriptional regulator proteins, synthetic modular polypeptides that are modular epigenetic regulator proteins, synthetic modular polypeptides that are modular recombinase or nuclease proteins, etc. Such libraries may be screened for a desired phenotype, e.g., according to the methods described herein.

Reporters

The libraries described herein include detectable signal producing proteins expressed from nucleic acid sequence encoding therefrom. The particular detectable signal producing proteins used in the library systems as described herein will vary and depend, in part, upon the preferred method of detection of the produced signal. For example, where the signal is optically detected, e.g., through use of fluorescent microscopy or flow cytometry (including fluorescently activated cell sorting (FACS), a fluorescent reporter is used.

Suitable detectable signal-producing proteins include, e.g., fluorescent proteins; enzymes that catalyze a reaction that generates a detectable signal as a product; epitope tags, surface markers, and the like. Detectable signal-producing proteins may be directly detected or indirectly detected. For example, where a fluorescent reporter is used, the fluorescence of the reporter may be directed detected. In some instances, where an epitope tag or a surface marker is used, the epitope tag or surface marker may be indirectly detected, e.g., through the use of a detectable binding agent that specifically binds the epitope tag or surface marker, e.g., a fluorescently labeled antibody that specifically binds the epitope tag or surface marker. In some instances, a reporter that is commonly indirectly detected, e.g., an epitope tag or surface marker, may be directed directly or a reporter that is commonly directly detected may be indirectly detected, e.g., through the use of a detectable antibody that specifically binds a fluorescent reporter.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Linkers and Junctions

Within individual library members, the junctions between modular components encoding a single polypeptide will generally be kept "in-frame", meaning the codon reading-frame of the multi-module coding sequence is maintained from one module unit to the next. Such junctions may be referred to herein as in-frame junctions and/or in-frame linkages. Linkers between module components of multi-module polypeptides will generally be flexible and/or will not contain amino acid residues that interfere with the function of the modular domains.

Such in-frame junctions may be achieved, as described in more detail below, by any convenient method of configuring the coding sequence and the nested assembly of the modular components to contain an in-frame linker.

Suitable linkers can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

Exemplary linkers include glycine polymers $(G)_n$, glycine-serine polymers (including, for example, $(GS)_n$, $(GSGGS)_n$ (SEQ ID NO:8) and $(GGGS)_n$ (SEQ ID NO:9), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, *Rev. Computational Chem.* 11173-142 (1992)). Exemplary linkers can comprise amino acid sequences including, but not limited to, GGSG (SEQ ID NO:10), GGSGG (SEQ ID NO:11), GSGSG (SEQ ID NO:12), GSGGG (SEQ ID NO:13), GGGSG (SEQ ID NO:14), GSSSG (SEQ ID NO:15), and the like.

In some instances, a linker comprises the BamHI restriction recognition site sequence for cloning purposes and as part of a linker because the BamHI site encodes GS.

In some instances, linker sequences may be eliminated through one or more cloning steps (e.g., through the use of TypeIIS restriction endonucleases or homologous recombination) or through direct digestion (e.g., BamHI digestion).

In some instances, an in-frame junction is achieved through the absence of linker at the junction of two modular components. As such, an in-frame junction may, in some instance, comprise no amino acid coding intervening nucleic acid between module coding sequences. In some instances, an in-frame junction may comprise two or fewer intervening nucleic acid base-pairs between module coding sequences. In some instances, an in-frame junction may comprise one or fewer intervening nucleic acid base-pairs between module coding sequences. In some instances, an in-frame junction may comprise no intervening nucleic acid base-pairs between module coding sequences.

Barcodes

Nucleic acid barcodes are specific unique nucleic acid sequences that may be identified by any convenient method of nucleic acid sequence identification including but not limited to, e.g., hybridization based identification (i.e., in situ hybridization), amplification based identification (i.e., PCR-based identification) and nucleic acid sequencing. Barcodes of the instant disclosure may be module specific barcodes meaning each unique module of a multi-module library is correlated with a specific unique barcode such that identification of a particular barcode is equivalent with positive identification of the associated module coding sequence.

A module specific barcode, as described herein, will be constrained by the library assembly method utilized. For example, where nested assembly of multi-module constructs is achieved by a restriction-enzyme-based method the barcodes will exclude any sequence that constitutes a restriction enzyme recognition site of the restriction enzymes utilized in assembly. As such, in some instances, the barcode sequences will not contain restriction enzyme recognition sequences. In some instances, the barcode sequences will not contain Type IIS restriction enzyme recognition sequences.

In instances where barcode identification and/or quantification is performed by sequencing, including e.g., Next Generation Sequencing methods, conventional considerations for barcodes detected by sequencing will be applied. In some instances, commercially available barcodes and/or kits containing barcodes and/or barcode adapters may be used or modified for use in the methods described herein, including e.g., those barcodes and/or barcode adapter kits commercially available from suppliers such as but not limited to, e.g., New England Biolabs (Ipswich, Mass.), Illumina, Inc. (Hayward, Calif.), Life Technologies, Inc. (Grand Island, N.Y.), Bioo Scientific Corporation (Austin, Tex.), and the like, or may be custom manufactured, e.g., as available from e.g., Integrated DNA Technologies, Inc. (Coralville, Iowa).

Barcode length will vary and will depend upon the complexity of the library and the barcode detection method utilized. As nucleic acid barcodes (e.g., DNA barcodes) are well-known, design, synthesis and use of nucleic acid barcodes is within the skill of the ordinary relevant artisan.

In some instances, the length of the utilized barcodes will further depend on the likelihood that an individual barcode sequence appears by chance in some other component of the library including but not limited to, e.g., a module coding sequence, a vector, a vector component, etc., or at the junction of two barcode units. For example, in some instances, where there a significant likelihood that a non-barcode sequence may be inadvertently detected as a barcode sequence, e.g., as in highly complex libraries, barcode units of longer length may be utilized. In some instances, the method of barcode detection may be taken into account when determining the necessary barcode length, e.g., in instances where hybridization barcode detection is used longer barcodes may be employed in comparison to where sequencing with specific sequencing primers is used.

As used herein, as it relates to individual members of a nucleic acid library, the term "barcode region" refers to the region of each nucleic acid that contains nucleic acid sequence specific to the variable modular portion of the synthetic polypeptide. In some instances, the barcode region may be used to specifically identify the variable module or modules present in the coding region of a particular member of a library. In some instances, the barcode region may be used to specifically identify the variable module(s) and identity the order of variable modules present in the coding region of a particular member of a library (i.e., architecture). In some instances, the barcode region may be used to quantify, e.g., semi-quantitatively, the frequency of a particular member of the library or the frequency of a particular module within a population containing a plurality of library members.

Within a barcoded synthetic module polypeptide of a library as described herein, the barcode units of the barcode region will be in reverse orientation as compared to the module coding sequences. In addition, the barcode units of the barcode region will be in reverse order as compared to their respective associated module coding sequence. However, with relationship to the encoded polypeptide, the barcode region may be positioned "N-terminal" or "C-terminal" to the nucleic acid sequence encoding the synthetic modular polypeptide.

Vector Specific Elements

By "vector specific elements" is meant elements that are used in making, constructing, propagating, maintaining and/or assaying the vector before, during or after its construction. Such vector specific elements include but are not limited to, e.g., vector elements necessary for the propagation, cloning and selection of the vector during its use and may include but are not limited to, e.g., an origin of replication, a multiple cloning site, a prokaryotic promoter, a phage promoter, a selectable marker (e.g., an antibiotic resistance gene, an encoded enzymatic protein, an encoded fluorescent or chromogenic protein, etc.), and the like. Any convenient vector specific elements may find use, as appropriate, in the vectors as described herein.

Suitable promoter and enhancer elements useful as vector specific elements are known in the art. For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some instances, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., *PNAS* (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. (2006) *Annual Review of Biochemistry*, 567-605 and Tropp (2012) Molecular Biology (Jones & Bartlett Publishers, Sudbury, Mass.), the disclosures of which are incorporated herein by reference.

Methods of Making Libraries

The instant disclosure provides methods of making libraries of nucleic acids encoding synthetic modular polypeptides wherein each nucleic acid of the library includes a multi-unit barcode that identifies the variable module(s) of the modular polypeptide and, where multiple variable modules are present, their orientation relative to one another. In numerous embodiments, the instant disclosure provides methods of step-wise combinatorial assembly of synthetic modular polypeptides from barcoded module encoding nucleic acids such that the resultant nucleic acids encoding the synthetic modular polypeptides each comprise a coding region of in-frame modules and a multi-unit barcode where the arrangement of barcode units corresponds to the arrangement of the in-frame modules. In general, where multiple variable modules are included in each member of a library, the co-assembled multi-unit barcode provides a record of the assembly of the variable modules of each library member.

Without being bound by theory, step-wise combinatorial assembly of the synthetic modular polypeptides as presented herein provides for the construction of larger and more complex libraries than would be possible or practical using conventional methods of individual (i.e., "one at a time") polypeptide engineering. The instant inventors recognized that conventional synthetic modular polypeptide engineering represented a significant technical obstacle to high-throughput synthetic modular polypeptide screening. The coordinated assembly of each multi-module synthetic polypeptide and with a corresponding multi-unit barcode, as presented herein, overcomes this obstacle and allows for "one-pot assembly" of a plurality of unique nucleic acids encoding screen-able synthetic modular polypeptides. Such high-throughput one-pot assembly could not be performed with conventional polypeptide engineering.

The instant inventors also recognized that conventional physically-arrayed synthetic polypeptide libraries also present major technical obstacles for high-throughput screening. In particular, where large libraries are screened, the number of the physically separated reaction chambers and the variability in assay conditions between each chamber present significant technical hurdles when attempting to perform a screen of the entire complexity of a large library and analyze the produced data. The instant inventors recognized that pooled library screening could overcome this issue but presents other significant obstacles, such as difficulty or impracticality of identifying and/or quantifying individual polypeptides producing a desired phenotype in a screen from a complex mixed pool of unique modular polypeptides. The use of the short multi-unit barcode overcomes this issue by allowing for the post hoc efficient positive identification and/or quantification of individual unique synthetic modular polypeptides that produce a desired phenotype within the complex pool by sequencing only the multi-unit barcode.

Cloning Strategies

In general, the instant disclosure provides a method of making libraries, as described herein, by nested assembly of barcode-linked polypeptide module encoding nucleic acids. For example, as depicted in FIG. 12, a nucleic acid vector (100) containing a sequence encoding a polypeptide module (101) linked to a module-specific barcode (102) is linearized (103) by cleaving the link between the sequence encoding a polypeptide module and the module-specific barcode. Following linearization of the vector containing the first module coding sequence and first module-specific barcode, nucleic acid containing a second module coding sequence (104) and a second barcode (105) specific to the second module is inserted (i.e., nested) between the first module coding sequence and the first barcode (106). The assembled nucleic acid contains a coding region encoding a synthetic modular polypeptide and a barcode region that contains a multi-unit barcode (i.e., "barcodes" (BCs)). In some instances, the module coding sequences are assembled such that they are joined by sequence encoding a desired linker, as described herein. In certain instances, the module coding sequences are assembled such that they are joined without the use of a linker sequence, e.g., without linker sequence encoding one or more linker amino acids, without any intervening non-coding nucleotides between the first and second module encoding sequences, etc. As such, the designation of a "desired linker sequence" or "linker", particularly as used in the figures, encompasses the complete absence of any linker or linker sequence and the direct joining of polypeptide modules and module encoding sequences.

Linearization of the vector sequence by cleavage between the first module encoding sequence and the first module-specific barcode may be achieved by any convenient and appropriate means. For example, the polynucleotide containing the module coding sequence and the barcode may be configured to contain a restriction enzyme (i.e., restriction endonuclease) cleavage site between the module coding sequence and the barcode. The cleavage site may be a Type II restriction enzyme cleavage site and, more specifically, may be a cleavage site contained within the recognition sequence of the Type II restriction enzyme used. Any convenient Type II restriction enzyme that cleaves within its recognition sequence may find use for this described purpose including those Type II restriction enzymes that cleave within their recognition sequences that are known in the art. In some instances, the cleavage site may be the cleavage site of BamHI which has the recognition sequence of 5'-GGATCC-3' and cleaves after the first G of the recognition sequence on both strands leaving a 5'-GATC-3' overhang. Other restriction enzymes that may be used for this purpose include but are not limited to, e.g., In some instances, nested assembly is achieved through the use of two restriction enzyme sites (RE1 and RE2) positioned between the first module coding sequence and the first module specific barcode and flanking the second barcoded module coding sequence (FIG. 13). In this two restriction enzyme assembly strategy, digestion at both RE1 and RE2 results in linearization of the vector and liberation of a fragment containing the second barcoded module coding sequence. Upon ligation of the linearized vector and the liberated fragment, a desired linker sequence is present between the first and second module coding sequences and the first and second barcodes are in reverse orientation as compared to the first and second module coding sequences.

In some instances, nested assembly is achieved through the use of four restriction enzyme sites (RE1, RE2, RE3 and RE4), where RE1 and RE2 are positioned between both module coding sequences and their respective barcodes and RE3 and RE4 are positioned flanking the second barcoded module coding sequence (FIG. 14). In this four restriction enzyme assembly strategy, separate digestion of the first vector, at RE1 and RE2, and the second vector, at RE3 and RE4, results in linearization of the vector and liberation of a fragment containing the second barcoded module coding sequence. Upon ligation of the linearized vector and the liberated fragment, a desired linker sequence is present between the first and second module coding sequences and the first and second barcodes are in reverse orientation as compared to the first and second module coding sequences.

In some instances, restriction enzymes are specifically chosen such that, upon ligation, the junctions between the first and second module coding sequences and the first and second barcodes do not contain RE1, RE2, RE3 or RE4 restriction enzyme recognition sequences. Generally, according to this strategy the utilized RE1, RE2, RE3 and RE4 sites are inactivated following ligation such that the resulting vector only contains active RE1 and RE2 sites between the second module coding sequence and its respective barcode. Thus, this strategy allows for sequential nested assembly beyond a two-dimensional construct by repeated linearization of the resulting vector by restriction digest at RE1 and RE2 of the most recently inserted barcoded module coding sequence.

In this four restriction enzyme method, RE1 is chosen such that, upon digestion, the resulting end of the linearized vector is compatible (i.e., able to be ligated) with the end of the liberated fragment generated by digestion with RE3. RE2 is chosen such that, upon digestion, the resulting end of the linearized vector is compatible (i.e., able to be ligated and/or able to hybridize completely or at least partially) with the end of the liberated fragment generated by digestion with RE4. In some instances, one or more ends generated by digestion with RE1, RE2, RE3 or RE4 may be modified, e.g., by the addition or deletion of one or more nucleotides or other chemical modification, in order to generate compatible ends between RE1 and RE3 or RE2 and RE4. Any convenient method of end-modification may find use in generating compatible ends including those end-modification methods that are well-known in the art including, but not limited to, e.g., end-blunting, phosphorylation, dephosphorylation, etc.

Figure 15:
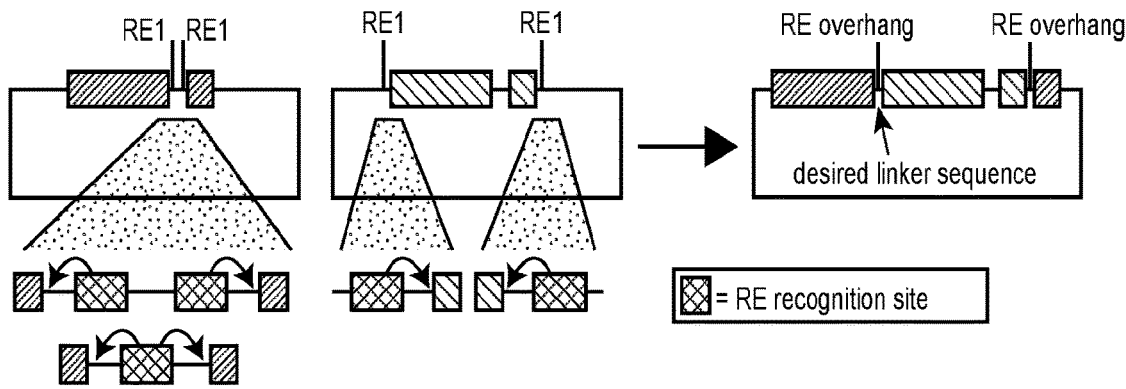
FIG. 15 depicts a schematized barcoded module coding sequence assembly strategy as described herein.

In some instances, nested assembly is achieved through the use of a Type IIS restriction enzyme recognition sequence (RE1), where two RE1 sites are present between the first module coding sequence and its barcode and two RE1 sites flank the second barcoded module coding sequence (FIG. 15). In this Type IIS restriction enzyme mediated strategy, digestion at sites adjacent to the RE1 recognition sites results in linearization of the vector and liberation of a fragment containing the second barcoded module coding sequence. The cleavage sites adjacent to the RE1 recognition sites are configured such that, upon cleavage, the 3' end of the vector is compatible with the 5' end of the fragment and the 5' end of the vector is compatible with the 3' end of the fragment. In some instances, these compatible ends may be referred to as compatible "overhangs". Thus, upon ligation of the linearized vector and the liberated fragment, a desired linker sequence is present between the first and second module coding sequences and the first and second barcodes are in reverse orientation as compared to the first and second module coding sequences.

Any convenient Type IIS restriction enzyme my find use in the assembly strategies utilizing such enzymes as described herein, including but not limited to, e.g., AceIII, AcuI, AlwI, AarI, BbsI, BbvI, BbvII, BccI, Bce83I, BceAI, BcefI, BciVI, BfuAI, BmrI, BmuI, BpmI, BpuEI, BsaI, BsbI, BseRI, BsgI, BslFI, BsmAI, BsmFI, BsoMAI, BspCNI, BspGI, BspMI, BspNCI, BspQI, BsrDI, Bst71I, BtgZI, BtsCI, BtsI, BveI, DrdII, EarI, EciI, FaqI, FinI, FokI, HgaI, Hin4II, HphI, HpyAV, LguI, MboII, MmeI, MnlI, NmeAIII, PleI, SapI, SfaNI, SgeI, and the like.

In some instances, a restriction enzyme utilized, e.g., in linearizing the vector and/or liberating the second module containing fragment, is a restriction enzyme that cleaves on both sides of its recognition site. Any convenient restriction enzyme with such functionality may find use in the assembly methods describe herein including but not limited to, e.g., BcgI.

Figure 16:
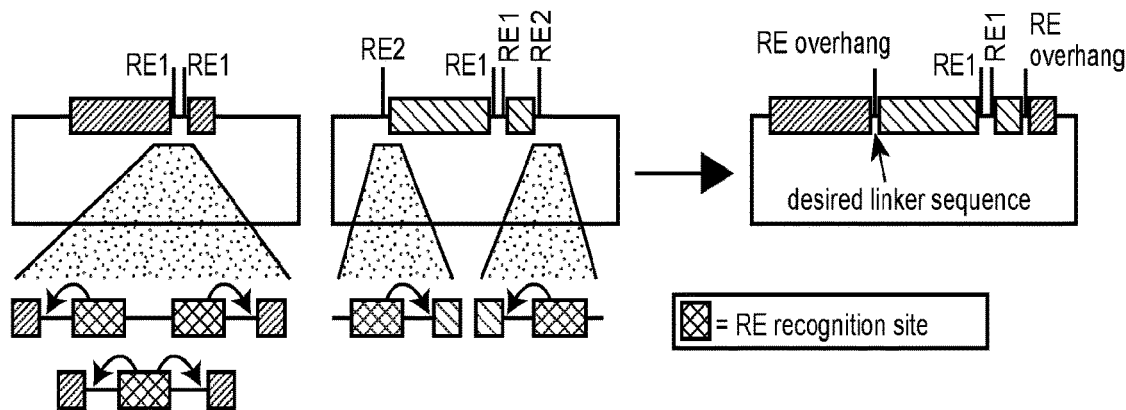
FIG. 16 depicts a schematized barcoded module coding sequence assembly strategy as described herein.

In some instances, nested assembly is achieved through the use of multiple Type IIS restriction enzyme recognition sequences, e.g., two Type IIS restriction enzyme recognition sequences (RE1 and RE2), where two RE1 sites are present between both module coding sequences and their respective barcodes and two RE2 sites flank the second barcoded module coding sequence (FIG. 16). In this two Type IIS restriction enzyme strategy, separate digestion of the first vector, at the RE1 sites, and the second vector, at the RE2 sites, results in linearization of the vector and liberation of a fragment containing the second barcoded module coding sequence. Upon ligation of the linearized vector and the liberated fragment, a desired linker sequence is present between the first and second module coding sequences and the first and second barcodes are in reverse orientation as compared to the first and second module coding sequences.

Generally, according to this strategy the RE1 and RE2 sites utilized in the first round of linearization and fragment liberation are lost to the vector and insert such that the resulting vector only contains active RE1 sites between the second module coding sequence and its respective barcode. Thus, this strategy allows for sequential nested assembly beyond a two-dimensional construct by repeated linearization of the resulting vector by restriction digest using the RE1 recognition sites of the most recently inserted barcoded module coding sequence.

In this two Type IIS restriction enzyme method, the cleave sites adjacent to RE1 and RE2 recognition sequences are configured such that, upon digestion, the resulting ends of the linearized vector are compatible (i.e., able to be ligated) with the ends of the liberated fragment. In some instances, one or more ends generated by digestion with RE1 and/or RE2 may be modified, e.g., by the addition or deletion of one or more nucleotides or other chemical modification, in order to generate compatible ends. Any convenient method of end-modification may find use in generating compatible ends including those end-modification methods that are well-known in the art including, but not limited to, e.g., end-blunting, phosphorylation, dephosphorylation, etc.

In some instances, compatible ends may be generated through the use of an enzyme with exonuclease activity, e.g., an exonuclease. For example, in some embodiments, the first vector and the second vector or nucleic acid fragment are configured such that upon restriction enzyme digestion of the first vector with a first restriction enzyme (RE1) and the second vector or nucleic acid with a second restriction enzyme (RE2), the newly generated ends are compatible for ligation following the use of an enzyme with exonuclease activity. Methods of generating compatible ends through the use of an enzyme with exonuclease activity are well known in the art and include but are not limited to, e.g., In-Fusion cloning, Gibson Assembly, and the like.

Figure 17:
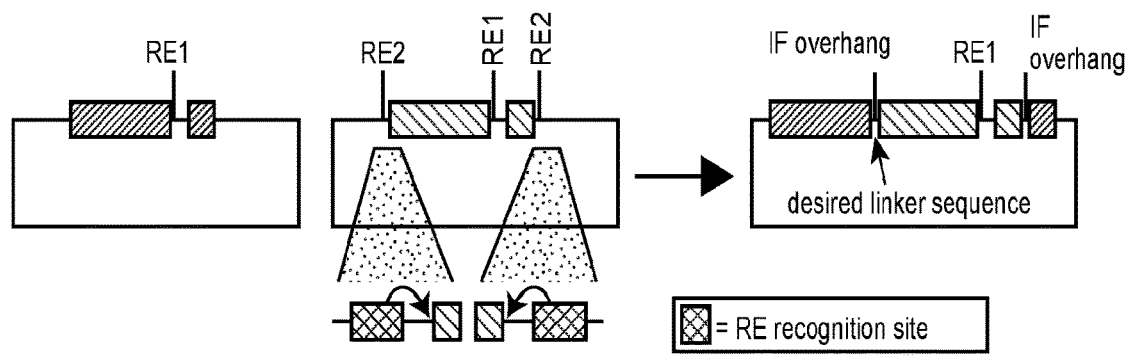
FIG. 17 depicts a schematized barcoded module coding sequence assembly strategy as described herein.

In some instances, assembly of restriction enzyme digested first vector and a second nucleic acid, e.g., a second vector of nucleic acid fragment, is achieved through the use of an In-Fusion reaction and, in such instances, compatible ends generated through the use of an enzyme with exonuclease activity may be referred to as In-Fusion overhangs (IF overhang) (FIG. 17). The joining of two IF overhangs may be configured to generate desirable linkers and/or desirable linker sequences between two joined ends of nucleic acid. For example, joined IF overhangs between a first module coding sequence and a second module coding sequence may be configured such that the first and second modules are in-frame. As described in more detail herein, in-frame module coding sequences may or may not be separated by sequence coding for one or more linker amino acids. For example, as depicted in FIG. 17, digestion of a first vector at the recognition site (RE1) of a first restriction enzyme generates ends that are In-Fusion compatible with the ends generated by digestion of a second vector or nucleic acid fragment by a Type IIS restriction enzyme at the cleavage sites determined by the recognition sites (RE2) present on the second vector or nucleic acid fragment. The compatible ends are ligated through an In-Fusion reaction, resulting in a desirable linker sequence between the first and second module coding sequences and a multi-unit barcode having first and second barcode units that are in reverse orientation as compared to the first and second module coding sequences. In some instances, following In-Fusion assembly of a first and second module coding sequence and a multi-unit barcode, a restriction enzyme site is present between the coding region and the barcode region in order to allow for insertion of further module coding sequences and barcode units.

Figure 18:
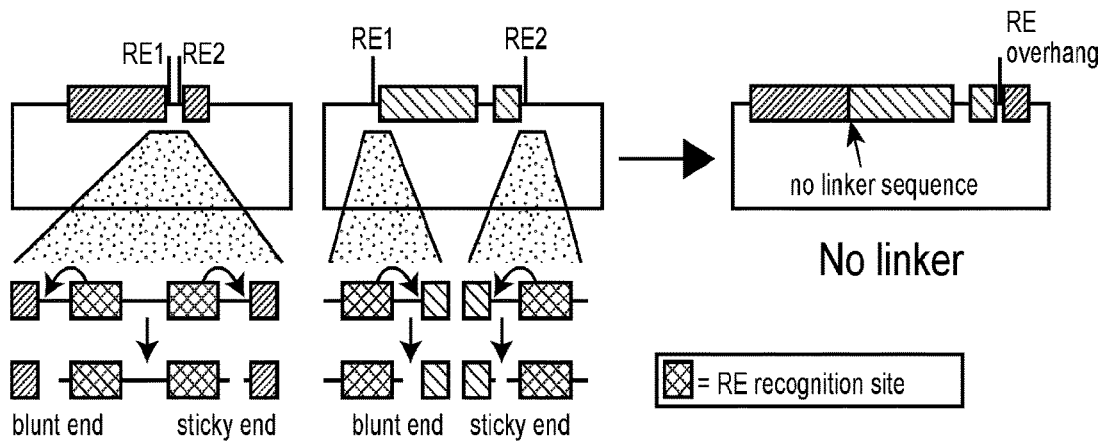
FIG. 18 depicts a schematized barcoded module coding sequence assembly strategy as described herein.

In some instances, upon ligation of a nucleic acid containing a first module coding sequence with a second nucleic acid containing a second module coding sequence, the first and second module coding sequences are joined such that no linker and no intervening non-coding nucleotides are present between the first and second module coding sequences. In one non-limiting example, a first vector containing a first module coding sequence and its respective barcode is joined without a linker or intervening non-coding nucleotides to a second vector or nucleic acid fragment containing a second module coding sequence and its respective barcode by means of restriction enzyme digestion (FIG. 18). Both the first vector and the second vector or nucleic acid fragment are digested using two different Type IIS restriction enzymes having two different recognition sites (RE1 and RE2) where the first restriction enzyme cleaves both strands of the nucleic acid at the same position at some distance from its recognition site (RE1) leaving a "blunt-end" and the second restriction enzyme cleaves both strands of the nucleic acid at different positions at some distance from its recognition site (RE2) leaving an overhang or "sticky end". The starting nucleic acids are configured such that upon cleavage of the first vector and the second vector with the second restriction enzyme, the generated sticky ends are compatible for ligation. Thus, upon ligation of the generated blunt ends and sticky ends, the resulting vector contains a first module coding sequence fused directly, with no linker or intervening non-coding nucleic acids, to a second module coding sequence and a multi-unit barcode containing the barcode of the first module coding sequence and the barcode of the second module coding sequence in reverse orientation as compared to the first and second module coding sequences.

Any convenient Type IIS restriction enzyme that results in blunt ends following digestion may find use in methods described herein utilizing blunt-end ligation, including those that are well known in the art including but are not limited to, e.g., SlyI, MlyI, etc. In addition, methods of generating a blunt end following digestion with a restriction endonuclease that does not generate blunt ends, i.e. "blunting", may be utilized where appropriate, including but not limited to "end-filling" with a DNA polymerase, such as, e.g., DNA Polymerase I Large Fragment (i.e., Klenow), T4 DNA Polymerase, Mung Bean Nuclease, etc., or terminal unpaired nucleotides may be removed by an enzyme with exonuclease activity.

In some instances, where sequence compatible with a non-Type IIS restriction enzyme is present at the terminal end of a module coding sequence, digestion may be performed with a non-Type IIS restriction enzyme, e.g., a Type II restriction enzyme that cleaves within its recognition sequence. In such instances, a restriction enzyme that produces a blunt end at the terminal end of the module coding sequence may be used where the module coding sequence contains all or a portion of the recognition sequence of the restriction enzyme at its 3' or 5' end. In some instances, where the module coding sequence contains all or a portion of a recognition sequence of a restriction enzyme that cuts within its recognition sequence and does not produce a blunt end, the non-blunt end restriction enzyme may be used and the generated overhang may be blunted, e.g., through any convenient method including but not limited to, e.g., those methods described herein.

As the sequences at the ends of the module coding sequences will be constrained by the terminal amino acids of the module, instances where appropriate restriction enzyme recognition sequences are, or can be modified to be, conveniently present at one or more terminal ends of the module coding sequence to allow for proper cleavage and/or generation of a blunt end may be infrequent depending on the particular module employed. Thus, in many instances, efficient generation of a large or multi-dimensional library of synthetic modular polypeptides will depend on enzyme recognition sites that are present outside of the module coding sequence. As such, in some instances, one or more, including all, of the enzyme recognition sequences utilized in library assembly will be present outside of the module coding sequence. In many instances, one or more, including all, of the enzyme recognition sequences utilized in library assembly will be present outside of the barcode sequence.

Figure 19:
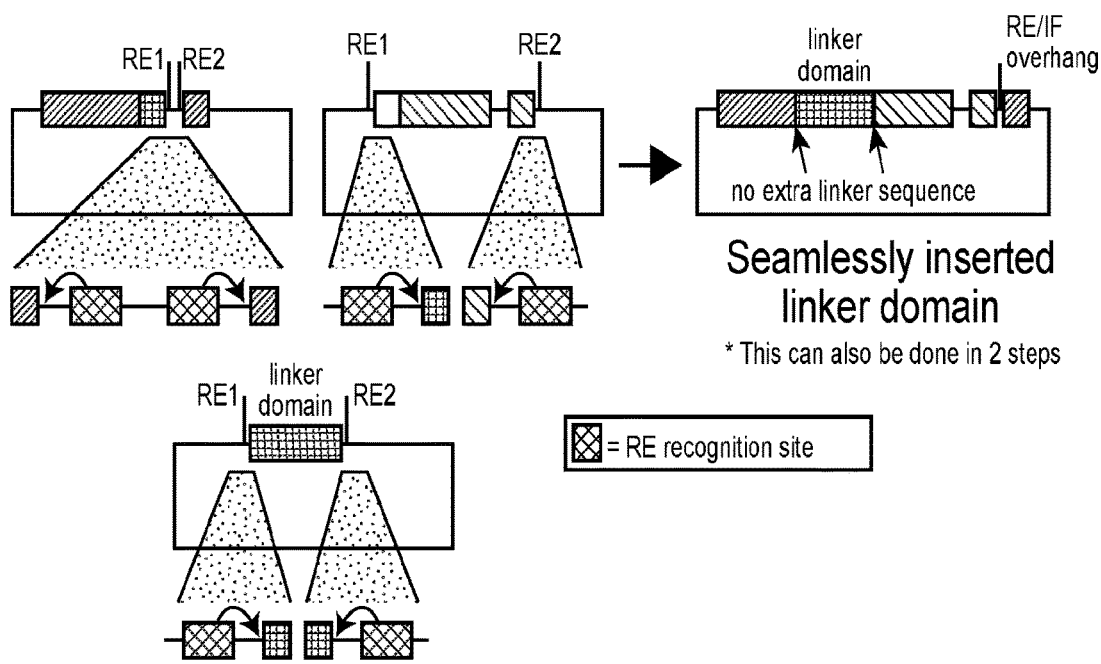
FIG. 19 depicts a schematized barcoded module coding sequence assembly strategy as described herein.

In some instances, a synthetic modular polypeptide is generated wherein module coding sequences are seamlessly joined to the ends of a linker domain such that no intervening sequence is present between the module coding sequences and their respective junctions with the linker domain. In one non-limiting example, such seamless joining of a module coding sequences to a linker domain is facilitated by a vector or a nucleic acid fragment configured to contain a portion of a desirable linker sequence seamlessly joined to either end of a module coding sequence. For example, a first vector may be configured to contain a first module coding sequence seamlessly joined to a first portion of a linker domain is ligated to a second vector, or nucleic acid fragment, configured to contain a second portion of the linker domain seamlessly joined to a second module coding sequence (FIG. 19). The first vector may be configured to contain two of a first Type IIS restriction enzyme recognition site (RE1) between the module coding sequence and its respective barcode. The second vector, or nucleic acid fragment, may be configured to contain two of a second Type IIS restriction enzyme recognition site (RE2) flanking the barcoded second module coding sequence. A third vector or nucleic acid fragment may be utilized containing the remaining, e.g., "middle" portion of the linker domain that is flanked by two of the second Type IIS restriction enzyme recognition site (RE2). The sequence of the pre-digested vectors and/or nucleic acid fragments is configured such that, upon digestion, compatible ends are generated between the first portion of the linker domain and the middle portion of the linker domain, the second portion of the linker domain and the middle portion of the linker domain, and the two barcodes. Upon digestion and ligation the resultant vector contains the first module coding sequence seamlessly joined to the linker domain seamlessly joined to the second module coding sequence joined to the barcode region containing the first and second barcodes in reverse orientation as compared to the first and second module coding sequences (FIG. 19). Seamless assembly, e.g., between modules and linker domains, may be achieved with or without the use of exonuclease mediated assembly (e.g., In-Fusion cloning, Gibson Assembly, etc.).

The above described digestion-based assembly strategies, in some instances, may be combined, in whole or in part, in any convenient and appropriate manner to arrive at a method useful to produce a synthetic modular polypeptide library as described herein. In addition, where substitute methods of digestion-based assembly are known in the art and would be compatible with the methods described herein, such substitute methods may find use in assembly of a synthetic modular polypeptide library as described herein. In some instances, the described digestion-based strategies may be combined, in whole or in part, with non-digestion-based methods of nucleic acid assembly.

Assembly of the nucleic acids encoding a synthetic modular polypeptide library as described herein is not limited to digestion-based, i.e., restriction enzyme-based, assembly strategies. In some instances, non-digestion based methods may find use in assembly of a library as described herein, including but not limited to, e.g., amplification-based strategies, recombination-based strategies, etc. Non-digestion-based methods may be used in place of digestion-based strategies, i.e., such that the entire assembly strategy as a whole does not involve restriction enzyme digestion, or may be used in combination with digestion-based strategies, i.e., such that the assembly strategy as a whole involves both restriction enzyme-based digestion and non-digestion-based methods.

In some instances, a synthetic modular polypeptide library as described herein may be assembled, in whole or in part, using amplification-based assembly, including but not limited to, e.g., PCR cloning, TA cloning, PCR overhang extension, and the like. Such amplification-based strategies will vary but will generally utilize a plurality of primer binding sites within the starting vectors and/or nucleic acid fragments. Such primer binding sites, depending on the desired final product, may be specifically added to the vectors and/or nucleic acid fragments or pre-existing sequence presence in a vector or nucleic acid fragment may be utilized as a primer binding site in accordance with various amplification-based assembly strategies. Primer binding sites may be positioned in any convenient configuration and/or orientation sufficient to produce the desired cloned product including but not limited to: positioned between a module encoding sequence and its respective barcode in a 5' to 3' orientation towards the module coding sequence; positioned between a module encoding sequence and its respective barcode in a 5' to 3' orientation towards the barcode; positioned upstream (i.e., 5') of the module encoding sequence in a 5' to 3' orientation towards the module encoding sequence; positioned downstream (i.e., 3') of the a module barcode sequence in a 5' to 3' orientation towards the module barcode sequence; and the like. The primer binding site sequences may be configured such that following the amplification-based cloning, including following one round of amplification-based cloning, one or more desired linker sequences is present between assembled elements including, e.g., assembled module coding sequences, assembled barcode sequences, etc.

Figure 20:
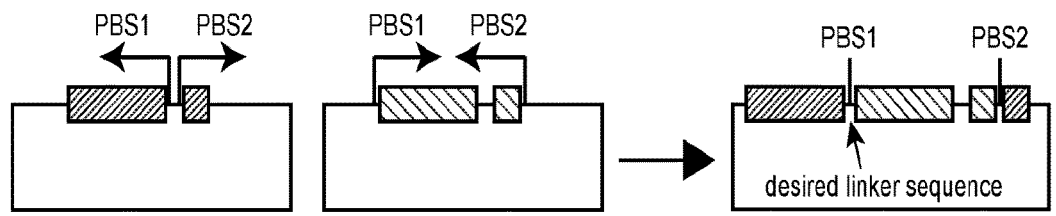
FIG. 20 depicts a schematized barcoded module coding sequence assembly strategy as described herein.

As a non-limiting example of amplification-based assembly strategies, a PCR overhang extension strategy may be employed (FIG. 20) wherein a first vector contains a first primer binding site (PBS1) and a second primer binding site (PBS2) positioned, in opposite 5' to 3' orientation, between a module coding sequence and its respective barcode sequence. A second vector or nucleic acid fragment having a second barcoded module coding sequence flanked by first and second primer binding sites (PBS1 and PBS2) is utilized. Upon extension and amplification by overhang extension PCR using the primers that specifically hybridize with the PBS1 and PBS2 sites, an assembled product is produced wherein the first module coding sequence is joined with a desired linker to the second module coding sequence which is joined to a multi-unit barcode containing the first and second barcodes in reverse orientation as compared to their respective module coding sequences (FIG. 20).

Figure 21:
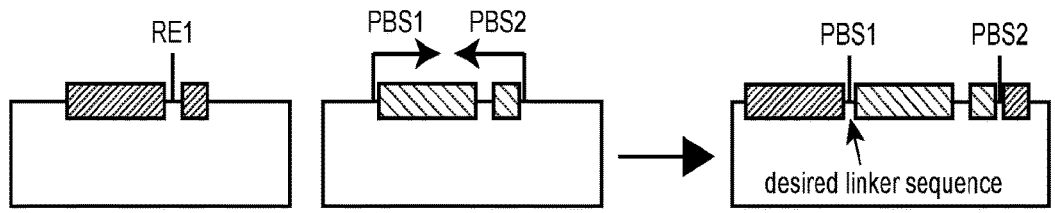
FIG. 21 depicts a schematized barcoded module coding sequence assembly strategy as described herein.

In view of the above described assembly strategies, the ordinary skilled artisan will readily comprehend how any of the above described strategies may be combined in whole or in part to result in a desired outcome and/or maximize the advantages and/or minimize the disadvantages of particular cloning techniques in accordance with the assembly with a desired library and/or library component. As a non-limiting example, amplification-based strategies may be combined with digestion-based strategies where the combination of such strategies results in assembly of a desired library and/or library components. For example, as depicted in FIG. 21, restriction enzyme digestion of a first vector according to a restriction recognition site enzyme site (RE1) positioned between a first module coding sequence and its barcode may be combined with PCR-based amplification using primer binding sites flanking a second barcoded module coding sequence contained within a second vector or nucleic acid fragment to allow for nested assembly. Upon assembly of the described hybrid assembly strategy, an assembled product is produced wherein the first module coding sequence is joined with a desired linker to the second module coding sequence which is joined to a multi-unit barcode containing the first and second barcodes in reverse orientation as compared to their respective module coding sequences (FIG. 21).

Hybrid strategies are not limited to the combination of digestion- and amplification-based strategies and may include other cloning and/or synthetic biology methods, in whole or in part, including but not limited to e.g., recombination-based cloning strategies (including but not limited to e.g., Gateway-based cloning strategies, Cre/Flp recombinase-based cloning (including wherein the site is inactivated upon recombination), etc.), de novo sequence assembly, de novo nucleic acid synthesis and the like. In some instances, recombination-based cloning strategies, de novo sequence assembly, de novo nucleic acid synthesis, and the like may be used independently, i.e., alone as a separate cloning strategy and not as part of a hybrid cloning strategy.

In some instances, where the particular cloning strategy employed results in the presence of undesired intervening sequence between two cloned elements, also known as cloning scars or seams, such cloning scars may be reduced and/or removed through unimolecular cleavage and religation of the scar containing vector. Unimolecular cleavage and religation may be achieved by any convenient method including but not limited to, e.g., restriction enzyme mediated unimolecular cleavage and religation, such as, e.g., Type IIS unimolecular cleavage and religation. For example, in some instances, a seam that includes all or part of a recombination site from a recombination-based assembly may be removed, in part or in whole, through unimolecular cleavage and religation. In some instances, a cleavage scar that includes all or part of a restriction enzyme recognition site from digestion based assembly may be removed, in part or in whole, through unimolecular cleavage and religation. In some instances, a seam that includes all or part of a primer binding site from amplification based assembly may be removed, in part or in whole, through unimolecular cleavage and religation.

Figure 22:
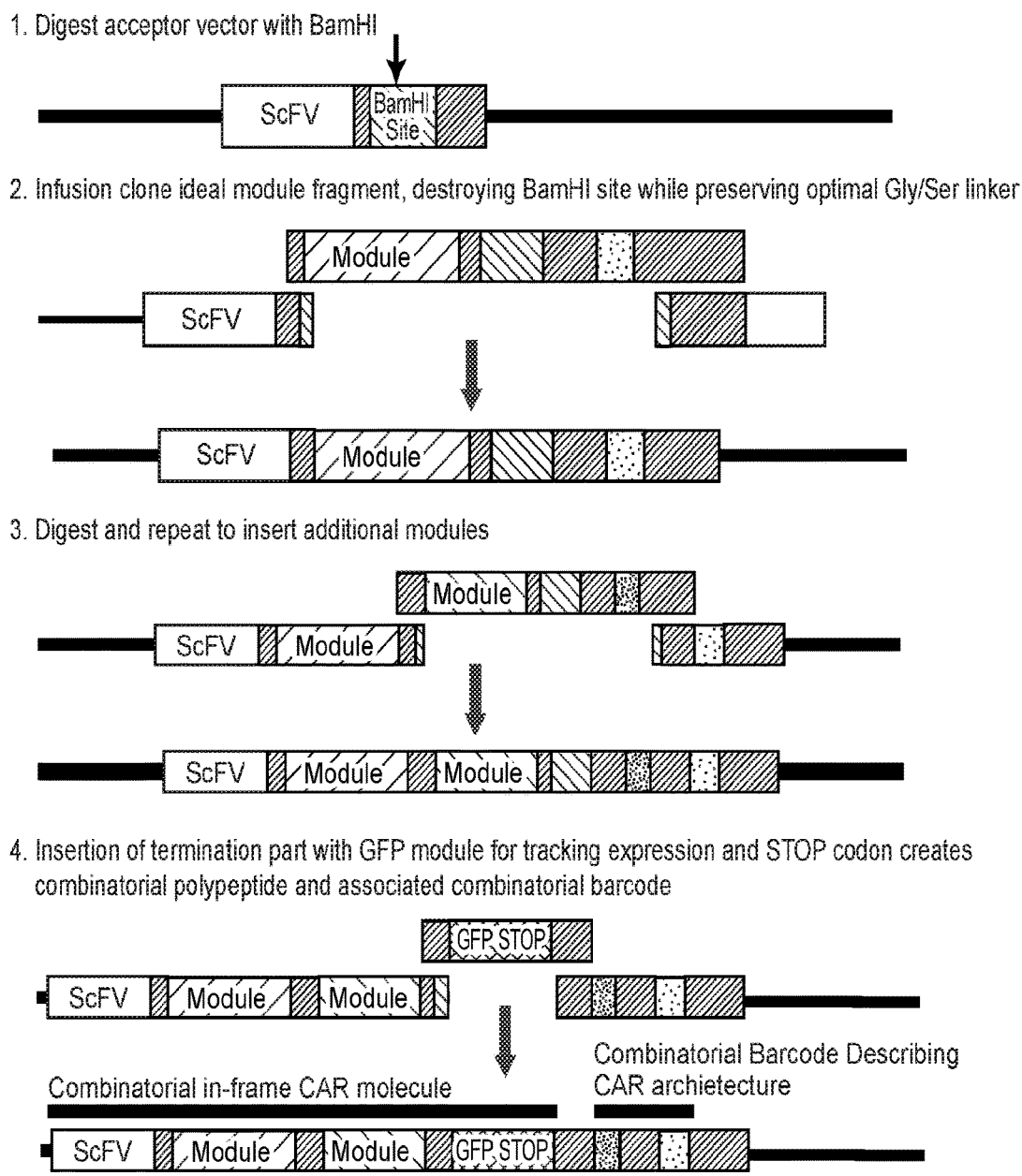
FIG. 22 depicts a schematized strategy for combinatorial nested assembly of a modular chimeric antigen receptor (CAR) library according to an embodiment of the instant disclosure.

In one non-limiting embodiment, a combinatorial library is produced by iterative cloning of each dimension of the library components through the use of digestion-based cloning and In-Fusion cloning. For example, as detailed in FIG. 22, in step one, a starting nucleic acid (e.g., a vector) containing a ScFv coding sequence and an adjacent Gly/Ser linker is digested at a BamHI site within or adjacent to the Gly/Ser linker. In step two, a nucleic acid fragment containing a first module coding sequence linked to a second Gly/Ser linker fused to a first module specific barcode is cloned into the digested BamHI site by In-Fusion cloning. Following ligation by In-Fusion cloning a Gly/Ser linker between the ScFv and the first module coding sequence is maintained. In the third step, the nucleic acid assembled in step 2 is digested at a BamHI site imported within or adjacent to the Gly/Ser linker of the first module coding sequence nucleic acid fragment and In-Fusion cloning is repeated with a second nucleic acid fragment containing a second module coding sequence containing linked to a third Gly/Ser linker fused to a second module specific barcode. Similar to step 2, following ligation by In-Fusion cloning a Gly/Ser linker between the first and second module coding sequences is maintained. Wherein higher dimension library members are desired, step 3 may be repeated iteratively. In step four, digestion at a BamHI site imported within or adjacent to the Gly/Ser linker of the last added module coding sequence containing nucleic acid allows for the In-Fusion cloning of a terminal reporter sequence (e.g., a GFP encoding sequence that also contains a "stop" signal sequence (e.g., a stop codon)) between the final module coding sequence and the downstream multi-unit barcode sequence. In this embodiment, each resulting library member contains a combinatorial in-frame CAR and a combinatorial barcode describing the architecture of the combinatorial in-frame CAR.

Pooled Libraries

The instant disclosure provides methods of making pooled libraries of barcoded synthetic modular polypeptides. By pooled library is meant that the library members are present in a common container and/or common solution and the individual library members need not be physically separated in space, e.g., the individual library members may be pooled during construction of the library (e.g., as in a "one-pot assembly") or following construction of the individual library members. For example, in the case of a pooled synthetic modular polypeptide library constructed by combinatorial nested assembly, the components of the library may be pooled during assembly of the library members, prior to completion of the assembly of the library members, and/or following completion of the assembly of the library members, etc. Pooled libraries as used herein is not limited to libraries of bare synthetic modular polypeptides but also includes pooled libraries of cells expressing synthetic modular polypeptides, pooled libraries of nucleic acids encoding synthetic modular polypeptides, and the like.

Accordingly, in some instances, individual nucleic acid components used to assemble the library members may be pooled prior to assembly and may remain pooled during assembly of the library members. In other instances, the assembled library members may be mixed following assembly to generate a pooled library.

As libraries and methods of library assembly described herein involve the production of library members that may be identified by sequencing the associated barcoding region, individual nucleic acids may be pooled at any point before, during or after assembly and identification and quantification of individual library members in downstream assays remains possible. In some instances, the final dimensionality of a library may be manipulated by pooling library components at particular points during assembly. For example, a mixed-dimensional library may be obtained by separately assembling partial libraries of different dimensionality and subsequently pooling the partial libraries (e.g., using a "split-and-pool" assembly). In some instances, e.g., after pooling partial libraries of differing dimensionality, further assembly, including the addition of further variable domains, may be performed.

Figure 23:
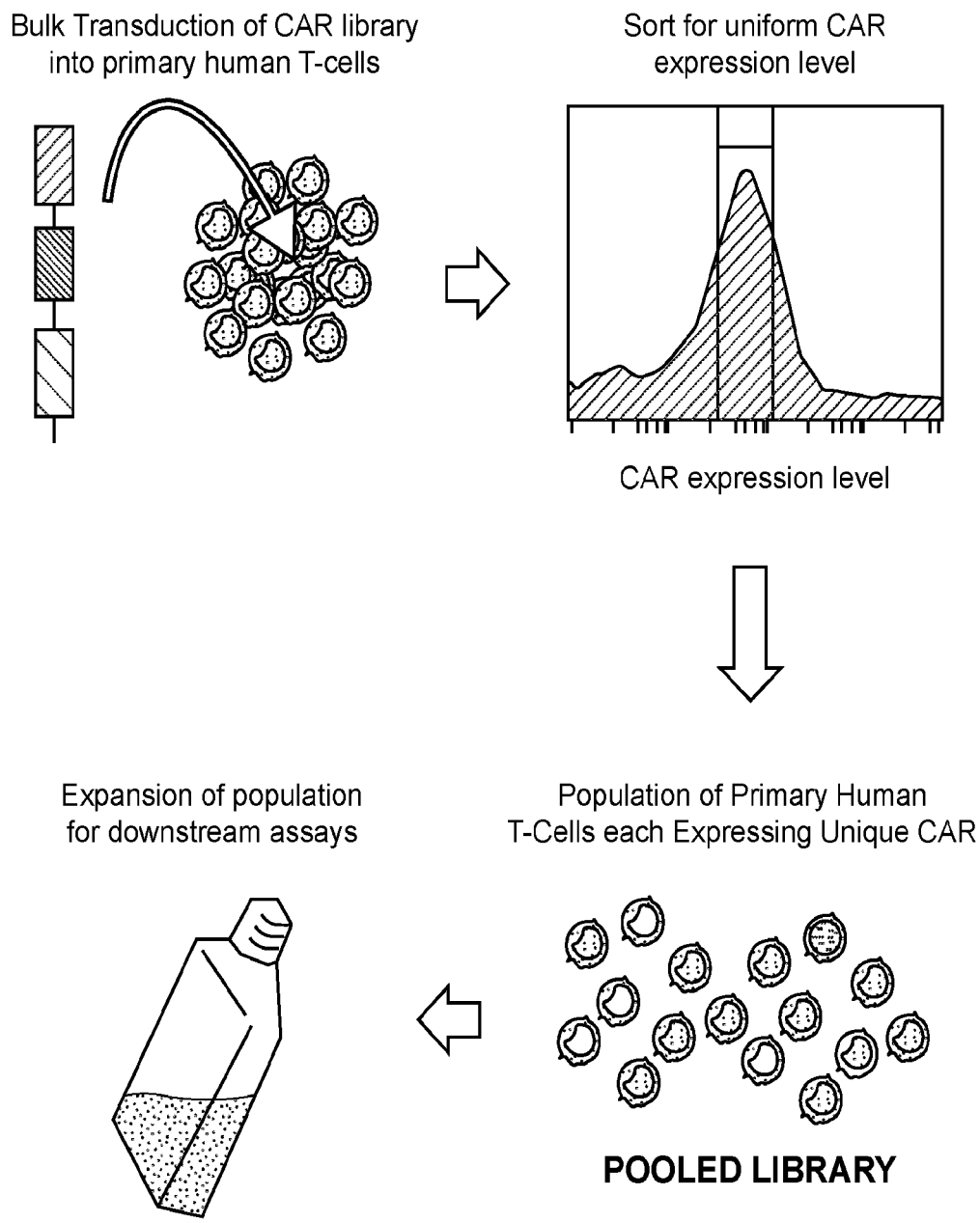
FIG. 23 depicts schematized production of a pooled cellular modular CAR library according to an embodiment of the instant disclosure.

In one non-limiting embodiment, as depicted in FIG. 23, a pooled library of synthetic modular CAR polypeptide encoding nucleic acids is transformed in bulk into human primary T-cells to generate synthetic modular CAR polypeptide expressing primary human T-cells. Optionally, where the encoded synthetic modular CAR polypeptide library members include one or more reporter modules, the transformed T-cells may be sorted based on their expression of the reporter module (which serves to indicate expression of the synthetic modular CAR polypeptide) so as to isolate transformed cells with uniform expression of the synthetic modular CAR polypeptide library members. Such sorted uniformly expressing transformed T-cells represent a pooled library of synthetic modular CAR polypeptide expressing T-cells.

In some instances, the transformation efficiency of the synthetic modular CAR polypeptide expressing nucleic acids and/or the primary human T-cells is modulated. Such modulation may be performed for various practical reasons, for example, to control the likelihood of expression of each member of the library and/or to control the likelihood that each cell expresses at most one library member. Such modulation may be achieved through any convenient method including but not limited to, e.g., modulating the initial amount of synthetic modular CAR polypeptide encoding nucleic acid present during transformation, controlling the initial amount of primary T-cells present during the transformation, controlling the ratio of encoding nucleic acid to primary T-cells during the transformation, and the like. As such, in some instances, the transformation efficiency is modulated such that essentially each transduced T-cell expresses one unique synthetic modular CAR polypeptide. In some instances, resulting pooled cellular libraries expressing unique synthetic modular CAR polypeptides may be cultured, expanded, stored, etc. according to the requirements of downstream assays.

Such pooled libraries, whether of pooled nucleic acids, pooled modular polypeptides, pooled transduced cells, etc. are not limited to nucleic acids encoding synthetic modular CAR polypeptides, synthetic modular CAR polypeptides, or cells (e.g., T-cells) expressing synthetic modular CAR polypeptides. Any library of nucleic acids encoding modular polypeptides, modular polypeptides and/or appropriate cells transduced expressing modular polypeptides produced according to the methods as described herein may be pooled in a similar fashion to generate a pooled library useful, e.g., in screening assays.

Individual members of the pooled libraries, as described herein, may be positively identified by virtue of the specific multi-unit barcode associated with each library member. Due to the specific combinatorial nested assembly that results in a predictable positional relationship between each module encoding sequence and its respective barcode sequence, the identity and architecture of each synthetic modular polypeptide can be reconstructed by simply sequencing the associated multi-unit barcode. As such, in some instances, the identities and/or architecture of individual members of a synthetic modular polypeptide library may be determined from sequence information related to the barcode regions of the library members. For example, in some instances, the complexity and/or each individual member of a pooled library as described herein may be determined, e.g., following construction of the library, following use of the library in a particular assay, etc.

Compartmentalized Library Components

Individual nucleic acid members comprising a coding region and a barcode region may, in some instances, be compartmentalized. Pooled libraries and libraries with compartmentalized components need not be mutually exclusive and, e.g., a library may in some instances be both pooled and contain compartmentalized components at different times, e.g., a library may be constructed, e.g., the library members may be assembled, as a pool, e.g., as in one-pot assembly, and then may be subsequently compartmentalized, e.g., by transfection of nucleic acid library members into individual cells or non-cellular compartments. In other instances, library members may be compartmentalized during a portion of their assembly and then subsequently pooled for further processes including but not limited to, e.g., further assembly or screening. In general, the barcoded synthetic polypeptide encoding nucleic acids assembled according the nested assembly and cloning strategies as described herein are assembled as a pool and may or may not be subsequently compartmentalized.

Compartmentalization of assembled barcoded synthetic polypeptide encoding nucleic acids may be achieved by any convenient method allowing for transcription and translation from individual nucleic acid library members such that each nucleic acid library member remains associated with the encoded product thereof. In some instances, as described in more detail below, compartmentalization may be achieved through the creation of cellular libraries, wherein individual cells serve as the "compartment" and provide for translation and transcription from the nucleic acid library members.

In some instances, compartmentalization may be achieved through the creation of non-cellular libraries, e.g., encapsulation-based libraries. Cell-free encapsulation-based libraries will generally comprise an emulsion of two or more immiscible liquids wherein the nucleic acid library members are soluble in a first liquid, e.g., an aqueous liquid such as water or aqueous buffer, and insoluble in a second liquid, e.g., an oil or other organic solvent, such that the first liquid forms compartments, e.g., droplets, containing individual library members. A library containing emulsion may be configured such that each compartment contains any desired number of individual library members, including but not limited to at most one member per compartment. The nucleic acid members of encapsulated libraries may be transcribed (e.g., in vitro transcribed) and translated (e.g., in vitro translated) under conditions such that the transcription and translation products remain associated, i.e., remain within the compartment, with the individual nucleic acid library member from which they were encoded. Any convenient and appropriate method of generating an encapsulated library of nucleic acid encoded polypeptides may find use in the methods described herein, including but not limited to, e.g., those described in Bernath et al. *Anal Biochem*. (2004) 325(1):151-7; the disclosure of which is incorporated herein by reference in its entirety.

Following production of the encoded product of the library member within the compartment, the nucleic acid library member and the encoded synthetic modular polypeptide may or may not be physically linked. For example, in some instances, the nucleic acid library member and the encoded product may be linked, e.g., through any convenient and appropriate method including chemical linkage or conjugation (i.e., the generation of a covalent bond between the nucleic acid library member and the encoded synthetic modular polypeptide) or through molecular binding (e.g., through direct binding between the library member and the encoded synthetic modular polypeptide or through indirect binding between the library member and the encoded product mediated by one or more binding intermediates (e.g., binding partners, substrates, etc.). Any convenient and appropriate method of linking compartmentalized encoded polypeptides to nucleic acid library members may find use in the methods describe herein including but not limited to e.g., the use of a substrate comprising an attached epitope tag binding agent that specifically binds to an epitope tag encoded by the nucleic acid library member, e.g., as described in Griffiths & Tawfik. *EMBO J* (20030 22(1):24-35, the disclosure of which is incorporated herein by reference in its entirety. In some instances, following linking the nucleic acid library members may be decompartmentalized, e.g., pooled, and further assayed as a pooled library.

In some instances, the nucleic acid library member and the encoded product remain sufficiently associated without being physically linked, e.g., through compartmentalization within the compartment, including cellular and non-cellular compartments.

Compartmentalization, whether cellular or non-cellular, generally allows for the identification of the synthetic modular polypeptide, or portion thereof, that correlates with a detected phenotype through the sequencing of the barcode region of the individual library member nucleic acid encoding the synthetic modular polypeptide which remains associated with the synthetic modular polypeptide by nature of their compartmentalization or as a result of a physical link formed during their compartmentalization.

Cellular Libraries

As described in some detail above, libraries as used herein include cellular libraries wherein the cells of the library express synthetic modular polypeptides. Transformation of nucleic acids encoding synthetic modular polypeptides may be performed by any convenient method including but not limited to, e.g., viral transfection, electroporation, lipofection, bombardment, chemical transformation, use of a transducible carrier (e.g., a transducible carrier protein), and the like. In some instances, the cell into which a synthetic modular polypeptide encoding nucleic acid is transformed is herein referred to as a host cell.

Host cells may express a single individual barcoded nucleic acid encoding a unique synthetic modular polypeptide or may express multiple, including two or more, individual barcoded nucleic acids encoding unique synthetic modular polypeptides. It will be understood that the number of individual barcoded nucleic acids expressed by a host cell may be controlled, e.g., by controlling the frequency or likelihood of delivery of the subject nucleic acids into host cell, e.g., by modulating the parameters of the delivery method. In some instances, the resulting number of individual barcoded nucleic acids encoding unique synthetic modular polypeptides present in a host cell may be referred to as the multiplicity of infection (MOI) and may be defined as the ratio of nucleic acids to host cells either before or following the delivery. Conventional methods of modulating the MOI, e.g., by increasing or decreasing the ratio of nucleic acids to host cells before delivery, may be employed to obtain a desired final number of individual barcoded nucleic acids encoding unique synthetic modular polypeptides per host cell following delivery.

Nucleic acids encoding synthetic modular polypeptides may transformed into any appropriate host cell or cell line, including e.g., prokaryotic and eukaryotic cells. Selection of a host cell type will depend on a number of factors, including the type of synthetic modular polypeptide library to be screened and the particular screening assay. In some instances, a host cell may be a prokaryotic cell, including but not limited to Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospirae, Planctomycetes, Proteobacteria, Spirochaetes, Synergistetes, Tenericutes, Thermodesulfobacteria, Thermotogae and Verrucomicrobia. In certain embodiments, a host cell may be a bacterial cell, e.g., *E. coli*. In some instances, a conventional bacterial strain may be used, including but not limited to e.g., those commercially available from supplies such as American Type Culture Collection (ATCC) (Manassas, Va.), Life Technologies, Inc. (Grand Island, N.Y.), and the like.

Suitable eukaryotic cells include primary cells and cultured cells originally derived from a host animal including but not limited to, e.g., mammals (including e.g., humans, primates, apes, ungulates, canines, felines, rabbits, rodents, etc.), reptiles, amphibians (e.g., xenopus, salamander, newt, etc.), fish (e.g., zebrafish, etc.), birds (e.g., chicken, etc.), invertebrates (e.g., insects (e.g., fruit fly, etc.), worms (e.g., nematodes, etc.), marine invertebrates (e.g., sea urchin, etc.), etc.), yeast, and the like. In certain embodiments, the cells may be primary rodent cells or cultured rodent cells derived from a mouse or rat. In other embodiments, the cells may be primary human cells or cultured human cells. Any convenient eukaryotic cell may find use as a host cell depending on the particular library to be screened and the particular screening assay, where in some instances, convention eukaryotic cell lines may be used, including but not limited to e.g., those commercially available from supplies such as American Type Culture Collection (ATCC) (Manassas, Va.), Life Technologies, Inc. (Grand Island, N.Y.), and the like.

In some instances, the cells of a cellular library are primary cells (e.g., primary monocytes, primary lymphocytes (e.g., primary T-cells, primary B cells, primary NK cells, etc.), primary dendritic cells, etc.), primary endothelial cells, primary epithelial cells, primary fibroblasts, primary hematopoietic stem cells, primary keratinocytes, primary melanocytes, primary mesenchymal stem cells, primary preadipocytes, primary muscle cells (e.g., primary smooth muscle cells, primary skeletal muscle cells, etc.), etc. In some instances, the cells of a cellular library are established cell lines (e.g., Jurkat cells, etc.). In some instances, the cells of a cellular library are patient specific cells (patient specific immune cells (e.g., primary T-cells, etc.), patient specific stem cells (e.g., hematopoietic stem cells, mesenchymal stem cells, adipose derived stem cells, etc.), patient specific cancer cells (e.g., tumor cells, blood cancer cells, etc.).

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, Hut-78, Jurkat, HL-60, NK cell lines (e.g., NKL, NK92, and YTS), and the like.

In some instances, the cell is not an immortalized cell line, but is instead a cell (e.g., a primary cell) obtained from an individual. For example, in some cases, the cell is an immune cell obtained from an individual. As an example, the cell is a T lymphocyte obtained from an individual. As another example, the cell is a cytotoxic cell obtained from an individual. As another example, the cell is a stem cell or progenitor cell obtained from an individual.

Following transformation of a plurality of nucleic acids encoding synthetic modular polypeptides of a library the transformed host cells may be sorted based on their expression of the synthetic modular polypeptides, e.g., to remove those cells not expressing synthetic modular polypeptides from the library, to isolate only those cells expressing synthetic modular polypeptides above a particular expression threshold, to isolate only those cells expressing synthetic modular polypeptides below a particular expression threshold, to isolate only those cells expressing synthetic modular polypeptides within a particular range of expression, etc. In some instances, sorting of transformed cells based on expression may be performed in order to isolate only those cells in the library having uniform expression, where uniform expression may vary according to particular applications and may, in some instances be defined as an expression level within a particular range above and below the mean expression of the population.

In certain embodiments, the sorting of transformed cells based on their expression of library members, e.g., the sorting of cells having expression or roughly equal expression of library members, allows for improved evaluation of the influence of the library member and/or the modules contained there. For example, by isolating only those cells expressing the library members within a defined range, identification of library members as influencing a particular phenotype will be based on the actual function of the library members and those modules contained within rather than how well the particular library member is expressed. In some embodiments, e.g., where semi-quantitative analysis of the frequency of individual library members and/or modules thereof is performed, sorting cell expressing the library members within a predefined range allows for more accurate quantitative analysis and quantitation of those library members and/or modules based on their influence of a particular phenotype and not on their relative level of expression.

In addition, sorting allows for the identification of library members and modules thereof that function to produce or influence a particular phenotype when expressed within a particular expression range or above or below a particular threshold including e.g., when expressed at a low level or when expressed at a high level.

Library Normalization

Libraries of the present disclosure may or may not be normalized depending on the context in which the library is made and/or the intended final use of the library. By "normalized", as used herein in reference to the described libraries, is meant that the relative amounts of each library member are adjusted to at least be closer to equal than the relative amounts of each library member were before the adjusting. In some instances, normalization of a library results in a library having a smaller range between the amount of the most represented members of the library and the amount of least represented members of the library. In some instances, normalization results in an increase in the amount of the least represented member(s) of the library. In some instances, normalization results in a decrease in the amount of the most represented member(s) of the library.

In some instances, library normalization may include quantifying all or most or a representative sampling (or all or most of a representative sampling) of the members of the library to determine the relative amount of each library member within the library. Following quantification, an adjustment is made based on the quantification to equalize the relative presence of each member of the library within the library. Depending on the context, such an adjustment may be made directly in the already produced library such that the library is directly normalized. Alternatively, an adjustment may be made in the library preparation method such that the next prepared library will be normalized.

Any library of the present disclosure may be normalized, including but not limited to e.g., nucleic acid libraries, polypeptide libraries, non-cellular encapsulated libraries, cellular libraries, etc., and depending on the library to be normalized various methods may be utilized. For example, depending on the type of library to be normalized, various methods of quantifying the relative amounts of library members may be utilized. Various methods of quantifying the members of a nucleic acid library that may be utilized include but are not limited to e.g., quantitative sequencing (e.g., Next Generation Sequencing), quantitative PCR, quantitative hybridization (e.g., microarray), and the like. Various methods of quantifying the members of a polypeptide library may be utilized including but not limited to e.g., quantitative mass spectrometry, ELISA, and the like. Various methods of quantifying the members of a cellular library may be utilized including but not limited to e.g., flow cytometry, immunohistochemistry, quantitative sequencing (e.g., Next Generation Sequencing), quantitative PCR, quantitative hybridization (e.g., microarray), and the like.

In some instances, once the members of a library are quantified the adjustment(s) needed for normalization may be calculated. Any convenient and appropriate method of normalization calculation may be employed depending on the type of library and/or the size of the library. In some instances, a linear equation may be used, including but not limited to e.g., the linear equation presented in FIG. 28.

In some instances, once the normalization is calculated for each member of the library, the library may be adjusted. Various methods for direct adjustment of a library may be employed. For example, in some instances, a cellular library may be normalized using FACS to sort an equal number of cells representing each member of the library either into a pool or into individually addressable compartments. In some instances, where a library is already compartmentalized, the library may be normalized by adjusting the volume of each compartment including e.g., where different concentrations of library members in each compartment are normalized by adding a specific volume of liquid to each compartment sufficient to equalize the concentrations.

In some instances, normalization of a pooled library of nucleic acids may be performed. Pooled libraries of nucleic acids may be normalized for various reasons. In one embodiment, a pooled library of nucleic acids may be normalized to compensate for the over or under representation of individual library members within the library, e.g., due to over or under efficient incorporation of particular nucleic acid modules into the library members during a combinatorial assembly.

In some instances, the members of a nucleic acid library and/or nucleic acid modules making up the library members may be quantified (e.g., by quantitative sequencing). Following such quantification, the adjustment of each member needed for normalization is calculated. In one embodiment, the calculated adjustment may be applied to the next combinatorial assembly of the library, e.g., the amount of each nucleic acid module used to assemble the nucleic acid library may be adjusted based on the relative representation of that module in the quantified library. Therefore, by adjusting the starting amount of the nucleic acid modules before the next assembly of the library the resulting combinatorial library will be normalized. Accordingly, in some instances, normalization of a library described herein may include assembly of the library, followed by quantification of the assembled library and reassembly of a normalized version of the library that is based on the quantification.

Methods of Screening

Methods of screening synthetic modular polypeptide libraries are provided including, but not limited to, e.g., in vitro screening methods and in vivo screening methods. By "in vivo screening" is generally meant that a library containing a plurality of unique synthetic modular polypeptides is assayed within the biological context of a living organism. Living organisms that may be assayed in vivo according to the methods described herein include unicellular and multicellular organisms.

In vivo screening of a unicellular organism generally involves contacting a unicellular organism with a synthetic modular polypeptide library, where the synthetic modular polypeptide library may be a polypeptide library or a cellular library expressing synthetic modular polypeptides, and detecting a phenotype in the unicellular organism. In other instances, in vivo screening of a unicellular organism may include contacting a unicellular organism or a plurality of unicellular organisms with a nucleic acid library encoding synthetic modular polypeptides under conditions sufficient for expression of the encoded synthetic modular polypeptides by the unicellular organisms.

In vivo screening of a multicellular organism generally involves contacting a multicellular organism with a synthetic modular polypeptide library, where the synthetic modular polypeptide library may be a polypeptide library or a cellular library expressing synthetic modular polypeptides, and detecting a phenotype in the multicellular organism. In other instances, in vivo screening of a multicellular organism may include contacting a multicellular organism or a plurality of multicellular organisms with a nucleic acid library encoding synthetic modular polypeptides under conditions sufficient for expression of the encoded synthetic modular polypeptides by the multicellular organism(s). Any convenient multicellular organism may be employed in in vivo screening of a library as described herein depending on the particular library to be screened and the particular in vivo assay employed, where particular multicellular organisms include but are not limited to, e.g., mammals (e.g., mice, rats, etc.).

By "in vitro screening" is generally meant that a library containing a plurality of unique synthetic modular polypeptides is assayed outside of the normal biological context, e.g., of the polypeptide modules of the library, the biological material used in the screen or the phenotype screened. For example, in some instances, in vitro screening may be performed using an artificial or synthetic experimental context including but not limited to, e.g., an isolated sample, an isolated cell, a cell culture, an isolated or dissected tissue, a defined sample, a defined medium, an artificial tissue, an artificial organ, a cell extract, a tissue extract, an array of samples, etc. In vitro screening may be performed in any convenient and appropriate vessel including but not limited to, e.g., a reaction vessel, a reaction chamber, a tube, a vial, a plate, a flask, a dish, a slide, and the like.

In vitro screening of a sample, including a cellular sample or a non-cellular sample, generally involves contacting the sample with a synthetic modular polypeptide library, where the synthetic modular polypeptide library may be a polypeptide library or a cellular library expressing synthetic modular polypeptides, and detecting a cellular phenotype or other reaction or molecular phenotype. Any convenient sample may be employed in in vitro screening of a library as described herein depending on the particular library to be screened and the particular in vitro assay employed, where particular samples include but are not limited to, e.g., biological samples, cellular samples, polypeptide samples, nucleic acid samples, chemical samples, and the like.

In some instances, cell-free synthetic modular polypeptide libraries may be in vitro screened. For example, a compartmentalized synthetic modular polypeptide library may be screened for a phenotype by contacting the compartmentalized synthetic modular polypeptide library with one or more agents with which individual members of the library are predicted to react. Any convenient methods of screening cell-free polypeptide libraries, whether encapsulated or pooled, may find use in the methods described herein, including but not limited to e.g., flow cytometry-based detection or FACS-based detection of a phenotype in cell-free encapsulation-based assays, e.g., as described in Griffiths & Tawfik. *EMBO J* (2003) 22(1):24-35 and Bernath et al. *Anal Biochem* (2004) 325(1):151-7; the disclosures of which are incorporated herein by reference in their entirety.

Phenotypes and Methods of Identifying

Methods of screening, whether in vivo or in vitro, will generally involve the detection of a phenotype and identification of the one or more library members associated with the phenotype. As used herein the term "phenotype" generally refers to a characteristic of a molecule, a cell, a tissue, an organ or an organism that is detected in a particular assay and thus may include but are not limited to, e.g., molecular phenotypes, cellular phenotypes, organismal phenotypes, tissue phenotypes, organ phenotypes, organismal phenotypes, etc. A phenotype detected in a particular assay may be a predetermined phenotype, e.g., a known or expected phenotype (e.g., including a known or expected level of a particular characteristic, the presence or absence of a known or expected level characteristic, etc.), or may be identified at the time of the assay, e.g., a newly detected or previously undetermined phenotype (e.g., including a newly detected or previously undetermined level of a particular characteristic, the presence or absence of a newly detected or previously undetermined characteristic, etc.). Any convenient assay for detecting a phenotype relevant to a synthetic modular polypeptide library as described herein may find use in screening such libraries.

Screening of a library of synthetic modular polypeptides or nucleic acids encoding a library of synthetic modular polypeptides allows for the identification of polypeptides and/or module portions thereof that effectively produce a desired phenotype. Accordingly, the instant disclosure generally includes polypeptides identified by screening the herein described libraries.

In some instances, a cellular phenotype is detected following contacting a population of cells with a library as described herein. Cellular phenotypes may include but are not limited to, e.g., cellular behaviors (including but not limited to e.g., cell viability, cell proliferation, cell activation, cell morphology, cell migration, cell adherence, cellular differentiation, cellular pluripotency, etc.), cellular expression (including but not limited to, e.g., gene expression, protein expression, non-coding RNA expression, gene activation, gene repression, etc.), reporter expression (including but not limited to, e.g., transgene reporter expression, marker expression) and the like.

In some instances, a tissue, organ or organismal phenotype is detected following contacting a tissue, an organ or organism with a library as described herein. Tissue phenotypes include but are not limited to, e.g., tissue viability, tissue morphology, physical tissue characteristics (including but not limited to e.g., boundary function, mechanical strength, elasticity, etc.), tissue expression (including but not limited to e.g., tissue gene expression, tissue protein expression, etc.), tissue reporter expression (including but not limited to, e.g., transgene reporter expression, marker expression) and the like. Organ phenotypes include but are not limited to, e.g., organ appearance, organ viability, organ morphology, organ function (including but not limited to e.g., biomolecule (e.g., enzyme, metabolite, protein, etc.) production, filtration, mechanical function, etc.). Organismal phenotypes include but are not limited to, e.g., organism appearance, organism viability (e.g., lifespan), organism physiology, organism fertility/fecundity, organism behavior, etc.

In some instances, a phenotype may be assayed in relationship to a disease state where the disease state may be a modeled disease state (e.g., a cell, tissue or organism that has been altered or treated to display characteristics of a particular disease) or may be a clinical disease state (e.g., organism displaying characteristics of a disease or diagnosed with a disease or cells or tissue derived therefrom). Disease related phenotypes may be assayed at any convenient level including but not limited to e.g., the cellular level, the tissue level, the organ level, the organismal level. In some instances disease phenotypes assayed may be phenotypes of the disease causing agent itself including but not limited to, e.g., tumor phenotypes, cancer cell phenotypes, autoimmune cell phenotypes, infectious agent (bacterial, virus, etc.) phenotypes, etc. In other instances, disease phenotypes assayed may be phenotypes of the cell, tissue or organism affected by the disease or associated with the disease model that provide information regarding disease presence and/or progression including but not limited to e.g., cell activation (e.g., immune cell activation), disease response (e.g., immune response), biomarkers, cell counts, organism physiology, clinical outcomes, etc.

In some instances, assessment of a phenotype may be performed at the population level, e.g., a population of cells may be assessed, a population of organisms is assessed, etc. In some instances, in a population-based phenotype assessment the effect of a particular library member on the presence or absence of a population phenotype may be measured. For example, the effect of a particular library member on a cellular phenotype of a population of cells may be assessed. In other instances, the effect of a particular library member on a organismal phenotype of a population of organisms may be assessed.

In some embodiments, a phenotype is assessed in response to an applied stimulus wherein application of the stimulus includes but is not limited to e.g., contacting cells with the stimulus, contacting tissue with the stimulus, contacting an organ with the stimulus, contacting an organism with the stimulus, etc. As such a test sample or test subject may be contacted with a stimulus in vitro or in vivo depending on the assay employed, depending on the stimulus and depending on the particular library being screened. Different stimuli may be used alone or in combination. A stimulus may be a free (e.g., a soluble stimulus, a free ligand, etc.) stimulus, bound (e.g., bound to a solid support), cellular expressed stimulus (e.g., an expressed co-stimulatory molecule, an expressed antigen, an expressed cellular ligand, etc.), and the like.

In some embodiments, a T-cell population expressing a synthetic modular CAR library is contacted in vitro with a stimulus and a resulting phenotype is detected. In vitro stimuli useful in screening a cellular library expressing synthetic modular CARs will generally be antigens including e.g., free antigen, bound antigen, cellular expressed antigen (e.g., expressed on an antigen presenting cell, expressed on a target cell, etc.), etc. Useful antigens will vary depending on the particular CAR library to be screened and the desired outcome of the screen. Non-limiting examples antigens include but are not limited to, e.g., soluble antigen, solid support bound antigen (e.g., plate bound antigen, bead bound antigen, slide bound antigen, etc.), expressed antigen (e.g., a transgenic cell expressing an antigen, a cell naturally expressing an antigen (e.g., a native antigen expressing cell, a cancer cell expressing a cancer antigen, etc.). Native antigen expressing cells useful in screening a library in vitro will vary and may include but are not limited to e.g., naïve tumor cells (e.g., obtained from a tumor biopsy).

In some embodiments, a T-cell population expressing a synthetic modular CAR library is contacted in vivo with a stimulus and a resulting phenotype is detected. The in vivo context of synthetic modular CAR library screening will vary greatly and may include but are not limited to animal models. In some instances, in vivo screening may be performed in small animal model such as, e.g., rodent models including but not limited to e.g., mouse models, rat models, etc. In some instances, in vivo screening is performed in a mouse tumor models, including transgenic and non-transgenic mouse tumor models.

In some instances, a utilized model may be a xenograft model. For example, a utilized model may be a "humanized" model wherein such humanized models are defined as having one or more human derived components, e.g., a humanized immune system, humanized T-cells, expressing a human protein, harboring human cancer cells, etc. As such, humanized models may be fully or partially humanized. In other instances, the model may not be fully or partially humanized but may instead be simply introduced with human cells or human tissue through injection or transplantation. For example, in some instances, human cancer cells or cells of a human cancer cell line are introduced into an animal model. Any convenient human tumor cells or human tumor cell line may find use in such models including but not limited to e.g., K562 cells, Daudi lymphoma cells, etc.

Animal models and/or cells or tissues introduced into animal models may or may not be transgenic, e.g., modified to express one or more transgenes. For example, in some instances, an animal model may be transgenically modified to express a heterologous gene, e.g., a reporter gene (e.g., to identify cells of the host animal), a target gene (e.g., a gene encoding a gene product that is to be targeted in an in vivo screen). In some instances, a cell introduced into an animal model may be transgenically modified to express a heterologous gene, e.g., a reporter gene (e.g., to identify the introduced cell), a target gene (e.g., a gene encoding a gene product that is to be targeted in an in vivo screen). As a non-limiting example, a mouse tumor model may be screened, according to the methods as described herein, where human tumor cells expressing a cancer target transgene (e.g., CD19, mesothelin, etc.) are introduced into the mouse.

The library members, introduced into in vivo systems, may be screened for any convenient phenotype where the phenotype may depend upon the particular library being screened, the particular in vivo context (e.g., the animal model), etc. In some instances, e.g., where the in vivo system is an animal tumor model, the library may be screened for phenotypes related to tumor selectivity of the library members, e.g., by introducing the library into an animal model containing two different tumors, by introducing the library into an animal model or multiple animal models containing tumors expressing different levels of tumor antigen, etc. Any convenient method of assaying for the phenotype, including those cellular and biochemical/molecular methods described herein, may find use in evaluating in vivo systems where such evaluations generally involve obtaining a biological sample from the animal model. In some instances, a biological sample useful in assessing an in vivo model may include a tissue sample (e.g., blood, tumor, etc.) or organ sample (e.g., spleen).

In some instances, a library may be screened in vitro or in vivo according to a T-cell phenotype. T-cell phenotypes will vary and will include stimulated T-cell phenotypes, i.e., antigen response. Non-limiting examples of T-cell phenotypes include but are not limited to, e.g., T-cell proliferation, cytokine production (e.g., IL-2, IFN-γ, TNF, LT-α, IFN-γ, LT-α, TNF IL-4, IL-5, IL-6, IL-13, IL-9, IL-10, IL-17A, IL-17F, IL-21, IL-22, IL-26, TNF, CCL20, IL-21, TGF-β, IL-10, etc.), T-cell surface marker expression (e.g., CD3, CD4, CD8, etc.), T-cell activation markers (e.g., CD69, etc.), markers of intracellular signaling (e.g., phosphorylated ERK1/2, phosphorylated p38MAPK, etc.) and the like.

T-cell phenotypes may be assayed in vitro and in vivo and may be detected by any convenient method. In some instances, a cell counter or flow cytometer may be used to assay a T-cell phenotype including, e.g., T-cell proliferation and/or T-cell quantification. For example, T-cell proliferation may be assayed by cell-trace dye dilution using flow cytometry. In some instances, expression of cell surface markers may also be assayed by flow cytometry. Intracellular markers expression may be determined by cellular methods (e.g., flow cytometry, phosphoflow, intracellular flow cytometry, immunofluorescence, in situ hybridization, fluorescent in situ hybridization, etc.) or may be assayed by molecular and/or biochemical methods (e.g., ELISA, cytokine capture, amplification-based methods (e.g., quantitative PCR), sequencing based methods (e.g., quantitative sequencing), quantitative mass spectrometry, etc.).

In some instances, T-cells may be assayed for a "natural killer" activation phenotype. Any convenient method for assessing natural killer activation may find use in such assays. For example, T-cells may be analyzed for expression of CD107a/b, e.g., by flow cytometry.

In some instances, T-cells may be assayed for one or more differentiation phenotypes. Any convenient method for assessing T-cell differentiation may find use in such assays. For example, differentiation to memory T-cell may be assessed, e.g., through assaying for markers of memory T-cells (e.g., Th1, Th2, Th17, Treg, etc.) using any convenient cellular or molecular/biochemical method. In some instances, the expression of one or more intracellular transcription factors indicative of memory T-cell differentiation may be assessed (e.g., Gata3, Tbet, RORyt, FoxP3, Bcl-6, CCR7, CD45RO, CD45RA, CD69, etc.).

Screening of a library of synthetic modular CAR polypeptides or nucleic acids encoding a library of synthetic modular CAR polypeptides allows for the identification of CARs and/or portions thereof (e.g., antigen-binding domains, primary signaling domains, co-modulatory domains, etc.) that effectively produce a desired T cell phenotype. Accordingly, the instant disclosure includes CARs identified by screening the herein described libraries as well as nucleic acids encoding such CARs. The instant disclosure also includes CARs containing useful CAR modules (e.g., antigen-binding domains, primary signaling domains, co-modulatory domains, etc.) identified by screening the herein described libraries as well as nucleic acids encoding such CARs.

In some instances, a CAR of the instant disclosure may include one or more of the co-modulatory domains identified as T cell stimulatory or T cell inhibitory from screening a library of synthetic modular CAR polypeptides or nucleic acids encoding synthetic modular CAR polypeptides as described herein. Accordingly, the overall T cell phenotype of a CAR may be to simulate T cell activity or to inhibit T cell activity. T cell activities that may be stimulated or inhibited include but are not limited to e.g., those T cell activities described herein.

In some instances, a CAR identified by screening a library may include at least one co-modulatory domain listed in Table 3 or Table 4, including but not limited to e.g., a co-modulatory domains comprising an amino acid sequence having at least about 75%, at least about 80%, at least about 85%, at least about 90%, at least about 95%, at least about 98% sequence identity to a listed domain sequence. In some instances, a CAR identified by screening a library may include two or more co-modulatory domains of those listed in Table 3 and Table 4, including but not limited to e.g., a co-modulatory domains comprising an amino acid sequence having at least about 75%, at least about 80%, at least about 85%, at least about 90%, at least about 95%, at least about 98% sequence identity to a listed domain sequence. In some instances, a CAR of the instant disclosure may include a co-modulatory domain identified in a herein described screen as a co-stimulatory domain including but not limited to e.g., those listed in Table 3, including but not limited to e.g., a co-modulatory domains comprising an amino acid sequence having at least about 75%, at least about 80%, at least about 85%, at least about 90%, at least about 95%, at least about 98% sequence identity to a listed domain sequence. In some instances, a CAR of the instant disclosure may include a co-modulatory domain identified in a herein described screen as a co-inhibitory domain including but not limited to e.g., those listed in Table 4, including but not limited to e.g., a co-modulatory domains comprising an amino acid sequence having at least about 75%, at least about 80%, at least about 85%, at least about 90%, at least about 95%, at least about 98% sequence identity to a listed domain sequence. In some instances, a CAR that includes one or more co-inhibitory domains may be an iCAR.

In some instances, a CAR having two or more co-modulatory domains may include two co-stimulatory domains including but not limited to e.g., two or more co-stimulatory domains listed in Table 3. In some instances, a CAR having two or more co-modulatory domains may include two co-inhibitory domains including but not limited to e.g., two or more co-inhibitory domains listed in Table 4. In some instances, a CAR having two or more co-modulatory domains may include a mix of co-stimulatory and co-inhibitory domains including but not limited to at least one co-stimulatory domain listed in Table 3 and at least one co-inhibitory domain listed in Table 4.

TABLE 3

| Co-modulatory domains showing stimulatory function (co-stimulatory domains) | | |
|---|---|---|
| Domain | Sequence | SEQ ID NO: |
| 4-1BB | KRGRKKLLYIFKQPFMRPVQTTQEEDGCSCRFPEEEEGGCEL | 26 |
| CD7 | ARTQIKKLCSWRDKNSAACVVYEDMSHSRCNTLSSPNQYQ | 25 |
| 2B4 | WRRKRKEKQSETSPKEFLTIYEDVKDLKTRRNHEQEQTFPGGGSTIYSMIQS QSSAPTSQEPAYTLYSLIQPSRKSGSRKRNHSPSFNSTIYEVIGKSQPKAQNP ARLSRKELENFDVYS | 41 |

TABLE 3-continued

Co-modulatory domains showing stimulatory function (co-stimulatory domains)

| Domain | Sequence | SEQ ID NO: |
|---|---|---|
| HVEM | MEESVVRPSVFVVDGQTDIPFTRLGRSHRRQSCSV | 23 |
| CRTAM | KLRKAHVIWKKENEVSEHTLESYRSRSNNEETSSEEKNGQSSHPMRCMNYI TKLYSEAKTKRKENVQHSKLEEKHIQVPESIV | 35 |
| CD30 | RRACRKRIRQKLHECYPVQTSQPKLELVDSRPRRSSTQLRSGASVTEPVAEE RGLMSQPLMETCHSVGAAYLESLPLQDASPAGGPSSPRDLPEPRVSTEHTN NKIEKIYIMKADTVIVGTVKAELPEGRGLAGPAEPELEEELEADHTPHYPEQ ETEPPLGSCSDVMLSVEEEGKEDPLPTAASGK | 42 |
| TLT2 | KKRHMASYSMCSDPSTRDPPGRPEPYVEVYLI | 21 |
| CD27 | HQRRKYRSNKGESPVEPAEPCHYSCPREEEGSTIPIQEDYRKPEPACSP | 28 |
| CTLA4 | SLSKMEKKRSPETTGVYVKMPPTEPECEKQFQPYFIPIN | 24 |

TABLE 4

Co-modulatory domains showing inhibitory function (co-inhibitory domains)

| Domain | Sequence | SEQ ID NO: |
|---|---|---|
| DNAM-1 | NRRRRERRDLFTESWDTQKAPNNYRSPISTSQPTNQSMDDTREDIYVNYPTFSRR PKTRV | 31 |
| CD80 | RCRERRRNERLRRESVRPV | 19 |
| PD-1 | ICSRAARGTIGARRTGQPLKEDPSAVPVFSVDYGELDFQWREKTPEPPVPCVPEQT EYATIVFPSGMGTSSPARRGSADGPRSAQPLRPEDGHCSWPL | 36 |
| TIM-3 | KWYSHSKEKIQNLSLISLANLPPSGLANAVAEGIRSEENIYTIEENVYEVEEPNEYY CYVSSRQQPSQPLGCRFAMP | 33 |
| BTLA | CCLRRHQGKQNELSDTAGREINLVDAHLKSEQTEASTRQNSQVLLSETGIYDNDPD LCFRMQEGSEVYSNPCLEENKPGIVYASLNHSVIGPNSRLARNVKEAPTEYASICV RS | 39 |
| CD40 | KKVAKKPTNKAPHPKQEPQEINFPDDLPGSNTAAPVQETLHGCQPVTQEDGKESRI SVQERQ | 32 |
| ICOS | TKKKYSSSVHDPNGEYMFMRAVNTAKKSRLTDVTL | 22 |
| LAG3 | RRQWRPRRFSALEQGIHPPQAQSKIEELEQEPEPEPEPEPEPEPEPEPEQL | 29 |
| GITR | HIWQLRSQCMWPRETQLLLEVPPSTEDARSCQFPEEERGERSAEEKGRLGDLWV | 30 |
| TIGIT | RKKKALRIHSVEGDLRRKSAGQEEWSPSAPSPPGSCVQAEAAPAGLCGEQRGEDC AELHDYFNVLSYRSLGNCSFFTETG | 34 |
| PD-L1 | RKGRMMDVKKCGIQDTNSKKQSDTHLEET | 20 |
| CD28 | WVRSKRSRLLHSDYMNMTPRRPGPTRKHYQPYAPPRDFAAYRS | 27 |
| LAIR1 | HRQNQIKQGPPPRSKDEEQKPQQRPDLAVDVLERTADKATVNGLPEKDRETDTSAL AAGSSQEVTYAQLDHWALTQRTARAVSPQSTKPMAESITYAAVARH | 37 |
| CAR | CCRKKRREEKYEKEVHHDIREDVPPPKSRTSTARSYIGSNHSSLGSMSPSNMEGYS KTQYNQVPSEDFERTPQSPTLPPAKVAAPNLSRMGAIPVMIPAQSKDGSIV | 38 |
| CD2 | TKRKKQRSRRNDEELETRAHRVATEERGRKPHQIPASTPQNPATSQHPPPPPGHRS QAPSHRPPPPGHRVQHQPQKRPPAPSGTQVHQQKGPPLPRPRVQPKPPHGAAENSL SPSSN | 40 |

A CAR identified by screening a library of synthetic modular CAR polypeptides or a library of synthetic modular CAR polypeptide encoding nucleic acids may include any useful antigen-binding domain including but not limited to e.g., those used clinically in various CAR constructs including e.g., an anti-BCMA antigen-binding domain, an anti-CD123 antigen-binding domain, an anti-CD138 antigen-binding domain, an anti-CD171 antigen-binding domain, an anti-CD19 antigen-binding domain, an anti-CD22 antigen-binding domain, an anti-CD30 antigen-binding domain, an anti-CD33 antigen-binding domain, an anti-CD7 antigen-binding domain, an anti-CD70 antigen-binding domain, an anti-CEA antigen-binding domain, an anti-EGFRvIII antigen-binding domain, an anti-EPCAM antigen-binding domain, an anti-EphA2 antigen-binding domain, an anti-ErbB antigen-binding domain, an anti-FAP antigen-binding domain, an anti-GD2 antigen-binding domain, an anti-GPC3 antigen-binding domain, an anti-HER2 antigen-binding domain, an anti-IL1RAP antigen-binding domain, an anti-Kappa antigen-binding domain, an anti-LeY antigen-binding domain, an anti-Meso antigen-binding domain, an anti-MG7 antigen-binding domain, an anti-MUC1 antigen-binding domain, an anti-NKG2D antigen-binding domain, an anti-PSCA antigen-binding domain, an anti-ROR1 antigen-binding domain, and the like.

A CAR identified by screening a library of synthetic modular CAR polypeptides or a library of synthetic modular CAR polypeptide encoding nucleic acids may include any useful primary signaling domain (also referred to herein as a intracellular signaling domain) including but not limited to e.g., those including one or more immunoreceptor tyrosine-based activation motifs (ITAM).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12; FCER1G (Fc epsilon receptor I gamma chain); CD3D (CD3 delta); CD3E (CD3 epsilon); CD3G (CD3 gamma); CD3Z (CD3 zeta); and CD79A (antigen receptor complex-associated protein alpha chain).

In some cases, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to any of the following amino acid sequences (4 isoforms):

(SEQ ID NO:107)
MGGLEPCSRLLLLPLLLAVSGLRPVQAQAQSDCSCSTVSPGVLAGIVMGD
LVLTVLIALAVYFLGRLVPRGRGAAEAATRKQRITETESPYQELQGQRSD
VYSDLNTQRPYYK;

(SEQ ID NO: 108)
MGGLEPCSRLLLLPLLLAVSGLRPVQAQAQSDCSCSTVSPGVLAGIVMGD
LVLTVLIALAVYFLGRLVPRGRGAAEAATRKQRITETESPYQELQGQRSDV
YSDLNTQRPYYK;

(SEQ ID NO: 109)
MGGLEPCSRLLLLPLLLAVSDCSCSTVSPGVLAGIVMGDLVLTVLIALAV
YFLGRLVPRGRGAAEAATRKQRITETESPYQELQGQRSDVYSDLNTQRPY
YK;
or (SEQ ID NO: 110)
MGGLEPCSRLLLLPLLLAVSDCSCSTVSPGVLAGIVMGDLVLTVLIALAV
YFLGRLVPRGRGAAEAATRKQRITETESPYQELQGQRSDVYSDLNTQRPYY
K, where the ITAM motifs are in bold and are underlined.

Likewise, a suitable intracellular signaling domain polypeptide can comprise an ITAM motif-containing portion of the full length DAP12 amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

(SEQ ID NO: 111)
ESPYQELQGQRSDVYSDLNTQ, where the ITAM motifs are in bold and are underlined.

In some cases, the intracellular signaling domain is derived from FCER1G (also known as FCRG; Fc epsilon receptor I gamma chain; Fc receptor gamma-chain; fc-epsilon RI-gamma; fcRgamma; fceRI gamma; high affinity immunoglobulin epsilon receptor subunit gamma; immunoglobulin E receptor, high affinity, gamma chain; etc.). For example, a suitable intracellular signaling domain polypeptide can comprise an amino acid sequence having at least about 75%, at least about 80%, at least about 85%, at least about 90%, at least about 95%, at least about 98%, or 100% amino acid sequence identity to the following amino acid sequence:

(SEQ ID NO: 112)
MIPAVVLLLLLLVEQAAALGEPQLCYILDAILFLYGIVLTLLYCRLKIQV
RKAAITSYEKSDGVYTGLSTRNQETYETLKHEKPPQ, where the ITAM motifs are in bold and are underlined.

Likewise, a suitable intracellular signaling domain polypeptide can comprise an ITAM motif-containing portion of the full length FCER1G amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

(SEQ ID NO: 113)
DGVYTGLSTRNQETYETLKHE, where the ITAM motifs are in bold and are underlined.

In some cases, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 170 aa, of either of the following amino acid sequences (2 isoforms):

(SEQ ID NO: 114)
MEHSTFLSGLVLATLLSQVSPFKIPIEELEDRVFVNCNTSITWVEGTVGT
LLSDITRLDLGKRILDPRGIYRCNGTDIYKDKESTVQVHYRMCQSCVELD

```
PATVAGIIVTDVIATLLLALGVFCFAGHETGRLSGAADTQALLRNDQVYQ

PLRDRDDAQYSHLGGNWARNK
or
                                        (SEQ ID NO: 115)
MEHSTFLSGLVLATLLSQVSPFKIPIEELEDRVFVNCNTSITWVEGTVGT

LLSDITRLDLGKRILDPRGIYRCNGTDIYKDKESTVQVHYRTADTQALLR

NDQVYQPLRDRDDAQYSHLGGNWARNK,
``` where the ITAM motifs are in bold and are underlined.

Likewise, a suitable intracellular signaling domain polypeptide can comprise an ITAM motif-containing portion of the full length CD3 delta amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

```
                                        (SEQ ID NO: 116)
             DQVYQPLRDRDDAQYSHLGGN,
``` where the ITAM motifs are in bold and are underlined.

In some cases, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 205 aa, of the following amino acid sequence:

```
                                        (SEQ ID NO: 117)
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI,
``` where the ITAM motifs are in bold and are underlined.

Likewise, a suitable intracellular signaling domain polypeptide can comprise an ITAM motif-containing portion of the full length CD3 epsilon amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

```
                                        (SEQ ID NO: 118)
             NPDYEPIRKGQRDLYSGLNQR,
``` where the ITAM motifs are in bold and are underlined.

In some cases, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 180 aa, of the following amino acid sequence:

```
                                        (SEQ ID NO: 119)
MEQGKGLAVLILAIILLQGTLAQSIKGNHLVKVYDYQEDGSVLLTCDAEA

KNITWFKDGKMIGFLTEDKKKWNLGSNAKDPRGMYQCKGSQNKSKPLQVY

YRMCQNCIELNAATISGFLFAEIVSIFVLAVGVYFIAGQDGVRQSRASDK

QTLLPNDQLYQPLKDREDDQYSHLQGNQLRRN,
``` where the ITAM motifs are in bold and are underlined.

Likewise, a suitable intracellular signaling domain polypeptide can comprise an ITAM motif-containing portion of the full length CD3 gamma amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

```
                                        (SEQ ID NO: 120)
             DQLYQPLKDREDDQYSHLQGN,
``` where the ITAM motifs are in bold and are underlined.

In some cases, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (2 isoforms):

```
                                        (SEQ ID NO: 121)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKD

TYDALHMQALPPR
or
                                        (SEQ ID NO: 122)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP
```

-continued

```
QRRKNPQEGLYNELQKDKMAEAYSEIGMKGERRRGKGHDGLYQGLSTATK

DTYDALHMQALPPR,
``` where the ITAM motifs are in bold and are underlined.

Likewise, a suitable intracellular signaling domain polypeptide can comprise an ITAM motif-containing portion of the full length CD3 zeta amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to any of the following amino acid sequences:

```
                                          (SEQ ID NO: 123)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR;

(SEQ ID NO: 124)
NQLYNELNLGRREEYDVLDKR;

(SEQ ID NO: 125)
EGLYNELQKDKMAEAYSEIGMK;
or (SEQ ID NO: 126)
DGLYQGLSTATKDTYDALHMQ,
``` where the ITAM motifs are in bold and are underlined.

In some cases, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 150 aa, from about 150 aa to about 200 aa, or from about 200 aa to about 220 aa, of either of the following amino acid sequences (2 isoforms):

```
                                          (SEQ ID NO: 127)
MPGGPGVLQALPATIFLLFLLSAVYLGPGCQALWMHKVPASLMVSLGED

AHFQCPHNSSNNANVTWWRVLHGNYTWPPEFLGPGEDPNGTLIIQNVNK

SHGGIYVCRVQEGNESYQQSCGTYLRVRQPPPRPFLDMGEGTKNRIITA

EGIILLFCAVVPGTLLLFRKRWQNEKLGLDAGDEYEDENLYEGLNLDDC

SMYEDISRGLQGTYQDVGSLNIGDVQLEKP;
or (SEQ ID NO: 128)
MPGGPGVLQALPATIFLLFLLSAVYLGPGCQALWMHKVPASLMVSLGED

AHFQCPHNSSNNANVTWWRVLHGNYTWPPEFLGPGEDPNEPPPRPFLDM

GEGTKNRIITAEGIILLFCAVVPGTLLLFRKRWQNEKLGLDAGDEYEDE

NLYEGLNLDDCSMYEDISRGLQGTYQDVGSLNIGDVQLEKP,
``` where the ITAM motifs are in bold and are underlined.

Likewise, a suitable intracellular signaling domain polypeptide can comprise an ITAM motif-containing portion of the full length CD79A amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

```
                                          (SEQ ID NO: 129)
ENLYEGLNLDDCSMYEDISRG,
``` where the ITAM motifs are in bold and are underlined.

Intracellular signaling domains suitable for use in a CAR of the present disclosure include a DAP10/CD28 type signaling chain.

An example of a DAP10 signaling chain is the amino acid sequence is:

```
                                          (SEQ ID NO: 130)
RPRRSPAQDGKVYINMPGRG.
```

In some embodiments, a suitable intracellular signaling domain comprises an amino acid sequence having at least about 85%, at least about 90%, at least about 95%, at least about 98%, or at least about 99%, amino acid sequence identity to the entire length of the amino acid sequence

```
                                          (SEQ ID NO: 130)
RPRRSPAQDGKVYINMPGRG.
```

An example of a CD28 signaling chain is the amino acid sequence is

```
                                          (SEQ ID NO: 131)
FWVLVVVGGVLACYSLLVTVAFIIFWVRSKRSRLLHSDYMNMTPRRPGP

TRKHYQPYAPPRDFAAYRS.
```

In some embodiments, a suitable intracellular signaling domain comprises an amino acid sequence having at least about 85%, at least about 90%, at least about 95%, at least about 98%, or at least about 99%, amino acid sequence identity to the entire length of the amino acid sequence

```
                                          (SEQ ID NO: 131)
FWVLVVVGGVLACYSLLVTVAFIIFWVRSKRSRLLHSDYMNM

TPRRPGPTRKHYQPYAPPRDFAAYRS.
```

Intracellular signaling domains suitable for use in a CAR of the present disclosure include a ZAP70 polypeptide, e.g., a polypeptide comprising an amino acid sequence having at least about 85%, at least about 90%, at least about 95%, at least about 98%, at least about 99%, or 100%, amino acid sequence identity to a contiguous stretch of from about 300 amino acids to about 400 amino acids, from about 400 amino acids to about 500 amino acids, or from about 500 amino acids to 619 amino acids, of the following amino acid sequence:

```
                                          (SEQ ID NO: 132)
MPDPAAHLPFFYGSISRAEAEEHLKLAGMADGLFLLRQCLRSLGGY

VLSLVHDVRFHHFPIERQLNGTYAIAGGKAHCGPAELCEFYSRDPD
```

```
GLPCNLRKPCNRPSGLEPQPGVFDCLRDAMVRDYVRQTWKLEGEAL

EQAIISQAPQVEKLIATTAHERMPWYHSSLTREEAERKLYSGAQTD

GKFLLRPRKEQGTYALSLIYGKTVYHYLISQDKAGKYCIPEGTKFD

TLWQLVEYLKLKADGLIYCLKEACPNSSASNASGAAAPTLPAHPST

LTHPQRRIDTLNSDGYTPEPARITSPDKPRPMPMDTSVYESPYSDP

EELKDKKLFLKRDNLLIADIELGCGNFGSVRQGVYRMRKKQIDVAI

KVLKQGTEKADTEEMMREAQIMHQLDNPYIVRLIGVCQAEALMLVM

EMAGGGPLHKFLVGKREEIPVSNVAELLHQVSMGMKYLEEKNFVHR

DLAARNVLLVNRHYAKISDFGLSKALGADDSYYTARSAGKWPLKWY

APECINFRKFSSRSDVWSYGVTMWEALSYGQKPYKKMKGPEVMAFI

EQGKRMECPPECPPELYALMSDCWIYKWEDRPDFLTVEQRMRACYY

SLASKVEGPPGSTQKAEAACA
```

In some instances, a CAR identified by screening a library of synthetic modular CAR polypeptides or a library of synthetic modular CAR polypeptide encoding nucleic acids encoding nucleic acids, including a CAR having at least one or two or more of the co-modulatory domains listed in Table 3 and Table 4, may be split into two polypeptide chains joinable, in the presence of a dimerizer, by a dimerization domain present in each chain. Such split CARs are conditionally active and pharmacologically inducible/repressible such as e.g., those described in PCT Patent Application Publication WO 2014/127261, the disclosure of which is incorporated herein by reference in its entirety.

Accordingly, in some instances, each polypeptide of the split CAR version of a CAR identified by screening a library as described herein may include one half of a dimerization pair (also referred to as a dimerizer-binding pair). Non-limiting examples of suitable dimers (e.g., dimerizer-binding pairs) include, but are not limited to: a) FK506 binding protein (FKBP) and FKBP; b) FKBP and calcineurin catalytic subunit A (CnA); c) FKBP and cyclophilin; d) FKBP and FKBP-rapamycin associated protein (FRB); e) gyrase B (GyrB) and GyrB; f) dihydrofolate reductase (DHFR) and DHFR; g) DmrB and DmrB; h) PYL and ABI; i) Cry2 and CIB1; and j) GAI and GID1.

In some cases, a member of a dimer (e.g., a dimerizer-binding pair) of a subject CAR is derived from FKBP. For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence:

```
                                       (SEQ ID NO: 78)
MGVQVETISPGDGRTFPKRGQTCVVHYTGMLEDGKKFDSSRDRNKP

FKFMLGKQEVIRGWEEGVAQMSVGQRAKLTISPDYAYGATGHPGII

PPHATLVFDVELLKLE.
```

In some cases, a member of a dimerizer-binding pair of a subject CAR is derived from calcineurin catalytic subunit A (also known as PPP3CA; CALN; CALNA; CALNA1; CCN1; CNA1; PPP2B; CAM-PRP catalytic subunit; calcineurin A alpha; calmodulin-dependent calcineurin A subunit alpha isoform; protein phosphatase 2B, catalytic subunit, alpha isoform; etc.). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence (PP2Ac domain):

```
                                       (SEQ ID NO: 79)
LEESVALRIITEGASILRQEKNLLDIDAPVTVCGDIHGQFFDLMKL

FEVGGSPANTRYLFLGDYVDRGYFSIECVLYLWALKILYPKTLFLL

RGNHECRHLTEYFTFKQECKIKYSERVYDACMDAFDCLPLAALMNQ

QFLCVHGGLSPEINTLDDIRKLDRFKEPPAYGPMCDILWSDPLEDF

GNEKTQEHFTHNTVRGCSYFYSYPAVCEFLQHNNLLSILRAHEAQD

AGYRMYRKSQTTGFPSLITIFSAPNYLDVYNNKAAVLKYENNVMNI

RQFNCSPHPYWLPNFM.
```

In some cases, a member of a dimer (e.g., a dimerizer-binding pair) is derived from cyclophilin (also known cyclophilin A, PPIA, CYPA, CYPH, PPIase A, etc.). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence:

```
                                       (SEQ ID NO: 80)
MVNPTVFFDIAVDGEPLGRVSFELFADKVPKTAENFRALSTGEKGF

GYKGSCFHRIIPGFMCQGGDFTRHNGTGGKSIYGEKFEDENFILKH

TGPGILSMANAGPNTNGSQFFICTAKTEWLDGKHVVFGKVKEGMNI

VEAMERFGSRNGKTSKKITIADCGQLE.
```

In some cases, a member of a dimer (e.g., a dimerizer-binding pair) is derived from MTOR (also known as FKBP-rapamycin associated protein; FK506 binding protein 12-rapamycin associated protein 1; FK506 binding protein 12-rapamycin associated protein 2; FK506-binding protein 12-rapamycin complex-associated protein 1; FRAP; FRAP1; FRAP2; RAFT1; and RAPT1). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence (also known as "Frb": Fkbp-Rapamycin Binding Domain):

```
                                       (SEQ ID NO: 81)
MILWHEMWHEGLEEASRLYFGERNVKGMFEVLEPLHAMMERGPQTL

KETSFNQAYGRDLMEAQEWCRKYMKSGNVKDLLQAWDLYYHVFRRI

SK.
```

In some cases, a member of a dimer (e.g., a dimerizer-binding pair) is derived from GyrB (also known as DNA gyrase subunit B). For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 200 amino acids (aa), from about 200 aa to about 300 aa, from about 300 aa to about 400 aa, from about 400 aa to about 500 aa, from about 500 aa to about 600 aa, from about 600 aa to about 700 aa, or from about 700 aa to about 800 aa, of the following GyrB amino acid sequence from *Escherichia coli* (or to the DNA gyrase subunit B sequence from any organism):

(SEQ ID NO: 82)
MSNSYDSSSIKVLKGLDAVRKRPGMYIGDTDDGTGLHHMVFEVVDN
AIDEALAGHCKEIIVTIHADNSVSVQDDGRGIPTGIHPEEGVSAAE
VIMTVLHAGGKFDDNSYKVSGGLHGVGVSVVNALSQKLELVIQREG
KIHRQIYEHGVPQAPLAVTGETEKTGTMVRFWPSLETFTNVTEFEY
EILAKRLRELSFLNSGVSIRLRDKRDGKEDHFHYEGGIKAFVEYLN
KNKTPIHPNIFYFSTEKDGIGVEVALQWNDGFQENIYCFTNNIPQR
DGGTHLAGFRAAMTRTLNAYMDKEGYSKKAKVSATGDDAREGLIAV
VSVKVPDPKFSSQTKDKLVSSEVKSAVEQQMNELLAEYLLENPTDA
KIVVGKIIDAARAREAARRAREMTRRKGALDLAGLPGKLADCQERD
PALSELYLVEGDSAGGSAKQGRNRKNQAILPLKGKILNVEKARFDK
MLSSQEVATLITALGCGIGRDEYNPDKLRYHSIIIMTDADVDGSHI
RTLLLTFFYRQMPEIVERGHVYIAQPPLYKVKKGKQEQYIKDDEAM
DQYQISIALDGATLHTNASAPALAGEALEKLVSEYNATQKMINRME
RRYPKAMLKELIYQPTLTEADLSDEQTVTRWVNALVSELNDKEQHG
SQWKFDVHTNAEQNLFEPIVRVRTHGVDTDYPLDHEFITGGEYRRI
CTLGEKLRGLLEEDAFIERGERRQPVASFEQALDWLVKESRRGLSI
QRYKGLGEMNPEQLWETTMDPESRRMLRVTVKDAIAADQLFTTLMG
DAVEPRRAFIEENALKAANIDI.

In some cases, a member of a dimerizer-binding pair comprises an amino acid sequence having at least about 75%, at least about 80%, at least about 85%, at least about 90%, at least about 95%, at least about 98%, or 100% amino acid sequence identity to amino acids 1-220 of the above-listed GyrB amino acid sequence from *Escherichia coli*.

In some cases, a member of a dimer (e.g., a dimerizer-binding pair) is derived from DHFR (also known as dihydrofolate reductase, DHFRP1, and DYR). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence:

(SEQ ID NO: 83)
MVGSLNCIVAVSQNMGIGKNGDLPWPPLRNEFRYFQRMTTTSSVEGK
QNLVIMGKKTWFSIPEKNRPLKGRINLVLSRELKEPPQGAHFLSRSL
DDALKLTEQPELANKVDMVWIVGGSSVYKEAMNHPGHLKLFVTRIMQ
DFESDTFFPEIDLEKYKLLPEYPGVLSDVQEEKGIKYKFEVYEKND.

In some cases, a member of a dimer (e.g., a dimerizer-binding pair) is derived from the DmrB binding domain (i.e., DmrB homodimerization domain). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence:

(SEQ ID NO: 84)
MASRGVQVETISPGDGRTFPKRGQTCVVHYTGMLEDGKKVDSSRDRN
KPFKFMLGKQEVIRGWEEGVAQMSVGQRAKLTISPDYAYGATGHPGI
IPPHATLVFDVELLKLE.

In some cases, a member of a dimer (e.g., a dimerizer-binding pair) is derived from a PYL protein (also known as abscisic acid receptor and as RCAR). For example a member of a subject dimerizer-binding pair can be derived from proteins such as those of *Arabidopsis thaliana*: PYR1, RCAR1(PYL9), PYL1, PYL2, PYL3, PYL4, PYL5, PYL6, PYL7, PYL8 (RCAR3), PYL10, PYL11, PYL12, PYL13. For example, a suitable dimerizer-binding pair member can comprise an amino acid sequence having at least about 75%, at least about 80%, at least about 85%, at least about 90%, at least about 95%, at least about 98%, or 100% amino acid sequence identity to any of the following amino acid sequences:

PYL10:
(SEQ ID NO: 85)
MNGDETKKVESEYIKKHHRHELVESQCSSTLVKHIKAPLHLVWSIVR
RFDEPQKYKPFISRCVVQGKKLEVGSVREVDLKSGLPATKSTEVLEI
LDDNEHILGIRIVGGDHRLKNYSSTISLHSETIDGKTGTLAIESFVV
DVPEGNTKEETCFFVEALIQCNLNSLADVTERLQAESMEKKI.

PYL11:
(SEQ ID NO: 86)
METSQKYHTCGSTLVQTIDAPLSLVWSILRRFDNPQAYKQFVKTCNL
SSGDGGEGSVREVTVVSGLPAEFSRERLDELDDESHVMMISIIGGDH
RLVNYRSKTMAFVAADTEEKTVVVESYVVDVPEGNSEEETTSFADTI
VGFNLKSLAKLSERVAHLKL

PYL12:
(SEQ ID NO: 87)
MKTSQEQHVCGSTVVQTINAPLPLVWSILRRFDNPKTFKHFVKTCKL
RSGDGGEGSVREVTVVSDLPASFSLERLDELDDESHVMVISIIGGDH
RLVNYQSKTTVFVAAEEEKTVVVESYVVDVPEGNTEEETTLFADTIV
GCNLRSLAKLSEKMMELT.

PYL13:
(SEQ ID NO: 88)
MESSKQKRCRSSVVETIEAPLPLVWSILRSFDKPQAYQRFVKSCTMR
SGGGGGKGGEGKGSVRDVTLVSGFPADFSTERLEELDDESHVMVVSI
IGGNHRLVNYKSKTKVVASPEDMAKKTVVVESYVVDVPEGTSEEDTI
FFVDNIIRYNLTSLAKLTKKMMK.

PYL1:
(SEQ ID NO: 89)
MANSESSSSPVNEEENSQRISTLHHQTMPSDLTQDEFTQLSQSIAEF
HTYQLGNGRCSSLLAQRIHAPPETVWSVVRRFDRPQIYKHFIKSCNV
SEDFEMRVGCTRDVNVISGLPANTSRERLDLLDDDRRVTGFSITGGE
HRLRNYKSVTTVHRFEKEEEEERIWTVVLESYVVDVPEGNSEEDTRL
FADTVIRLNLQKLASITEAMNRNNNNNNSSQVR.

-continued

PYL2:
(SEQ ID NO: 90)
MSSSPAVKGLTDEEQKTLEPVIKTYHQFEPDPTTCTSLITQRIHAPA

SVVWPLIRRFDNPERYKHFVKRCRLISGDGDVGSVREVTVISGLPAS

TSTERLEFVDDDHRVLSFRVVGGEHRLKNYKSVTSVNEFLNQDSGKV

YTVVLESYTVDIPEGNTEEDTKMFVDTVVKLNLQKLGVAATSAPMHD

DE.

PYL3:
(SEQ ID NO: 91)
MNLAPIHDPSSSSTTTTSSSTPYGLTKDEFSTLDSIIRTHHTFPRSP

NTCTSLIAHRVDAPAHAIWRFVRDFANPNKYKHFIKSCTIRVNGNGI

KEIKVGTIREVSVVSGLPASTSVEILEVLDEEKRILSFRVLGGEHRL

NNYRSVTSVNEFVVLEKDKKKRVYSVVLESYIVDIPQGNTEEDTRMF

VDTVVKSNLQNLAVISTASPT.

PYL4:
(SEQ ID NO: 92)
MLAVHRPSSAVSDGDSVQIPMMIASFQKRFPSLSRDSTAARFHTHEV

GPNQCCSAVIQEISAPISTVWSVVRRFDNPQAYKHFLKSCSVIGGDG

DNVGSLRQVHVVSGLPAASSTERLDILDDERHVISFSVVGGDHRLSN

YRSVTTLHPSPISGTVVVESYVVDVPPGNTKEETCDFVDVIVRCNLQ

SLAKIAENTAAESKKKMSL.

PYL5:
(SEQ ID NO: 93)
MRSPVQLQHGSDATNGFHTLQPHDQTDGPIKRVCLTRGMHVPEHVAM

HHTHDVGPDQCCSSVVQMIHAPPESVWALVRRFDNPKVYKNFIRQCR

IVQGDGLHVGDLREVMVVSGLPAVSSTERLEILDEERHVISFSVVGG

DHRLKNYRSVTTLHASDDEGTVVVESYIVDVPPGNTEEETLSFVDTI

VRCNLQSLARSTNRQ.

PYL6:
(SEQ ID NO: 94)
MPTSIQFQRSSTAAEAANATVRNYPHHHQKQVQKVSLTRGMADVPEH

VELSHTHVVGPSQCFSVVVQDVEAPVSTVWSILSRFEHPQAYKHFVK

SCHVVIGDGREVGSVREVRVVSGLPAAFSLERLEIMDDDRHVISFSV

VGGDHRLMNYKSVTTVHESEEDSDGKKRTRVVESYVVDVPAGNDKEE

TCSFADTIVRCNLQSLAKLAENTSKFS.

PYL7:
(SEQ ID NO: 95)
MEMIGGDDTDTEMYGALVTAQSLRLRHLHHCRENQCTSVLVKYIQAP

VHLVWSLVRRFDQPQKYKPFISRCTVNGDPEIGCLREVNVKSGLPAT

TSTERLEQLDDEEHILGINIIGGDHRLKNYSSILTVHPEMIDGRSGT

MVMESFVVDVPQGNTKDDTCYFVESLIKCNLKSLACVSERLAAQDIT

NSIATFCNASNGYREKNHTETNL.

PYL8:
(SEQ ID NO: 96)
MEANGIENLTNPNQEREFIRRHHKHELVDNQCSSTLVKHINAPVHIV

WSLVRRFDQPQKYKPFISRCVVKGNMEIGTVREVDVKSGLPATRSTE

RLELLDDNEHILSIRIVGGDHRLKNYSSIISLHPETIEGRIGTLVIE

SFVVDVPEGNTKDETCYFVEALIKCNLKSLADISERLAVQDTTESRV.

PYL9:
(SEQ ID NO: 97)
MMDGVEGGTAMYGGLETVQYVRTHHQHLCRENQCTSALVKHIKAPLHL

VWSLVRRFDQPQKYKPFVSRCTVIGDPEIGSLREVNVKSGLPATTSTE

RLELLDDEEHILGIKIIGGDHRLKNYSSILTVHPEIIEGRAGTMVIES

FVVDVPQGNTKDETCYFVEALIRCNLKSLADVSERLASQDITQ.

PYR1:
(SEQ ID NO: 98)
MPSELTPEERSELKNSIAEFHTYQLDPGSCSSLHAQRIHAPPELVWSI

VRRFDKPQTYKHFIKSCSVEQNFEMRVGCTRDVIVISGLPANTSTERL

DILDDERRVTGFSIIGGEHRLTNYKSVTTVHRFEKENRIWTVVLESYV

VDMPEGNSEDDTRMFADTVVKLNLQKLATVAEAMARNSGDGSGSQVT.

In some cases, a member of a dimer (e.g., a dimerizer-binding pair) is derived from an ABI protein (also known as Abscisic Acid-Insensitive). For example a member of a subject dimerizer-binding pair can be derived from proteins such as those of *Arabidopsis thaliana*: ABI1 (Also known as ABSCISIC ACID-INSENSITIVE 1, Protein phosphatase 2C 56, AtPP2C56, P2C56, and PP2C ABI1) and/or ABI2 (also known as P2C77, Protein phosphatase 2C 77, AtPP2C77, ABSCISIC ACID-INSENSITIVE 2, Protein phosphatase 2C ABI2, and PP2C ABI2). For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

ABI1:
(SEQ ID NO: 99)
MEEVSPAIAGPFRPFSETQMDFTGIRLGKGYCNNQYSNQDSENGDLMV

SLPETSSCSVSGSHGSESRKVLISRINSPNLNMKESAAADIVVVDISA

GDEINGSDITSEKKMISRTESRSLFEFKSVPLYGFTSICGRRPEMEDA

VSTIPRFLQSSSGSMLDGRFDPQSAAHFFGVYDGHGGSQVANYCRERM

HLALAEEIAKEKPMLCDGDTWLEKWKKALFNSFLRVDSEIESVAPETV

GSTSVVAVVFPSHIFVANCGDSRAVLCRGKTALPLSVDHKPDREDEAA

RIEAAGGKVIQWNGARVFGVLAMSRSIGDRYLKPSIIPDPEVTAVKRV

KEDDCLILASDGVWDVMTDEEACEMARKRILLWHKKNAVAGDASLLAD

ERRKEGKDPAAMSAAEYLSKLAIQRGSKDNISVVVVDLKPRRKLKSKP

LN.

ABI2:
(SEQ ID NO: 100)
MDEVSPAVAVPFRPFTDPHAGLRGYCNGESRVTLPESSCSGDGAMKDS

SFEINTRQDSLTSSSSAMAGVDISAGDEINGSDEFDPRSMNQSEKKVL

-continued

SRTESRSLFEFKCVPLYGVTSICGRRPEMEDSVSTIPRFLQVSSSSLL

DGRVTNGFNPHLSAHFFGVYDGHGGSQVANYCRERMHLALTEEIVKEK

PEFCDGDTWQEKWKKALFNSFMRVDSEIETVAHAPETVGSTSVVAVVF

PTHIFVANCGDSRAVLCRGKTPLALSVDHKPDRDDEAARIEAAGGKVI

RWNGARVFGVLAMSRSIGDRYLKPSVIPDPEVTSVRRVKEDDCLILAS

DGLWDVMTNEEVCDLARKRILLWHKKNAMAGEALLPAEKRGEGKDPAA

MSAAEYLSKMALQKGSKDNISVVVVDLKGIRKFKSKSLN.

In some cases, a member of a dimer (e.g., a dimerizer-binding pair) is derived from a Cry2 protein (also known as cryptochrome 2). For example a member of a subject dimer (e.g., a dimerizer-binding pair) can be derived from Cry2 proteins from any organism (e.g., a plant) such as, but not limited to, those of *Arabidopsis thaliana*. For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

Cry2 (Arabidopsis thaliana)
(SEQ ID NO: 101)
MKMDKKTIVWFRRDLRIEDNPALAAAAHEGSVFPVFIWCPEEEGQFYP

GRASRWWMKQSLAHLSQSLKALGSDLTLIKTHNTISAILDCIRVTGAT

KVVFNHLYDPVSLVRDHTVKEKLVERGISVQSYNGDLLYEPWEIYCEK

GKPFTSFNSYWKKCLDMSIESVMLPPPWRLMPITAAAEAIWACSIEEL

GLENEAEKPSNALLTRAWSPGWSNADKLLNEFIEKQLIDYAKNSKKVV

GNSTSLLSPYLHFGEISVRHVFQCARMKQIIWARDKNSEGEESADLFL

RGIGLREYSRYICFNFPFTHEQSLLSHLRFFPWDADVDKFKAWRQGRT

GYPLVDAGMRELWATGWMHNRIRVIVSSFAVKFLLLPWKWGMKYFWDT

LLDADLECDILGWQYISGSIPDGHELDRLDNPALQGAKYDPEGEYIRQ

WLPELARLPTEWIHHPWDAPLTVLKASGVELGTNYAKPIVDIDTAREL

LAKAISRTREAQIMIGAAPDEIVADSFEALGANTIKEPGLCPSVSSND

QQVPSAVRYNGSKRVKPEEEEERDMKKSRGFDERELFSTAESSSSSSV

FFVSQSCSLASEGKNLEGIQDSSDQITTSLGKNGCK.

In some cases, a member of a dimer (e.g., a dimerizer-binding pair) is derived from the CIB1 *Arabidopsis thaliana* protein (also known as transcription factor bHLH63). For example, a suitable dimer (e.g., a dimerizer-binding pair) member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence:

(SEQ ID NO: 102)
MNGAIGGDLLLNFPDMSVLERQRAHLKYLNPTFDSPLAGFFADSSMIT

GGEMDSYLSTAGLNLPMMYGETTVEGDSRLSISPETTLGTGNFKKRKF

DTETKDCNEKKKKMTMNRDDLVEEGEEEKSKITEQNNGSTKSIKKMKH

KAKKEENNFSNDSSKVTKELEKTDYIHVRARRGQATDSHSIAERVRRE

KISERMKFLQDLVPGCDKITGKAGMLDEIINYVQSLQRQIEFLSMKLA

IVNPRPDFDMDDIFAKEVASTPMTVVPSPEMVLSGYSHEMVHSGYSSE

MVNSGYLHVNPMQQVNTSSDPLSCFNNGEAPSMWDSHVQNLYGNLGV.

In some cases, a member of a dimer (e.g., a dimerizer-binding pair) is derived from the GAI *Arabidopsis thaliana* protein (also known as Gibberellic Acid Insensitive, and DELLA protein GAI). For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence:

(SEQ ID NO: 103)
MKRDHHHHHQDKKTMMMNEEDDGNGMDELLAVLGYKVRSSEMADVAQ

KLEQLEVMMSNVQEDDLSQLATETVHYNPAELYTWLDSMLTDLNPPSS

NAEYDLKAIPGDAILNQFAIDSASSSNQGGGGDTYTTNKRLKCSNGVV

ETTTATAESTRHVVLVDSQENGVRLVHALLACAEAVQKENLTVAEALV

KQIGFLAVSQIGAMRKVATYFAEALARRIYRLSPSQSPIDHSLSDTLQ

MHFYETCPYLKFAHFTANQAILEAFQGKKRVHVIDFSMSQGLQWPALM

QALALRPGGPPVFRLTGIGPPAPDNFDYLHEVGCKLAHLAEAIHVEFE

YRGFVANTLADLDASMLELRPSEIESVAVNSVFELHKLLGRPGAIDKV

LGVVNQIKPEIFTVVEQESNHNSPIFLDRFTESLHYYSTLFDSLEGVP

SGQDKVMSEVYLGKQICNVVACDGPDRVERHETLSQWRNRFGSAGFAA

AHIGSNAFKQASMLLALFNGGEGYRVEESDGCLMLGWHTRPLIATSAW

KLSTN.

In some cases, a member of a dimer (e.g., a dimerizer-binding pair) is derived from a GID1 *Arabidopsis thaliana* protein (also known as Gibberellin receptor GID1). For example, a suitable dimer member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

GID 1A:
(SEQ ID NO: 104)
MAASDEVNLIESRTVVPLNTWVLISNFKVAYNILRRPDGTFNRHLAEY

LDRKVTANANPVDGVFSFDVLIDRRINLLSRVYRPAYADQEQPPSILD

LEKPVDGDIVPVILFFHGGSFAHSSANSAIYDTLCRRLVGLCKCVVVS

VNYRRAPENPYPCAYDDGWIALNWVNSRSWLKSKKDSKVHIFLAGDSS

GGNIAHNVALRAGESGIDVLGNILLNPMFGGNERTESEKSLDGKYFVT

VRDRDWYWKAFLPEGEDREHPACNPFSPRGKSLEGVSFPKSLVVVAGL

DLIRDWQLAYAEGLKKAGQEVKLMHLEKATVGFYLLPNNNHFHNVMDE

ISAFVNAEC.

GID 1B:
(SEQ ID NO: 105)
MAGGNEVNLNECKRIVPLNTWVLISNFKLAYKVLRRPDGSFNRDLAEF

LDRKVPANSFPLDGVFSFDHVDSTTNLLTRIYQPASLLHQTRHGTLEL

TKPLSTTEIVPVLIFFHGGSFTHSSANSAIYDTFCRRLVTICGVVVVS

VDYRRSPEHRYPCAYDDGWNALNWVKSRVWLQSGKDSNVYVYLAGDSS

GGNIAHNVAVRATNEGVKVLGNILLHPMFGGQERTQSEKTLDGKYFVT

IQDRDWYWRAYLPEGEDRDHPACNPFGPRGQSLKGVNFPKSLVVVAGL

DLVQDWQLAYVDGLKKTGLEVNLLYLKQATIGFYFLPNNDHFHCLMEE

LNKFVHSIEDSQSKSSPVLLTP

GID1C:
(SEQ ID NO: 106)
MAGSEEVNLIESKTVVPLNTWVLISNFKLAYNLLRRPDGTFNRHLAEF

LDRKVPANANPVNGVFSFDVIIDRQTNLLSRVYRPADAGTSPSITDLQ

NPVDGEIVPVIVFFHGGSFAHSSANSAIYDTLCRRLVGLCGAVVVSVN

YRRAPENRYPCAYDDGWAVLKWVNSSSWLRSKKDSKVRIFLAGDSSGG

NIVHNVAVRAVESRIDVLGNILLNPMFGGTERTESEKRLDGKYFVTVR

DRDWYWRAFLPEGEDREHPACSPFGPRSKSLEGLSFPKSLVVVAGLDL

IQDWQLKYAEGLKKAGQEVKLLYLEQATIGFYLLPNNNHFHTVMDEIA

AFVNAECQ.

As will be readily understood, a CAR identified by screening a library of synthetic modular CAR polypeptide encoding nucleic acids or a library of synthetic modular CAR polypeptides may be modified, e.g., by the addition of one or more domains (e.g., co-modulatory domains), by the removal of one or more domains (e.g., the removal of a fluorescent reporter utilized in the screening procedure), by splitting the CAR into two polypeptides (and adding a dimerization domains), by rearrangement of the domains, etc.

In some instances, a library may be screened for a phenotype related to a cellular response to a particular cellular environment. As such, a cellular phenotype may be defined by a cell's response (e.g., activation or inhibition) to exposure to a particular environment. For example, a T-cell response may be assessed according to exposure to a particular cellular environment. In some embodiments, T-cell inhibition may be assessed in response to exposure to a tumor microenvironment.

In some instances, a library may be screened for a phenotype related to cellular localization, e.g., as influenced by homing or cellular targeting. As such, the influence of library members on cellular targeting may screened. For example, a cellular library may be introduced into a host organism and library cells may be recovered from a targeted location of the host organism after some amount of time in order to assess which cells were successfully directed to the targeted location. In some instances, T-cells may assayed for targeting to a tumor in vivo.

In some instances, a library may be screened for a phenotype to a patient specific condition. Patient specific conditions screened in this manner will vary greatly and may include conditions related to a particular disease state of a patient and involve the screening of a library to identify the particular library member(s) showing an increased or optimal phenotype to the patient specific condition. In some instances, the localization of cellular library members may be assessed after exposure to a patient derived explant or xenograft. For example, T-cell localization of a CAR expressing cellular T-cell library may be assessed following exposure to a patient specific tumor xenograft. In some instances, the proliferation of cellular library members may be assessed after exposure to a patient derived explant or xenograft. For example, T-cell proliferation of a CAR expressing cellular T-cell library may be assessed following exposure to a patient specific tumor xenograft. In some instances, a patient specific explant or xenograft may be assayed for an increase or decrease in viability following exposure to a cellular library or particular cellular library members. For example, the T-cell killing of a CAR expressing cellular T-cell library may be assessed following exposure to a patient specific tumor xenograft. As such, a library may be screened to identify the optimal library member(s) for treating a particular patient.

In some instances, phenotypes may be assayed in vitro by dynamic antigen challenge. By dynamic antigen challenge is meant that the phenotype is assessed beyond mere presence or absence of the antigen and thus the antigen may be dynamically varied, e.g., dynamically varied across a range of concentrations, dynamically varied across a range of time, etc. For example, antigen levels may be titrated (e.g., through various concentrations) in order to assess the screening phenotype at various doses, i.e., to assess dose response. Antigen may be presented at different concentrations by any convenient means. As a non-limiting example, the different amounts of antigen may be presented using cells expressing the antigen at different levels including a range of levels. In some instances, the timing of antigen application may be dynamically varied, e.g., in order to assess the phenotype in a time-point assay or to assess the kinetics of the screened phenotype.

In some instances, a library may be screened for a phenotypic signature. The term "phenotypic signature" as used herein generally refers to a combination of individual phenotypes. For example, in some instances, a cell may have a phenotypic signature that includes a particular morphology combined with expression of a particular marker. A phenotypic signature may combine phenotypes from similar or different phenotypic categories, e.g., a phenotypic signature may include expression of two related but different cell surface markers or a phenotypic signature may include expression of a cell surface marker and a marker of cell proliferation or a phenotypic signature may include expression of a cell surface marker and a particular secreted marker (e.g., a cytokine) or a phenotypic signature may include expression of two different cytokines, etc. Any convenient phenotype, including those described herein, may find use as a component of a phenotypic signature.

Identifying Phenotype Associated Synthetic Module Polypeptides

The instant disclosure includes methods of identifying the library members that are associated with a particular detected phenotype. Without being bound by theory, the coordinated assembly of each multi-module synthetic polypeptide along with each corresponding multi-unit barcode allows for the assembly and subsequent identification of each unique synthetic module polypeptide. As described above, the barcode region of each synthetic modular polypeptide encoding nucleic acid provides not only the identity of the individual modules that make up each synthetic modular polypeptide but also the specific arrangement (referred to herein as architecture) of the modules. As such, the identity and architecture of each library member can be determined by sequencing the barcode region.

Accordingly, library screening need not be performed with physically separated library members and library members may be "pooled" and screened simultaneously. Pooling of library members may be performed in vitro, e.g., in a test tube or in a sample of cells outside of an associated organism, or in vivo, in an animal or in a tissue. Following simultaneous screening, phenotype associated library members and/or modules thereof may be identified by identification and/or quantification of the associated barcode region. In some instances, pooled screening allows for the screening of large numbers of unique library members that is not practical by conventional sequential or parallel screening. The number of unique library members that may be screened for a phenotype will depend on the size and complexity of the library and thus may vary but may range from 96 or less to millions or more, including but not limited to e.g., 100 or more, 200 or more, 300 or more, 400 or more, 500 or more, 1000 or more, 2000 or more, 3000 or more, 4000 or more, 5000 or more, 6000 or more, 7000 or more, 8000 or more, 9000 or more, 10,000 or more, 20,000 or more, 30,000 or more, 40,000 or more, 50,000 or more, 60,000 or more, 70,000 or more, 80,000 or more, 90,000 or more, 100,000 or more, etc.

In some instances, the quantity or frequency of a particular barcode may be measured to identify a highly represented module. For example, the frequency of each barcode may be quantified from a pooled sample containing library members and the associated nucleic acids encoding the library members such that the barcodes with the highest frequency identify those modules most highly represented in the sample. In certain embodiments, such samples may be cellular samples.

In some instances, the quantity or frequency of a particular multi-unit barcode (e.g., barcode region) may be measured to identify a highly represented modular polypeptide. For example, the frequency of each multi-unit barcode may be quantified from a pooled sample containing library members and the associated nucleic acids encoding the library members such that the multi-unit barcodes with the highest frequency identify those modular polypeptides most highly represented in the sample. In certain embodiments, such samples may be cellular samples.

Figure 24:
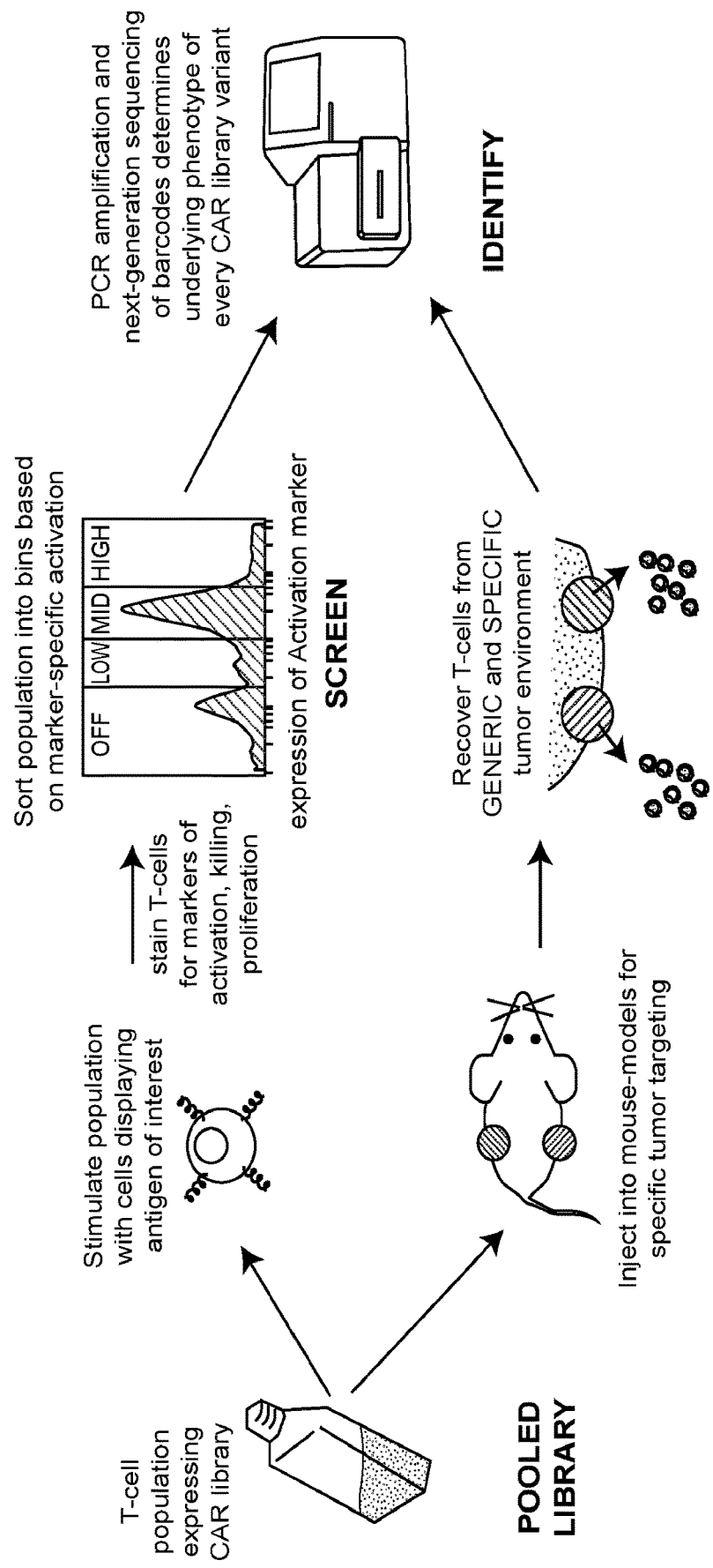
FIG. 24 depicts a schematized example of an integrated phenotype detection and modular polypeptide identification method for in vitro and/or in vivo use according to an embodiment of the instant disclosure.

In some instances, detection of phenotype and identification of the library members and their components may be performed as part of an integrated method. For example, in some instances, the phenotype may be detected by flow cytometry and the library members may be identified by sequencing. Such integrated methods may be performed in conjunction with in vitro and/or in vivo assays, e.g., as depicted in FIG. 24 where FLOW-Seq is used as a non-limiting example of an integrated method.

As used herein, the term "FLOW-seq" generally refers to the combination of sorting flow cytometry methods (e.g., FACS) with sequencing methods (e.g., Next Generation Sequencing) in a single linked workflow. Any convenient and appropriate method of sorting flow cytometry and any convenient and appropriate sequencing method may find use in such a FLOW-Seq method. For example, in some instances, a cellular library expressing barcoded synthetic modular polypeptides, as described herein, may be assayed for a phenotype by flow cytometry and those cells having a particular phenotype may be sorted and their barcodes subsequently sequenced to identify particular library members and/or quantify the frequency of particular library members and/or modules thereof appearing in the sorted cells. Sorting may be performed in any convenient and appropriate manner including, e.g., sorting into one or more bins based on a flow cytometrically detected phenotype. Following sorting, sequencing may be performed directly on the sorted sample and/or sorted cell or the sorted sample and/or sorted cell may be expanded and/or cultured prior to sorting, e.g., to increase the copies of the nucleic acids encoding the library members. FLOW-seq methods have been used, e.g., for phenotypically measuring protein levels and identifying related genetic elements in bacteria (see e.g., Kosuri et al. *Proc Natl Acad Sci USA* (2013) 110(34): 14024-9 and Goodman et al. *Science* (2013) 342(6157):475-479) in addition the coupling of sequencing with FACS has also been performed to correlate T-cells sorted based on function with their respective sequenced T cell receptor genes (see e.g., Han et al. Nature Biotechnology (2014) 32:684-692).

In some instances, identification of a synthetic module polypeptide associated with a particular phenotype may involve surgical isolation of a tissue or organ from an in vivo model into which the library has been introduced. For example, in some instances, following a sufficient time for the assay, an organ or tissue may be removed from a host animal and nucleic acids present in the organ or tissue may be sequenced in order to identify individual library members present in the organ or tissue, In other instances, nucleic acid isolated from an organ or tissue or a host animal may be quantitatively, including semi-quantitatively, sequenced so as to quantify the relative frequency or presence of a particular library member in the organ or tissue. In yet other instances, nucleic acid isolated from an organ or tissue or a host animal may be quantitatively, including semi-quantitatively, sequenced so as to quantify the relative frequency or presence of a particular module in the organ or tissue.

In some instances, e.g., where a particular module is highly represented following semi-quantification or an individual module is identified as contributing to a desired phenotype, a subsequent round of new library assembly may be performed where the identified module is included in all newly produced library members (i.e., the identified variable module is used subsequently as a non-variable module) and the newly generated library is screened to identify further modules that cooperatively influence the phenotype together with the originally identified module. An ordinary skilled artisan will readily understand where iterative library assembly and screening may be performed to evolve libraries and individual library members with desired phenotypes.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Construction and Screening of Co-Modulatory Domain Modular Libraries

To prepare barcoded module-encoding nucleic acid fragments containing the necessary elements for library construction, nucleic acids encoding the polypeptide modules (i.e., co-modulatory domains (i.e., co-stimulatory or co-inhibitory)) were subcloned into a cloning vector suitable for sequencing and Type IIS restriction enzyme digestion. Following the subcloning the vector contained: the module-encoding sequence, optimal Gly/Ser linker sequences flanking the module-encoding sequence, a module-specific barcode sequence, 3' cloning homology arms flanking the module-specific barcode sequence, a BamHI restriction site between the module-encoding sequence and the module-specific barcode sequence and Type IIS restriction enzyme sites on both the 5' end of the module-encoding sequence and the 3' end of the module-specific barcode sequence (FIG. 1). The subcloned vector inserts were sequenced to confirm identity of the inserted co-modulatory domains. The co-modulatory domains used in this combinatorial library and their respective protein sequences are provided in Table 1.

Figure 2:
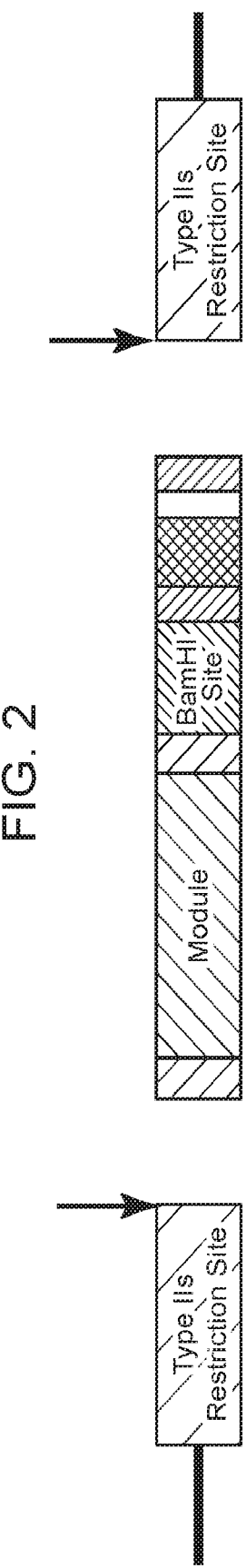
FIG. 2 depicts the barcoded module sequence of FIG. 1 following Type IIS restriction enzyme digestion in preparation for library assembly.

The cloning vectors containing the barcoded module-encoding sequence were digested using Type IIS restriction enzyme to release "sequence perfect" nucleic acids coding for each polypeptide module (FIG. 2). An example of a portion of a cloning vector containing the described elements and sequence encoding a CD28 co-stimulatory domain, before and after Type IIS restriction enzyme digestion, is provided (FIG. 3) and represents the general configuration of each module plasmid/fragment used in constructing the library.

Figure 5:
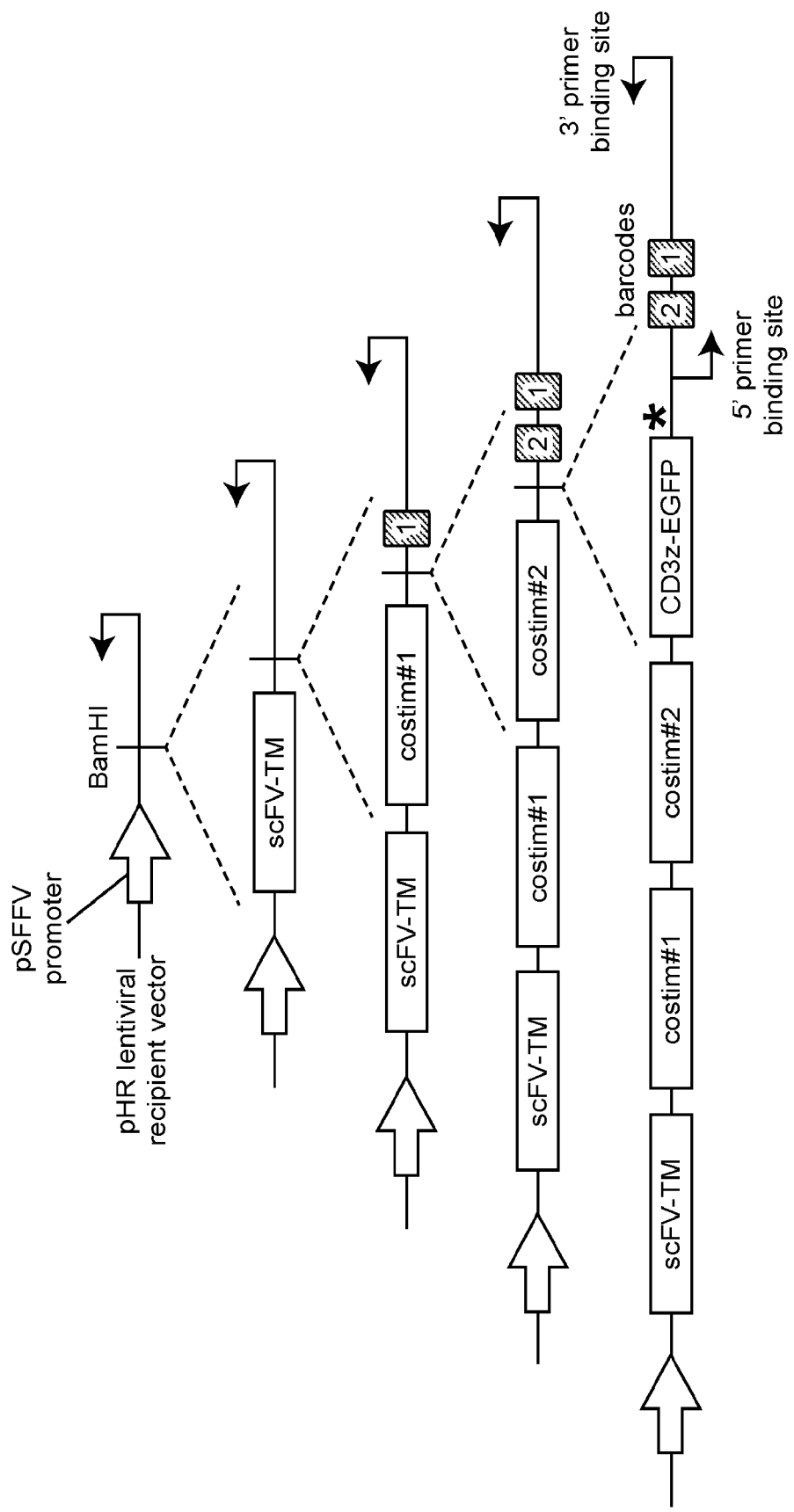
FIG. 5 depicts the general scheme of step-wise assembly of a barcoded two-dimensional co-modulatory module library according to one embodiment of the instant disclosure.

Preparation of the expression vector (i.e., lentiviral packaging vector pHR (also referred to as the recipient vector)) was performed by restriction enzyme digestion at the BamHI site 3' of the spleen focus-forming virus promoter (pSFFV). The library member constructs were assembled in step-wise fashion (FIG. 5). In-Fusion cloning was first used to insert into the expression vector sequence encoding the single-chain variable fragment (scFv) and transmembrane (TM) domains (scFV-TM) common to all members of the library. The In-Fusion reaction mixture was transformed in competent E. coli. The transformed cells were plated. Colonies were selected and Minipreps were performed to extract DNA to recover the constructed plasmid. Following successful construction of the scFV-TM containing expression plasmid, each successive component of the multi-modular polypeptide, including the EGFP reporter, was inserted 3' to the previous component in individual steps according to FIG. 5. Each step included digestion with BamHI and In-Fusion assembly followed by transfection of the In-Fusion reaction, colony selection, and plasmid purification.

As shown in FIG. 5, each resultant library member of the final In-Fusion reaction contained the common scFV-TM linked to a member-specific combination of two co-modulatory domains linked to the common reporter (CD3z-EGFP) and a pair of module-specific barcodes in reverse orientation relative to the co-modulatory domains. The barcodes were flanked by primer binding sites allowing the amplification and/or sequencing of the particular barcode combination corresponding to the library member-specific combination of co-modulatory domains.

Following competition of the final plasmid library, the individual library members were transfected into HEK-293 cells and lentivirus was generated by conventional means. The generated lentivirus was used to infect T-cells to produce engineered immune cells expressing the multi-modular polypeptides.

The engineered immune cells were FACS sorted based on EGFP expression of the reporter. Sorting was performed to isolate a population of engineered cells with uniform expression levels. The sorted cells with uniform expression of the multi-modular polypeptides were utilized in subsequent functional screens.

Figure 6:
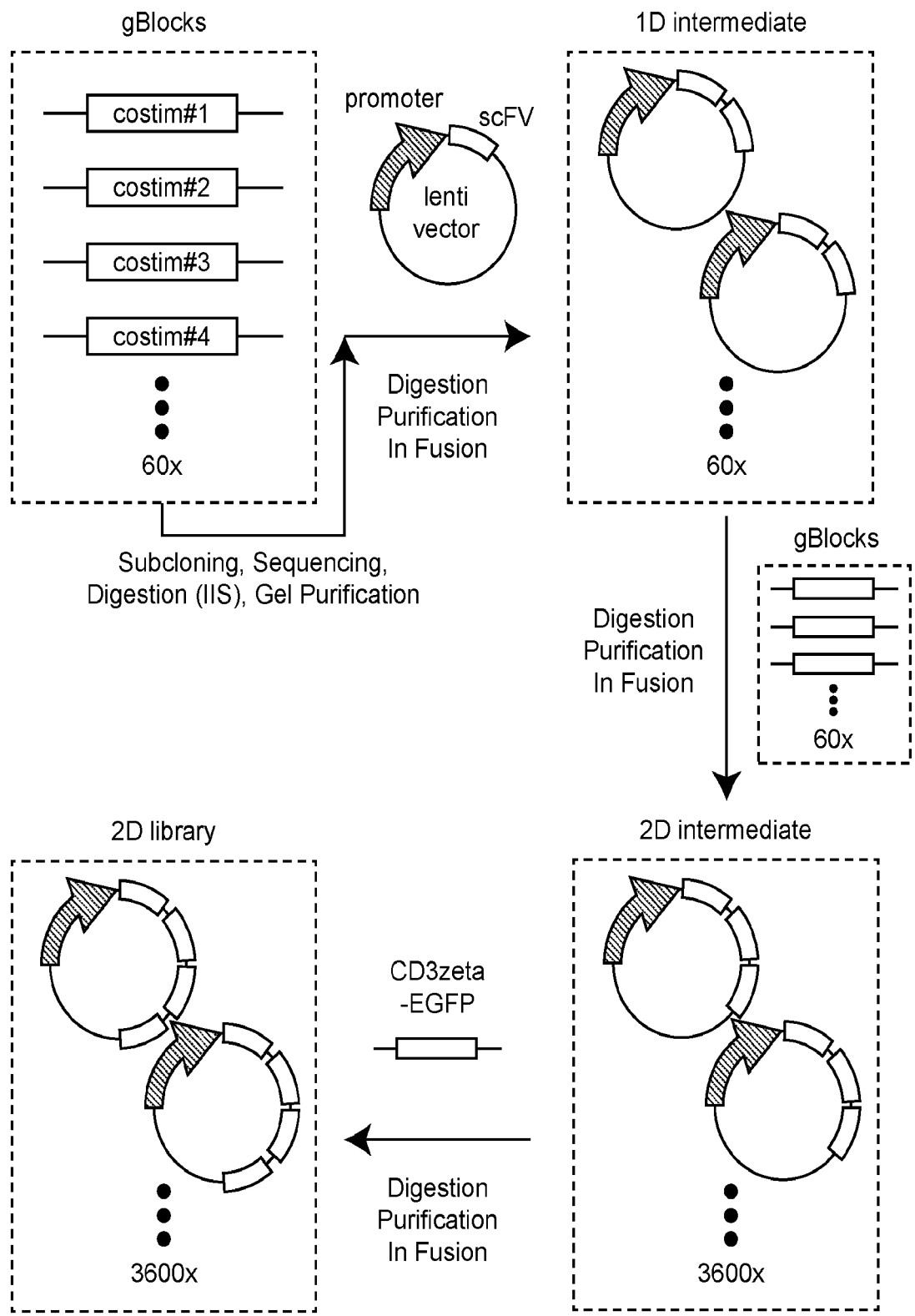
FIG. 6 depicts the general scheme of generation of a 62-by-62 two-dimensional co-modulatory module library according to one embodiment of the instant disclosure.

This general strategy was used to generate four separate libraries. One-dimensional libraries (i.e., where each library member contained a single co-modulatory domain) and two-dimensional libraries (i.e., where each library member contained two co-modulatory domains) were constructed. The members of the two-dimensional libraries were assembled according to the general scheme presented in FIG. 6. The four libraries and associated screens performed were as follows:

1) A 20 member one-dimensional library was constructed and used to test feasibility of FLOWseq analysis of T-cell function. Each library member was configured to contain a CD8 domain fused to a co-modulatory domain module fused to a CD3Z domain. Engineered T-cells were binned according to their reporter expression by FACS and the library was screened to measure dose response of T-cell activation (CD69) to plate-bound antigens.

2) A 62 member one-dimensional anti-CD19 library was constructed and screened in an in vivo mouse tumor model. Each library member was configured to contain an anti-CD19 domain fused to a co-modulatory domain module fused to a CD3Z domain fused to the EGFP reporter.

3) A 62-by-62 member two-dimensional library was constructed. Each library member contained an anti-CD19 domain fused to a first co-modulatory domain module fused to a second co-modulatory domain module fused to a CD3Z domain fused to the EGFP reporter.

4) A 62 member one-dimensional anti-mesothelin library was constructed. Each library member contained an anti-mesothelin domain fused to a co-modulatory domain module fused to a CD3Z domain fused to the EGFP reporter.

Figure 7:
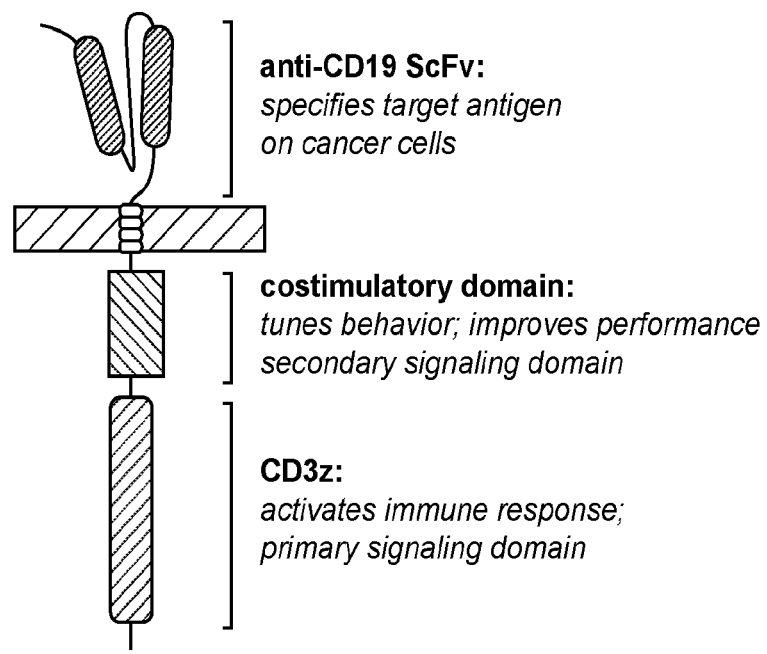
FIG. 7 depicts the general configuration of the members of a one-dimensional chimeric antigen receptor (CAR) library according to one embodiment of the instant disclosure.

The pooled 62 member one-dimensional anti-CD19 library was functionally screened for alternative co-modulatory sequences in chimeric antigen receptors (CARs). Each member of the library contained an anti-CD19 scFv that specifies the target cancer cell antigen, one of the co-modulatory domain modules of Table 1 and a CD3Z primary signaling domain (FIG. 7).

Figure 8:
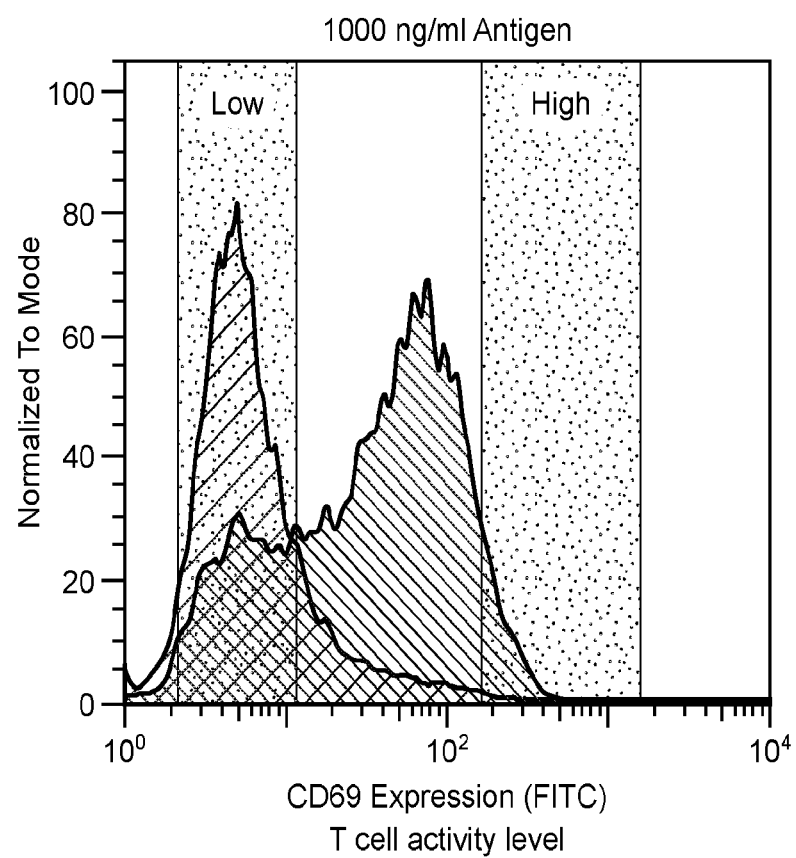
FIG. 8 depicts functional sorting (i.e., binning) of stimulated CAR expressing T-cells based on the resultant level of activation.
Figure 9:
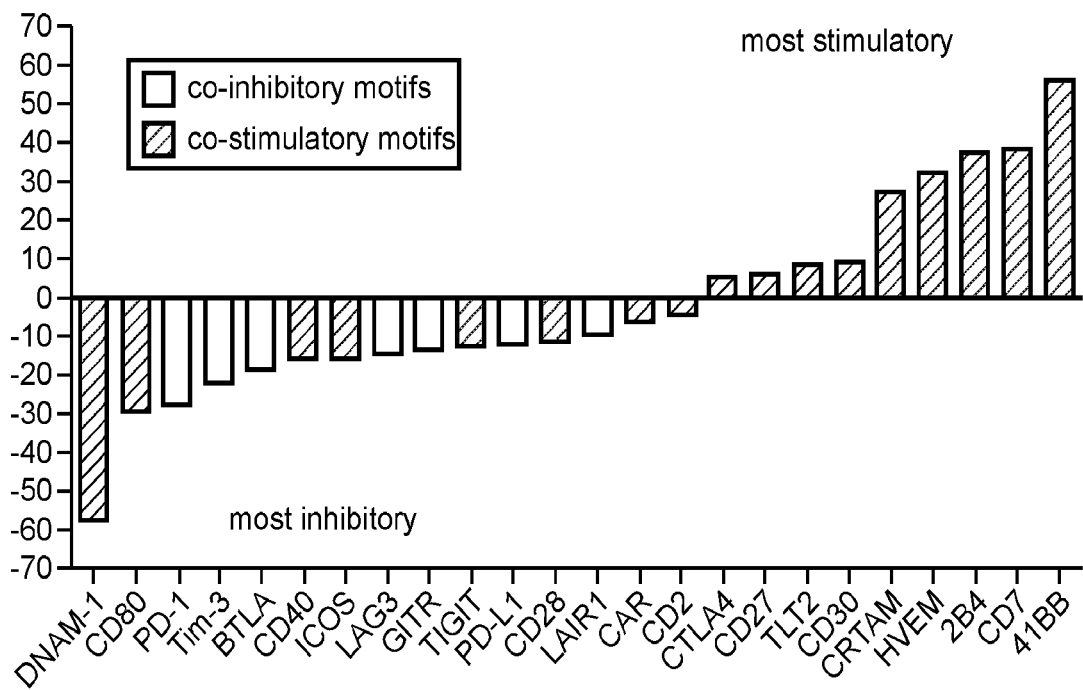
FIG. 9 depicts quantification of the relative influence on T-cell activity of each co-modulatory domain of the library as performed by quantitatively sequencing module-specific barcodes.
Figure 10:
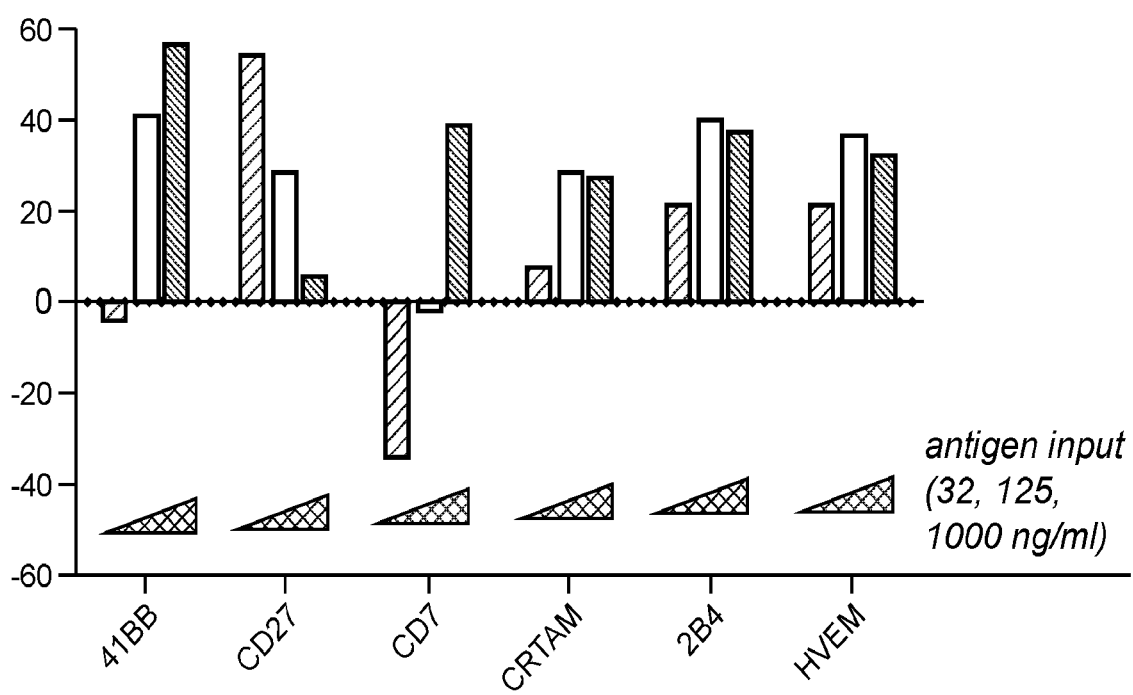
FIG. 10 depicts the dose-response characteristics of six co-modulatory domains across three increasing antigen input levels obtained using a 62 member one-dimensional library.

Following antigen stimulation (at 32 ng/ml, 125 ng/ml and 1000 ng/ml antigen) of the engineered T-cells of the pooled library, the T-cells were functionally sorted by FACS into "high" or "low" stimulation bins based on CD69 expression (FIG. 8). The relative enrichment of specific barcodes corresponding to individual co-modulatory domains was quantitated, in both the high- and low-stimulation bins, by sequencing (at antigen level 1000 ng/ml) (FIG. 9). This approach allowed for the comparison of the stimulatory and inhibitory outcome of each co-modulatory domain within the anti-CD19-CD3Z CAR and in the particular context of antigen stimulation used. For example, the results of the screen were further analyzed across different antigen input levels, allowing for the rapid assessment of the dose-response of individual co-modulatory domains (FIG. 10).

Figures 25, 26:
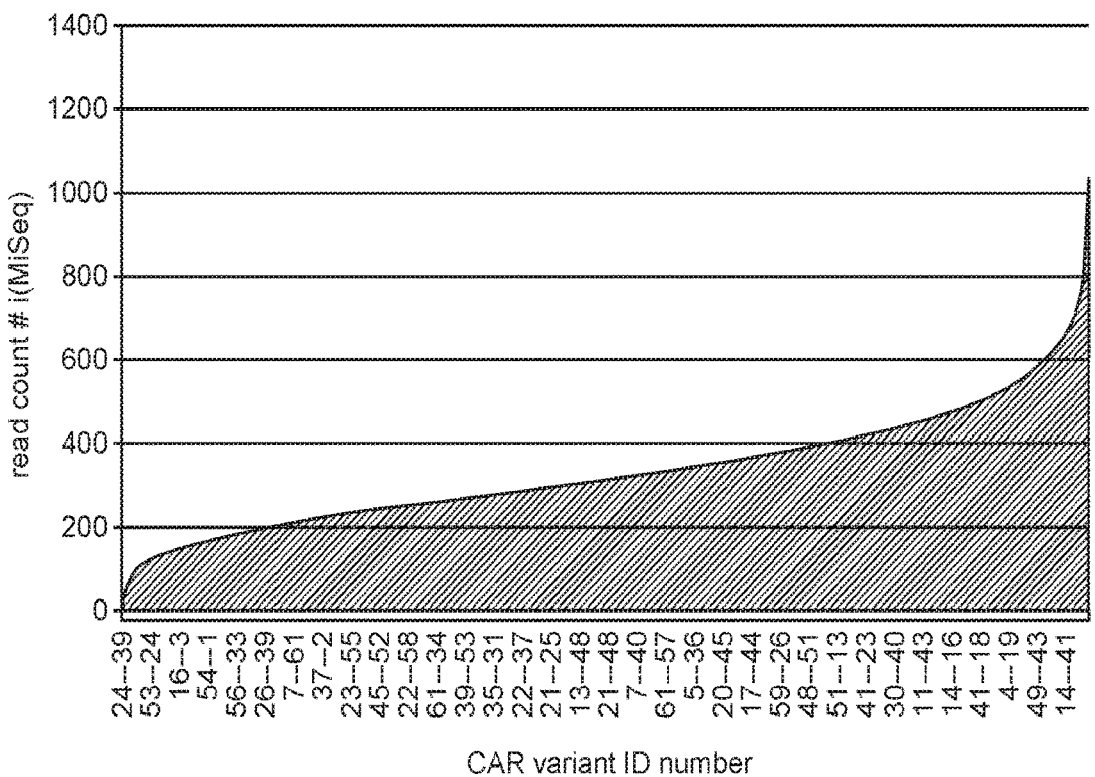
FIG. 25 provides Table 2.
FIG. 26 depicts the complete representation of each member of a 61×61 two dimensional library as determined by deep sequencing the assembled library.

Example 2: Confirmation of Comprehensive Assembly of a 61×61 Two Dimensional Library Sixty-one variable CAR modules (Table 2, provided in FIG. 25) were assembled into a barcoded nucleic acid library encoding two dimensional (2D) synthetic modular CAR polypeptides by nested assembly. The library was deep sequenced by a sequencing by synthesis (SBS) method utilizing a MiSeq system (Illumina Inc., Hayward, Calif.) and the read count of each assembled library member was determined (FIG. 26).

Of the 3,721 total possible library members (i.e., CAR variants) all possible library members were detected by sequencing, with a maximum frequency of 1216 counts and a minimum of 2 counts. The average number of counts across the library was 333 with a median of 311 counts and a standard deviation of 140. 90% of the library members were represented with counts that were within 2-fold of the median and 98% within 3-fold of the median.

As such, sequencing confirms that the nested assembly method is capable of generating a 2D library containing library members that represent all possible combinations of the variable modules.

Example 3: Library Part Normalization

A method was developed to enhance the distribution of clones in the combinatorial library using library part normalization.

In any combinatorial assembly reaction, some parts (e.g., modules) are integrated into the assembled products more efficiently than others. As a consequence, assembled products (e.g., protein variants) that contain parts that integrate relatively inefficiently are underrepresented in or absent from the final combinatorial library. For similar reasons, other assembled products (e.g., those protein variants containing parts that integrate efficiently) are overly abundant, and, consequently, oversampled in all downstream assays.

To address this problem, a method for improving library assembly was developed. In the method, an initial assembly reaction is carried out in which every part (DNA insert) is present at the same volume. For this purpose, a master mix was created containing 1 uL of each part. After the combinatorial assembly is completed, the mixture of products is determined by any convenient quantitative assay. For instance, in the instant example, Next Generation Sequencing was used (see FIG. 27), and the fraction of each part in the total library was calculated (denoted as $e_1$, $e_2$ . . . in the linear equation shown in the FIG. 28). Linear algebra was then used to simultaneously calculate a new, optimized volume for each part (in the master mix), and the library was then resynthesized to achieve a more uniform distribution of variants.

Figures 27, 28:
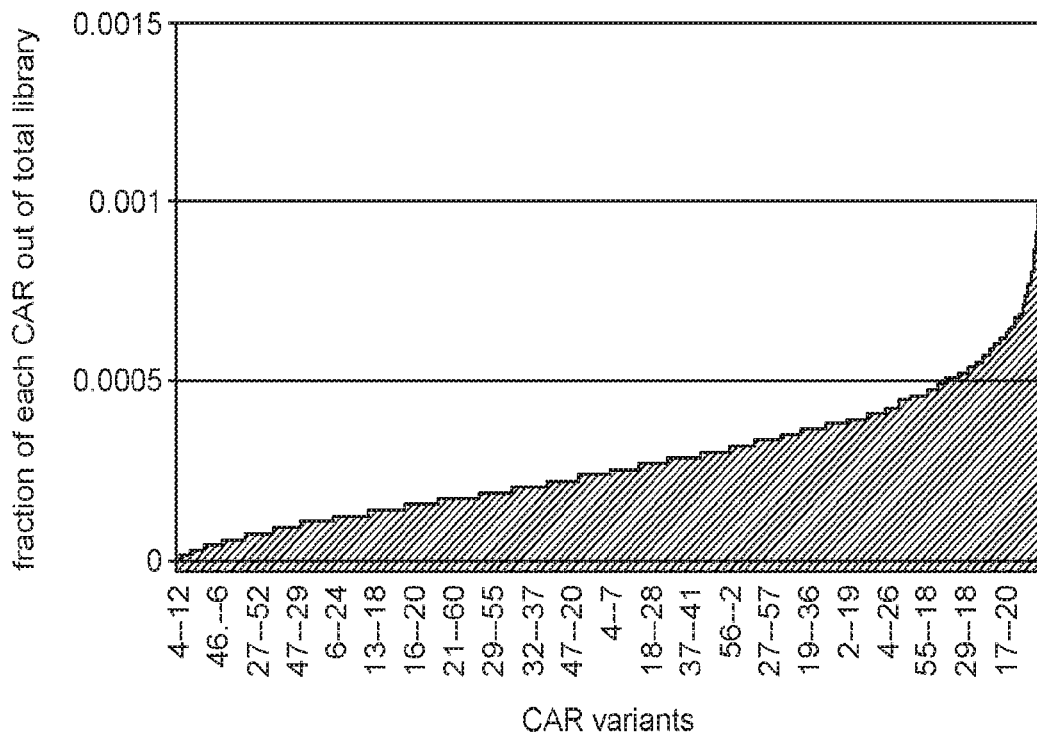
FIG. 27 depicts the sequencing quantification of members of a pre-normalized combinatorial nucleic acid library as described herein.
FIG. 28 depicts a linear equation used in calculating normalization adjustments related to the library members quantified in FIG. 27.
Figure 29:
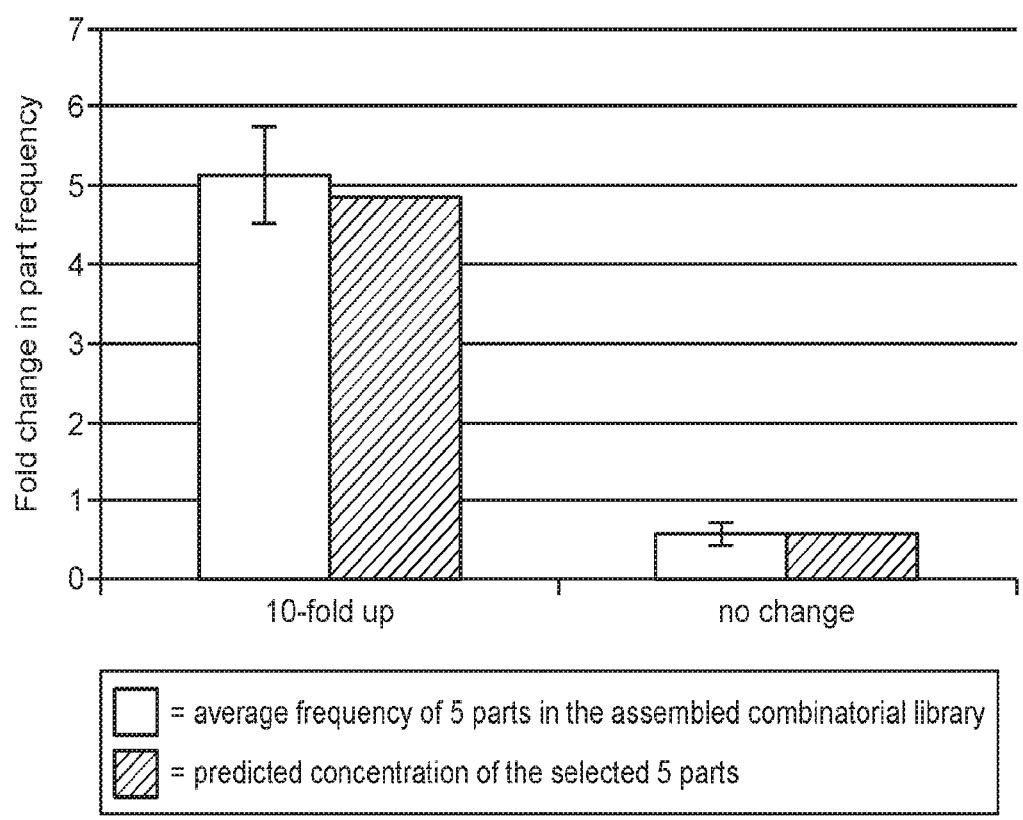
FIG. 29 shows the predictability of normalization adjustments performed according to the method described herein.

This approach was validated by synthesizing a combinatorial library of CARs in which each CAR contains two of 61 different co-stimulatory domains, linked in tandem ($61^2$ for 3721 protein variants). By capitalizing on the simple, linear relationship between part efficiency, concentration, and abundance in the assembled combinatorial library, it was demonstrated that this method can be used to quantitatively control the relative frequency of particular parts. As depicted in FIG. 29, it was predicted (black bars) that a 10-fold change in the relative concentration of a set of parts in the assembly master mix would result in a 10-fold change in the part frequency in the resulting composition of the combinatorial library. When the average frequency of 5 parts in the assembled combinatorial library was measured (white bars) the predicted impact of the 10-fold change was indeed observed. The resulting normalized large combinatorial library (as depicted in FIG. 26) demonstrated a significant improvement in the distribution of variants in the library (e.g., as compared to the variant distribution in the library before normalization (FIG. 27).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of screening, comprising:
    (a) introducing a library of nucleic acids into a population of cells, wherein:
        (i) the members of the library each comprise a barcode region and a coding sequence that is operably linked to a promoter;
        (ii) within each member, the barcode region is separate from the coding sequence;
        (iii) the coding sequence encodes a modular protein having at least a first domain, a second domain, and a third domain;
        (iv) the sequences of the first domain, the second domain and the third domain independently vary in the library;
        (v) the barcode region comprises at least a first barcode, a second barcode and a third barcode, and
        (vi) within each member, the first barcode, the second barcode and the third barcode correspond to and identify the sequence of the first domain, the sequence of the second domain, and the sequence of the third domain of the modular protein, respectively;
    (b) exposing the cells to a stimulus;
    (c) sequencing the barcode region from a cell that exhibits a phenotype in response the stimulus, thereby determining the identity of the first, second, third domains of the modular protein in the cell.
2. The method of claim 1, wherein the modular protein is a receptor.

3. The method of claim 1, wherein the receptor comprises an antigen binding domain, a transmembrane domain, and an intracellular signaling domain.

4. The method of claim 2, wherein the receptor is a chimeric antigen receptor (CAR).

5. The method of claim 4, wherein the stimulus is an antigen-presenting cell that displays on its surface an antigen that is bound by the CAR.

6. The method of claim 1, wherein the cells are eukaryotic cells.

7. The method of claim 6, wherein the eukaryotic cells are human cells.

8. The method of claim 7, wherein the human cells are human T cells.

9. The method of claim 1, wherein, within each member, the barcode region is 3' of the coding sequence.

10. The method of claim 1, wherein the members of the library contain, from 5' to 3',
    a sequence that encodes the first domain of the modular protein;
    a sequence that encodes the second domain of the modular protein;
    a sequence that encodes the third domain of the modular protein;
    the third barcode;
    the second barcode; and
    the first barcode.

11. The method of claim 1, wherein the library comprises at least 100 members.

* * * * *

SEQUENCE LISTING

```
<160> NUMBER OF SEQ ID NOS: 132

<210> SEQ ID NO 1
<211> LENGTH: 24
<212> TYPE: PRT
<213> ORGANISM: Artificial Sequence
<220> FEATURE:
<223> OTHER INFORMATION: Synthetic polypeptide sequence.

<400> SEQUENCE: 1

Ile Tyr Ile Trp Ala Pro Leu Ala Gly Thr Cys Gly Val Leu Leu Leu
```

```
                1               5                   10                  15
Ser Leu Val Ile Thr Leu Tyr Cys
                20

<210> SEQ ID NO 2
<211> LENGTH: 23
<212> TYPE: PRT
<213> ORGANISM: Artificial Sequence
<220> FEATURE:
<223> OTHER INFORMATION: Synthetic polypeptide sequence.

<400> SEQUENCE: 2

Leu Gly Leu Leu Val Ala Gly Val Leu Val Leu Val Ser Leu Gly
1               5                   10                  15

Val Ala Ile His Leu Cys Cys
                20

<210> SEQ ID NO 3
<211> LENGTH: 25
<212> TYPE: PRT
<213> ORGANISM: Artificial Sequence
<220> FEATURE:
<223> OTHER INFORMATION: Synthetic polypeptide sequence.

<400> SEQUENCE: 3

Ala Leu Ile Val Leu Gly Gly Val Ala Gly Leu Leu Leu Phe Ile Gly
1               5                   10                  15

Leu Gly Ile Phe Phe Cys Val Arg Cys
                20              25

<210> SEQ ID NO 4
<211> LENGTH: 23
<212> TYPE: PRT
<213> ORGANISM: Artificial Sequence
<220> FEATURE:
<223> OTHER INFORMATION: Synthetic polypeptide sequence.

<400> SEQUENCE: 4

Leu Cys Tyr Leu Leu Asp Gly Ile Leu Phe Ile Tyr Gly Val Ile Leu
1               5                   10                  15

Thr Ala Leu Phe Leu Arg Val
                20

<210> SEQ ID NO 5
<211> LENGTH: 26
<212> TYPE: PRT
<213> ORGANISM: Artificial Sequence
<220> FEATURE:
<223> OTHER INFORMATION: Synthetic polypeptide sequence.

<400> SEQUENCE: 5

Trp Val Leu Val Val Val Gly Gly Val Leu Ala Cys Tyr Ser Leu Leu
1               5                   10                  15

Val Thr Val Ala Phe Ile Ile Phe Trp Val
                20              25

<210> SEQ ID NO 6
<211> LENGTH: 26
<212> TYPE: PRT
<213> ORGANISM: Artificial Sequence
<220> FEATURE:
<223> OTHER INFORMATION: Synthetic polypeptide sequence.

<400> SEQUENCE: 6
```

```
Val Ala Ala Ile Leu Gly Leu Gly Leu Val Leu Gly Leu Leu Gly Pro
1               5                   10                  15

Leu Ala Ile Leu Leu Ala Leu Tyr Leu Leu
            20                  25

<210> SEQ ID NO 7
<211> LENGTH: 24
<212> TYPE: PRT
<213> ORGANISM: Artificial Sequence
<220> FEATURE:
<223> OTHER INFORMATION: Synthetic polypeptide sequence.

<400> SEQUENCE: 7

Ala Leu Pro Ala Ala Leu Ala Val Ile Ser Phe Leu Leu Gly Leu Gly
1               5                   10                  15

Leu Gly Val Ala Cys Val Leu Ala
            20

<210> SEQ ID NO 8
<211> LENGTH: 5
<212> TYPE: PRT
<213> ORGANISM: Artificial Sequence
<220> FEATURE:
<223> OTHER INFORMATION: Synthetic polypeptide sequence.
<220> FEATURE:
<221> NAME/KEY: MISC_FEATURE
<222> LOCATION: (1)..(5)
<223> OTHER INFORMATION: This stretch of residues may be repeated.

<400> SEQUENCE: 8

Gly Ser Gly Gly Ser
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic polypeptide sequence.
<220> FEATURE:
<221> NAME/KEY: MISC_FEATURE
<222> LOCATION: (1)..(4)
<223> OTHER INFORMATION: This stretch of residues may be repeated.

<400> SEQUENCE: 9

Gly Gly Gly Ser
1

<210> SEQ ID NO 10
<211> LENGTH: 4
<212> TYPE: PRT
<213> ORGANISM: Artificial Sequence
<220> FEATURE:
<223> OTHER INFORMATION: Synthetic polypeptide sequence.

<400> SEQUENCE: 10

Gly Gly Ser Gly
1

<210> SEQ ID NO 11
<211> LENGTH: 5
<212> TYPE: PRT
<213> ORGANISM: Artificial Sequence
<220> FEATURE:
<223> OTHER INFORMATION: Synthetic polypeptide sequence.

<400> SEQUENCE: 11
```

Gly Gly Ser Gly Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic polypeptide sequence.

<400> SEQUENCE: 12

Gly Ser Gly Ser Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic polypeptide sequence.

<400> SEQUENCE: 13

Gly Ser Gly Gly Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic polypeptide sequence.

<400> SEQUENCE: 14

Gly Gly Gly Ser Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide sequence.

<400> SEQUENCE: 15

Gly Ser Ser Ser Gly
1               5

<210> SEQ ID NO 16
<211> LENGTH: 228
<212> TYPE: DNA
<213> ORGANISM: Artificial Sequence
<220> FEATURE:
<223> OTHER INFORMATION: Synthetic nucleic acid sequence.

<400> SEQUENCE: 16
acctgcaaca ctccggatca ggatctggtt cgtgggtgcg cagcaagaga agcagactgc      60
tgcacagcga ctacatgaac atgacccca gacggcctgg ccccaccaga aagcactacc     120
agccttcgcc cctcccagag acttcgccgc ctacagatct ggctccggat caggatccgg     180
cagtggtaac acatatgtct gcagatccgg cagtggtaca aggcaggt                 228

<210> SEQ ID NO 17
<211> LENGTH: 208
<212> TYPE: DNA
<213> ORGANISM: Artificial Sequence
<220> FEATURE:

<223> OTHER INFORMATION: Synthetic nucleic acid sequence.

<400> SEQUENCE: 17

```
ctccggatca ggatctggtt cgtgggtgcg cagcaagaga agcagactgc tgcacagcga    60
ctacatgaac atgaccccca gacggcctgg ccccaccaga aagcactacc agccttacgc   120
ccctccagag acttcgccgc ctacagatct ggctccggat caggatccgg cagtggtaac   180
acatatgtct gcagatccgg cagtggta                                      208
```

<210> SEQ ID NO 18
<211> LENGTH: 58
<212> TYPE: PRT
<213> ORGANISM: Artificial Sequence
<220> FEATURE:
<223> OTHER INFORMATION: Synthetic polypeptide sequence.

<400> SEQUENCE: 18

```
Ser Gly Ser Gly Ser Gly Ser Trp Val Arg Ser Lys Arg Ser Arg Leu
1               5                  10                  15

Leu His Ser Asp Tyr Met Asn Met Thr Pro Arg Arg Pro Gly Pro Thr
            20                  25                  30

Arg Lys His Tyr Gln Pro Tyr Ala Pro Pro Arg Asp Phe Ala Ala Tyr
        35                  40                  45

Arg Ser Gly Ser Gly Ser Gly Ser
    50                  55
```

<210> SEQ ID NO 19
<211> LENGTH: 19
<212> TYPE: PRT
<213> ORGANISM: Artificial Sequence
<220> FEATURE:
<223> OTHER INFORMATION: Synthetic polypeptide sequence.

<400> SEQUENCE: 19

```
Arg Cys Arg Glu Arg Arg Asn Glu Arg Leu Arg Arg Glu Ser Val
1               5                  10                  15

Arg Pro Val
```

<210> SEQ ID NO 20
<211> LENGTH: 29
<212> TYPE: PRT
<213> ORGANISM: Artificial Sequence
<220> FEATURE:
<223> OTHER INFORMATION: Synthetic polypeptide sequence.

<400> SEQUENCE: 20

```
Arg Lys Gly Arg Met Met Asp Val Lys Lys Cys Gly Ile Gln Asp Thr
1               5                  10                  15

Asn Ser Lys Lys Gln Ser Asp Thr His Leu Glu Glu Thr
            20                  25
```

<210> SEQ ID NO 21
<211> LENGTH: 32
<212> TYPE: PRT
<213> ORGANISM: Artificial Sequence
<220> FEATURE:
<223> OTHER INFORMATION: Synthetic polypeptide sequence.

<400> SEQUENCE: 21

```
Lys Lys Arg His Met Ala Ser Tyr Ser Met Cys Ser Asp Pro Ser Thr
1               5                  10                  15

Arg Asp Pro Pro Gly Arg Pro Glu Pro Tyr Val Glu Val Tyr Leu Ile
```

20                  25                  30

<210> SEQ ID NO 22
<211> LENGTH: 35
<212> TYPE: PRT
<213> ORGANISM: Artificial Sequence
<220> FEATURE:
<223> OTHER INFORMATION: Synthetic polypeptide sequence.

<400> SEQUENCE: 22

Thr Lys Lys Lys Tyr Ser Ser Val His Asp Pro Asn Gly Glu Tyr
1               5                   10                  15

Met Phe Met Arg Ala Val Asn Thr Ala Lys Lys Ser Arg Leu Thr Asp
                20                  25                  30

Val Thr Leu
        35

<210> SEQ ID NO 23
<211> LENGTH: 35
<212> TYPE: PRT
<213> ORGANISM: Artificial Sequence
<220> FEATURE:
<223> OTHER INFORMATION: Synthetic polypeptide sequence.

<400> SEQUENCE: 23

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
                20                  25                  30

Cys Ser Val
        35

<210> SEQ ID NO 24
<211> LENGTH: 39
<212> TYPE: PRT
<213> ORGANISM: Artificial Sequence
<220> FEATURE:
<223> OTHER INFORMATION: Synthetic polypeptide sequence.

<400> SEQUENCE: 24

Ser Leu Ser Lys Met Leu Lys Lys Arg Ser Pro Leu Thr Thr Gly Val
1               5                   10                  15

Tyr Val Lys Met Pro Pro Thr Glu Pro Glu Cys Glu Lys Gln Phe Gln
                20                  25                  30

Pro Tyr Phe Ile Pro Ile Asn
        35

<210> SEQ ID NO 25
<211> LENGTH: 40
<212> TYPE: PRT
<213> ORGANISM: Artificial Sequence
<220> FEATURE:
<223> OTHER INFORMATION: Synthetic polypeptide sequence.

<400> SEQUENCE: 25

Ala Arg Thr Gln Ile Lys Lys Leu Cys Ser Trp Arg Asp Lys Asn Ser
1               5                   10                  15

Ala Ala Cys Val Val Tyr Glu Asp Met Ser His Ser Arg Cys Asn Thr
                20                  25                  30

Leu Ser Ser Pro Asn Gln Tyr Gln
        35                  40

<210> SEQ ID NO 26
<211> LENGTH: 42
<212> TYPE: PRT
<213> ORGANISM: Artificial Sequence
<220> FEATURE:
<223> OTHER INFORMATION: Synthetic polypeptide sequence.

<400> SEQUENCE: 26

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 27
<211> LENGTH: 43
<212> TYPE: PRT
<213> ORGANISM: Artificial Sequence
<220> FEATURE:
<223> OTHER INFORMATION: Synthetic polypeptide sequence.

<400> SEQUENCE: 27

Trp Val Arg Ser Lys Arg Ser Arg Leu Leu His Ser Asp Tyr Met Asn
1               5                   10                  15

Met Thr Pro Arg Arg Pro Gly Pro Thr Arg Lys His Tyr Gln Pro Tyr
            20                  25                  30

Ala Pro Pro Arg Asp Phe Ala Ala Tyr Arg Ser
        35                  40

<210> SEQ ID NO 28
<211> LENGTH: 49
<212> TYPE: PRT
<213> ORGANISM: Artificial Sequence
<220> FEATURE:
<223> OTHER INFORMATION: Synthetic polypeptide sequence.

<400> SEQUENCE: 28

His Gln Arg Arg Lys Tyr Arg Ser Asn Lys Gly Glu Ser Pro Val Glu
1               5                   10                  15

Pro Ala Glu Pro Cys His Tyr Ser Cys Pro Arg Glu Glu Gly Ser
            20                  25                  30

Thr Ile Pro Ile Gln Glu Asp Tyr Arg Lys Pro Glu Pro Ala Cys Ser
        35                  40                  45

Pro

<210> SEQ ID NO 29
<211> LENGTH: 51
<212> TYPE: PRT
<213> ORGANISM: Artificial Sequence
<220> FEATURE:
<223> OTHER INFORMATION: Synthetic polypeptide sequence.

<400> SEQUENCE: 29

Arg Arg Gln Trp Arg Pro Arg Arg Phe Ser Ala Leu Glu Gln Gly Ile
1               5                   10                  15

His Pro Pro Gln Ala Gln Ser Lys Ile Glu Glu Leu Glu Gln Glu Pro
            20                  25                  30

Glu Pro Glu Pro Glu Pro Glu Pro Glu Pro Glu Pro Glu Pro Glu Pro
        35                  40                  45

Glu Gln Leu
    50

```
<210> SEQ ID NO 30
<211> LENGTH: 54
<212> TYPE: PRT
<213> ORGANISM: Artificial Sequence
<220> FEATURE:
<223> OTHER INFORMATION: Synthetic polypeptide sequence.

<400> SEQUENCE: 30

His Ile Trp Gln Leu Arg Ser Gln Cys Met Trp Pro Arg Glu Thr Gln
1               5                   10                  15

Leu Leu Leu Glu Val Pro Pro Ser Thr Glu Asp Ala Arg Ser Cys Gln
            20                  25                  30

Phe Pro Glu Glu Glu Arg Gly Glu Arg Ser Ala Glu Glu Lys Gly Arg
        35                  40                  45

Leu Gly Asp Leu Trp Val
    50

<210> SEQ ID NO 31
<211> LENGTH: 61
<212> TYPE: PRT
<213> ORGANISM: Artificial Sequence
<220> FEATURE:
<223> OTHER INFORMATION: Synthetic polypeptide sequence.

<400> SEQUENCE: 31

Asn Arg Arg Arg Arg Arg Glu Arg Arg Asp Leu Phe Thr Glu Ser Trp
1               5                   10                  15

Asp Thr Gln Lys Ala Pro Asn Asn Tyr Arg Ser Pro Ile Ser Thr Ser
            20                  25                  30

Gln Pro Thr Asn Gln Ser Met Asp Asp Thr Arg Glu Asp Ile Tyr Val
        35                  40                  45

Asn Tyr Pro Thr Phe Ser Arg Arg Pro Lys Thr Arg Val
    50                  55                  60

<210> SEQ ID NO 32
<211> LENGTH: 62
<212> TYPE: PRT
<213> ORGANISM: Artificial Sequence
<220> FEATURE:
<223> OTHER INFORMATION: Synthetic polypeptide sequence.

<400> SEQUENCE: 32

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 33
<211> LENGTH: 77
<212> TYPE: PRT
<213> ORGANISM: Artificial Sequence
<220> FEATURE:
<223> OTHER INFORMATION: Synthetic polypeptide sequence.

<400> SEQUENCE: 33

Lys Trp Tyr Ser His Ser Lys Glu Lys Ile Gln Asn Leu Ser Leu Ile
1               5                   10                  15
```

```
Ser Leu Ala Asn Leu Pro Pro Ser Gly Leu Ala Asn Ala Val Ala Glu
            20                  25                  30

Gly Ile Arg Ser Glu Glu Asn Ile Tyr Thr Ile Glu Glu Asn Val Tyr
            35                  40                  45

Glu Val Glu Glu Pro Asn Glu Tyr Tyr Cys Tyr Val Ser Ser Arg Gln
50                      55                  60

Gln Pro Ser Gln Pro Leu Gly Cys Arg Phe Ala Met Pro
65                  70                  75
```

<210> SEQ ID NO 34
<211> LENGTH: 80
<212> TYPE: PRT
<213> ORGANISM: Artificial Sequence
<220> FEATURE:
<223> OTHER INFORMATION: Synthetic polypeptide sequence.

<400> SEQUENCE: 34

```
Arg Lys Lys Lys Ala Leu Arg Ile His Ser Val Glu Gly Asp Leu Arg
1               5                   10                  15

Arg Lys Ser Ala Gly Gln Glu Glu Trp Ser Pro Ser Ala Pro Ser Pro
            20                  25                  30

Pro Gly Ser Cys Val Gln Ala Glu Ala Ala Pro Ala Gly Leu Cys Gly
            35                  40                  45

Glu Gln Arg Gly Glu Asp Cys Ala Glu Leu His Asp Tyr Phe Asn Val
50                      55                  60

Leu Ser Tyr Arg Ser Leu Gly Asn Cys Ser Phe Phe Thr Glu Thr Gly
65                  70                  75                  80
```

<210> SEQ ID NO 35
<211> LENGTH: 83
<212> TYPE: PRT
<213> ORGANISM: Artificial Sequence
<220> FEATURE:
<223> OTHER INFORMATION: Synthetic polypeptide sequence.

<400> SEQUENCE: 35

```
Lys Leu Arg Lys Ala His Val Ile Trp Lys Lys Glu Asn Glu Val Ser
1               5                   10                  15

Glu His Thr Leu Glu Ser Tyr Arg Ser Arg Ser Asn Asn Glu Glu Thr
            20                  25                  30

Ser Ser Glu Glu Lys Asn Gly Gln Ser Ser His Pro Met Arg Cys Met
            35                  40                  45

Asn Tyr Ile Thr Lys Leu Tyr Ser Glu Ala Lys Thr Lys Arg Lys Glu
50                      55                  60

Asn Val Gln His Ser Lys Leu Glu Glu Lys His Ile Gln Val Pro Glu
65                  70                  75                  80

Ser Ile Val
```

<210> SEQ ID NO 36
<211> LENGTH: 98
<212> TYPE: PRT
<213> ORGANISM: Artificial Sequence
<220> FEATURE:
<223> OTHER INFORMATION: Synthetic polypeptide sequence.

<400> SEQUENCE: 36

```
Ile Cys Ser Arg Ala Ala Arg Gly Thr Ile Gly Ala Arg Arg Thr Gly
1               5                   10                  15

Gln Pro Leu Lys Glu Asp Pro Ser Ala Val Pro Val Phe Ser Val Asp
```

```
                20                  25                  30

Tyr Gly Glu Leu Asp Phe Gln Trp Arg Glu Lys Thr Pro Glu Pro Pro
            35                  40                  45

Val Pro Cys Val Pro Glu Gln Thr Glu Tyr Ala Thr Ile Val Phe Pro
 50                  55                  60

Ser Gly Met Gly Thr Ser Ser Pro Ala Arg Arg Gly Ser Ala Asp Gly
 65                  70                  75                  80

Pro Arg Ser Ala Gln Pro Leu Arg Pro Glu Asp Gly His Cys Ser Trp
                85                  90                  95

Pro Leu

<210> SEQ ID NO 37
<211> LENGTH: 101
<212> TYPE: PRT
<213> ORGANISM: Artificial Sequence
<220> FEATURE:
<223> OTHER INFORMATION: Synthetic polypeptide sequence.

<400> SEQUENCE: 37

His Arg Gln Asn Gln Ile Lys Gln Gly Pro Pro Arg Ser Lys Asp Glu
 1               5                  10                  15

Glu Gln Lys Pro Gln Gln Arg Pro Asp Leu Ala Val Asp Val Leu Glu
                20                  25                  30

Arg Thr Ala Asp Lys Ala Thr Val Asn Gly Leu Pro Glu Lys Asp Arg
            35                  40                  45

Glu Thr Asp Thr Ser Ala Leu Ala Ala Gly Ser Ser Gln Glu Val Thr
 50                  55                  60

Tyr Ala Gln Leu Asp His Trp Ala Leu Thr Gln Arg Thr Ala Arg Ala
 65                  70                  75                  80

Val Ser Pro Gln Ser Thr Lys Pro Met Ala Glu Ser Ile Thr Tyr Ala
                85                  90                  95

Ala Val Ala Arg His
            100

<210> SEQ ID NO 38
<211> LENGTH: 107
<212> TYPE: PRT
<213> ORGANISM: Artificial Sequence
<220> FEATURE:
<223> OTHER INFORMATION: Synthetic polypeptide sequence.

<400> SEQUENCE: 38

Cys Cys Arg Lys Lys Arg Arg Glu Glu Lys Tyr Glu Lys Glu Val His
 1               5                  10                  15

His Asp Ile Arg Glu Asp Val Pro Pro Pro Lys Ser Arg Thr Ser Thr
                20                  25                  30

Ala Arg Ser Tyr Ile Gly Ser Asn His Ser Ser Leu Gly Ser Met Ser
            35                  40                  45

Pro Ser Asn Met Glu Gly Tyr Ser Lys Thr Gln Tyr Asn Gln Val Pro
 50                  55                  60

Ser Glu Asp Phe Glu Arg Thr Pro Gln Ser Pro Thr Leu Pro Pro Ala
 65                  70                  75                  80

Lys Val Ala Ala Pro Asn Leu Ser Arg Met Gly Ala Ile Pro Val Met
                85                  90                  95

Ile Pro Ala Gln Ser Lys Asp Gly Ser Ile Val
            100                 105
```

```
<210> SEQ ID NO 39
<211> LENGTH: 114
<212> TYPE: PRT
<213> ORGANISM: Artificial Sequence
<220> FEATURE:
<223> OTHER INFORMATION: Synthetic polypeptide sequence.

<400> SEQUENCE: 39

Cys Cys Leu Arg Arg His Gln Gly Lys Gln Asn Glu Leu Ser Asp Thr
1               5                   10                  15

Ala Gly Arg Glu Ile Asn Leu Val Asp Ala His Leu Lys Ser Glu Gln
            20                  25                  30

Thr Glu Ala Ser Thr Arg Gln Asn Ser Gln Val Leu Leu Ser Glu Thr
        35                  40                  45

Gly Ile Tyr Asp Asn Asp Pro Asp Leu Cys Phe Arg Met Gln Glu Gly
    50                  55                  60

Ser Glu Val Tyr Ser Asn Pro Cys Leu Glu Glu Asn Lys Pro Gly Ile
65                  70                  75                  80

Val Tyr Ala Ser Leu Asn His Ser Val Ile Gly Pro Asn Ser Arg Leu
                85                  90                  95

Ala Arg Asn Val Lys Glu Ala Pro Thr Glu Tyr Ala Ser Ile Cys Val
            100                 105                 110

Arg Ser

<210> SEQ ID NO 40
<211> LENGTH: 117
<212> TYPE: PRT
<213> ORGANISM: Artificial Sequence
<220> FEATURE:
<223> OTHER INFORMATION: Synthetic polypeptide sequence.

<400> SEQUENCE: 40

Thr Lys Arg Lys Lys Gln Arg Ser Arg Arg Asn Asp Glu Glu Leu Glu
1               5                   10                  15

Thr Arg Ala His Arg Val Ala Thr Glu Glu Arg Gly Arg Lys Pro His
            20                  25                  30

Gln Ile Pro Ala Ser Thr Pro Gln Asn Pro Ala Thr Ser Gln His Pro
        35                  40                  45

Pro Pro Pro Pro Gly His Arg Ser Gln Ala Pro Ser His Arg Pro Pro
    50                  55                  60

Pro Pro Gly His Arg Val Gln His Gln Pro Gln Lys Arg Pro Pro Ala
65                  70                  75                  80

Pro Ser Gly Thr Gln Val His Gln Gln Lys Gly Pro Pro Leu Pro Arg
                85                  90                  95

Pro Arg Val Gln Pro Lys Pro Pro His Gly Ala Ala Glu Asn Ser Leu
            100                 105                 110

Ser Pro Ser Ser Asn
        115

<210> SEQ ID NO 41
<211> LENGTH: 120
<212> TYPE: PRT
<213> ORGANISM: Artificial Sequence
<220> FEATURE:
<223> OTHER INFORMATION: Synthetic polypeptide sequence.

<400> SEQUENCE: 41

Trp Arg Arg Lys Arg Lys Glu Lys Gln Ser Glu Thr Ser Pro Lys Glu
1               5                   10                  15
```

```
Phe Leu Thr Ile Tyr Glu Asp Val Lys Asp Leu Lys Thr Arg Arg Asn
             20                  25                  30

His Glu Gln Glu Gln Thr Phe Pro Gly Gly Gly Ser Thr Ile Tyr Ser
         35                  40                  45

Met Ile Gln Ser Gln Ser Ser Ala Pro Thr Ser Gln Glu Pro Ala Tyr
     50                  55                  60

Thr Leu Tyr Ser Leu Ile Gln Pro Ser Arg Lys Ser Gly Ser Arg Lys
 65                  70                  75                  80

Arg Asn His Ser Pro Ser Phe Asn Ser Thr Ile Tyr Glu Val Ile Gly
                 85                  90                  95

Lys Ser Gln Pro Lys Ala Gln Asn Pro Ala Arg Leu Ser Arg Lys Glu
            100                 105                 110

Leu Glu Asn Phe Asp Val Tyr Ser
            115                 120
```

<210> SEQ ID NO 42
<211> LENGTH: 187
<212> TYPE: PRT
<213> ORGANISM: Artificial Sequence
<220> FEATURE:
<223> OTHER INFORMATION: Synthetic polypeptide sequence.

<400> SEQUENCE: 42

```
Arg Arg Ala Cys Arg Lys Arg Ile Arg Gln Lys Leu His Leu Cys Tyr
 1               5                  10                  15

Pro Val Gln Thr Ser Gln Pro Lys Leu Glu Leu Val Asp Ser Arg Pro
             20                  25                  30

Arg Arg Ser Ser Thr Gln Leu Arg Ser Gly Ala Ser Val Thr Glu Pro
         35                  40                  45

Val Ala Glu Glu Arg Gly Leu Met Ser Gln Pro Leu Met Glu Thr Cys
     50                  55                  60

His Ser Val Gly Ala Ala Tyr Leu Glu Ser Leu Pro Leu Gln Asp Ala
 65                  70                  75                  80

Ser Pro Ala Gly Gly Pro Ser Ser Pro Arg Asp Leu Pro Glu Pro Arg
                 85                  90                  95

Val Ser Thr Glu His Thr Asn Asn Lys Ile Glu Lys Ile Tyr Ile Met
            100                 105                 110

Lys Ala Asp Thr Val Ile Val Gly Thr Val Lys Ala Glu Leu Pro Glu
            115                 120                 125

Gly Arg Gly Leu Ala Gly Pro Ala Glu Pro Glu Leu Glu Glu Glu Leu
        130                 135                 140

Glu Ala Asp His Thr Pro His Tyr Pro Glu Gln Glu Thr Glu Pro Pro
145                 150                 155                 160

Leu Gly Ser Cys Ser Asp Val Met Leu Ser Val Glu Gly Glu Gly Lys
                165                 170                 175

Glu Asp Pro Leu Pro Thr Ala Ala Ser Gly Lys
            180                 185
```

<210> SEQ ID NO 43
<211> LENGTH: 108
<212> TYPE: PRT
<213> ORGANISM: Artificial Sequence
<220> FEATURE:
<223> OTHER INFORMATION: Synthetic polypeptide sequence.

<400> SEQUENCE: 43

```
Thr Tyr Arg His Cys Trp Pro His Lys Pro Leu Val Thr Ala Asp Glu
 1               5                  10                  15
```

Ala Gly Met Glu Ala Leu Thr Pro Pro Ala Thr His Leu Ser Pro
            20                  25                  30

Leu Asp Ser Ala His Thr Leu Leu Ala Pro Pro Asp Ser Ser Glu Lys
        35                  40                  45

Ile Cys Thr Val Gln Leu Val Gly Asn Ser Trp Thr Pro Gly Tyr Pro
 50                  55                  60

Glu Thr Gln Glu Ala Leu Cys Pro Gln Val Thr Trp Ser Trp Asp Gln
 65                  70                  75                  80

Leu Pro Ser Arg Ala Leu Gly Pro Ala Ala Pro Thr Leu Ser Pro
                85                  90                  95

Glu Ser Pro Ala Gly Ser Pro Ala Met Met Leu Gln
            100                 105

<210> SEQ ID NO 44
<211> LENGTH: 42
<212> TYPE: PRT
<213> ORGANISM: Artificial Sequence
<220> FEATURE:
<223> OTHER INFORMATION: Synthetic polypeptide sequence.

<400> SEQUENCE: 44

Ala Leu Tyr Leu Leu Arg Arg Asp Gln Arg Leu Pro Pro Asp Ala His
 1               5                  10                  15

Lys Pro Pro Gly Gly Gly Ser Phe Arg Thr Pro Ile Gln Glu Glu Gln
                20                  25                  30

Ala Asp Ala His Ser Thr Leu Ala Lys Ile
            35                  40

<210> SEQ ID NO 45
<211> LENGTH: 51
<212> TYPE: PRT
<213> ORGANISM: Artificial Sequence
<220> FEATURE:
<223> OTHER INFORMATION: Synthetic polypeptide sequence.

<400> SEQUENCE: 45

Met Gly Trp Ile Arg Gly Arg Arg Ser Arg His Ser Trp Glu Met Ser
 1               5                  10                  15

Glu Phe His Asn Tyr Asn Leu Asp Leu Lys Lys Ser Asp Phe Ser Thr
                20                  25                  30

Arg Trp Gln Lys Gln Arg Cys Pro Val Val Lys Ser Lys Cys Arg Glu
            35                  40                  45

Asn Ala Ser
    50

<210> SEQ ID NO 46
<211> LENGTH: 48
<212> TYPE: PRT
<213> ORGANISM: Artificial Sequence
<220> FEATURE:
<223> OTHER INFORMATION: Synthetic polypeptide sequence.

<400> SEQUENCE: 46

Lys Lys Tyr Phe Phe Lys Lys Glu Val Gln Gln Leu Ser Val Ser Phe
 1               5                  10                  15

Ser Ser Leu Gln Ile Lys Ala Leu Gln Asn Ala Val Glu Lys Glu Val
                20                  25                  30

Gln Ala Glu Asp Asn Ile Tyr Ile Glu Asn Ser Leu Tyr Ala Thr Asp
            35                  40                  45

<210> SEQ ID NO 47
<211> LENGTH: 22
<212> TYPE: PRT
<213> ORGANISM: Artificial Sequence
<220> FEATURE:
<223> OTHER INFORMATION: Synthetic polypeptide sequence.

<400> SEQUENCE: 47

Ser Gly Phe Leu Gln Glu Lys Val Trp Val Met Leu Val Thr Ser Leu
1               5                   10                  15

Val Ala Leu Gln Ala Leu
            20

<210> SEQ ID NO 48
<211> LENGTH: 85
<212> TYPE: PRT
<213> ORGANISM: Artificial Sequence
<220> FEATURE:
<223> OTHER INFORMATION: Synthetic polypeptide sequence.

<400> SEQUENCE: 48

Ser Trp Arg Arg Gln Arg Arg Leu Arg Gly Ala Ser Ser Ala Glu
1               5                   10                  15

Ala Pro Asp Gly Asp Lys Asp Ala Pro Glu Pro Leu Asp Lys Val Ile
            20                  25                  30

Ile Leu Ser Pro Gly Ile Ser Asp Ala Thr Ala Pro Ala Trp Pro Pro
        35                  40                  45

Pro Gly Glu Asp Pro Gly Thr Thr Pro Pro Gly His Ser Val Pro Val
    50                  55                  60

Pro Ala Thr Glu Leu Gly Ser Thr Glu Leu Val Thr Thr Lys Thr Ala
65                  70                  75                  80

Gly Pro Glu Gln Gln
            85

<210> SEQ ID NO 49
<211> LENGTH: 111
<212> TYPE: PRT
<213> ORGANISM: Artificial Sequence
<220> FEATURE:
<223> OTHER INFORMATION: Synthetic polypeptide sequence.

<400> SEQUENCE: 49

Ala Cys Phe Leu Lys Lys Arg Gly Asp Pro Cys Ser Cys Gln Pro Arg
1               5                   10                  15

Ser Arg Pro Arg Gln Ser Pro Ala Lys Ser Ser Gln Asp His Ala Met
            20                  25                  30

Glu Ala Gly Ser Pro Val Ser Thr Ser Pro Glu Pro Val Glu Thr Cys
        35                  40                  45

Ser Phe Cys Phe Pro Glu Cys Arg Ala Pro Thr Gln Glu Ser Ala Val
    50                  55                  60

Thr Pro Gly Thr Pro Asp Pro Thr Cys Ala Gly Arg Trp Gly Cys His
65                  70                  75                  80

Thr Arg Thr Thr Val Leu Gln Pro Cys Pro His Ile Pro Asp Ser Gly
            85                  90                  95

Leu Gly Ile Val Cys Val Pro Ala Gln Glu Gly Pro Gly Ala
        100                 105                 110

<210> SEQ ID NO 50
<211> LENGTH: 95
<212> TYPE: PRT

<213> ORGANISM: Artificial Sequence
<220> FEATURE:
<223> OTHER INFORMATION: Synthetic polypeptide sequence.

<400> SEQUENCE: 50

Met Ala Glu Ala Ile Thr Tyr Ala Asp Leu Arg Phe Val Lys Ala Pro
1               5                   10                  15

Leu Lys Lys Ser Ile Ser Ser Arg Leu Gly Gln Asp Pro Gly Ala Asp
            20                  25                  30

Asp Asp Gly Glu Ile Thr Tyr Glu Asn Val Gln Val Pro Ala Val Leu
        35                  40                  45

Gly Val Pro Ser Ser Leu Ala Ser Ser Val Leu Gly Asp Lys Ala Ala
    50                  55                  60

Val Lys Ser Glu Gln Pro Thr Ala Ser Trp Arg Ala Val Thr Ser Pro
65                  70                  75                  80

Ala Val Gly Arg Ile Leu Pro Cys Arg Thr Thr Cys Leu Arg Tyr
                85                  90                  95

<210> SEQ ID NO 51
<211> LENGTH: 141
<212> TYPE: PRT
<213> ORGANISM: Artificial Sequence
<220> FEATURE:
<223> OTHER INFORMATION: Synthetic polypeptide sequence.

<400> SEQUENCE: 51

Lys Leu Gln Arg Arg Trp Lys Arg Thr Gln Ser Gln Gly Leu Gln
1               5                   10                  15

Glu Asn Ser Ser Gly Gln Ser Phe Phe Val Arg Asn Lys Lys Val Arg
            20                  25                  30

Arg Ala Pro Leu Ser Glu Gly Pro His Ser Leu Gly Cys Tyr Asn Pro
        35                  40                  45

Met Met Glu Asp Gly Ile Ser Tyr Thr Thr Leu Arg Phe Pro Glu Met
    50                  55                  60

Asn Ile Pro Arg Thr Gly Asp Ala Glu Ser Ser Glu Met Gln Arg Pro
65                  70                  75                  80

Pro Pro Asp Cys Asp Asp Thr Val Thr Tyr Ser Ala Leu His Lys Arg
                85                  90                  95

Gln Val Gly Asp Tyr Glu Asn Val Ile Pro Asp Phe Pro Glu Asp Glu
            100                 105                 110

Gly Ile His Tyr Ser Glu Leu Ile Gln Phe Gly Val Gly Glu Arg Pro
        115                 120                 125

Gln Ala Gln Glu Asn Val Asp Tyr Val Ile Leu Lys His
    130                 135                 140

<210> SEQ ID NO 52
<211> LENGTH: 45
<212> TYPE: PRT
<213> ORGANISM: Artificial Sequence
<220> FEATURE:
<223> OTHER INFORMATION: Synthetic polypeptide sequence.

<400> SEQUENCE: 52

Arg Lys Trp Cys Gln Tyr Gln Lys Glu Ile Met Glu Arg Pro Pro Pro
1               5                   10                  15

Phe Lys Pro Pro Pro Pro Pro Ile Lys Tyr Thr Cys Ile Gln Glu Pro
            20                  25                  30

Asn Glu Ser Asp Leu Pro Tyr His Glu Met Glu Thr Leu
        35                  40                  45

<210> SEQ ID NO 53
<211> LENGTH: 84
<212> TYPE: PRT
<213> ORGANISM: Artificial Sequence
<220> FEATURE:
<223> OTHER INFORMATION: Synthetic polypeptide sequence.

<400> SEQUENCE: 53

Leu Arg Lys Arg Arg Asp Ser Leu Ser Leu Ser Thr Gln Arg Thr Gln
1               5                   10                  15

Gly Pro Ala Glu Ser Ala Arg Asn Leu Glu Tyr Val Ser Val Ser Pro
            20                  25                  30

Thr Asn Asn Thr Val Tyr Ala Ser Val Thr His Ser Asn Arg Glu Thr
        35                  40                  45

Glu Ile Trp Thr Pro Arg Glu Asn Asp Thr Ile Thr Ile Tyr Ser Thr
    50                  55                  60

Ile Asn His Ser Lys Glu Ser Lys Pro Thr Phe Ser Arg Ala Thr Ala
65                  70                  75                  80

Leu Asp Asn Val

<210> SEQ ID NO 54
<211> LENGTH: 88
<212> TYPE: PRT
<213> ORGANISM: Artificial Sequence
<220> FEATURE:
<223> OTHER INFORMATION: Synthetic polypeptide sequence.

<400> SEQUENCE: 54

Trp Phe Leu Lys Arg Glu Arg Gln Glu Glu Tyr Ile Glu Glu Lys Lys
1               5                   10                  15

Arg Val Asp Ile Cys Arg Glu Thr Pro Asn Ile Cys Pro His Ser Gly
            20                  25                  30

Glu Asn Thr Glu Tyr Asp Thr Ile Pro His Thr Asn Arg Thr Ile Leu
        35                  40                  45

Lys Glu Asp Pro Ala Asn Thr Val Tyr Ser Thr Val Glu Ile Pro Lys
    50                  55                  60

Lys Met Glu Asn Pro His Ser Leu Leu Thr Met Pro Asp Thr Pro Arg
65                  70                  75                  80

Leu Phe Ala Tyr Glu Asn Val Ile
                85

<210> SEQ ID NO 55
<211> LENGTH: 82
<212> TYPE: PRT
<213> ORGANISM: Artificial Sequence
<220> FEATURE:
<223> OTHER INFORMATION: Synthetic polypeptide sequence.

<400> SEQUENCE: 55

Lys Thr His Arg Arg Lys Ala Ala Arg Thr Ala Val Gly Arg Asn Asp
1               5                   10                  15

Thr His Pro Thr Thr Gly Ser Ala Ser Pro Lys His Gln Lys Lys Ser
            20                  25                  30

Lys Leu His Gly Pro Thr Glu Thr Ser Ser Cys Ser Gly Ala Ala Pro
        35                  40                  45

Thr Val Glu Met Asp Glu Glu Leu His Tyr Ala Ser Leu Asn Phe His
    50                  55                  60

Gly Met Asn Pro Ser Lys Asp Thr Ser Thr Glu Tyr Ser Glu Val Arg

Thr Gln

<210> SEQ ID NO 56
<211> LENGTH: 38
<212> TYPE: PRT
<213> ORGANISM: Artificial Sequence
<220> FEATURE:
<223> OTHER INFORMATION: Synthetic polypeptide sequence.

<400> SEQUENCE: 56

```
Met Thr Asp Ser Val Ile Tyr Ser Met Leu Glu Leu Pro Thr Ala Thr
1               5                   10                  15
Gln Ala Gln Asn Asp Tyr Gly Pro Gln Gln Lys Ser Ser Ser Ser Arg
                20                  25                  30
Pro Ser Cys Ser Cys Leu
                35
```

<210> SEQ ID NO 57
<211> LENGTH: 45
<212> TYPE: PRT
<213> ORGANISM: Artificial Sequence
<220> FEATURE:
<223> OTHER INFORMATION: Synthetic polypeptide sequence.

<400> SEQUENCE: 57

```
Met Asp Gln Gln Ala Ile Tyr Ala Glu Leu Asn Leu Pro Thr Asp Ser
1               5                   10                  15
Gly Pro Glu Ser Ser Ser Pro Ser Ser Leu Pro Arg Asp Val Cys Gln
                20                  25                  30
Gly Ser Pro Trp His Gln Phe Ala Leu Lys Leu Ser Cys
            35                  40                  45
```

<210> SEQ ID NO 58
<211> LENGTH: 168
<212> TYPE: PRT
<213> ORGANISM: Artificial Sequence
<220> FEATURE:
<223> OTHER INFORMATION: Synthetic polypeptide sequence.

<400> SEQUENCE: 58

```
Leu Arg His Arg Arg Gln Gly Lys His Trp Thr Ser Thr Gln Arg Lys
1               5                   10                  15
Ala Asp Phe Gln His Pro Ala Gly Ala Val Gly Pro Glu Pro Thr Asp
                20                  25                  30
Arg Gly Leu Gln Trp Arg Ser Ser Pro Ala Ala Asp Ala Gln Glu Glu
            35                  40                  45
Asn Leu Tyr Ala Ala Val Lys His Thr Gln Pro Glu Asp Gly Val Glu
        50                  55                  60
Met Asp Thr Arg Ser Pro His Asp Glu Asp Pro Gln Ala Val Thr Tyr
65                  70                  75                  80
Ala Glu Val Lys His Ser Arg Pro Arg Arg Glu Met Ala Ser Pro Pro
                85                  90                  95
Ser Pro Leu Ser Gly Glu Phe Leu Asp Thr Lys Asp Arg Gln Ala Glu
                100                 105                 110
Glu Asp Arg Gln Met Asp Thr Glu Ala Ala Ala Ser Glu Ala Pro Gln
            115                 120                 125
Asp Val Thr Tyr Ala Gln Leu His Ser Leu Thr Leu Arg Arg Glu Ala
        130                 135                 140
```

Thr Glu Pro Pro Pro Ser Gln Glu Gly Pro Ser Pro Ala Val Pro Ser
145                 150                 155                 160

Ile Tyr Ala Thr Leu Ala Ile His
                165

<210> SEQ ID NO 59
<211> LENGTH: 83
<212> TYPE: PRT
<213> ORGANISM: Artificial Sequence
<220> FEATURE:
<223> OTHER INFORMATION: Synthetic polypeptide sequence.

<400> SEQUENCE: 59

Arg Trp Cys Ser Asn Lys Lys Asn Ala Ala Val Met Asp Gln Glu Ser
1               5                   10                  15

Ala Gly Asn Arg Thr Ala Asn Ser Glu Asp Ser Asp Glu Gln Asp Pro
            20                  25                  30

Gln Glu Val Thr Tyr Thr Gln Leu Asn His Cys Val Phe Thr Gln Arg
        35                  40                  45

Lys Ile Thr Arg Pro Ser Gln Arg Pro Lys Thr Pro Pro Thr Asp Ile
    50                  55                  60

Ile Val Tyr Thr Glu Leu Pro Asn Ala Glu Ser Arg Ser Lys Val Val
65                  70                  75                  80

Ser Cys Pro

<210> SEQ ID NO 60
<211> LENGTH: 84
<212> TYPE: PRT
<213> ORGANISM: Artificial Sequence
<220> FEATURE:
<223> OTHER INFORMATION: Synthetic polypeptide sequence.

<400> SEQUENCE: 60

His Leu Trp Cys Ser Asn Lys Lys Asn Ala Ala Val Met Asp Gln Glu
1               5                   10                  15

Pro Ala Gly Asn Arg Thr Ala Asn Ser Glu Asp Ser Asp Glu Gln Asp
            20                  25                  30

Pro Glu Glu Val Thr Tyr Ala Gln Leu Asp His Cys Val Phe Thr Gln
        35                  40                  45

Arg Lys Ile Thr Arg Pro Ser Gln Arg Pro Lys Thr Pro Pro Thr Asp
    50                  55                  60

Thr Ile Leu Tyr Thr Glu Leu Pro Asn Ala Lys Pro Arg Ser Lys Val
65                  70                  75                  80

Val Ser Cys Pro

<210> SEQ ID NO 61
<211> LENGTH: 10
<212> TYPE: PRT
<213> ORGANISM: Artificial Sequence
<220> FEATURE:
<223> OTHER INFORMATION: Synthetic polypeptide sequence.

<400> SEQUENCE: 61

Met Ala Val Phe Lys Thr Thr Leu Trp Arg
1               5                   10

<210> SEQ ID NO 62
<211> LENGTH: 29
<212> TYPE: PRT
<213> ORGANISM: Artificial Sequence
<220> FEATURE:

<223> OTHER INFORMATION: Synthetic polypeptide sequence.

<400> SEQUENCE: 62

Lys Gly Ser Gln Arg Val Pro Glu Glu Pro Gly Glu Gln Pro Ile Tyr
1               5                   10                  15

Met Asn Phe Ser Glu Pro Leu Thr Lys Asp Met Ala Thr
            20                  25

<210> SEQ ID NO 63
<211> LENGTH: 11
<212> TYPE: PRT
<213> ORGANISM: Artificial Sequence
<220> FEATURE:
<223> OTHER INFORMATION: Synthetic polypeptide sequence.

<400> SEQUENCE: 63

Val Asn Arg Pro Gln Trp Ala Pro Pro Gly Arg
1               5                   10

<210> SEQ ID NO 64
<211> LENGTH: 8
<212> TYPE: PRT
<213> ORGANISM: Artificial Sequence
<220> FEATURE:
<223> OTHER INFORMATION: Synthetic polypeptide sequence.

<400> SEQUENCE: 64

Val Thr Leu Arg Ser Phe Val Pro
1               5

<210> SEQ ID NO 65
<211> LENGTH: 35
<212> TYPE: PRT
<213> ORGANISM: Artificial Sequence
<220> FEATURE:
<223> OTHER INFORMATION: Synthetic polypeptide sequence.

<400> SEQUENCE: 65

Ala Ala Trp His Gly Gln Lys Pro Gly Thr His Pro Pro Ser Glu Leu
1               5                   10                  15

Asp Cys Gly His Asp Pro Gly Tyr Gln Leu Gln Thr Leu Pro Gly Leu
            20                  25                  30

Arg Asp Thr
        35

<210> SEQ ID NO 66
<211> LENGTH: 32
<212> TYPE: PRT
<213> ORGANISM: Artificial Sequence
<220> FEATURE:
<223> OTHER INFORMATION: Synthetic polypeptide sequence.

<400> SEQUENCE: 66

Gln His Ser Gln Arg Ser Pro Pro Arg Cys Ser Gln Glu Ala Asn Ser
1               5                   10                  15

Arg Lys Asp Asn Ala Pro Phe Arg Val Val Glu Pro Trp Glu Gln Ile
            20                  25                  30

<210> SEQ ID NO 67
<211> LENGTH: 168
<212> TYPE: PRT
<213> ORGANISM: Artificial Sequence
<220> FEATURE:
<223> OTHER INFORMATION: Synthetic polypeptide sequence.

<400> SEQUENCE: 67

Gln His Trp Arg Gln Gly Lys His Arg Thr Leu Ala Gln Arg Gln Ala
1               5                   10                  15

Asp Phe Gln Arg Pro Pro Gly Ala Ala Glu Pro Glu Pro Lys Asp Gly
            20                  25                  30

Gly Leu Gln Arg Arg Ser Ser Pro Ala Ala Asp Val Gln Gly Glu Asn
        35                  40                  45

Phe Cys Ala Ala Val Lys Asn Thr Gln Pro Glu Asp Gly Val Glu Met
    50                  55                  60

Asp Thr Arg Gln Ser Pro His Asp Glu Asp Pro Gln Ala Val Thr Tyr
65                  70                  75                  80

Ala Lys Val Lys His Ser Arg Pro Arg Glu Met Ala Ser Pro Pro
                85                  90                  95

Ser Pro Leu Ser Gly Glu Phe Leu Asp Thr Lys Asp Arg Gln Ala Glu
                100                 105                 110

Glu Asp Arg Gln Met Asp Thr Glu Ala Ala Ser Glu Ala Pro Gln
            115                 120                 125

Asp Val Thr Tyr Ala Gln Leu His Ser Phe Thr Leu Arg Gln Lys Ala
    130                 135                 140

Thr Glu Pro Pro Pro Ser Gln Glu Gly Ala Ser Pro Ala Glu Pro Ser
145                 150                 155                 160

Val Tyr Ala Thr Leu Ala Ile His
                165

<210> SEQ ID NO 68
<211> LENGTH: 116
<212> TYPE: PRT
<213> ORGANISM: Artificial Sequence
<220> FEATURE:
<223> OTHER INFORMATION: Synthetic polypeptide sequence.

<400> SEQUENCE: 68

Leu Arg His Arg Arg Gln Gly Lys His Trp Thr Ser Thr Gln Arg Lys
1               5                   10                  15

Ala Asp Phe Gln His Pro Ala Gly Ala Val Gly Pro Glu Pro Thr Asp
            20                  25                  30

Arg Gly Leu Gln Trp Arg Ser Ser Pro Ala Ala Asp Ala Gln Glu Glu
        35                  40                  45

Asn Leu Tyr Ala Ala Val Lys Asp Thr Gln Pro Glu Asp Gly Val Glu
    50                  55                  60

Met Asp Thr Arg Ala Ala Ala Ser Glu Ala Pro Gln Asp Val Thr Tyr
65                  70                  75                  80

Ala Gln Leu His Ser Leu Thr Leu Arg Arg Lys Ala Thr Glu Pro Pro
                85                  90                  95

Pro Ser Gln Glu Arg Glu Pro Pro Ala Glu Pro Ser Ile Tyr Ala Thr
                100                 105                 110

Leu Ala Ile His
        115

<210> SEQ ID NO 69
<211> LENGTH: 128
<212> TYPE: PRT
<213> ORGANISM: Artificial Sequence
<220> FEATURE:
<223> OTHER INFORMATION: Synthetic polypeptide sequence.

<400> SEQUENCE: 69

```
Met Ala Lys Arg Lys Gln Gly Asn Arg Leu Gly Val Cys Gly Arg Phe
1               5                   10                  15

Leu Ser Ser Arg Val Ser Gly Met Asn Pro Ser Val Val His His
            20                  25                  30

Val Ser Asp Ser Gly Pro Ala Ala Glu Leu Pro Leu Asp Val Pro His
        35                  40                  45

Ile Arg Leu Asp Ser Pro Pro Ser Phe Asp Asn Thr Thr Tyr Thr Ser
50                  55                  60

Leu Pro Leu Asp Ser Pro Ser Gly Lys Pro Ser Leu Pro Ala Pro Ser
65                  70                  75                  80

Ser Leu Pro Pro Leu Pro Pro Lys Val Leu Val Cys Ser Lys Pro Val
            85                  90                  95

Thr Tyr Ala Thr Val Ile Phe Pro Gly Gly Asn Lys Gly Gly Gly Thr
            100                 105                 110

Ser Cys Gly Pro Ala Gln Asn Pro Pro Asn Asn Gln Thr Pro Ser Ser
            115                 120                 125
```

<210> SEQ ID NO 70
<211> LENGTH: 61
<212> TYPE: PRT
<213> ORGANISM: Artificial Sequence
<220> FEATURE:
<223> OTHER INFORMATION: Synthetic polypeptide sequence.

<400> SEQUENCE: 70

```
Lys Val Asn Gly Cys Arg Lys Tyr Lys Leu Asn Lys Thr Glu Ser Thr
1               5                   10                  15

Pro Val Val Glu Glu Asp Glu Met Gln Pro Tyr Ala Ser Tyr Thr Glu
            20                  25                  30

Lys Asn Asn Pro Leu Tyr Asp Thr Thr Asn Lys Val Lys Ala Ser Glu
            35                  40                  45

Ala Leu Gln Ser Glu Val Asp Thr Asp Leu His Thr Leu
50                  55                  60
```

<210> SEQ ID NO 71
<211> LENGTH: 98
<212> TYPE: PRT
<213> ORGANISM: Artificial Sequence
<220> FEATURE:
<223> OTHER INFORMATION: Synthetic polypeptide sequence.

<400> SEQUENCE: 71

```
Arg Met Phe Gln Lys Trp Ile Lys Ala Gly Asp His Ser Glu Leu Ser
1               5                   10                  15

Gln Asn Pro Lys Gln Ala Ala Thr Gln Ser Glu Leu His Tyr Ala Asn
            20                  25                  30

Leu Glu Leu Leu Met Trp Pro Leu Gln Glu Lys Pro Ala Pro Pro Arg
            35                  40                  45

Glu Val Glu Val Glu Tyr Ser Thr Val Ala Ser Pro Arg Glu Glu Leu
50                  55                  60

His Tyr Ala Ser Val Val Phe Asp Ser Asn Thr Asn Arg Ile Ala Ala
65                  70                  75                  80

Gln Arg Pro Arg Glu Glu Glu Pro Asp Ser Asp Tyr Ser Val Ile Arg
            85                  90                  95

Lys Thr
```

<210> SEQ ID NO 72
<211> LENGTH: 113

```
<212> TYPE: PRT
<213> ORGANISM: Artificial Sequence
<220> FEATURE:
<223> OTHER INFORMATION: Synthetic polypeptide sequence.

<400> SEQUENCE: 72

Trp Arg Met Met Lys Tyr Gln Gln Lys Ala Ala Gly Met Ser Pro Glu
1               5                   10                  15

Gln Val Leu Gln Pro Leu Glu Gly Asp Leu Cys Tyr Ala Asp Leu Thr
            20                  25                  30

Leu Gln Leu Ala Gly Thr Ser Pro Gln Lys Ala Thr Thr Lys Leu Ser
        35                  40                  45

Ser Ala Gln Val Asp Gln Val Glu Val Glu Tyr Val Thr Met Ala Ser
    50                  55                  60

Leu Pro Lys Glu Asp Ile Ser Tyr Ala Ser Leu Thr Leu Gly Ala Glu
65                  70                  75                  80

Asp Gln Glu Pro Thr Tyr Cys Asn Met Gly His Leu Ser Ser His Leu
                85                  90                  95

Pro Gly Arg Gly Pro Glu Pro Thr Glu Tyr Ser Thr Ile Ser Arg
            100                 105                 110

Pro

<210> SEQ ID NO 73
<211> LENGTH: 37
<212> TYPE: PRT
<213> ORGANISM: Artificial Sequence
<220> FEATURE:
<223> OTHER INFORMATION: Synthetic polypeptide sequence.

<400> SEQUENCE: 73

Met Ser Asp Ser Lys Glu Pro Arg Leu Gln Gln Leu Gly Leu Leu Glu
1               5                   10                  15

Glu Glu Gln Leu Arg Gly Leu Gly Phe Arg Gln Thr Arg Gly Tyr Lys
            20                  25                  30

Ser Leu Ala Gly Cys
        35

<210> SEQ ID NO 74
<211> LENGTH: 29
<212> TYPE: PRT
<213> ORGANISM: Artificial Sequence
<220> FEATURE:
<223> OTHER INFORMATION: Synthetic polypeptide sequence.

<400> SEQUENCE: 74

Arg Lys Ser Ser Gly Gly Lys Gly Gly Ser Tyr Ser Gln Ala Ala Cys
1               5                   10                  15

Ser Asp Ser Ala Gln Gly Ser Asp Val Ser Leu Thr Ala
            20                  25

<210> SEQ ID NO 75
<211> LENGTH: 95
<212> TYPE: PRT
<213> ORGANISM: Artificial Sequence
<220> FEATURE:
<223> OTHER INFORMATION: Synthetic polypeptide sequence.

<400> SEQUENCE: 75

Leu Pro Lys Tyr Lys Thr Arg Lys Ala Met Arg Asn Asn Val Pro Arg
1               5                   10                  15

Asp Arg Gly Asp Thr Ala Met Glu Val Gly Ile Tyr Ala Asn Ile Leu
```

```
                 20                  25                  30

Glu Lys Gln Ala Lys Glu Glu Ser Val Pro Glu Val Gly Ser Arg Pro
             35                  40                  45

Cys Val Ser Thr Ala Gln Asp Glu Ala Lys His Ser Gln Glu Leu Gln
         50                  55                  60

Tyr Ala Thr Pro Val Phe Gln Glu Val Ala Pro Arg Glu Gln Glu Ala
 65                  70                  75                  80

Cys Asp Ser Tyr Lys Ser Gly Tyr Val Tyr Ser Glu Leu Asn Phe
                 85                  90                  95

<210> SEQ ID NO 76
<211> LENGTH: 178
<212> TYPE: PRT
<213> ORGANISM: Artificial Sequence
<220> FEATURE:
<223> OTHER INFORMATION: Synthetic polypeptide sequence.

<400> SEQUENCE: 76

Arg Arg Arg His Arg Gly Lys Phe Arg Lys Asp Val Gln Lys Glu Lys
 1               5                  10                  15

Asp Leu Gln Leu Ser Ser Gly Ala Glu Glu Pro Ile Thr Arg Lys Gly
             20                  25                  30

Glu Leu Gln Lys Arg Pro Asn Pro Ala Ala Thr Gln Glu Glu Ser
         35                  40                  45

Leu Tyr Ala Ser Val Glu Asp Met Gln Thr Glu Asp Gly Val Glu Leu
 50                  55                  60

Asn Ser Trp Thr Pro Pro Glu Glu Asp Pro Gln Gly Glu Thr Tyr Ala
 65                  70                  75                  80

Gln Val Lys Pro Ser Arg Leu Arg Lys Ala Gly His Val Ser Pro Ser
                 85                  90                  95

Val Met Ser Arg Glu Gln Leu Asn Thr Glu Tyr Glu Gln Ala Glu Glu
             100                 105                 110

Gly Gln Gly Ala Asn Asn Gln Ala Ala Glu Ser Gly Glu Ser Gln Asp
         115                 120                 125

Val Thr Tyr Ala Gln Leu Cys Ser Arg Thr Leu Arg Gln Gly Ala Ala
130                 135                 140

Ala Ser Pro Leu Ser Gln Ala Gly Glu Ala Pro Glu Glu Pro Ser Val
145                 150                 155                 160

Tyr Ala Thr Leu Ala Ala Arg Pro Glu Ala Val Pro Lys Asp Met
                 165                 170                 175

Glu Gln

<210> SEQ ID NO 77
<211> LENGTH: 42
<212> TYPE: PRT
<213> ORGANISM: Artificial Sequence
<220> FEATURE:
<223> OTHER INFORMATION: Synthetic polypeptide sequence.

<400> SEQUENCE: 77

Ser Ala Gly Ser Ala Gly Ser Ala Gly Ser Ala Gly Ser Ala Gly Ser
 1               5                  10                  15

Ala Gly Ser Ala Gly Ser Ala Gly Ser Ala Gly Ser Ala Gly Ser Ala
             20                  25                  30

Gly Ser Ala Gly Ser Ala Gly Ser Ala Gly
         35                  40
```

```
<210> SEQ ID NO 78
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 78

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 79
<211> LENGTH: 292
<212> TYPE: PRT
<213> ORGANISM: Artificial Sequence
<220> FEATURE:
<223> OTHER INFORMATION: synthetic polypeptide

<400> SEQUENCE: 79

Leu Glu Glu Ser Val Ala Leu Arg Ile Ile Thr Glu Gly Ala Ser Ile
1               5                   10                  15

Leu Arg Gln Glu Lys Asn Leu Leu Asp Ile Asp Ala Pro Val Thr Val
            20                  25                  30

Cys Gly Asp Ile His Gly Gln Phe Phe Asp Leu Met Lys Leu Phe Glu
        35                  40                  45

Val Gly Gly Ser Pro Ala Asn Thr Arg Tyr Leu Phe Leu Gly Asp Tyr
    50                  55                  60

Val Asp Arg Gly Tyr Phe Ser Ile Glu Cys Val Leu Tyr Leu Trp Ala
65                  70                  75                  80

Leu Lys Ile Leu Tyr Pro Lys Thr Leu Phe Leu Leu Arg Gly Asn His
                85                  90                  95

Glu Cys Arg His Leu Thr Glu Tyr Phe Thr Phe Lys Gln Glu Cys Lys
            100                 105                 110

Ile Lys Tyr Ser Glu Arg Val Tyr Asp Ala Cys Met Asp Ala Phe Asp
        115                 120                 125

Cys Leu Pro Leu Ala Ala Leu Met Asn Gln Gln Phe Leu Cys Val His
    130                 135                 140

Gly Gly Leu Ser Pro Glu Ile Asn Thr Leu Asp Asp Ile Arg Lys Leu
145                 150                 155                 160

Asp Arg Phe Lys Glu Pro Pro Ala Tyr Gly Pro Met Cys Asp Ile Leu
                165                 170                 175

Trp Ser Asp Pro Leu Glu Asp Phe Gly Asn Glu Lys Thr Gln Glu His
            180                 185                 190

Phe Thr His Asn Thr Val Arg Gly Cys Ser Tyr Phe Tyr Ser Tyr Pro
        195                 200                 205
```

```
Ala Val Cys Glu Phe Leu Gln His Asn Asn Leu Leu Ser Ile Leu Arg
210                 215                 220

Ala His Glu Ala Gln Asp Ala Gly Tyr Arg Met Tyr Arg Lys Ser Gln
225                 230                 235                 240

Thr Thr Gly Phe Pro Ser Leu Ile Thr Ile Phe Ser Ala Pro Asn Tyr
            245                 250                 255

Leu Asp Val Tyr Asn Asn Lys Ala Ala Val Leu Lys Tyr Glu Asn Asn
            260                 265                 270

Val Met Asn Ile Arg Gln Phe Asn Cys Ser Pro His Pro Tyr Trp Leu
            275                 280                 285

Pro Asn Phe Met
            290

<210> SEQ ID NO 80
<211> LENGTH: 165
<212> TYPE: PRT
<213> ORGANISM: Artificial Sequence
<220> FEATURE:
<223> OTHER INFORMATION: synthetic polypeptide

<400> SEQUENCE: 80

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
                20                  25                  30

Ala Glu Asn Phe Arg Ala Leu Ser Thr Gly Glu Lys Gly Phe Gly Tyr
            35                  40                  45

Lys Gly Ser Cys Phe His Arg Ile Ile Pro Gly Phe Met Cys Gln Gly
50                  55                  60

Gly Asp Phe Thr Arg His Asn Gly Thr Gly Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
130                 135                 140

Phe Gly Ser Arg Asn Gly Lys Thr Ser Lys Lys Ile Thr Ile Ala Asp
145                 150                 155                 160

Cys Gly Gln Leu Glu
            165

<210> SEQ ID NO 81
<211> LENGTH: 94
<212> TYPE: PRT
<213> ORGANISM: Artificial Sequence
<220> FEATURE:
<223> OTHER INFORMATION: synthetic polypeptide

<400> SEQUENCE: 81

Met Ile Leu Trp His Glu Met Trp His Glu Gly Leu Glu Glu Ala Ser
1               5                   10                  15

Arg Leu Tyr Phe Gly Glu Arg Asn Val Lys Gly Met Phe Glu Val Leu
                20                  25                  30

Glu Pro Leu His Ala Met Met Glu Arg Gly Pro Gln Thr Leu Lys Glu
            35                  40                  45
```

-continued

```
Thr Ser Phe Asn Gln Ala Tyr Gly Arg Asp Leu Met Glu Ala Gln Glu
     50                  55                  60
Trp Cys Arg Lys Tyr Met Lys Ser Gly Asn Val Lys Asp Leu Leu Gln
 65                  70                  75                  80
Ala Trp Asp Leu Tyr Tyr His Val Phe Arg Arg Ile Ser Lys
                 85                  90

<210> SEQ ID NO 82
<211> LENGTH: 804
<212> TYPE: PRT
<213> ORGANISM: Artificial Sequence
<220> FEATURE:
<223> OTHER INFORMATION: synthetic polypeptide

<400> SEQUENCE: 82

Met Ser Asn Ser Tyr Asp Ser Ser Ile Lys Val Leu Lys Gly Leu
  1               5                  10                  15

Asp Ala Val Arg Lys Arg Pro Gly Met Tyr Ile Gly Asp Thr Asp Asp
                 20                  25                  30

Gly Thr Gly Leu His His Met Val Phe Glu Val Val Asp Asn Ala Ile
             35                  40                  45

Asp Glu Ala Leu Ala Gly His Cys Lys Glu Ile Ile Val Thr Ile His
 50                  55                  60

Ala Asp Asn Ser Val Ser Val Gln Asp Gly Arg Gly Ile Pro Thr
 65                  70                  75                  80

Gly Ile His Pro Glu Glu Gly Val Ser Ala Ala Glu Val Ile Met Thr
                 85                  90                  95

Val Leu His Ala Gly Gly Lys Phe Asp Asp Asn Ser Tyr Lys Val Ser
                100                 105                 110

Gly Gly Leu His Gly Val Gly Val Ser Val Val Asn Ala Leu Ser Gln
             115                 120                 125

Lys Leu Glu Leu Val Ile Gln Arg Glu Gly Lys Ile His Arg Gln Ile
130                 135                 140

Tyr Glu His Gly Val Pro Gln Ala Pro Leu Ala Val Thr Gly Glu Thr
145                 150                 155                 160

Glu Lys Thr Gly Thr Met Val Arg Phe Trp Pro Ser Leu Glu Thr Phe
                165                 170                 175

Thr Asn Val Thr Glu Phe Glu Tyr Glu Ile Leu Ala Lys Arg Leu Arg
                180                 185                 190

Glu Leu Ser Phe Leu Asn Ser Gly Val Ser Ile Arg Leu Arg Asp Lys
             195                 200                 205

Arg Asp Gly Lys Glu Asp His Phe His Tyr Glu Gly Gly Ile Lys Ala
210                 215                 220

Phe Val Glu Tyr Leu Asn Lys Asn Lys Thr Pro Ile His Pro Asn Ile
225                 230                 235                 240

Phe Tyr Phe Ser Thr Glu Lys Asp Gly Ile Gly Val Glu Val Ala Leu
                245                 250                 255

Gln Trp Asn Asp Gly Phe Gln Glu Asn Ile Tyr Cys Phe Thr Asn Asn
                260                 265                 270

Ile Pro Gln Arg Asp Gly Gly Thr His Leu Ala Gly Phe Arg Ala Ala
             275                 280                 285

Met Thr Arg Thr Leu Asn Ala Tyr Met Asp Lys Glu Gly Tyr Ser Lys
290                 295                 300

Lys Ala Lys Val Ser Ala Thr Gly Asp Asp Ala Arg Glu Gly Leu Ile
305                 310                 315                 320
```

-continued

```
Ala Val Val Ser Val Lys Val Pro Asp Pro Lys Phe Ser Ser Gln Thr
            325                 330                 335

Lys Asp Lys Leu Val Ser Ser Glu Val Lys Ser Ala Val Glu Gln Gln
            340                 345                 350

Met Asn Glu Leu Leu Ala Glu Tyr Leu Leu Glu Asn Pro Thr Asp Ala
            355                 360                 365

Lys Ile Val Val Gly Lys Ile Ile Asp Ala Ala Arg Ala Arg Glu Ala
            370                 375                 380

Ala Arg Arg Ala Arg Glu Met Thr Arg Arg Lys Gly Ala Leu Asp Leu
385                 390                 395                 400

Ala Gly Leu Pro Gly Lys Leu Ala Asp Cys Gln Glu Arg Asp Pro Ala
            405                 410                 415

Leu Ser Glu Leu Tyr Leu Val Glu Gly Asp Ser Ala Gly Gly Ser Ala
            420                 425                 430

Lys Gln Gly Arg Asn Arg Lys Asn Gln Ala Ile Leu Pro Leu Lys Gly
            435                 440                 445

Lys Ile Leu Asn Val Glu Lys Ala Arg Phe Asp Lys Met Leu Ser Ser
            450                 455                 460

Gln Glu Val Ala Thr Leu Ile Thr Ala Leu Gly Cys Gly Ile Gly Arg
465                 470                 475                 480

Asp Glu Tyr Asn Pro Asp Lys Leu Arg Tyr His Ser Ile Ile Met
            485                 490                 495

Thr Asp Ala Asp Val Asp Gly Ser His Ile Arg Thr Leu Leu Leu Thr
            500                 505                 510

Phe Phe Tyr Arg Gln Met Pro Glu Ile Val Glu Arg Gly His Val Tyr
            515                 520                 525

Ile Ala Gln Pro Pro Leu Tyr Lys Val Lys Lys Gly Lys Gln Glu Gln
            530                 535                 540

Tyr Ile Lys Asp Asp Glu Ala Met Asp Gln Tyr Gln Ile Ser Ile Ala
545                 550                 555                 560

Leu Asp Gly Ala Thr Leu His Thr Asn Ala Ser Ala Pro Ala Leu Ala
            565                 570                 575

Gly Glu Ala Leu Glu Lys Leu Val Ser Glu Tyr Asn Ala Thr Gln Lys
            580                 585                 590

Met Ile Asn Arg Met Glu Arg Arg Tyr Pro Lys Ala Met Leu Lys Glu
            595                 600                 605

Leu Ile Tyr Gln Pro Thr Leu Thr Glu Ala Asp Leu Ser Asp Glu Gln
            610                 615                 620

Thr Val Thr Arg Trp Val Asn Ala Leu Val Ser Glu Leu Asn Asp Lys
625                 630                 635                 640

Glu Gln His Gly Ser Gln Trp Lys Phe Asp Val His Thr Asn Ala Glu
            645                 650                 655

Gln Asn Leu Phe Glu Pro Ile Val Arg Val Arg Thr His Gly Val Asp
            660                 665                 670

Thr Asp Tyr Pro Leu Asp His Glu Phe Ile Thr Gly Gly Glu Tyr Arg
            675                 680                 685

Arg Ile Cys Thr Leu Gly Glu Lys Leu Arg Gly Leu Leu Glu Glu Asp
            690                 695                 700

Ala Phe Ile Glu Arg Gly Glu Arg Arg Gln Pro Val Ala Ser Phe Glu
705                 710                 715                 720

Gln Ala Leu Asp Trp Leu Val Lys Glu Ser Arg Arg Gly Leu Ser Ile
            725                 730                 735
```

Gln Arg Tyr Lys Gly Leu Gly Glu Met Asn Pro Glu Gln Leu Trp Glu
            740                 745                 750

Thr Thr Met Asp Pro Glu Ser Arg Arg Met Leu Arg Val Thr Val Lys
        755                 760                 765

Asp Ala Ile Ala Ala Asp Gln Leu Phe Thr Thr Leu Met Gly Asp Ala
    770                 775                 780

Val Glu Pro Arg Arg Ala Phe Ile Glu Glu Asn Ala Leu Lys Ala Ala
785                 790                 795                 800

Asn Ile Asp Ile

<210> SEQ ID NO 83
<211> LENGTH: 187
<212> TYPE: PRT
<213> ORGANISM: Artificial Sequence
<220> FEATURE:
<223> OTHER INFORMATION: synthetic polypeptide

<400> SEQUENCE: 83

Met Val Gly Ser Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185

<210> SEQ ID NO 84
<211> LENGTH: 111
<212> TYPE: PRT
<213> ORGANISM: Artificial Sequence
<220> FEATURE:
<223> OTHER INFORMATION: synthetic polypeptide

<400> SEQUENCE: 84

Met Ala Ser Arg Gly Val Gln Val Glu Thr Ile Ser Pro Gly Asp Gly
1               5                   10                  15

Arg Thr Phe Pro Lys Arg Gly Gln Thr Cys Val Val His Tyr Thr Gly
            20                  25                  30

Met Leu Glu Asp Gly Lys Lys Val Asp Ser Ser Arg Asp Arg Asn Lys
        35                  40                  45

```
Pro Phe Lys Phe Met Leu Gly Lys Gln Glu Val Ile Arg Gly Trp Glu
 50                  55                  60

Glu Gly Val Ala Gln Met Ser Val Gly Gln Arg Ala Lys Leu Thr Ile
 65                  70                  75                  80

Ser Pro Asp Tyr Ala Tyr Gly Ala Thr Gly His Pro Gly Ile Ile Pro
                 85                  90                  95

Pro His Ala Thr Leu Val Phe Asp Val Glu Leu Leu Lys Leu Glu
            100                 105                 110

<210> SEQ ID NO 85
<211> LENGTH: 183
<212> TYPE: PRT
<213> ORGANISM: Artificial Sequence
<220> FEATURE:
<223> OTHER INFORMATION: synthetic polypeptide

<400> SEQUENCE: 85

Met Asn Gly Asp Glu Thr Lys Lys Val Glu Ser Glu Tyr Ile Lys Lys
 1               5                  10                  15

His His Arg His Glu Leu Val Glu Ser Gln Cys Ser Ser Thr Leu Val
                20                  25                  30

Lys His Ile Lys Ala Pro Leu His Leu Val Trp Ser Ile Val Arg Arg
             35                  40                  45

Phe Asp Glu Pro Gln Lys Tyr Lys Pro Phe Ile Ser Arg Cys Val Val
 50                  55                  60

Gln Gly Lys Lys Leu Glu Val Gly Ser Val Arg Glu Val Asp Leu Lys
 65                  70                  75                  80

Ser Gly Leu Pro Ala Thr Lys Ser Thr Glu Val Leu Glu Ile Leu Asp
                 85                  90                  95

Asp Asn Glu His Ile Leu Gly Ile Arg Ile Val Gly Gly Asp His Arg
            100                 105                 110

Leu Lys Asn Tyr Ser Ser Thr Ile Ser Leu His Ser Glu Thr Ile Asp
            115                 120                 125

Gly Lys Thr Gly Thr Leu Ala Ile Glu Ser Phe Val Val Asp Val Pro
130                 135                 140

Glu Gly Asn Thr Lys Glu Glu Thr Cys Phe Phe Val Glu Ala Leu Ile
145                 150                 155                 160

Gln Cys Asn Leu Asn Ser Leu Ala Asp Val Thr Glu Arg Leu Gln Ala
                165                 170                 175

Glu Ser Met Glu Lys Lys Ile
            180

<210> SEQ ID NO 86
<211> LENGTH: 161
<212> TYPE: PRT
<213> ORGANISM: Artificial Sequence
<220> FEATURE:
<223> OTHER INFORMATION: synthetic polypeptide

<400> SEQUENCE: 86

Met Glu Thr Ser Gln Lys Tyr His Thr Cys Gly Ser Thr Leu Val Gln
 1               5                  10                  15

Thr Ile Asp Ala Pro Leu Ser Leu Val Trp Ser Ile Leu Arg Arg Phe
                20                  25                  30

Asp Asn Pro Gln Ala Tyr Lys Gln Phe Val Lys Thr Cys Asn Leu Ser
             35                  40                  45

Ser Gly Asp Gly Gly Glu Gly Ser Val Arg Glu Val Thr Val Val Ser
 50                  55                  60
```

```
Gly Leu Pro Ala Glu Phe Ser Arg Glu Arg Leu Asp Glu Leu Asp Asp
65                  70                  75                  80

Glu Ser His Val Met Met Ile Ser Ile Ile Gly Gly Asp His Arg Leu
                85                  90                  95

Val Asn Tyr Arg Ser Lys Thr Met Ala Phe Val Ala Asp Thr Glu
            100                 105                 110

Glu Lys Thr Val Val Val Glu Ser Tyr Val Val Asp Val Pro Glu Gly
            115                 120                 125

Asn Ser Glu Glu Glu Thr Thr Ser Phe Ala Asp Thr Ile Val Gly Phe
        130                 135                 140

Asn Leu Lys Ser Leu Ala Lys Leu Ser Glu Arg Val Ala His Leu Lys
145                 150                 155                 160

Leu

<210> SEQ ID NO 87
<211> LENGTH: 159
<212> TYPE: PRT
<213> ORGANISM: Artificial Sequence
<220> FEATURE:
<223> OTHER INFORMATION: synthetic polypeptide

<400> SEQUENCE: 87

Met Lys Thr Ser Gln Glu Gln His Val Cys Gly Ser Thr Val Val Gln
1               5                   10                  15

Thr Ile Asn Ala Pro Leu Pro Leu Val Trp Ser Ile Leu Arg Arg Phe
            20                  25                  30

Asp Asn Pro Lys Thr Phe Lys His Phe Val Lys Thr Cys Lys Leu Arg
        35                  40                  45

Ser Gly Asp Gly Gly Glu Gly Ser Val Arg Glu Val Thr Val Val Ser
    50                  55                  60

Asp Leu Pro Ala Ser Phe Ser Leu Glu Arg Leu Asp Glu Leu Asp Asp
65                  70                  75                  80

Glu Ser His Val Met Val Ile Ser Ile Ile Gly Gly Asp His Arg Leu
                85                  90                  95

Val Asn Tyr Gln Ser Lys Thr Thr Val Phe Val Ala Ala Glu Glu Glu
            100                 105                 110

Lys Thr Val Val Val Glu Ser Tyr Val Val Asp Val Pro Glu Gly Asn
            115                 120                 125

Thr Glu Glu Glu Thr Thr Leu Phe Ala Asp Thr Ile Val Gly Cys Asn
            130                 135                 140

Leu Arg Ser Leu Ala Lys Leu Ser Glu Lys Met Met Glu Leu Thr
145                 150                 155

<210> SEQ ID NO 88
<211> LENGTH: 164
<212> TYPE: PRT
<213> ORGANISM: Artificial Sequence
<220> FEATURE:
<223> OTHER INFORMATION: synthetic polypeptide

<400> SEQUENCE: 88

Met Glu Ser Ser Lys Gln Lys Arg Cys Arg Ser Ser Val Glu Thr
1               5                   10                  15

Ile Glu Ala Pro Leu Pro Leu Val Trp Ser Ile Leu Arg Ser Phe Asp
            20                  25                  30

Lys Pro Gln Ala Tyr Gln Arg Phe Val Lys Ser Cys Thr Met Arg Ser
        35                  40                  45
```

```
Gly Gly Gly Gly Gly Lys Gly Glu Gly Lys Gly Ser Val Arg Asp
            50                  55                  60
Val Thr Leu Val Ser Gly Phe Pro Ala Asp Phe Ser Thr Glu Arg Leu
 65                  70                  75                  80
Glu Glu Leu Asp Asp Glu Ser His Val Met Val Val Ser Ile Ile Gly
                 85                  90                  95
Gly Asn His Arg Leu Val Asn Tyr Lys Ser Lys Thr Lys Val Val Ala
                100                 105                 110
Ser Pro Glu Asp Met Ala Lys Lys Thr Val Val Glu Ser Tyr Val
             115                 120                 125
Val Asp Val Pro Glu Gly Thr Ser Glu Glu Asp Thr Ile Phe Phe Val
             130                 135                 140
Asp Asn Ile Ile Arg Tyr Asn Leu Thr Ser Leu Ala Lys Leu Thr Lys
145                 150                 155                 160
Lys Met Met Lys
```

<210> SEQ ID NO 89
<211> LENGTH: 221
<212> TYPE: PRT
<213> ORGANISM: Artificial Sequence
<220> FEATURE:
<223> OTHER INFORMATION: synthetic polypeptide

<400> SEQUENCE: 89

```
Met Ala Asn Ser Glu Ser Ser Ser Pro Val Asn Glu Glu Glu Asn
  1               5                  10                  15
Ser Gln Arg Ile Ser Thr Leu His His Gln Thr Met Pro Ser Asp Leu
                 20                  25                  30
Thr Gln Asp Glu Phe Thr Gln Leu Ser Gln Ser Ile Ala Glu Phe His
                 35                  40                  45
Thr Tyr Gln Leu Gly Asn Gly Arg Cys Ser Ser Leu Leu Ala Gln Arg
             50                  55                  60
Ile His Ala Pro Pro Glu Thr Val Trp Ser Val Val Arg Arg Phe Asp
 65                  70                  75                  80
Arg Pro Gln Ile Tyr Lys His Phe Ile Lys Ser Cys Asn Val Ser Glu
                 85                  90                  95
Asp Phe Glu Met Arg Val Gly Cys Thr Arg Asp Val Asn Val Ile Ser
                100                 105                 110
Gly Leu Pro Ala Asn Thr Ser Arg Glu Arg Leu Asp Leu Leu Asp Asp
             115                 120                 125
Asp Arg Arg Val Thr Gly Phe Ser Ile Thr Gly Gly Glu His Arg Leu
         130                 135                 140
Arg Asn Tyr Lys Ser Val Thr Thr Val His Arg Phe Glu Lys Glu Glu
145                 150                 155                 160
Glu Glu Glu Arg Ile Trp Thr Val Val Leu Glu Ser Tyr Val Val Asp
                165                 170                 175
Val Pro Glu Gly Asn Ser Glu Glu Asp Thr Arg Leu Phe Ala Asp Thr
             180                 185                 190
Val Ile Arg Leu Asn Leu Gln Lys Leu Ala Ser Ile Thr Glu Ala Met
         195                 200                 205
Asn Arg Asn Asn Asn Asn Asn Ser Ser Gln Val Arg
         210                 215                 220
```

<210> SEQ ID NO 90
<211> LENGTH: 190

```
<212> TYPE: PRT
<213> ORGANISM: Artificial Sequence
<220> FEATURE:
<223> OTHER INFORMATION: synthetic polypeptide

<400> SEQUENCE: 90

Met Ser Ser Ser Pro Ala Val Lys Gly Leu Thr Asp Glu Glu Gln Lys
1               5                   10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

His Phe Val Lys Arg Cys Arg Leu Ile Ser Gly Asp Gly Asp Val Gly
65                  70                  75                  80

Ser Val Arg Glu Val Thr Val Ile Ser Gly Leu Pro Ala Ser Thr Ser
                85                  90                  95

Thr Glu Arg Leu Glu Phe Val Asp Asp Asp His Arg Val Leu Ser Phe
            100                 105                 110

Arg Val Val Gly Gly Glu His Arg Leu Lys Asn Tyr Lys Ser Val Thr
        115                 120                 125

Ser Val Asn Glu Phe Leu Asn Gln Asp Ser Gly Lys Val Tyr Thr Val
    130                 135                 140

Val Leu Glu Ser Tyr Thr Val Asp Ile Pro Glu Gly Asn Thr Glu Glu
145                 150                 155                 160

Asp Thr Lys Met Phe Val Asp Thr Val Val Lys Leu Asn Leu Gln Lys
                165                 170                 175

Leu Gly Val Ala Ala Thr Ser Ala Pro Met His Asp Asp Glu
            180                 185                 190

<210> SEQ ID NO 91
<211> LENGTH: 209
<212> TYPE: PRT
<213> ORGANISM: Artificial Sequence
<220> FEATURE:
<223> OTHER INFORMATION: synthetic polypeptide

<400> SEQUENCE: 91

Met Asn Leu Ala Pro Ile His Asp Pro Ser Ser Ser Thr Thr Thr Thr
1               5                   10                  15

Thr Ser Ser Ser Thr Pro Tyr Gly Leu Thr Lys Asp Glu Phe Ser Thr
            20                  25                  30

Leu Asp Ser Ile Ile Arg Thr His His Thr Phe Pro Arg Ser Pro Asn
        35                  40                  45

Thr Cys Thr Ser Leu Ile Ala His Arg Val Asp Ala Pro Ala His Ala
    50                  55                  60

Ile Trp Arg Phe Val Arg Asp Phe Ala Asn Pro Asn Lys Tyr Lys His
65                  70                  75                  80

Phe Ile Lys Ser Cys Thr Ile Arg Val Asn Gly Asn Gly Ile Lys Glu
                85                  90                  95

Ile Lys Val Gly Thr Ile Arg Glu Val Ser Val Ser Gly Leu Pro
            100                 105                 110

Ala Ser Thr Ser Val Glu Ile Leu Glu Val Leu Asp Glu Glu Lys Arg
        115                 120                 125

Ile Leu Ser Phe Arg Val Leu Gly Gly Glu His Arg Leu Asn Asn Tyr
    130                 135                 140
```

```
Arg Ser Val Thr Ser Val Asn Glu Phe Val Val Leu Glu Lys Asp Lys
145                 150                 155                 160

Lys Lys Arg Val Tyr Ser Val Val Leu Glu Ser Tyr Ile Val Asp Ile
                165                 170                 175

Pro Gln Gly Asn Thr Glu Glu Asp Thr Arg Met Phe Val Asp Thr Val
            180                 185                 190

Val Lys Ser Asn Leu Gln Asn Leu Ala Val Ile Ser Thr Ala Ser Pro
        195                 200                 205

Thr
```

<210> SEQ ID NO 92
<211> LENGTH: 207
<212> TYPE: PRT
<213> ORGANISM: Artificial Sequence
<220> FEATURE:
<223> OTHER INFORMATION: synthetic polypeptide

<400> SEQUENCE: 92

```
Met Leu Ala Val His Arg Pro Ser Ser Ala Val Ser Asp Gly Asp Ser
1               5                   10                  15

Val Gln Ile Pro Met Met Ile Ala Ser Phe Gln Lys Arg Phe Pro Ser
            20                  25                  30

Leu Ser Arg Asp Ser Thr Ala Ala Arg Phe His Thr His Glu Val Gly
        35                  40                  45

Pro Asn Gln Cys Cys Ser Ala Val Ile Gln Glu Ile Ser Ala Pro Ile
    50                  55                  60

Ser Thr Val Trp Ser Val Val Arg Arg Phe Asp Asn Pro Gln Ala Tyr
65                  70                  75                  80

Lys His Phe Leu Lys Ser Cys Ser Val Ile Gly Gly Asp Gly Asp Asn
                85                  90                  95

Val Gly Ser Leu Arg Gln Val His Val Val Ser Gly Leu Pro Ala Ala
            100                 105                 110

Ser Ser Thr Glu Arg Leu Asp Ile Leu Asp Asp Glu Arg His Val Ile
        115                 120                 125

Ser Phe Ser Val Val Gly Gly Asp His Arg Leu Ser Asn Tyr Arg Ser
    130                 135                 140

Val Thr Thr Leu His Pro Ser Pro Ile Ser Gly Thr Val Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
            180                 185                 190

Ile Ala Glu Asn Thr Ala Ala Glu Ser Lys Lys Lys Met Ser Leu
        195                 200                 205
```

<210> SEQ ID NO 93
<211> LENGTH: 203
<212> TYPE: PRT
<213> ORGANISM: Artificial Sequence
<220> FEATURE:
<223> OTHER INFORMATION: synthetic polypeptide

<400> SEQUENCE: 93

```
Met Arg Ser Pro Val Gln Leu Gln His Gly Ser Asp Ala Thr Asn Gly
1               5                   10                  15

Phe His Thr Leu Gln Pro His Asp Gln Thr Asp Gly Pro Ile Lys Arg
            20                  25                  30
```

```
Val Cys Leu Thr Arg Gly Met His Val Pro Glu His Val Ala Met His
         35                  40                  45

His Thr His Asp Val Gly Pro Asp Gln Cys Cys Ser Ser Val Val Gln
 50                  55                  60

Met Ile His Ala Pro Pro Glu Ser Val Trp Ala Leu Val Arg Arg Phe
 65                  70                  75                  80

Asp Asn Pro Lys Val Tyr Lys Asn Phe Ile Arg Gln Cys Arg Ile Val
                 85                  90                  95

Gln Gly Asp Gly Leu His Val Gly Asp Leu Arg Glu Val Met Val Val
                100                 105                 110

Ser Gly Leu Pro Ala Val Ser Ser Thr Glu Arg Leu Glu Ile Leu Asp
            115                 120                 125

Glu Glu Arg His Val Ile Ser Phe Ser Val Val Gly Gly Asp His Arg
130                 135                 140

Leu Lys Asn Tyr Arg Ser Val Thr Thr Leu His Ala Ser Asp Asp Glu
145                 150                 155                 160

Gly Thr Val Val Val Glu Ser Tyr Ile Val Asp Val Pro Pro Gly Asn
                165                 170                 175

Thr Glu Glu Glu Thr Leu Ser Phe Val Asp Thr Ile Val Arg Cys Asn
            180                 185                 190

Leu Gln Ser Leu Ala Arg Ser Thr Asn Arg Gln
            195                 200

<210> SEQ ID NO 94
<211> LENGTH: 215
<212> TYPE: PRT
<213> ORGANISM: Artificial Sequence
<220> FEATURE:
<223> OTHER INFORMATION: synthetic polypeptide

<400> SEQUENCE: 94

Met Pro Thr Ser Ile Gln Phe Gln Arg Ser Ser Thr Ala Ala Glu Ala
 1               5                  10                  15

Ala Asn Ala Thr Val Arg Asn Tyr Pro His His His Gln Lys Gln Val
             20                  25                  30

Gln Lys Val Ser Leu Thr Arg Gly Met Ala Asp Val Pro Glu His Val
         35                  40                  45

Glu Leu Ser His Thr His Val Val Gly Pro Ser Gln Cys Phe Ser Val
 50                  55                  60

Val Val Gln Asp Val Glu Ala Pro Val Ser Thr Val Trp Ser Ile Leu
 65                  70                  75                  80

Ser Arg Phe Glu His Pro Gln Ala Tyr Lys His Phe Val Lys Ser Cys
                 85                  90                  95

His Val Val Ile Gly Asp Gly Arg Glu Val Gly Ser Val Arg Glu Val
                100                 105                 110

Arg Val Val Ser Gly Leu Pro Ala Ala Phe Ser Leu Glu Arg Leu Glu
            115                 120                 125

Ile Met Asp Asp Asp Arg His Val Ile Ser Phe Ser Val Val Gly Gly
130                 135                 140

Asp His Arg Leu Met Asn Tyr Lys Ser Val Thr Thr His Glu Ser
145                 150                 155                 160

Glu Glu Asp Ser Asp Gly Lys Lys Arg Thr Arg Val Val Glu Ser Tyr
                165                 170                 175

Val Val Asp Val Pro Ala Gly Asn Asp Lys Glu Glu Thr Cys Ser Phe
            180                 185                 190
```

```
Ala Asp Thr Ile Val Arg Cys Asn Leu Gln Ser Leu Ala Lys Leu Ala
        195                 200                 205

Glu Asn Thr Ser Lys Phe Ser
        210                 215

<210> SEQ ID NO 95
<211> LENGTH: 211
<212> TYPE: PRT
<213> ORGANISM: Artificial Sequence
<220> FEATURE:
<223> OTHER INFORMATION: synthetic polypeptide

<400> SEQUENCE: 95

Met Glu Met Ile Gly Gly Asp Asp Thr Asp Thr Glu Met Tyr Gly Ala
1               5                   10                  15

Leu Val Thr Ala Gln Ser Leu Arg Leu Arg His Leu His His Cys Arg
            20                  25                  30

Glu Asn Gln Cys Thr Ser Val Leu Val Lys Tyr Ile Gln Ala Pro Val
        35                  40                  45

His Leu Val Trp Ser Leu Val Arg Arg Phe Asp Gln Pro Gln Lys Tyr
    50                  55                  60

Lys Pro Phe Ile Ser Arg Cys Thr Val Asn Gly Asp Pro Glu Ile Gly
65                  70                  75                  80

Cys Leu Arg Glu Val Asn Val Lys Ser Gly Leu Pro Ala Thr Thr Ser
                85                  90                  95

Thr Glu Arg Leu Glu Gln Leu Asp Asp Glu His Ile Leu Gly Ile
            100                 105                 110

Asn Ile Ile Gly Gly Asp His Arg Leu Lys Asn Tyr Ser Ser Ile Leu
        115                 120                 125

Thr Val His Pro Glu Met Ile Asp Gly Arg Ser Gly Thr Met Val Met
    130                 135                 140

Glu Ser Phe Val Val Asp Val Pro Gln Gly Asn Thr Lys Asp Asp Thr
145                 150                 155                 160

Cys Tyr Phe Val Glu Ser Leu Ile Lys Cys Asn Leu Lys Ser Leu Ala
                165                 170                 175

Cys Val Ser Glu Arg Leu Ala Ala Gln Asp Ile Thr Asn Ser Ile Ala
            180                 185                 190

Thr Phe Cys Asn Ala Ser Asn Gly Tyr Arg Gly Lys Asn His Thr Glu
        195                 200                 205

Thr Asn Leu
    210

<210> SEQ ID NO 96
<211> LENGTH: 188
<212> TYPE: PRT
<213> ORGANISM: Artificial Sequence
<220> FEATURE:
<223> OTHER INFORMATION: synthetic polypeptide

<400> SEQUENCE: 96

Met Glu Ala Asn Gly Ile Glu Asn Leu Thr Asn Pro Asn Gln Glu Arg
1               5                   10                  15

Glu Phe Ile Arg Arg His His Lys His Glu Leu Val Asp Asn Gln Cys
            20                  25                  30

Ser Ser Thr Leu Val Lys His Ile Asn Ala Pro Val His Ile Val Trp
        35                  40                  45

Ser Leu Val Arg Arg Phe Asp Gln Pro Gln Lys Tyr Lys Pro Phe Ile
```

```
            50                  55                  60
Ser Arg Cys Val Val Lys Gly Asn Met Glu Ile Gly Thr Val Arg Glu
 65                  70                  75                  80

Val Asp Val Lys Ser Gly Leu Pro Ala Thr Arg Ser Thr Glu Arg Leu
                 85                  90                  95

Glu Leu Leu Asp Asp Asn Glu His Ile Leu Ser Ile Arg Ile Val Gly
             100                 105                 110

Gly Asp His Arg Leu Lys Asn Tyr Ser Ser Ile Ser Leu His Pro
         115                 120                 125

Glu Thr Ile Glu Gly Arg Ile Gly Thr Leu Val Ile Glu Ser Phe Val
     130                 135                 140

Val Asp Val Pro Glu Gly Asn Thr Lys Asp Glu Thr Cys Tyr Phe Val
145                 150                 155                 160

Glu Ala Leu Ile Lys Cys Asn Leu Lys Ser Leu Ala Asp Ile Ser Glu
                165                 170                 175

Arg Leu Ala Val Gln Asp Thr Thr Glu Ser Arg Val
            180                 185
```

<210> SEQ ID NO 97
<211> LENGTH: 187
<212> TYPE: PRT
<213> ORGANISM: Artificial Sequence
<220> FEATURE:
<223> OTHER INFORMATION: synthetic polypeptide

<400> SEQUENCE: 97

```
Met Met Asp Gly Val Glu Gly Gly Thr Ala Met Tyr Gly Gly Leu Glu
  1               5                  10                  15

Thr Val Gln Tyr Val Arg Thr His His Gln His Leu Cys Arg Glu Asn
                 20                  25                  30

Gln Cys Thr Ser Ala Leu Val Lys His Ile Lys Ala Pro Leu His Leu
             35                  40                  45

Val Trp Ser Leu Val Arg Arg Phe Asp Gln Pro Gln Lys Tyr Lys Pro
 50                  55                  60

Phe Val Ser Arg Cys Thr Val Ile Gly Asp Pro Glu Ile Gly Ser Leu
 65                  70                  75                  80

Arg Glu Val Asn Val Lys Ser Gly Leu Pro Ala Thr Thr Ser Thr Glu
                 85                  90                  95

Arg Leu Glu Leu Leu Asp Asp Glu Glu His Ile Leu Gly Ile Lys Ile
             100                 105                 110

Ile Gly Gly Asp His Arg Leu Lys Asn Tyr Ser Ser Ile Leu Thr Val
         115                 120                 125

His Pro Glu Ile Ile Glu Gly Arg Ala Gly Thr Met Val Ile Glu Ser
     130                 135                 140

Phe Val Val Asp Val Pro Gln Gly Asn Thr Lys Asp Glu Thr Cys Tyr
145                 150                 155                 160

Phe Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185
```

<210> SEQ ID NO 98
<211> LENGTH: 191
<212> TYPE: PRT
<213> ORGANISM: Artificial Sequence
<220> FEATURE:
<223> OTHER INFORMATION: synthetic polypeptide

<400> SEQUENCE: 98

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 99
<211> LENGTH: 434
<212> TYPE: PRT
<213> ORGANISM: Artificial Sequence
<220> FEATURE:
<223> OTHER INFORMATION: synthetic polypeptide

<400> SEQUENCE: 99

Met Glu Glu Val Ser Pro Ala Ile Ala Gly Pro Phe Arg Pro Phe Ser
1               5                   10                  15

Glu Thr Gln Met Asp Phe Thr Gly Ile Arg Leu Gly Lys Gly Tyr Cys
            20                  25                  30

Asn Asn Gln Tyr Ser Asn Gln Asp Ser Glu Asn Gly Asp Leu Met Val
        35                  40                  45

Ser Leu Pro Glu Thr Ser Ser Cys Ser Val Ser Gly Ser His Gly Ser
    50                  55                  60

Glu Ser Arg Lys Val Leu Ile Ser Arg Ile Asn Ser Pro Asn Leu Asn
65                  70                  75                  80

Met Lys Glu Ser Ala Ala Ala Asp Ile Val Val Asp Ile Ser Ala
                85                  90                  95

Gly Asp Glu Ile Asn Gly Ser Asp Ile Thr Ser Glu Lys Lys Met Ile
            100                 105                 110

Ser Arg Thr Glu Ser Arg Ser Leu Phe Glu Phe Lys Ser Val Pro Leu
        115                 120                 125

Tyr Gly Phe Thr Ser Ile Cys Gly Arg Arg Pro Glu Met Glu Asp Ala
    130                 135                 140

Val Ser Thr Ile Pro Arg Phe Leu Gln Ser Ser Gly Ser Met Leu
145                 150                 155                 160

```
Asp Gly Arg Phe Asp Pro Gln Ser Ala Ala His Phe Gly Val Tyr
                165                 170                 175

Asp Gly His Gly Gly Ser Gln Val Ala Asn Tyr Cys Arg Glu Arg Met
            180                 185                 190

His Leu Ala Leu Ala Glu Glu Ile Ala Lys Glu Lys Pro Met Leu Cys
        195                 200                 205

Asp Gly Asp Thr Trp Leu Glu Lys Trp Lys Ala Leu Phe Asn Ser
    210                 215                 220

Phe Leu Arg Val Asp Ser Glu Ile Glu Ser Val Ala Pro Glu Thr Val
225                 230                 235                 240

Gly Ser Thr Ser Val Val Ala Val Val Phe Pro Ser His Ile Phe Val
                245                 250                 255

Ala Asn Cys Gly Asp Ser Arg Ala Val Leu Cys Arg Gly Lys Thr Ala
            260                 265                 270

Leu Pro Leu Ser Val Asp His Lys Pro Asp Arg Glu Asp Glu Ala Ala
        275                 280                 285

Arg Ile Glu Ala Ala Gly Gly Lys Val Ile Gln Trp Asn Gly Ala Arg
    290                 295                 300

Val Phe Gly Val Leu Ala Met Ser Arg Ser Ile Gly Asp Arg Tyr Leu
305                 310                 315                 320

Lys Pro Ser Ile Ile Pro Asp Pro Glu Val Thr Ala Val Lys Arg Val
                325                 330                 335

Lys Glu Asp Asp Cys Leu Ile Leu Ala Ser Asp Gly Val Trp Asp Val
            340                 345                 350

Met Thr Asp Glu Glu Ala Cys Glu Met Ala Arg Lys Arg Ile Leu Leu
        355                 360                 365

Trp His Lys Lys Asn Ala Val Ala Gly Asp Ala Ser Leu Leu Ala Asp
    370                 375                 380

Glu Arg Arg Lys Glu Gly Lys Asp Pro Ala Ala Met Ser Ala Ala Glu
385                 390                 395                 400

Tyr Leu Ser Lys Leu Ala Ile Gln Arg Gly Ser Lys Asp Asn Ile Ser
                405                 410                 415

Val Val Val Val Asp Leu Lys Pro Arg Arg Lys Leu Lys Ser Lys Pro
            420                 425                 430

Leu Asn
```

<210> SEQ ID NO 100
<211> LENGTH: 423
<212> TYPE: PRT
<213> ORGANISM: Artificial Sequence
<220> FEATURE:
<223> OTHER INFORMATION: synthetic polypeptide

<400> SEQUENCE: 100

```
Met Asp Glu Val Ser Pro Ala Val Ala Val Pro Phe Arg Pro Phe Thr
1               5                   10                  15

Asp Pro His Ala Gly Leu Arg Gly Tyr Cys Asn Gly Glu Ser Arg Val
            20                  25                  30

Thr Leu Pro Glu Ser Ser Cys Ser Gly Asp Gly Ala Met Lys Asp Ser
        35                  40                  45

Ser Phe Glu Ile Asn Thr Arg Gln Asp Ser Leu Thr Ser Ser Ser Ser
    50                  55                  60

Ala Met Ala Gly Val Asp Ile Ser Ala Gly Asp Glu Ile Asn Gly Ser
65                  70                  75                  80

Asp Glu Phe Asp Pro Arg Ser Met Asn Gln Ser Glu Lys Lys Val Leu
```

```
                85                  90                  95
Ser Arg Thr Glu Ser Arg Ser Leu Phe Glu Phe Lys Cys Val Pro Leu
                100                 105                 110

Tyr Gly Val Thr Ser Ile Cys Gly Arg Arg Pro Glu Met Glu Asp Ser
                115                 120                 125

Val Ser Thr Ile Pro Arg Phe Leu Gln Val Ser Ser Ser Leu Leu
130                 135                 140

Asp Gly Arg Val Thr Asn Gly Phe Asn Pro His Leu Ser Ala His Phe
145                 150                 155                 160

Phe Gly Val Tyr Asp Gly His Gly Gly Ser Gln Val Ala Asn Tyr Cys
                165                 170                 175

Arg Glu Arg Met His Leu Ala Leu Thr Glu Glu Ile Val Lys Glu Lys
                180                 185                 190

Pro Glu Phe Cys Asp Gly Asp Thr Trp Gln Glu Lys Trp Lys Lys Ala
                195                 200                 205

Leu Phe Asn Ser Phe Met Arg Val Asp Ser Glu Ile Glu Thr Val Ala
210                 215                 220

His Ala Pro Glu Thr Val Gly Ser Thr Ser Val Val Ala Val Val Phe
225                 230                 235                 240

Pro Thr His Ile Phe Val Ala Asn Cys Gly Asp Ser Arg Ala Val Leu
                245                 250                 255

Cys Arg Gly Lys Thr Pro Leu Ala Leu Ser Val Asp His Lys Pro Asp
                260                 265                 270

Arg Asp Asp Glu Ala Ala Arg Ile Glu Ala Ala Gly Gly Lys Val Ile
                275                 280                 285

Arg Trp Asn Gly Ala Arg Val Phe Gly Val Leu Ala Met Ser Arg Ser
                290                 295                 300

Ile Gly Asp Arg Tyr Leu Lys Pro Ser Val Ile Pro Asp Pro Glu Val
305                 310                 315                 320

Thr Ser Val Arg Arg Val Lys Glu Asp Asp Cys Leu Ile Leu Ala Ser
                325                 330                 335

Asp Gly Leu Trp Asp Val Met Thr Asn Glu Glu Val Cys Asp Leu Ala
                340                 345                 350

Arg Lys Arg Ile Leu Leu Trp His Lys Lys Asn Ala Met Ala Gly Glu
                355                 360                 365

Ala Leu Leu Pro Ala Glu Lys Arg Gly Glu Gly Lys Asp Pro Ala Ala
370                 375                 380

Met Ser Ala Ala Glu Tyr Leu Ser Lys Met Ala Leu Gln Lys Gly Ser
385                 390                 395                 400

Lys Asp Asn Ile Ser Val Val Val Asp Leu Lys Gly Ile Arg Lys
                405                 410                 415

Phe Lys Ser Lys Ser Leu Asn
                420

<210> SEQ ID NO 101
<211> LENGTH: 612
<212> TYPE: PRT
<213> ORGANISM: Artificial Sequence
<220> FEATURE:
<223> OTHER INFORMATION: synthetic polypeptide

<400> SEQUENCE: 101

Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
```

-continued

```
                20                  25                  30
Phe Pro Val Phe Ile Trp Cys Pro Glu Glu Gly Gln Phe Tyr Pro
            35                  40                  45
Gly Arg Ala Ser Arg Trp Trp Met Lys Gln Ser Leu Ala His Leu Ser
50                  55                  60
Gln Ser Leu Lys Ala Leu Gly Ser Asp Leu Thr Leu Ile Lys Thr His
65                  70                  75                  80
Asn Thr Ile Ser Ala Ile Leu Asp Cys Ile Arg Val Thr Gly Ala Thr
                85                  90                  95
Lys Val Val Phe Asn His Leu Tyr Asp Pro Val Ser Leu Val Arg Asp
                100                 105                 110
His Thr Val Lys Glu Lys Leu Val Glu Arg Gly Ile Ser Val Gln Ser
            115                 120                 125
Tyr Asn Gly Asp Leu Leu Tyr Glu Pro Trp Glu Ile Tyr Cys Glu Lys
        130                 135                 140
Gly Lys Pro Phe Thr Ser Phe Asn Ser Tyr Trp Lys Lys Cys Leu Asp
145                 150                 155                 160
Met Ser Ile Glu Ser Val Met Leu Pro Pro Pro Trp Arg Leu Met Pro
                165                 170                 175
Ile Thr Ala Ala Ala Glu Ala Ile Trp Ala Cys Ser Ile Glu Glu Leu
                180                 185                 190
Gly Leu Glu Asn Glu Ala Glu Lys Pro Ser Asn Ala Leu Leu Thr Arg
            195                 200                 205
Ala Trp Ser Pro Gly Trp Ser Asn Ala Asp Lys Leu Leu Asn Glu Phe
        210                 215                 220
Ile Glu Lys Gln Leu Ile Asp Tyr Ala Lys Asn Ser Lys Lys Val Val
225                 230                 235                 240
Gly Asn Ser Thr Ser Leu Leu Ser Pro Tyr Leu His Phe Gly Glu Ile
                245                 250                 255
Ser Val Arg His Val Phe Gln Cys Ala Arg Met Lys Gln Ile Ile Trp
                260                 265                 270
Ala Arg Asp Lys Asn Ser Glu Gly Glu Glu Ser Ala Asp Leu Phe Leu
            275                 280                 285
Arg Gly Ile Gly Leu Arg Glu Tyr Ser Arg Tyr Ile Cys Phe Asn Phe
        290                 295                 300
Pro Phe Thr His Glu Gln Ser Leu Leu Ser His Leu Arg Phe Phe Pro
305                 310                 315                 320
Trp Asp Ala Asp Val Asp Lys Phe Lys Ala Trp Arg Gln Gly Arg Thr
                325                 330                 335
Gly Tyr Pro Leu Val Asp Ala Gly Met Arg Glu Leu Trp Ala Thr Gly
            340                 345                 350
Trp Met His Asn Arg Ile Arg Val Ile Val Ser Ser Phe Ala Val Lys
        355                 360                 365
Phe Leu Leu Leu Pro Trp Lys Trp Gly Met Lys Tyr Phe Trp Asp Thr
        370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
            420                 425                 430
Trp Leu Pro Glu Leu Ala Arg Leu Pro Thr Glu Trp Ile His His Pro
        435                 440                 445
```

Trp Asp Ala Pro Leu Thr Val Leu Lys Ala Ser Gly Val Glu Leu Gly
        450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Pro Asp Glu Ile Val Ala Asp Ser Phe Glu Ala Leu Gly Ala
                500                 505                 510

Asn Thr Ile Lys Glu Pro Gly Leu Cys Pro Ser Val Ser Ser Asn Asp
            515                 520                 525

Gln Gln Val Pro Ser Ala Val Arg Tyr Asn Gly Ser Lys Arg Val Lys
530                 535                 540

Pro Glu Glu Glu Glu Arg Asp Met Lys Lys Ser Arg Gly Phe Asp
545                 550                 555                 560

Glu Arg Glu Leu Phe Ser Thr Ala Glu Ser Ser Ser Ser Ser Val
                565                 570                 575

Phe Phe Val Ser Gln Ser Cys Ser Leu Ala Ser Glu Gly Lys Asn Leu
                580                 585                 590

Glu Gly Ile Gln Asp Ser Ser Asp Gln Ile Thr Thr Ser Leu Gly Lys
            595                 600                 605

Asn Gly Cys Lys
        610

<210> SEQ ID NO 102
<211> LENGTH: 335
<212> TYPE: PRT
<213> ORGANISM: Artificial Sequence
<220> FEATURE:
<223> OTHER INFORMATION: synthetic polypeptide

<400> SEQUENCE: 102

Met Asn Gly Ala Ile Gly Gly Asp Leu Leu Asn Phe Pro Asp Met
1               5                   10                  15

Ser Val Leu Glu Arg Gln Arg Ala His Leu Lys Tyr Leu Asn Pro Thr
            20                  25                  30

Phe Asp Ser Pro Leu Ala Gly Phe Phe Ala Asp Ser Ser Met Ile Thr
        35                  40                  45

Gly Gly Glu Met Asp Ser Tyr Leu Ser Thr Ala Gly Leu Asn Leu Pro
    50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Lys Arg Lys Phe
                85                  90                  95

Asp Thr Glu Thr Lys Asp Cys Asn Glu Lys Lys Lys Met Thr Met
            100                 105                 110

Asn Arg Asp Asp Leu Val Glu Glu Gly Glu Glu Glu Lys Ser Lys Ile
        115                 120                 125

Thr Glu Gln Asn Asn Gly Ser Thr Lys Ser Ile Lys Lys Met Lys His
    130                 135                 140

Lys Ala Lys Lys Glu Glu Asn Asn Phe Ser Asn Asp Ser Ser Lys Val
145                 150                 155                 160

Thr Lys Glu Leu Glu Lys Thr Asp Tyr Ile His Val Arg Ala Arg Arg
                165                 170                 175

Gly Gln Ala Thr Asp Ser His Ser Ile Ala Glu Arg Val Arg Arg Glu
            180                 185                 190

```
Lys Ile Ser Glu Arg Met Lys Phe Leu Gln Asp Leu Val Pro Gly Cys
        195                 200                 205

Asp Lys Ile Thr Gly Lys Ala Gly Met Leu Asp Glu Ile Ile Asn Tyr
    210                 215                 220

Val Gln Ser Leu Gln Arg Gln Ile Glu Phe Leu Ser Met Lys Leu Ala
225                 230                 235                 240

Ile Val Asn Pro Arg Pro Asp Phe Asp Met Asp Asp Ile Phe Ala Lys
                245                 250                 255

Glu Val Ala Ser Thr Pro Met Thr Val Val Pro Ser Pro Glu Met Val
                260                 265                 270

Leu Ser Gly Tyr Ser His Glu Met Val His Ser Gly Tyr Ser Ser Glu
            275                 280                 285

Met Val Asn Ser Gly Tyr Leu His Val Asn Pro Met Gln Gln Val Asn
    290                 295                 300

Thr Ser Ser Asp Pro Leu Ser Cys Phe Asn Asn Gly Glu Ala Pro Ser
305                 310                 315                 320

Met Trp Asp Ser His Val Gln Asn Leu Tyr Gly Asn Leu Gly Val
                325                 330                 335

<210> SEQ ID NO 103
<211> LENGTH: 533
<212> TYPE: PRT
<213> ORGANISM: Artificial Sequence
<220> FEATURE:
<223> OTHER INFORMATION: synthetic polypeptide

<400> SEQUENCE: 103

Met Lys Arg Asp His His His His His Gln Asp Lys Lys Thr Met
1               5                   10                  15

Met Met Asn Glu Glu Asp Gly Asn Gly Met Asp Glu Leu Leu Ala
                20                  25                  30

Val Leu Gly Tyr Lys Val Arg Ser Ser Glu Met Ala Asp Val Ala Gln
            35                  40                  45

Lys Leu Glu Gln Leu Glu Val Met Met Ser Asn Val Gln Glu Asp Asp
    50                  55                  60

Leu Ser Gln Leu Ala Thr Glu Thr Val His Tyr Asn Pro Ala Glu Leu
65                  70                  75                  80

Tyr Thr Trp Leu Asp Ser Met Leu Thr Asp Leu Asn Pro Pro Ser Ser
                85                  90                  95

Asn Ala Glu Tyr Asp Leu Lys Ala Ile Pro Gly Asp Ala Ile Leu Asn
                100                 105                 110

Gln Phe Ala Ile Asp Ser Ala Ser Ser Asn Gln Gly Gly Gly Gly
            115                 120                 125

Asp Thr Tyr Thr Thr Asn Lys Arg Leu Lys Cys Ser Asn Gly Val Val
    130                 135                 140

Glu Thr Thr Thr Ala Thr Ala Glu Ser Thr Arg His Val Val Leu Val
145                 150                 155                 160

Asp Ser Gln Glu Asn Gly Val Arg Leu Val His Ala Leu Leu Ala Cys
                165                 170                 175

Ala Glu Ala Val Gln Lys Glu Asn Leu Thr Val Ala Glu Ala Leu Val
                180                 185                 190

Lys Gln Ile Gly Phe Leu Ala Val Ser Gln Ile Gly Ala Met Arg Lys
            195                 200                 205

Val Ala Thr Tyr Phe Ala Glu Ala Leu Ala Arg Arg Ile Tyr Arg Leu
    210                 215                 220
```

```
Ser Pro Ser Gln Ser Pro Ile Asp His Ser Leu Ser Asp Thr Leu Gln
225                 230                 235                 240

Met His Phe Tyr Glu Thr Cys Pro Tyr Leu Lys Phe Ala His Phe Thr
            245                 250                 255

Ala Asn Gln Ala Ile Leu Glu Ala Phe Gln Gly Lys Lys Arg Val His
        260                 265                 270

Val Ile Asp Phe Ser Met Ser Gln Gly Leu Gln Trp Pro Ala Leu Met
    275                 280                 285

Gln Ala Leu Ala Leu Arg Pro Gly Pro Val Phe Arg Leu Thr
290                 295                 300

Gly Ile Gly Pro Pro Ala Pro Asp Asn Phe Asp Tyr Leu His Glu Val
305                 310                 315                 320

Gly Cys Lys Leu Ala His Leu Ala Glu Ala Ile His Val Glu Phe Glu
            325                 330                 335

Tyr Arg Gly Phe Val Ala Asn Thr Leu Ala Asp Leu Asp Ala Ser Met
        340                 345                 350

Leu Glu Leu Arg Pro Ser Glu Ile Glu Ser Val Ala Val Asn Ser Val
    355                 360                 365

Phe Glu Leu His Lys Leu Leu Gly Arg Pro Gly Ala Ile Asp Lys Val
370                 375                 380

Leu Gly Val Val Asn Gln Ile Lys Pro Glu Ile Phe Thr Val Glu
385                 390                 395                 400

Gln Glu Ser Asn His Asn Ser Pro Ile Phe Leu Asp Arg Phe Thr Glu
            405                 410                 415

Ser Leu His Tyr Tyr Ser Thr Leu Phe Asp Ser Leu Glu Gly Val Pro
        420                 425                 430

Ser Gly Gln Asp Lys Val Met Ser Glu Val Tyr Leu Gly Lys Gln Ile
    435                 440                 445

Cys Asn Val Val Ala Cys Asp Gly Pro Asp Arg Val Glu Arg His Glu
450                 455                 460

Thr Leu Ser Gln Trp Arg Asn Arg Phe Gly Ser Ala Gly Phe Ala Ala
465                 470                 475                 480

Ala His Ile Gly Ser Asn Ala Phe Lys Gln Ala Ser Met Leu Leu Ala
            485                 490                 495

Leu Phe Asn Gly Gly Glu Gly Tyr Arg Val Glu Glu Ser Asp Gly Cys
        500                 505                 510

Leu Met Leu Gly Trp His Thr Arg Pro Leu Ile Ala Thr Ser Ala Trp
    515                 520                 525

Lys Leu Ser Thr Asn
        530

<210> SEQ ID NO 104
<211> LENGTH: 345
<212> TYPE: PRT
<213> ORGANISM: Artificial Sequence
<220> FEATURE:
<223> OTHER INFORMATION: synthetic polypeptide

<400> SEQUENCE: 104

Met Ala Ala Ser Asp Glu Val Asn Leu Ile Glu Ser Arg Thr Val Val
1               5                   10                  15

Pro Leu Asn Thr Trp Val Leu Ile Ser Asn Phe Lys Val Ala Tyr Asn
            20                  25                  30

Ile Leu Arg Arg Pro Asp Gly Thr Phe Asn Arg His Leu Ala Glu Tyr
        35                  40                  45
```

-continued

Leu Asp Arg Lys Val Thr Ala Asn Ala Asn Pro Val Asp Gly Val Phe
 50                  55                  60

Ser Phe Asp Val Leu Ile Asp Arg Arg Ile Asn Leu Leu Ser Arg Val
 65                  70                  75                  80

Tyr Arg Pro Ala Tyr Ala Asp Gln Glu Gln Pro Pro Ser Ile Leu Asp
                 85                  90                  95

Leu Glu Lys Pro Val Asp Gly Asp Ile Val Pro Val Ile Leu Phe Phe
            100                 105                 110

His Gly Gly Ser Phe Ala His Ser Ser Ala Asn Ser Ala Ile Tyr Asp
            115                 120                 125

Thr Leu Cys Arg Arg Leu Val Gly Leu Cys Lys Cys Val Val Val Ser
130                 135                 140

Val Asn Tyr Arg Arg Ala Pro Glu Asn Pro Tyr Pro Cys Ala Tyr Asp
145                 150                 155                 160

Asp Gly Trp Ile Ala Leu Asn Trp Val Asn Ser Arg Ser Trp Leu Lys
                165                 170                 175

Ser Lys Lys Asp Ser Lys Val His Ile Phe Leu Ala Gly Asp Ser Ser
            180                 185                 190

Gly Gly Asn Ile Ala His Asn Val Ala Leu Arg Ala Gly Glu Ser Gly
            195                 200                 205

Ile Asp Val Leu Gly Asn Ile Leu Leu Asn Pro Met Phe Gly Gly Asn
210                 215                 220

Glu Arg Thr Glu Ser Glu Lys Ser Leu Asp Gly Lys Tyr Phe Val Thr
225                 230                 235                 240

Val Arg Asp Arg Asp Trp Tyr Trp Lys Ala Phe Leu Pro Glu Gly Glu
                245                 250                 255

Asp Arg Glu His Pro Ala Cys Asn Pro Phe Ser Pro Arg Gly Lys Ser
            260                 265                 270

Leu Glu Gly Val Ser Phe Pro Lys Ser Leu Val Val Ala Gly Leu
            275                 280                 285

Asp Leu Ile Arg Asp Trp Gln Leu Ala Tyr Ala Glu Gly Leu Lys Lys
290                 295                 300

Ala Gly Gln Glu Val Lys Leu Met His Leu Glu Lys Ala Thr Val Gly
305                 310                 315                 320

Phe Tyr Leu Leu Pro Asn Asn Asn His Phe His Asn Val Met Asp Glu
                325                 330                 335

Ile Ser Ala Phe Val Asn Ala Glu Cys
            340                 345

<210> SEQ ID NO 105
<211> LENGTH: 358
<212> TYPE: PRT
<213> ORGANISM: Artificial Sequence
<220> FEATURE:
<223> OTHER INFORMATION: synthetic polypeptide

<400> SEQUENCE: 105

Met Ala Gly Gly Asn Glu Val Asn Leu Asn Glu Cys Lys Arg Ile Val
 1               5                  10                  15

Pro Leu Asn Thr Trp Val Leu Ile Ser Asn Phe Lys Leu Ala Tyr Lys
                20                  25                  30

Val Leu Arg Arg Pro Asp Gly Ser Phe Asn Arg Asp Leu Ala Glu Phe
             35                  40                  45

Leu Asp Arg Lys Val Pro Ala Asn Ser Phe Pro Leu Asp Gly Val Phe
 50                  55                  60

```
Ser Phe Asp His Val Asp Ser Thr Thr Asn Leu Leu Thr Arg Ile Tyr
 65                  70                  75                  80

Gln Pro Ala Ser Leu Leu His Gln Thr Arg His Gly Thr Leu Glu Leu
                 85                  90                  95

Thr Lys Pro Leu Ser Thr Thr Glu Ile Val Pro Val Leu Ile Phe Phe
            100                 105                 110

His Gly Gly Ser Phe Thr His Ser Ser Ala Asn Ser Ala Ile Tyr Asp
            115                 120                 125

Thr Phe Cys Arg Arg Leu Val Thr Ile Cys Gly Val Val Val Val Ser
130                 135                 140

Val Asp Tyr Arg Arg Ser Pro Glu His Arg Tyr Pro Cys Ala Tyr Asp
145                 150                 155                 160

Asp Gly Trp Asn Ala Leu Asn Trp Val Lys Ser Arg Val Trp Leu Gln
                165                 170                 175

Ser Gly Lys Asp Ser Asn Val Tyr Val Tyr Leu Ala Gly Asp Ser Ser
            180                 185                 190

Gly Gly Asn Ile Ala His Asn Val Ala Val Arg Ala Thr Asn Glu Gly
        195                 200                 205

Val Lys Val Leu Gly Asn Ile Leu Leu His Pro Met Phe Gly Gly Gln
210                 215                 220

Glu Arg Thr Gln Ser Glu Lys Thr Leu Asp Gly Lys Tyr Phe Val Thr
225                 230                 235                 240

Ile Gln Asp Arg Asp Trp Tyr Trp Arg Ala Tyr Leu Pro Glu Gly Glu
                245                 250                 255

Asp Arg Asp His Pro Ala Cys Asn Pro Phe Gly Pro Arg Gly Gln Ser
            260                 265                 270

Leu Lys Gly Val Asn Phe Pro Lys Ser Leu Val Val Val Ala Gly Leu
        275                 280                 285

Asp Leu Val Gln Asp Trp Gln Leu Ala Tyr Val Asp Gly Leu Lys Lys
290                 295                 300

Thr Gly Leu Glu Val Asn Leu Leu Tyr Leu Lys Gln Ala Thr Ile Gly
305                 310                 315                 320

Phe Tyr Phe Leu Pro Asn Asn Asp His Phe His Cys Leu Met Glu Glu
                325                 330                 335

Leu Asn Lys Phe Val His Ser Ile Glu Asp Ser Gln Ser Lys Ser Ser
            340                 345                 350

Pro Val Leu Leu Thr Pro
        355

<210> SEQ ID NO 106
<211> LENGTH: 344
<212> TYPE: PRT
<213> ORGANISM: Artificial Sequence
<220> FEATURE:
<223> OTHER INFORMATION: synthetic polypeptide

<400> SEQUENCE: 106

Met Ala Gly Ser Glu Glu Val Asn Leu Ile Glu Ser Lys Thr Val Val
 1               5                  10                  15

Pro Leu Asn Thr Trp Val Leu Ile Ser Asn Phe Lys Leu Ala Tyr Asn
             20                  25                  30

Leu Leu Arg Arg Pro Asp Gly Thr Phe Asn Arg His Leu Ala Glu Phe
         35                  40                  45

Leu Asp Arg Lys Val Pro Ala Asn Ala Asn Pro Val Asn Gly Val Phe
 50                  55                  60
```

```
Ser Phe Asp Val Ile Ile Asp Arg Gln Thr Asn Leu Leu Ser Arg Val
 65                  70                  75                  80

Tyr Arg Pro Ala Asp Ala Gly Thr Ser Pro Ser Ile Thr Asp Leu Gln
                 85                  90                  95

Asn Pro Val Asp Gly Glu Ile Val Pro Val Ile Val Phe Phe His Gly
            100                 105                 110

Gly Ser Phe Ala His Ser Ser Ala Asn Ser Ala Ile Tyr Asp Thr Leu
        115                 120                 125

Cys Arg Arg Leu Val Gly Leu Cys Gly Ala Val Val Ser Val Asn
130                 135                 140

Tyr Arg Arg Ala Pro Glu Asn Arg Tyr Pro Cys Ala Tyr Asp Asp Gly
145                 150                 155                 160

Trp Ala Val Leu Lys Trp Val Asn Ser Ser Trp Leu Arg Ser Lys
                165                 170                 175

Lys Asp Ser Lys Val Arg Ile Phe Leu Ala Gly Asp Ser Ser Gly Gly
            180                 185                 190

Asn Ile Val His Asn Val Ala Val Arg Ala Val Glu Ser Arg Ile Asp
            195                 200                 205

Val Leu Gly Asn Ile Leu Leu Asn Pro Met Phe Gly Gly Thr Glu Arg
210                 215                 220

Thr Glu Ser Glu Lys Arg Leu Asp Gly Lys Tyr Phe Val Thr Val Arg
225                 230                 235                 240

Asp Arg Asp Trp Tyr Trp Arg Ala Phe Leu Pro Gly Glu Asp Arg
                245                 250                 255

Glu His Pro Ala Cys Ser Pro Phe Gly Pro Arg Ser Lys Ser Leu Glu
            260                 265                 270

Gly Leu Ser Phe Pro Lys Ser Leu Val Val Ala Gly Leu Asp Leu
            275                 280                 285

Ile Gln Asp Trp Gln Leu Lys Tyr Ala Glu Gly Leu Lys Lys Ala Gly
290                 295                 300

Gln Glu Val Lys Leu Leu Tyr Leu Glu Gln Ala Thr Ile Gly Phe Tyr
305                 310                 315                 320

Leu Leu Pro Asn Asn His Phe His Thr Val Met Asp Glu Ile Ala
                325                 330                 335

Ala Phe Val Asn Ala Glu Cys Gln
            340

<210> SEQ ID NO 107
<211> LENGTH: 113
<212> TYPE: PRT
<213> ORGANISM: Artificial Sequence
<220> FEATURE:
<223> OTHER INFORMATION: synthetic polypeptide

<400> SEQUENCE: 107

Met Gly Gly Leu Glu Pro Cys Ser Arg Leu Leu Leu Leu Pro Leu Leu
 1               5                  10                  15

Leu Ala Val Ser Gly Leu Arg Pro Val Gln Ala Gln Ala Gln Ser Asp
                20                  25                  30

Cys Ser Cys Ser Thr Val Ser Pro Gly Val Leu Ala Gly Ile Val Met
            35                  40                  45

Gly Asp Leu Val Leu Thr Val Leu Ile Ala Leu Ala Val Tyr Phe Leu
        50                  55                  60

Gly Arg Leu Val Pro Arg Gly Arg Gly Ala Ala Glu Ala Ala Thr Arg
 65                  70                  75                  80
```

```
Lys Gln Arg Ile Thr Glu Thr Glu Ser Pro Tyr Gln Leu Gln Gly
                85                  90                  95

Gln Arg Ser Asp Val Tyr Ser Asp Leu Asn Thr Gln Arg Pro Tyr Tyr
            100                 105                 110

Lys

<210> SEQ ID NO 108
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 108

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Thr Arg Lys
65                  70                  75                  80

Gln Arg Ile Thr Glu Thr Glu Ser Pro Tyr Gln Glu Leu Gln Gly Gln
                85                  90                  95

Arg Ser Asp Val Tyr Ser Asp Leu Asn Thr Gln Arg Pro Tyr Tyr Lys
            100                 105                 110

<210> SEQ ID NO 109
<211> LENGTH: 102
<212> TYPE: PRT
<213> ORGANISM: Artificial Sequence
<220> FEATURE:
<223> OTHER INFORMATION: synthetic polypeptide

<400> SEQUENCE: 109

Met Gly Gly Leu Glu Pro Cys Ser Arg Leu Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Ala Thr Arg Lys Gln Arg Ile Thr Glu Thr Glu Ser Pro Tyr
65                  70                  75                  80

Gln Glu Leu Gln Gly Gln Arg Ser Asp Val Tyr Ser Asp Leu Asn Thr
                85                  90                  95

Gln Arg Pro Tyr Tyr Lys
            100

<210> SEQ ID NO 110
<211> LENGTH: 101
<212> TYPE: PRT
<213> ORGANISM: Artificial Sequence
<220> FEATURE:
<223> OTHER INFORMATION: synthetic polypeptide
```

```
<400> SEQUENCE: 110

Met Gly Gly Leu Glu Pro Cys Ser Arg Leu Leu Leu Pro Leu Leu
1               5                   10                  15

Leu Ala Val Ser Asp Cys Ser Cys Ser Thr Val Ser Pro Gly Val Leu
                20                  25                  30

Ala Gly Ile Val Met Gly Asp Leu Val Leu Thr Val Leu Ile Ala Leu
            35                  40                  45

Ala Val Tyr Phe Leu Gly Arg Leu Val Pro Arg Gly Arg Gly Ala Ala
        50                  55                  60

Glu Ala Thr Arg Lys Gln Arg Ile Thr Glu Thr Glu Ser Pro Tyr Gln
65                  70                  75                  80

Glu Leu Gln Gly Gln Arg Ser Asp Val Tyr Ser Asp Leu Asn Thr Gln
                85                  90                  95

Arg Pro Tyr Tyr Lys
            100

<210> SEQ ID NO 111
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 111

Glu Ser Pro Tyr Gln Glu Leu Gln Gly Gln Arg Ser Asp Val Tyr Ser
1               5                   10                  15

Asp Leu Asn Thr Gln
            20

<210> SEQ ID NO 112
<211> LENGTH: 86
<212> TYPE: PRT
<213> ORGANISM: Artificial Sequence
<220> FEATURE:
<223> OTHER INFORMATION: synthetic polypeptide

<400> SEQUENCE: 112

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
                20                  25                  30

Phe Leu Tyr Gly Ile Val Leu Thr Leu Leu Tyr Cys Arg Leu Lys Ile
            35                  40                  45

Gln Val Arg Lys Ala Ala Ile Thr Ser Tyr Glu Lys Ser Asp Gly Val
        50                  55                  60

Tyr Thr Gly Leu Ser Thr Arg Asn Gln Glu Thr Tyr Glu Thr Leu Lys
65                  70                  75                  80

His Glu Lys Pro Pro Gln
                85

<210> SEQ ID NO 113
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 113

Asp Gly Val Tyr Thr Gly Leu Ser Thr Arg Asn Gln Glu Thr Tyr Glu
1               5                   10                  15
```

Thr Leu Lys His Glu
            20

<210> SEQ ID NO 114
<211> LENGTH: 171
<212> TYPE: PRT
<213> ORGANISM: Artificial Sequence
<220> FEATURE:
<223> OTHER INFORMATION: synthetic polypeptide

<400> SEQUENCE: 114

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 115
<211> LENGTH: 127
<212> TYPE: PRT
<213> ORGANISM: Artificial Sequence
<220> FEATURE:
<223> OTHER INFORMATION: synthetic polypeptide

<400> SEQUENCE: 115

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Thr Ala Asp Thr Gln
                85                  90                  95

Ala Leu Leu Arg Asn Asp Gln Val Tyr Gln Pro Leu Arg Asp Arg Asp
            100                 105                 110

Asp Ala Gln Tyr Ser His Leu Gly Gly Asn Trp Ala Arg Asn Lys

-continued

<210> SEQ ID NO 116
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 116

Asp Gln Val Tyr Gln Pro Leu Arg Asp Arg Asp Ala Gln Tyr Ser
1               5                   10                  15

His Leu Gly Gly Asn
            20

<210> SEQ ID NO 117
<211> LENGTH: 207
<212> TYPE: PRT
<213> ORGANISM: Artificial Sequence
<220> FEATURE:
<223> OTHER INFORMATION: synthetic polypeptide

<400> SEQUENCE: 117

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 118
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 118

Asn Pro Asp Tyr Glu Pro Ile Arg Lys Gly Gln Arg Asp Leu Tyr Ser
1               5                   10                  15

Gly Leu Asn Gln Arg
            20

<210> SEQ ID NO 119
<211> LENGTH: 182
<212> TYPE: PRT
<213> ORGANISM: Artificial Sequence
<220> FEATURE:
<223> OTHER INFORMATION: synthetic polypeptide

<400> SEQUENCE: 119

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 120
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 120

Asp Gln Leu Tyr Gln Pro Leu Lys Asp Arg Glu Asp Asp Gln Tyr Ser
1               5                   10                  15

His Leu Gln Gly Asn
            20

<210> SEQ ID NO 121
<211> LENGTH: 163
<212> TYPE: PRT
<213> ORGANISM: Artificial Sequence
<220> FEATURE:
<223> OTHER INFORMATION: synthetic polypeptide

<400> SEQUENCE: 121

Met Lys Trp Lys Ala Leu Phe Thr Ala Ala Ile Leu Gln Ala Gln Leu
1               5                   10                  15

```
Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
                100                 105                 110

Leu Gln Lys Asp Lys Met Ala Glu Ala Tyr Ser Glu Ile Gly Met Lys
            115                 120                 125

Gly Glu Arg Arg Arg Gly Lys Gly His Asp Gly Leu Tyr Gln Gly Leu
        130                 135                 140

Ser Thr Ala Thr Lys Asp Thr Tyr Asp Ala Leu His Met Gln Ala Leu
145                 150                 155                 160

Pro Pro Arg

<210> SEQ ID NO 122
<211> LENGTH: 164
<212> TYPE: PRT
<213> ORGANISM: Artificial Sequence
<220> FEATURE:
<223> OTHER INFORMATION: synthetic polypeptide

<400> SEQUENCE: 122

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
                100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
        130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 123
<211> LENGTH: 112
<212> TYPE: PRT
<213> ORGANISM: Artificial Sequence
<220> FEATURE:
<223> OTHER INFORMATION: synthetic polypeptide
```

<400> SEQUENCE: 123

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 124
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 124

```
Asn Gln Leu Tyr Asn Glu Leu Asn Leu Gly Arg Arg Glu Glu Tyr Asp
1               5                   10                  15

Val Leu Asp Lys Arg
            20
```

<210> SEQ ID NO 125
<211> LENGTH: 22
<212> TYPE: PRT
<213> ORGANISM: Artificial Sequence
<220> FEATURE:
<223> OTHER INFORMATION: synthetic polypeptide

<400> SEQUENCE: 125

```
Glu Gly Leu Tyr Asn Glu Leu Gln Lys Asp Lys Met Ala Glu Ala Tyr
1               5                   10                  15

Ser Glu Ile Gly Met Lys
            20
```

<210> SEQ ID NO 126
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 126

```
Asp Gly Leu Tyr Gln Gly Leu Ser Thr Ala Thr Lys Asp Thr Tyr Asp
1               5                   10                  15

Ala Leu His Met Gln
            20
```

<210> SEQ ID NO 127
<211> LENGTH: 226
<212> TYPE: PRT
<213> ORGANISM: Artificial Sequence
<220> FEATURE:
<223> OTHER INFORMATION: synthetic polypeptide

<400> SEQUENCE: 127

```
Met Pro Gly Gly Pro Gly Val Leu Gln Ala Leu Pro Ala Thr Ile Phe
1               5                   10                  15
Leu Leu Phe Leu Leu Ser Ala Val Tyr Leu Gly Pro Gly Cys Gln Ala
            20                  25                  30
Leu Trp Met His Lys Val Pro Ala Ser Leu Met Val Ser Leu Gly Glu
        35                  40                  45
Asp Ala His Phe Gln Cys Pro His Asn Ser Ser Asn Asn Ala Asn Val
    50                  55                  60
Thr Trp Trp Arg Val Leu His Gly Asn Tyr Thr Trp Pro Pro Glu Phe
65                  70                  75                  80
Leu Gly Pro Gly Glu Asp Pro Asn Gly Thr Leu Ile Ile Gln Asn Val
                85                  90                  95
Asn Lys Ser His Gly Gly Ile Tyr Val Cys Arg Val Gln Glu Gly Asn
            100                 105                 110
Glu Ser Tyr Gln Gln Ser Cys Gly Thr Tyr Leu Arg Val Arg Gln Pro
        115                 120                 125
Pro Pro Arg Pro Phe Leu Asp Met Gly Glu Gly Thr Lys Asn Arg Ile
    130                 135                 140
Ile Thr Ala Glu Gly Ile Ile Leu Leu Phe Cys Ala Val Val Pro Gly
145                 150                 155                 160
Thr Leu Leu Leu Phe Arg Lys Arg Trp Gln Asn Glu Lys Leu Gly Leu
                165                 170                 175
Asp Ala Gly Asp Glu Tyr Glu Asp Glu Asn Leu Tyr Glu Gly Leu Asn
            180                 185                 190
Leu Asp Asp Cys Ser Met Tyr Glu Asp Ile Ser Arg Gly Leu Gln Gly
        195                 200                 205
Thr Tyr Gln Asp Val Gly Ser Leu Asn Ile Gly Asp Val Gln Leu Glu
    210                 215                 220
Lys Pro
225
```

<210> SEQ ID NO 128
<211> LENGTH: 188
<212> TYPE: PRT
<213> ORGANISM: Artificial Sequence
<220> FEATURE:
<223> OTHER INFORMATION: synthetic polypeptide

<400> SEQUENCE: 128

```
Met Pro Gly Gly Pro Gly Val Leu Gln Ala Leu Pro Ala Thr Ile Phe
1               5                   10                  15
Leu Leu Phe Leu Leu Ser Ala Val Tyr Leu Gly Pro Gly Cys Gln Ala
            20                  25                  30
Leu Trp Met His Lys Val Pro Ala Ser Leu Met Val Ser Leu Gly Glu
        35                  40                  45
Asp Ala His Phe Gln Cys Pro His Asn Ser Ser Asn Asn Ala Asn Val
    50                  55                  60
Thr Trp Trp Arg Val Leu His Gly Asn Tyr Thr Trp Pro Pro Glu Phe
65                  70                  75                  80
Leu Gly Pro Gly Glu Asp Pro Asn Glu Pro Pro Arg Pro Phe Leu
                85                  90                  95
Asp Met Gly Glu Gly Thr Lys Asn Arg Ile Ile Thr Ala Glu Gly Ile
            100                 105                 110
Ile Leu Leu Phe Cys Ala Val Val Pro Gly Thr Leu Leu Leu Phe Arg
```

```
                115                 120                 125
Lys Arg Trp Gln Asn Glu Lys Leu Gly Leu Asp Ala Gly Asp Glu Tyr
    130                 135                 140

Glu Asp Glu Asn Leu Tyr Glu Gly Leu Asn Leu Asp Asp Cys Ser Met
145                 150                 155                 160

Tyr Glu Asp Ile Ser Arg Gly Leu Gln Gly Thr Tyr Gln Asp Val Gly
                165                 170                 175

Ser Leu Asn Ile Gly Asp Val Gln Leu Glu Lys Pro
            180                 185
```

<210> SEQ ID NO 129
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 129

```
Glu Asn Leu Tyr Glu Gly Leu Asn Leu Asp Asp Cys Ser Met Tyr Glu
1               5                   10                  15

Asp Ile Ser Arg Gly
            20
```

<210> SEQ ID NO 130
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 130

```
Arg Pro Arg Arg Ser Pro Ala Gln Asp Gly Lys Val Tyr Ile Asn Met
1               5                   10                  15

Pro Gly Arg Gly
            20
```

<210> SEQ ID NO 131
<211> LENGTH: 68
<212> TYPE: PRT
<213> ORGANISM: Artificial Sequence
<220> FEATURE:
<223> OTHER INFORMATION: synthetic polypeptide

<400> SEQUENCE: 131

```
Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
        50                  55                  60

Ala Tyr Arg Ser
65
```

<210> SEQ ID NO 132
<211> LENGTH: 619
<212> TYPE: PRT
<213> ORGANISM: Artificial Sequence
<220> FEATURE:
<223> OTHER INFORMATION: synthetic polypeptide

```
<400> SEQUENCE: 132

Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
            20                  25                  30

Leu Phe Leu Leu Arg Gln Cys Leu Arg Ser Leu Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
            115                 120                 125

Gln Thr Trp Lys Leu Glu Gly Glu Ala Leu Glu Gln Ala Ile Ile Ser
130                 135                 140

Gln Ala Pro Gln Val Glu Lys Leu Ile Ala Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
        210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
    290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
            405                 410                 415
```

```
Ala Gly Gly Gly Pro Leu His Lys Phe Leu Val Gly Lys Arg Glu Glu
            420             425             430
Ile Pro Val Ser Asn Val Ala Glu Leu Leu His Gln Val Ser Met Gly
        435             440             445
Met Lys Tyr Leu Glu Gly Lys Asn Phe Val His Arg Asp Leu Ala Ala
    450             455             460
Arg Asn Val Leu Leu Val Asn Arg His Tyr Ala Lys Ile Ser Asp Phe
465             470             475             480
Gly Leu Ser Lys Ala Leu Gly Ala Asp Asp Ser Tyr Tyr Thr Ala Arg
            485             490             495
Ser Ala Gly Lys Trp Pro Leu Lys Trp Tyr Ala Pro Glu Cys Ile Asn
            500             505             510
Phe Arg Lys Phe Ser Ser Arg Ser Asp Val Trp Ser Tyr Gly Val Thr
            515             520             525
Met Trp Glu Ala Leu Ser Tyr Gly Gln Lys Pro Tyr Lys Lys Met Lys
    530             535             540
Gly Pro Glu Val Met Ala Phe Ile Glu Gln Gly Lys Arg Met Glu Cys
545             550             555             560
Pro Pro Glu Cys Pro Pro Glu Leu Tyr Ala Leu Met Ser Asp Cys Trp
            565             570             575
Ile Tyr Lys Trp Glu Asp Arg Pro Asp Phe Leu Thr Val Glu Gln Arg
            580             585             590
Met Arg Ala Cys Tyr Tyr Ser Leu Ala Ser Lys Val Glu Gly Pro Pro
            595             600             605
Gly Ser Thr Gln Lys Ala Glu Ala Ala Cys Ala
    610             615
```